(12) United States Patent
Hermann et al.

(10) Patent No.: US 8,921,383 B2
(45) Date of Patent: Dec. 30, 2014

(54) THIAZOLOPYRIMIDINE COMPOUNDS

(75) Inventors: Johannes Cornelius Hermann, Jersey City, NJ (US); Lee Edwin Lowrie, Jr., Andover, NJ (US); Matthew C. Lucas, Verona, NJ (US); Kin-Chun Thomas Luk, North Caldwell, NJ (US); Fernando Padilla, Verona, NJ (US); Jutta Wanner, Montclair, NJ (US); Wenwei Xie, Beijing (CN); Xiaohu Zhang, Beijing (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 274 days.

(21) Appl. No.: 13/429,484

(22) Filed: Mar. 26, 2012

(65) Prior Publication Data
US 2012/0252777 A1    Oct. 4, 2012

Related U.S. Application Data

(63) Continuation of application No. PCT/CN2011/072211, filed on Mar. 28, 2011.

(51) Int. Cl.
| | | |
|---|---|---|
| *A01N 43/90* | (2006.01) | |
| *A61K 31/519* | (2006.01) | |
| *C07D 471/00* | (2006.01) | |
| *C07D 487/00* | (2006.01) | |
| *C07D 513/04* | (2006.01) | |
| *A61K 45/06* | (2006.01) | |

(52) U.S. Cl.
CPC ............. *C07D 513/04* (2013.01); *A61K 45/06* (2013.01)
USPC ........................................ 514/260.1; 544/255

(58) Field of Classification Search
None
See application file for complete search history.

*Primary Examiner* — Jeffrey H Murray

(57) ABSTRACT

The present invention relates to the use of novel thiazolopyrimidine derivatives of formula I:

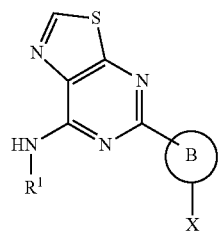

wherein all variable substituents are defined as described herein, which are SYK inhibitors and are useful for the treatment of auto-immune and inflammatory diseases.

15 Claims, No Drawings

THIAZOLOPYRIMIDINE COMPOUNDS

PRIORITY TO RELATED APPLICATION(S)

This application claims the benefit of International Patent Application No. PCT/CN2011/072211, filed Mar. 28, 2011, which is hereby incorporated by reference in its entirety.

FIELD OF THE INVENTION

Protein kinases constitute one of the largest families of human enzymes and regulate many different signaling processes by adding phosphate groups to proteins; particularly tyrosine kinases phosphorylate proteins on the alcohol moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a means to modulate cellular function with small molecule inhibitors of kinase activity and thus make good drug design targets. In addition to treatment of kinase-mediated disease processes, selective and efficacious inhibitors of kinase activity are also useful for investigation of cell signaling processes and identification of other cellular targets of therapeutic interest.

SYK (Spleen Tyrosine Kinase) is a non-receptor tyrosine kinase that is essential for B-cell activation through BCR signaling. SYK becomes activated upon binding to phosphorylated BCR and thus initiates the early signaling events following BCR activation. Mice deficient in SYK exhibit an early block in B-cell development. Therefore inhibition of SYK enzymatic activity in cells is proposed as a treatment for autoimmune disease through its effects on autoantibody production.

In addition to the role of SYK in BCR signaling and B-cell activation, it also plays a key role in FcεRI mediated mast cell degranulation and eosinophil activation. Thus, SYK is implicated in allergic disorders including asthma SYK binds to the phosphorylated gamma chain of FcγRI via its SH2 domains and is essential for downstream signaling SYK deficient mast cells demonstrate defective degranulation, arachidonic acid and cytokine secretion This also has been shown for pharmacologic agents that inhibit SYK activity in mast cells Treatment with SYK antisense oligonucleotides inhibits antigen-induced infiltration of eosinophils and neutrophils in an animal model of asthma. SYK deficient eosinophils also show impaired activation in response to FcεR stimulation. Therefore, small molecule inhibitors of SYK will be useful for treatment of allergy-induced inflammatory diseases including asthma.

In view of the numerous conditions that are contemplated to benefit by treatment involving modulation of the SYK pathway it is immediately apparent that new compounds that modulate the SYK pathway and methods of using these compounds should provide substantial therapeutic benefits to a wide variety of patients. Provided herein are novel compounds for use in the treatment of conditions in which targeting of the SYK pathway or inhibition of SYK kinases, and are therapeutically useful for the treatment of auto-immune and inflammatory diseases.

The present application provides a compound of Formula I

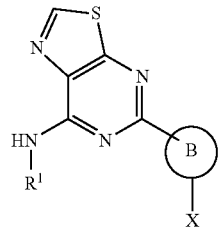

wherein:
$R^1$ is phenyl, optionally substituted with one or more lower alkyl, lower haloalkyl, hydroxy, hydroxy lower alkyl, lower alkoxy, lower alkyl sulfonyl, halo, nitro, amino, aminoalkyl, amido, cyano, oxo, or $R^{1'}$;
$R^{1'}$ is heterocycloalkyl or spiro heterocycloalkyl, each optionally substituted with one or more $R^{1''}$;
$R^{1''}$ is hydroxy, halo, lower alkyl, lower alkoxy, or lower haloalkyl;
B is phenyl, pyridinyl, pyrrolidinyl, or piperidinyl;
X is OH, lower alkoxy, NHC(=O)Y, C(=O)NH$_2$, C(=O)NHY, C(=O)X', C(=O)Y, CH$_2$NHY, CH$_2$CH$_2$Y, CF=CHY, CH=CHY, CH$_2$OH, C(=O)NHCH$_2$CH$_2$N(CH$_3$)$_2$, or C(=O)NHCH$_2$CH$_2$Y;
X' is OH or lower alkoxy;
Y is cycloalkyl, heterocycloalkyl, aryl, or heteroaryl, each optionally substituted with one or more $Y^3$;
$Y^3$ is hydroxy, lower alkyl, lower alkoxy, halo, oxo, lower haloalkyl, hydroxy lower alkyl, amino, amido, C(=O)NH(CH$_3$), C(=O)OH, C(=O)OY$^4$, or heteroaryl optionally substituted by with one or more lower alkyl, oxo or SH;
$Y^4$ is lower alkyl;
or a pharmaceutically acceptable salt thereof.

The present application provides a method for treating an inflammatory or autoimmune condition comprising administering to a patient in need thereof a therapeutically effective amount of the compound of any one of claims 1-12.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

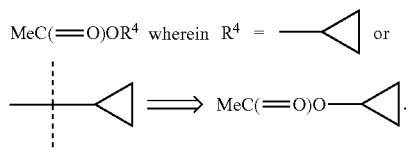

A bond drawn into ring system (as opposed to connected at a distinct vertex) indicates that the bond may be attached to any of the suitable ring atoms The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— $\leftrightarrows$ —C(—OH)=CH—), amide/imidic acid (—C(=O)—NH— $\leftrightarrows$ —C(—OH)=N—) and amidine (—C(=NR)—NH— $\leftrightarrows$ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro[3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —$CH_2CH(i-Pr)CH_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "$PCy_3$" refers to a phosphine trisubstituted with three cyclic moieties.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term carboxy-alkyl as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —$CO_2H$ moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N, O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of SYK

In certain embodiment, the present application provides a compound of Formula I

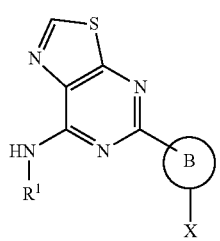

I wherein:
$R^1$ is phenyl, optionally substituted with one or more lower alkyl, lower haloalkyl, hydroxy, hydroxy lower alkyl, lower alkoxy, lower alkyl sulfonyl, halo, nitro, amino, aminoalkyl, amido, cyano, oxo, or $R^{1'}$;

R$^{1'}$ is heterocycloalkyl or spiro heterocycloalkyl, each optionally substituted with one or more R$^{1''}$;
  R$^{1''}$ is hydroxy, halo, lower alkyl, lower alkoxy, or lower haloalkyl;
B is phenyl, pyridinyl, pyrrolidinyl, or piperidinyl;
X is OH, lower alkoxy, NHC(=O)Y, C(=O)NH$_2$, C(=O)NHY, C(=O)X', C(=O)Y, CH$_2$NHY, CH$_2$CH$_2$Y, CF=CHY, CH=CHY, CH$_2$OH, C(=O)NHCH$_2$CH$_2$N(CH$_3$)$_2$, or C(=O)NHCH$_2$CH$_2$Y;
X' is OH or lower alkoxy;
Y is cycloalkyl, heterocycloalkyl, aryl, or heteroaryl, each optionally substituted with one or more Y$^3$;
Y$^3$ is hydroxy, lower alkyl, lower alkoxy, halo, oxo, lower haloalkyl, hydroxy lower alkyl, amino, amido, C(=O)NH(CH$_3$), C(=O)OH, C(=O)OY$^4$, or heteroaryl optionally substituted by with one or more lower alkyl, oxo or SH;
  Y$^4$ is lower alkyl;
or a pharmaceutically acceptable salt thereof.

The present application provides the above compound of Formula I, wherein B is phenyl.

The present application also provides the above compound of Formula I, wherein B is pyrrolidinyl.

The present application further provides the above compound of Formula I, wherein B is piperidinyl.

The present application provides the compound of formula I, wherein X is NHC(=O)Y, C(=O)NH$_2$, C(=O)NHY, C(=O)X', C(=O)Y, C(=O)NHCH$_2$CH$_2$N(CH$_3$)$_2$, or C(=O)NHCH$_2$CH$_2$Y.

The present application provides the compound of formula I, wherein X is NHC(=O)Y, C(=O)NHY, CH$_2$NHY or CH$_2$OH.

The present application provides the compound of Formula I, wherein X is NH and Y is C=O.

The present application provides the compound of Formula I, wherein B is pyrrolidinyl, X is NH and Y is C=O.

The present application provides the compound of Formula I, wherein B is piperidinyl, X is NH and Y is C=O.

The present application provides the compound of Formula I, wherein X is C=O and Y is NH.

The present application provides the compound of Formula I, wherein B is phenyl, X is C=O and Y is NH.

The present application provides the compound of Formula I, wherein R$^1$ is 3,4-dimethoxy-phenyl.

The present application provides the compound of Formula I, wherein Y is phenyl, pyridinyl or indazolyl optionally substituted with one or more Y$^3$.

The present application provides the compound of Formula I, wherein Y is phenyl optionally substituted with one or more Y$^3$.

The present application provides the compound of Formula I, wherein Y is heteroaryl optionally substituted with one or more Y$^3$.

The present application provides the compound of Formula I, wherein Y is heterocycloalkyl optionally substituted with one or more Y$^3$.

The present application provides the compound of Formula I, wherein Y$^3$ is hydroxy, lower alkoxy, C(=O)OH, or C(=O)OY4.

The present application provides a compound selected from the group consisting of:
3-[7-(3,4-Dimethoxy-phenylamino)-thiazolo[5,4-d]pyrimidin-5-yl]-benzoic acid;
[1,4]Diazepan-1-yl-{3-[7-(3,4-dimethoxy-phenylamino)-thiazolo[5,4-d]pyrimidin-5-yl]-phenyl}-methanone;
3-(7-(3,4-Dimethoxyphenylamino)thiazolo[5,4-d]pyrimidin-5-yl)-N-(4-(methylcarbamoyl)phenyl)benzamide;
4-{3-[7-(3,4-Dimethoxy-phenylamino)-thiazolo[5,4-d]pyrimidin-5-yl]-benzoylamino}-benzoic acid;
4-(1-(7-(3,4-Dimethoxyphenylamino)thiazolo[5,4-d]pyrimidin-5-yl)pyrrolidin-3-ylcarbamoyl)benzoic acid;
4-(1-(7-(3,4-Dimethoxyphenylamino)thiazolo[5,4-d]pyrimidin-5-yl)piperidin-3-ylcarbamoyl)benzoic acid;
4-({1-[7-(3,4-Dimethoxy-phenylamino)-thiazolo[5,4-d]pyrimidin-5-yl]-piperidine-3-carbonyl}-amino)-benzoic acid;
N-(1-(7-(3,4-Dimethoxyphenylamino)thiazolo[5,4-d]pyrimidin-5-yl)pyrrolidin-3-yl)-2-oxoindoline-6-carboxamide;
4-(1-(7-(3,4-Dimethoxyphenylamino)thiazolo[5,4-d]pyrimidin-5-yl)pyrrolidin-3-ylcarbamoyl)-2-hydroxybenzoic acid;
4-(1-(7-(3,4-Dimethoxyphenylamino)thiazolo[5,4-d]pyrimidin-5-yl)pyrrolidin-3-ylcarbamoyl)-2-methoxybenzoic acid;
N-(1-(7-(3,4-Dimethoxyphenylamino)thiazolo[5,4-d]pyrimidin-5-yl)pyrrolidin-3-yl)-1H-indazole-6-carboxamide;
N-(1-(7-(3,4-Dimethoxyphenylamino)thiazolo[5,4-d]pyrimidin-5-yl)pyrrolidin-3-yl)pyrazine-2-carboxamide;
6-Amino-N-{1-[7-(3,4-dimethoxy-phenylamino)-thiazolo[5,4-d]pyrimidin-5-yl]-pyrrolidin-3-yl}-nicotinamide;
N-(1-(7-(3,4-Dimethoxyphenylamino)thiazolo[5,4-d]pyrimidin-5-yl)pyrrolidin-3-yl)-2-oxo-2,3-dihydro-1H-benzo[d]imidazole-5-carboxamide;
3-[7-(3,4-Dimethoxy-phenylamino)-thiazolo[5,4-d]pyrimidin-5-yl]-N-[4-(5-mercapto-[1,3,4]oxadiazol-2-yl)-phenyl]-benzamide;
4-(3-(7-(3,4-Dimethoxyphenylamino)thiazolo[5,4-d]pyrimidin-5-yl)benzamido)-2-methoxybenzoic acid;
3-[7-(3,4-Dimethoxy-phenylamino)-thiazolo[5,4-d]pyrimidin-5-yl]-N-[4-(5-oxo-4,5-dihydro-[1,2,4]oxadiazol-3-yl)-phenyl]-benzamide;
3-[7-(3,4-Dimethoxy-phenylamino)-thiazolo[5,4-d]pyrimidin-5-yl]-N-(1H-indazol-5-yl)-benzamide;
3-[7-(3,4-Dimethoxy-phenylamino)-thiazolo[5,4-d]pyrimidin-5-yl]-N-(1H-indazol-6-yl)-benzamide;
4-[7-(3,4-Dimethoxy-phenylamino)-thiazolo[5,4-d]pyrimidin-5-yl]-N-(2-pyridin-4-yl-ethyl)-benzamide;
1-(7-(3,4-Dimethoxyphenylamino)thiazolo[5,4-d]pyrimidin-5-yl)-N-(2-(pyridin-4-yl)ethyl)piperidine-4-carboxamide;
1-(7-(3,4-Dimethoxyphenylamino)thiazolo[5,4-d]pyrimidin-5-yl)-N-(2-(2-oxo-1,2-dihydropyridin-4-yl)ethyl)piperidine-4-carboxamide;
4-(7-(3,4-Dimethoxyphenylamino)thiazolo[5,4-d]pyrimidin-5-yl)-N-(2-(2-oxo-1,2-dihydropyridin-4-yl)ethyl)benzamide;
4-[7-(3,4-Dimethoxy-phenylamino)-thiazolo[5,4-d]pyrimidin-5-yl]-N-[2-(1-methyl-2-oxo-1,2-dihydro-pyridin-4-yl)-ethyl]-benzamide;
1-(7-(3,4-Dimethoxyphenylamino)thiazolo[5,4-d]pyrimidin-5-yl)-N-(2-(pyridin-4-yl)ethyl)piperidine-3-carboxamide;
Methyl 3-(7-(3-(methylsulfonyl)phenylamino)thiazolo[5,4-d]pyrimidin-5-yl)benzoate;
3-[7-(3-Methanesulfonyl-phenylamino)-thiazolo[5,4-d]pyrimidin-5-yl]-benzoic acid;
3-{7-[3-(2-Methoxymethyl-pyrrolidin-1-yl)-phenylamino]-thiazolo[5,4-d]pyrimidin-5-yl}-benzoic acid;
tert-Butyl 4-(3-(7-(3,4-dimethoxyphenylamino)thiazolo[5,4-d]pyrimidin-5-yl)benzoate;
4-(3-(7-(3,4-Dimethoxyphenylamino)thiazolo[5,4-d]pyrimidin-5-yl)benzylamino)benzoic acid;

4-((E)-2-{3-[7-(3,4-Dimethoxy-phenylamino)-thiazolo[5,4-d]pyrimidin-5-yl]-phenyl}-2-fluoro-vinyl)-benzoic acid;
(E)-4-(3-(7-(3,4-Dimethoxyphenylamino)thiazolo[5,4-d]pyrimidin-5-yl)styryl)benzoic acid;
4-(3-(7-(3,4-Dimethoxyphenylamino)thiazolo[5,4-d]pyrimidin-5-yl)phenethyl)benzoic acid;
3-{7-[(1R,5S)-3-(8-Oxa-3-aza-bicyclo[3.2.1]oct-3-yl)-phenylamino]-thiazolo[5,4-d]pyrimidin-5-yl}-benzoic acid;
N-(1-(7-(3,4-Dimethoxyphenylamino)thiazolo[5,4-d]pyrimidin-5-yl)pyrrolidin-3-yl)-1H-indazole-5-carboxamide;
(S)—N-(3-(2-Methylpyrrolidin-1-yl)phenyl)-5-(3-((piperidin-4-ylamino)methyl)phenyl)thiazolo[5,4-d]pyrimidin-7-amine;
N5-(1-(7-(3,4-Dimethoxyphenylamino)thiazolo[5,4-d]pyrimidin-5-yl)pyrrolidin-3-yl)pyridine-2,5-dicarboxamide;
Methyl 5-(1-(7-(3,4-dimethoxyphenylamino)thiazolo[5,4-d]pyrimidin-5-yl)pyrrolidin-3-ylcarbamoyl)picolinate;
5-(1-(7-(3,4-Dimethoxyphenylamino)thiazolo[5,4-d]pyrimidin-5-yl)pyrrolidin-3-ylcarbamoyl)picolinic acid;
1-(7-(3,4-Dimethoxyphenylamino)thiazolo[5,4-d]pyrimidin-5-yl)-N-(2-oxoindolin-5-yl)piperidine-3-carboxamide;
1-(7-(3,4-Dimethoxyphenylamino)thiazolo[5,4-d]pyrimidin-5-yl)-N-(1H-indazol-5-yl)piperidine-3-carboxamide;
5-(1-(7-(3,4-Dimethoxyphenylamino)thiazolo[5,4-d]pyrimidin-5-yl)piperidine-3-carboxamido)picolinic acid;
4-({1-[7-(3,4-Dimethoxy-phenylamino)-thiazolo[5,4-d]pyrimidin-5-yl]-piperidine-3-carbonyl}-amino)-2-methoxybenzoic acid;
1-(7-(3,4-Dimethoxyphenylamino)thiazolo[5,4-d]pyrimidin-5-yl)-N-(4-(5-oxo-4,5-dihydro-1,2,4-oxadiazol-3-yl)phenyl)piperidine-3-carboxamide;
1-(7-(3,4-Dimethoxyphenylamino)thiazolo[5,4-d]pyrimidin-5-yl)-N-(1H-indazol-6-yl)piperidine-3-carboxamide;
1-(7-(3,4-Dimethoxyphenylamino)thiazolo[5,4-d]pyrimidin-5-yl)-N-(1-oxoisoindolin-5-yl)piperidine-3-carboxamide;
4-(1-(7-(3,4-Dimethoxyphenylamino)thiazolo[5,4-d]pyrimidin-5-yl)piperidine-3-carboxamido)-2-hydroxybenzoic acid;
1-(7-(3,4-Dimethoxyphenylamino)thiazolo[5,4-d]pyrimidin-5-yl)-N-(5-oxopyrrolidin-3-yl)piperidine-3-carboxamide;
1-(7-(3,4-Dimethoxyphenylamino)thiazolo[5,4-d]pyrimidin-5-yl)-N-(pyrazin-2-yl)piperidine-3-carboxamide;
1-(7-(3,4-Dimethoxyphenylamino)thiazolo[5,4-d]pyrimidin-5-yl)-N-(1,3-dioxoisoindolin-5-yl)piperidine-3-carboxamide;
1-(7-(3,4-Dimethoxyphenylamino)thiazolo[5,4-d]pyrimidin-5-yl)-N-(4-(5-mercapto-1,3,4-oxadiazol-2-yl)phenyl)piperidine-3-carboxamide;
1-(7-(3,4-Dimethoxyphenylamino)thiazolo[5,4-d]pyrimidin-5-yl)-N-(4-(5-mercapto-4-methyl-4H-1,2,4-triazol-3-yl)phenyl)piperidine-3-carboxamide;
3-{7-[3-(2-Oxa-6-aza-spiro[3.3]hept-6-yl)-phenylamino]-thiazolo[5,4-d]pyrimidin-5-yl}-benzoic acid;
4-(1-(7-(3,4-Dimethoxyphenylamino)thiazolo[5,4-d]pyrimidin-5-yl)pyrrolidine-3-carboxamido)benzoic acid;
4-(1-(7-(5,6-Dimethoxypyridin-2-ylamino)thiazolo[5,4-d]pyrimidin-5-yl)pyrrolidin-3-ylcarbamoyl)benzoic acid;
Methyl 3-(7-(3-(trifluoromethyl)phenylamino)thiazolo[5,4-d]pyrimidin-5-yl)benzoate;
3-[7-(3-Trifluoromethyl-phenylamino)-thiazolo[5,4-d]pyrimidin-5-yl]-benzoic acid;
3-[7-(3,4,5-Trimethoxy-phenylamino)-thiazolo[5,4-d]pyrimidin-5-yl]-benzamide;
1-(7-(3-((S)-2-Methylpyrrolidin-1-yl)phenylamino)thiazolo[5,4-d]pyrimidin-5-yl)piperidin-3-ol;
4-{7-[3-Methoxy-5-((S)-2-methyl-pyrrolidin-1-yl)-phenylamino]-thiazolo[5,4-d]pyrimidin-5-yl}-benzamide;
(S)-5-(6-Methoxypyridin-3-yl)-N-(3-(2-methylpyrrolidin-1-yl)phenyl)thiazolo[5,4-d]pyrimidin-7-amine;
4-{7-[3-((S)-2-Methyl-pyrrolidin-1-yl)-phenylamino]-thiazolo[5,4-d]pyrimidin-5-yl}-benzamide;
3-[7-(3,4-Dimethoxy-phenylamino)-thiazolo[5,4-d]pyrimidin-5-yl]-N-[4-(2,4-dioxo-thiazolidin-5-yl)-phenyl]-benzamide;
4-[7-(3,4-Dimethoxy-phenylamino)-thiazolo[5,4-d]pyrimidin-5-yl]-benzamide;
(S)—N-(2-(Dimethylamino)ethyl)-4-(7-(3-(2-methylpyrrolidin-1-yl)phenylamino)thiazolo[5,4-d]pyrimidin-5-yl)benzamide;
4-(7-(3,4-Dimethoxyphenylamino)thiazolo[5,4-d]pyrimidin-5-yl)-N-(2-(dimethylamino)ethyl)benzamide;
{3-[7-(3,4-Dimethoxy-phenylamino)-thiazolo[5,4-d]pyrimidin-5-yl]-phenyl}-methanol; and
3-[7-(3,4-Dimethoxy-phenylamino)-thiazolo[5,4-d]pyrimidin-5-yl]-benzamide.

The present application provides a method for treating an inflammatory or autoimmune condition comprising administering to a patient in need thereof a therapeutically effective amount of the compound of Formula I.

The present application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The present application provides a method for treating an inflammatory condition comprising administering to a patient in need thereof a therapeutically effective amount of the compound of Formula I.

The present application provides a method for treating rheumatoid arthritis comprising administering to a patient in need thereof a therapeutically effective amount of the compound of Formula I.

The present application provides a method for treating asthma comprising administering to a patient in need thereof a therapeutically effective amount of the compound of Formula I.

The present application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The present application provides a method for treating an inflammatory condition comprising co-administering to a patient in need thereof a therapeutically effective amount of an anti-inflammatory compound in combination with the compound of Formula I.

The present application provides a method for treating an immune disorder comprising co-administering to a patient in need thereof a therapeutically effective amount of an immunosuppressant compound in combination with the compound of Formula I.

The present application provides a pharmaceutical composition comprising the compound of Formula I, admixed with at least one pharmaceutically acceptable carrier, excipient or diluent.

The present application provides the above pharmaceutical composition, further comprising an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, and an agent for treating immunodeficiency disorders.

The present application provides the use of the compound of formula I for the manufacture of a medicament useful for the treatment of disorders associated with Syk.

The present application provides the use of the compound of formula I for the manufacture of a medicament useful for the treatment of rheumatoid arthritis.

A compound, method, or composition as described herein.

Compounds

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system or Struct=Name, a CambridgeSoft® application, for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of pyridinone compounds according to generic Formula I.

TABLE I

| Compound | Nomenclature | Structure |
|---|---|---|
| I-1 | 3-[7-(3,4-Dimethoxy-phenylamino)-thiazolo[5,4-d]pyrimidin-5-yl]-benzoic acid | 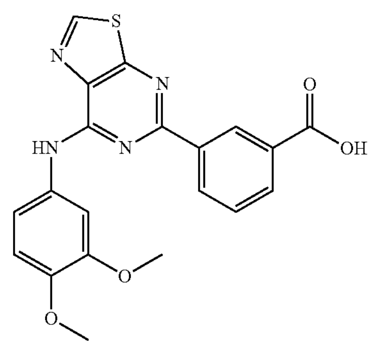 [SMILES: COc1ccc(Nc2nc(-c3cccc(C(=O)O)c3)nc3scnc23)cc1OC] |
| I-2 | [1,4]Diazepan-1-yl-{3-[7-(3,4-dimethoxy-phenylamino)-thiazolo[5,4-d]pyrimidin-5-yl]-phenyl}-methanone | 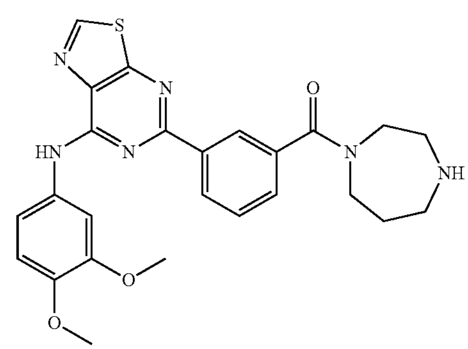 [SMILES: COc1ccc(Nc2nc(-c3cccc(C(=O)N4CCCNCC4)c3)nc3scnc23)cc1OC] |
| I-3 | 3-(7-(3,4-Dimethoxyphenylamino)thiazolo[5,4-d]pyrimidin-5-yl)-N-(4-(methylcarbamoyl)phenyl)benzamide | 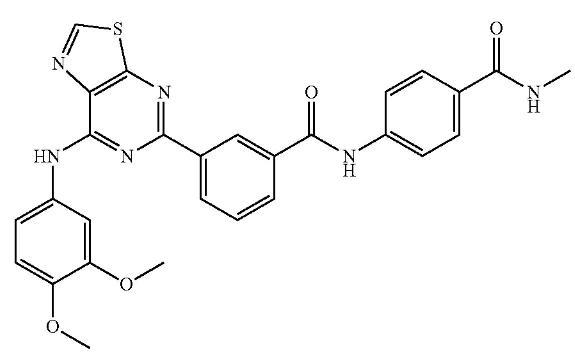 [SMILES: CNC(=O)c1ccc(NC(=O)c2cccc(-c3nc(Nc4ccc(OC)c(OC)c4)c4ncsc4n3)c2)cc1] |

TABLE I-continued

| Compound | Nomenclature | Structure |
|---|---|---|
| I-4 | 4-{3-[7-(3,4-Dimethoxy-phenylamino)-thiazolo[5,4-d]pyrimidin-5-yl]-benzoylamino}-benzoic acid | 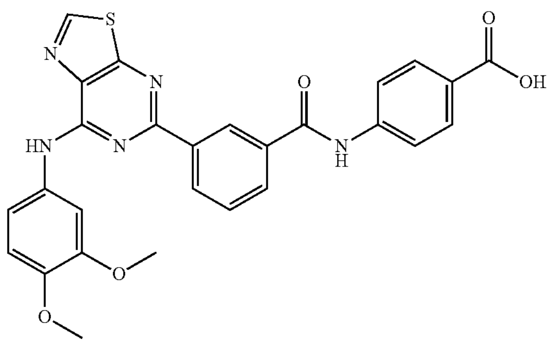 [SMILES: COc1ccc(Nc2nc(-c3cccc(C(=O)Nc4ccc(C(=O)O)cc4)c3)nc3scnc23)cc1OC] |
| I-5 | 4-(1-(7-(3,4-Dimethoxyphenylamino)thiazolo[5,4-d]pyrimidin-5-yl)pyrrolidin-3-ylcarbamoyl)benzoic acid | 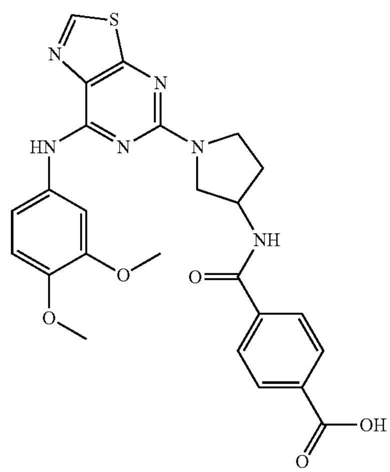 [SMILES: COc1ccc(Nc2nc(N3CCC(NC(=O)c4ccc(C(=O)O)cc4)C3)nc3scnc23)cc1OC] |
| I-6 | 4-(1-(7-(3,4-Dimethoxyphenylamino)thiazolo[5,4-d]pyrimidin-5-yl)piperidin-3-ylcarbamoyl)benzoic acid | 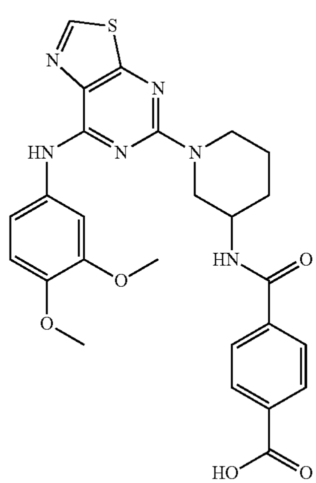 [SMILES: COc1ccc(Nc2nc(N3CCCC(NC(=O)c4ccc(C(=O)O)cc4)C3)nc3scnc23)cc1OC] |

TABLE I-continued

| Compound | Nomenclature | Structure |
|---|---|---|
| I-7 | 4-({1-[7-(3,4-Dimethoxy-phenylamino)-thiazolo[5,4-d]pyrimidin-5-yl]-piperidine-3-carbonyl}-amino)-benzoic acid | 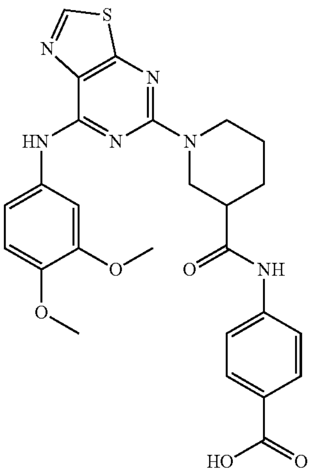 [SMILES: COc1ccc(Nc2nc(N3CCCC(C(=O)Nc4ccc(C(=O)O)cc4)C3)nc3scnc23)cc1OC] |
| I-8 | N-(1-(7-(3,4-Dimethoxyphenylamino)thiazolo[5,4-d]pyrimidin-5-yl)pyrrolidin-3-yl)-2-oxoindoline-6-carboxamide | 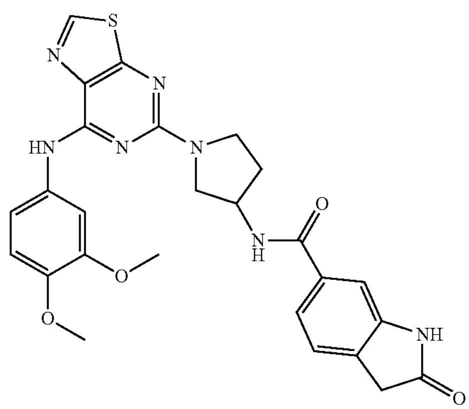 [SMILES: COc1ccc(Nc2nc(N3CCC(NC(=O)c4ccc5c(c4)NC(=O)C5)C3)nc3scnc23)cc1OC] |
| I-9 | 4-(1-(7-(3,4-Dimethoxyphenylamino)thiazolo[5,4-d]pyrimidin-5-yl)pyrrolidin-3-ylcarbamoyl)-2-hydroxybenzoic acid | 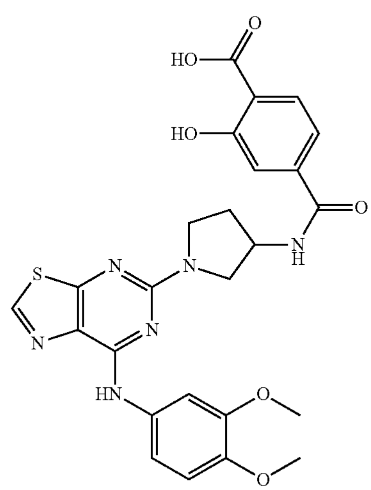 [SMILES: COc1ccc(Nc2nc(N3CCC(NC(=O)c4ccc(C(=O)O)c(O)c4)C3)nc3scnc23)cc1OC] |

TABLE I-continued

| Compound | Nomenclature | Structure |
|---|---|---|
| I-10 | 4-(1-(7-(3,4-Dimethoxyphenylamino)thiazolo[5,4-d]pyrimidin-5-yl)pyrrolidin-3-ylcarbamoyl)-2-methoxybenzoic acid | 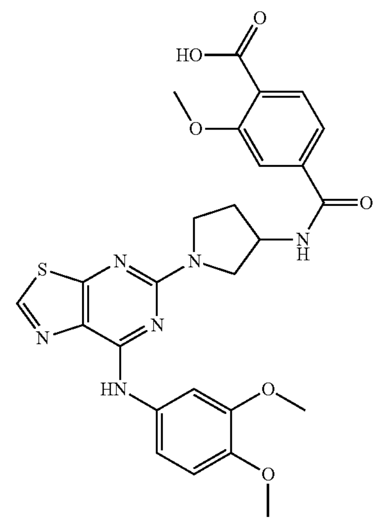 [SMILES: COc1ccc(Nc2nc(N3CCC(NC(=O)c4ccc(C(=O)O)c(OC)c4)C3)nc3scnc23)cc1OC] |
| I-11 | N-(1-(7-(3,4-Dimethoxyphenylamino)thiazolo[5,4-d]pyrimidin-5-yl)pyrrolidin-3-yl)-1H-indazole-6-carboxamide | 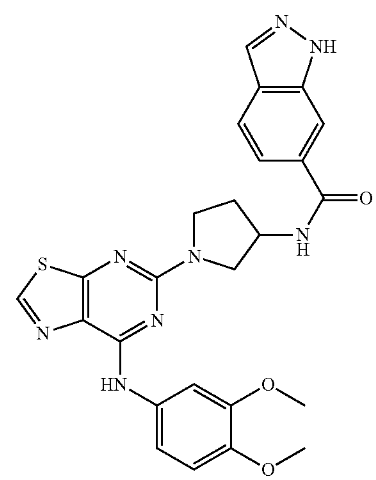 [SMILES: COc1ccc(Nc2nc(N3CCC(NC(=O)c4ccc5cn[nH]c5c4)C3)nc3scnc23)cc1OC] |
| I-12 | N-(1-(7-(3,4-Dimethoxyphenylamino)thiazolo[5,4-d]pyrimidin-5-yl)pyrrolidin-3-yl)pyrazine-2-carboxamide | 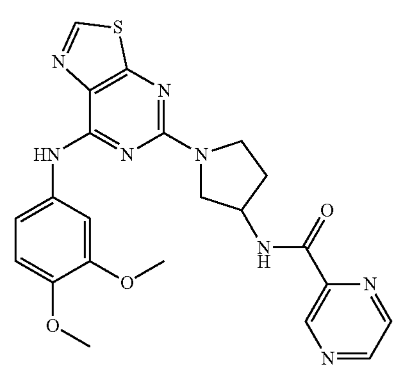 [SMILES: COc1ccc(Nc2nc(N3CCC(NC(=O)c4cnccn4)C3)nc3scnc23)cc1OC] |

TABLE I-continued

| Compound | Nomenclature | Structure |
|---|---|---|
| I-13 | 6-Amino-N-{1-[7-(3,4-dimethoxy-phenylamino)-thiazolo[5,4-d]pyrimidin-5-yl]-pyrrolidin-3-yl}-nicotinamide | 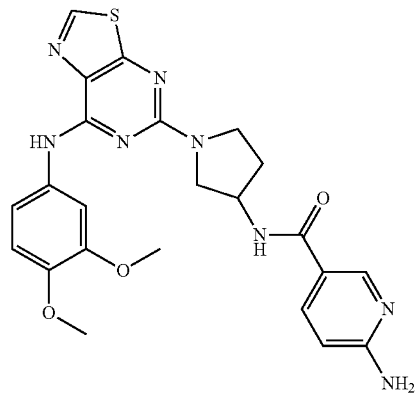 [SMILES: COc1ccc(Nc2nc(N3CCC(NC(=O)c4ccc(N)nc4)C3)nc3scnc23)cc1OC] |
| I-14 | N-(1-(7-(3,4-Dimethoxyphenylamino)thiazolo[5,4-d]pyrimidin-5-yl)pyrrolidin-3-yl)-2-oxo-2,3-dihydro-1H-benzo[d]imidazole-5-carboxamide | 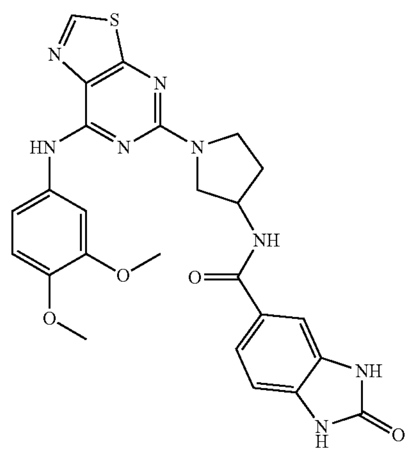 [SMILES: COc1ccc(Nc2nc(N3CCC(NC(=O)c4ccc5[nH]c(=O)[nH]c5c4)C3)nc3scnc23)cc1OC] |
| I-15 | 3-[7-(3,4-Dimethoxy-phenylamino)-thiazolo[5,4-d]pyrimidin-5-yl]-N-[4-(5-mercapto-[1,3,4]oxadiazol-2-yl)-phenyl]-benzamide | 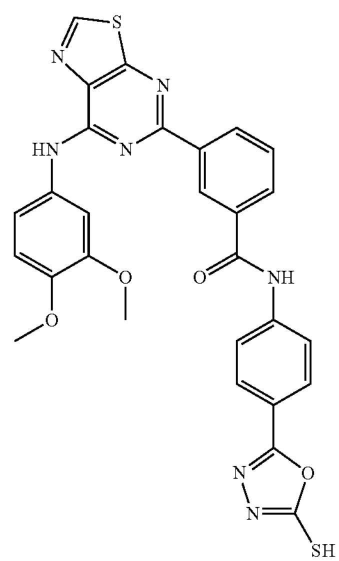 [SMILES: COc1ccc(Nc2nc(-c3cccc(C(=O)Nc4ccc(-c5nnc(S)o5)cc4)c3)nc3scnc23)cc1OC] |

TABLE I-continued

| Compound | Nomenclature | Structure |
|---|---|---|
| I-16 | 4-(3-(7-(3,4-Dimethoxyphenylamino)thiazolo[5,4-d]pyrimidin-5-yl)benzamido)-2-methoxybenzoic acid | 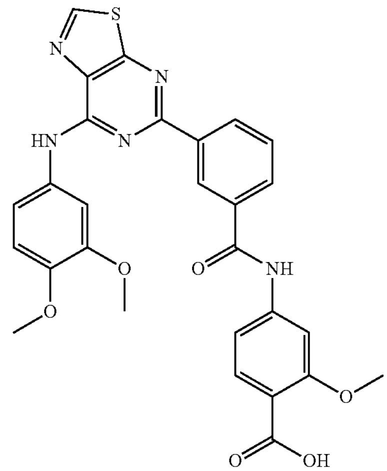 [SMILES: COc1ccc(Nc2nc(-c3cccc(C(=O)Nc4ccc(C(=O)O)c(OC)c4)c3)nc3scnc23)cc1OC] |
| I-17 | 3-[7-(3,4-Dimethoxy-phenylamino)-thiazolo[5,4-d]pyrimidin-5-yl]-N-[4-(5-oxo-4,5-dihydro-[1,2,4]oxadiazol-3-yl)-phenyl]-benzamide | 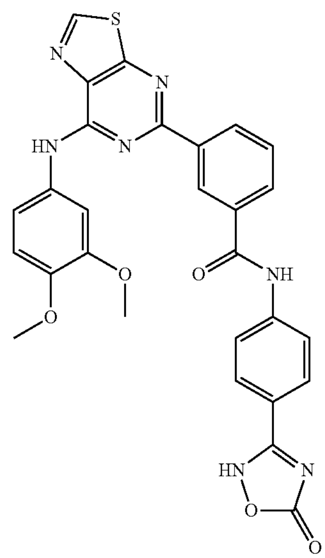 [SMILES: COc1ccc(Nc2nc(-c3cccc(C(=O)Nc4ccc(-c5nc(=O)o[nH]5)cc4)c3)nc3scnc23)cc1OC] |
| I-18 | 3-[7-(3,4-Dimethoxy-phenylamino)-thiazolo[5,4-d]pyrimidin-5-yl]-N-(1H-indazol-5-yl)-benzamide | 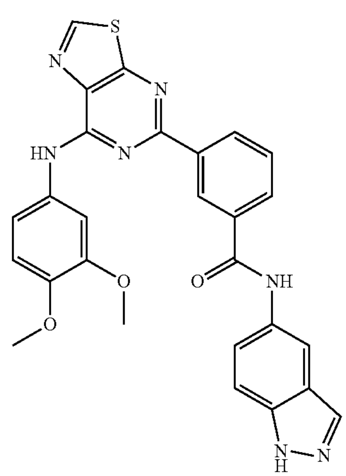 [SMILES: COc1ccc(Nc2nc(-c3cccc(C(=O)Nc4ccc5[nH]ncc5c4)c3)nc3scnc23)cc1OC] |

TABLE I-continued

| Compound | Nomenclature | Structure |
|---|---|---|
| I-19 | 3-[7-(3,4-Dimethoxy-phenylamino)-thiazolo[5,4-d]pyrimidin-5-yl]-N-(1H-indazol-6-yl)-benzamide | 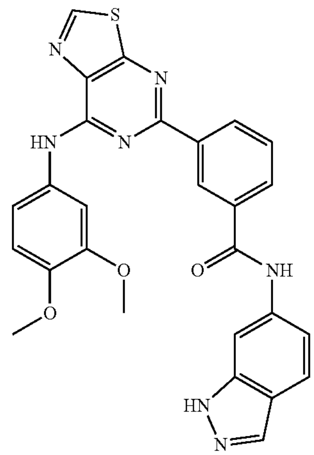 [SMILES: COc1ccc(Nc2nc(-c3cccc(C(=O)Nc4ccc5cn[nH]c5c4)c3)nc3scnc23)cc1OC] |
| I-20 | 4-[7-(3,4-Dimethoxy-phenylamino)-thiazolo[5,4-d]pyrimidin-5-yl]-N-(2-pyridin-4-yl-ethyl)-benzamide | 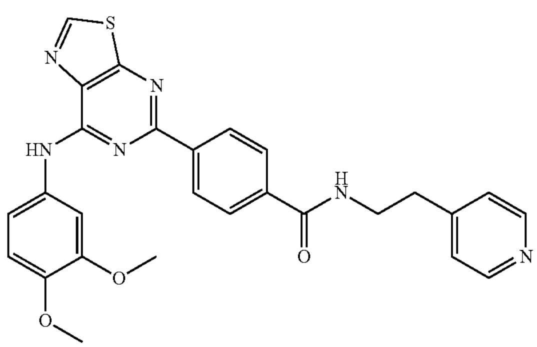 [SMILES: COc1ccc(Nc2nc(-c3ccc(C(=O)NCCc4ccncc4)cc3)nc3scnc23)cc1OC] |
| I-21 | 1-(7-(3,4-Dimethoxyphenylamino)thiazolo[5,4-d]pyrimidin-5-yl)-N-(2-(pyridin-4-yl)ethyl)piperidine-4-carboxamide | 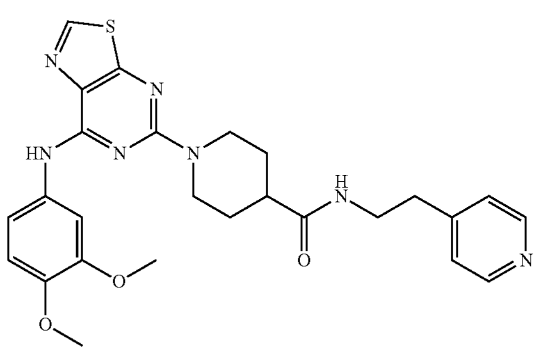 [SMILES: COc1ccc(Nc2nc(N3CCC(C(=O)NCCc4ccncc4)CC3)nc3scnc23)cc1OC] |
| I-22 | 1-(7-(3,4-Dimethoxyphenylamino)thiazolo[5,4-d]pyrimidin-5-yl)-N-(2-(2-oxo-1,2-dihydropyridin-4-yl)ethyl)piperidine-4-carboxamide | 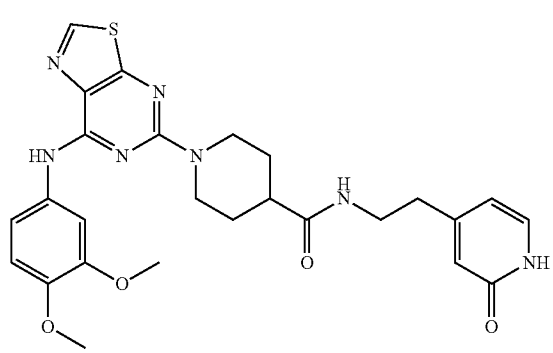 [SMILES: COc1ccc(Nc2nc(N3CCC(C(=O)NCCc4cc[nH]c(=O)c4)CC3)nc3scnc23)cc1OC] |

TABLE I-continued

| Compound | Nomenclature | Structure |
|---|---|---|
| I-23 | 4-(7-(3,4-Dimethoxyphenylamino)thiazolo[5,4-d]pyrimidin-5-yl)-N-(2-(2-oxo-1,2-dihydropyridin-4-yl)ethyl)benzamide | 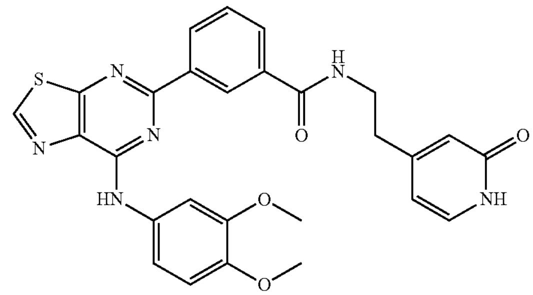 [SMILES: COc1ccc(Nc2nc(-c3cccc(C(=O)NCCc4cc[nH]c(=O)c4)c3)nc3scnc23)cc1OC] |
| I-24 | 4-[7-(3,4-Dimethoxy-phenylamino)-thiazolo[5,4-d]pyrimidin-5-yl]-N-[2-(1-methyl-2-oxo-1,2-dihydro-pyridin-4-yl)-ethyl]-benzamide | 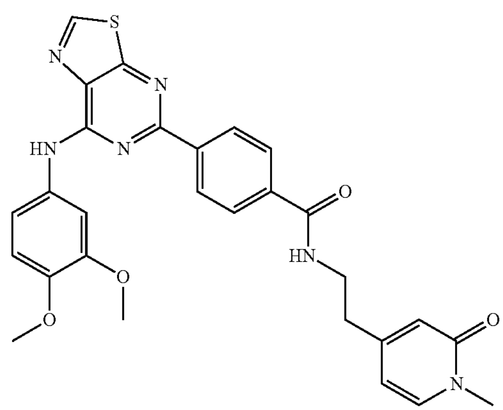 [SMILES: COc1ccc(Nc2nc(-c3ccc(C(=O)NCCc4ccn(C)c(=O)c4)cc3)nc3scnc23)cc1OC] |
| I-25 | 1-(7-(3,4-Dimethoxyphenylamino)thiazolo[5,4-d]pyrimidin-5-yl)-N-(2-(pyridin-4-yl)ethyl)piperidine-3-carboxamide | 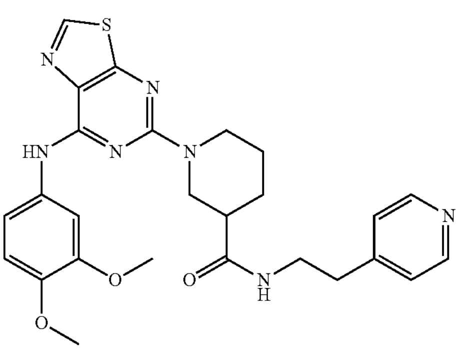 [SMILES: COc1ccc(Nc2nc(N3CCCC(C(=O)NCCc4ccncc4)C3)nc3scnc23)cc1OC] |
| I-26 | Methyl 3-(7-(3-(methylsulfonyl)phenylamino)thiazolo[5,4-d]pyrimidin-5-yl)benzoate | 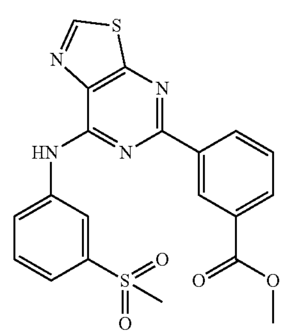 [SMILES: COC(=O)c1cccc(-c2nc(Nc3cccc(S(C)(=O)=O)c3)c3ncsc3n2)c1] |

TABLE I-continued

| Compound | Nomenclature | Structure |
|---|---|---|
| I-27 | 3-[7-(3-Methanesulfonyl-phenylamino)-thiazolo[5,4-d]pyrimidin-5-yl]-benzoic acid | 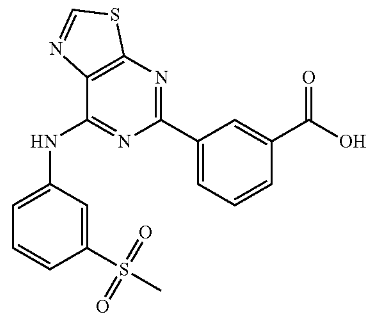 [SMILES: CS(=O)(=O)c1cccc(Nc2nc(-c3cccc(C(=O)O)c3)nc3scnc23)c1] |
| I-28 | 3-{7-[3-(2-Methoxymethyl-pyrrolidin-1-yl)-phenylamino]-thiazolo[5,4-d]pyrimidin-5-yl}-benzoic acid | 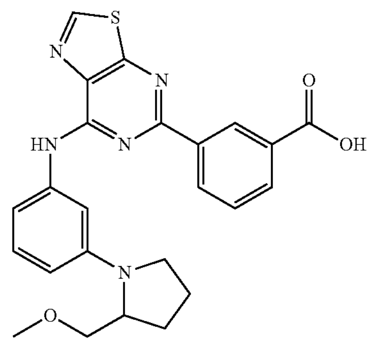 [SMILES: COCC1CCCN1c1cccc(Nc2nc(-c3cccc(C(=O)O)c3)nc3scnc23)c1] |
| I-29 | tert-Butyl 4-(3-(7-(3,4-dimethoxyphenylamino)thiazolo[5,4-d]pyrimidin-5-yl)benzylamino)benzoate | 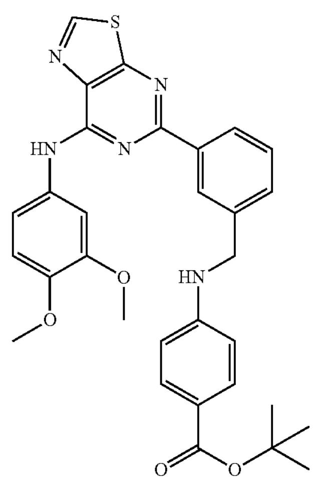 [SMILES: COc1ccc(Nc2nc(-c3cccc(CNc4ccc(C(=O)OC(C)(C)C)cc4)c3)nc3scnc23)cc1OC] |
| I-30 | 4-(3-(7-(3,4-Dimethoxyphenylamino)thiazolo[5,4-d]pyrimidin-5-yl)benzylamino)benzoic acid | 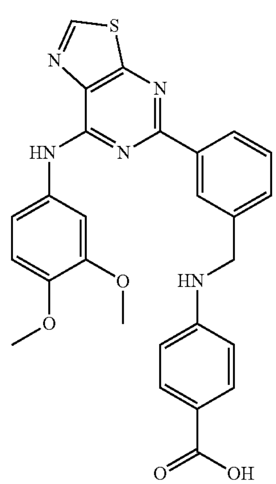 [SMILES: COc1ccc(Nc2nc(-c3cccc(CNc4ccc(C(=O)O)cc4)c3)nc3scnc23)cc1OC] |

TABLE I-continued

| Compound | Nomenclature | Structure |
|---|---|---|
| I-31 | 4-((E)-2-{3-[7-(3,4-Dimethoxy-phenylamino)-thiazolo[5,4-d]pyrimidin-5-yl]-phenyl}-2-fluoro-vinyl)-benzoic acid | 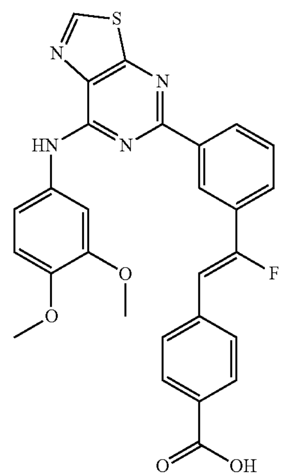 [SMILES: COc1ccc(Nc2nc(-c3cccc(/C(F)=C/c4ccc(C(=O)O)cc4)c3)nc3scnc23)cc1OC] |
| I-32 | (E)-4-(3-(7-(3,4-Dimethoxyphenylamino)thiazolo[5,4-d]pyrimidin-5-yl)styryl)benzoic acid | 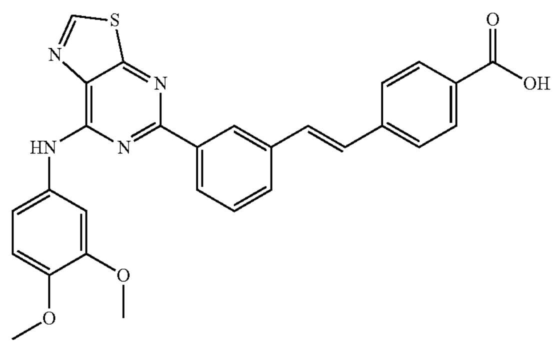 [SMILES: COc1ccc(Nc2nc(-c3cccc(/C=C/c4ccc(C(=O)O)cc4)c3)nc3scnc23)cc1OC] |
| I-33 | 4-(3-(7-(3,4-Dimethoxyphenylamino)thiazolo[5,4-d]pyrimidin-5-yl)phenethyl)benzoic acid | 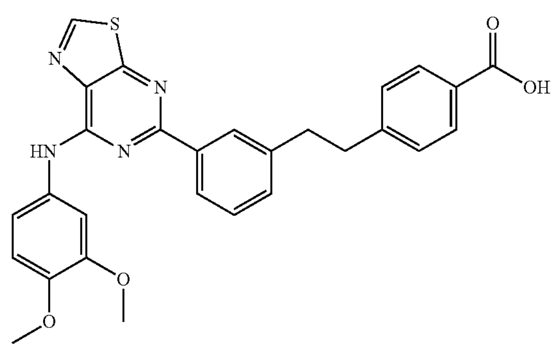 [SMILES: COc1ccc(Nc2nc(-c3cccc(CCc4ccc(C(=O)O)cc4)c3)nc3scnc23)cc1OC] |
| I-34 | 3-{7-[(1R,5S)-3-(8-Oxa-3-aza-bicyclo[3.2.1]oct-3-yl)-phenylamino]-thiazolo[5,4-d]pyrimidin-5-yl}-benzoic acid | 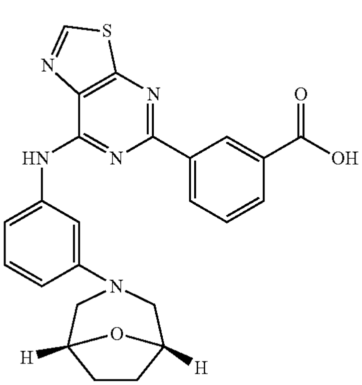 [SMILES: O=C(O)c1cccc(-c2nc(Nc3cccc(N4C[C@H]5CC[C@@H](C4)O5)c3)c3ncsc3n2)c1] |

TABLE I-continued

| Compound | Nomenclature | Structure |
|---|---|---|
| I-35 | N-(1-(7-(3,4-Dimethoxyphenylamino)thiazolo[5,4-d]pyrimidin-5-yl)pyrrolidin-3-yl)-1H-indazole-5-carboxamide | 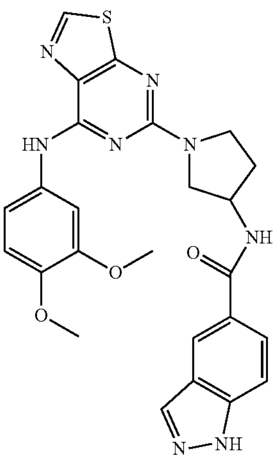 [SMILES: COc1ccc(Nc2nc(N3CCC(NC(=O)c4ccc5[nH]ncc5c4)C3)nc3scnc23)cc1OC] |
| I-36 | (S)-N-(3-(2-Methylpyrrolidin-1-yl)phenyl)-5-(3-((piperidin-4-ylamino)methyl)phenyl)thiazolo[5,4-d]pyrimidin-7-amine | 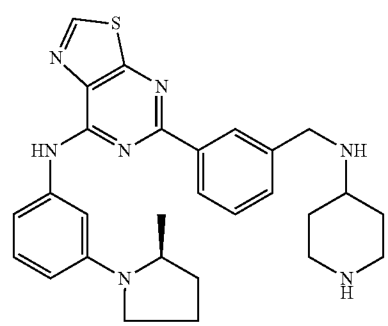 [SMILES: C[C@H]1CCCN1c1cccc(Nc2nc(-c3cccc(CNC4CCNCC4)c3)nc3scnc23)c1] |
| I-37 | N5-(1-(7-(3,4-Dimethoxyphenylamino)thiazolo[5,4-d]pyrimidin-5-yl)pyrrolidin-3-yl)pyridine-2,5-dicarboxamide | 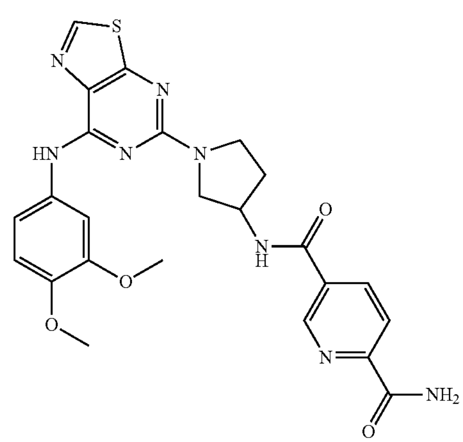 [SMILES: COc1ccc(Nc2nc(N3CCC(NC(=O)c4ccc(C(N)=O)nc4)C3)nc3scnc23)cc1OC] |

TABLE I-continued

| Compound | Nomenclature | Structure |
|---|---|---|
| I-38 | Methyl 5-(1-(7-(3,4-dimethoxyphenylamino)thiazolo[5,4-d]pyrimidin-5-yl)pyrrolidin-3-ylcarbamoyl)picolinate | 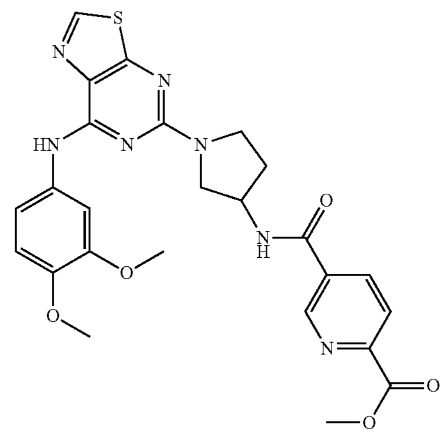 [SMILES: COC(=O)c1ccc(C(=O)NC2CCN(c3nc(Nc4ccc(OC)c(OC)c4)c4ncsc4n3)C2)cn1] |
| I-39 | 5-(1-(7-(3,4-Dimethoxyphenylamino)thiazolo[5,4-d]pyrimidin-5-yl)pyrrolidin-3-ylcarbamoyl)picolinic acid | 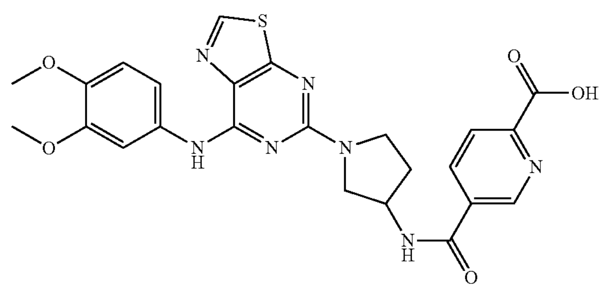 [SMILES: COc1ccc(Nc2nc(N3CCC(NC(=O)c4ccc(C(=O)O)nc4)C3)nc3scnc23)cc1OC] |
| I-40 | 1-(7-(3,4-Dimethoxyphenylamino)thiazolo[5,4-d]pyrimidin-5-yl)-N-(2-oxoindolin-5-yl)piperidine-3-carboxamide | 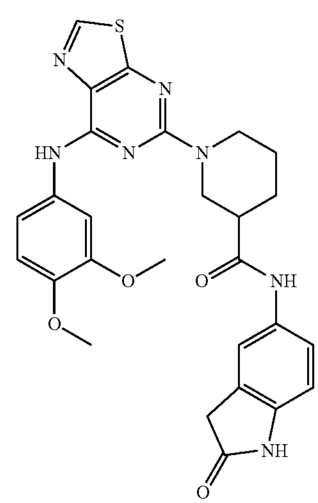 [SMILES: COc1ccc(Nc2nc(N3CCCC(C(=O)Nc4ccc5c(c4)CC(=O)N5)C3)nc3scnc23)cc1OC] |

TABLE I-continued

| Compound | Nomenclature | Structure |
|---|---|---|
| I-41 | 1-(7-(3,4-Dimethoxyphenylamino)thiazolo[5,4-d]pyrimidin-5-yl)-N-(1H-indazol-5-yl)piperidine-3-carboxamide | 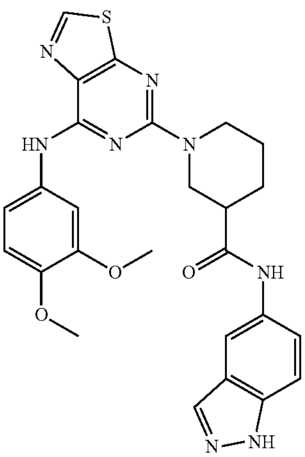 [SMILES: COc1ccc(Nc2nc(N3CCCC(C(=O)Nc4ccc5[nH]ncc5c4)C3)nc3scnc23)cc1OC] |
| I-42 | 5-(1-(7-(3,4-Dimethoxyphenylamino)thiazolo[5,4-d]pyrimidin-5-yl)piperidine-3-carboxamido)picolinic acid | 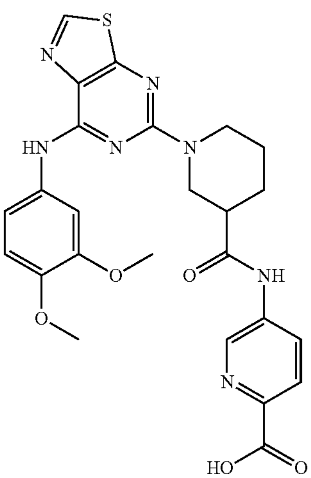 [SMILES: COc1ccc(Nc2nc(N3CCCC(C(=O)Nc4ccc(C(=O)O)nc4)C3)nc3scnc23)cc1OC] |
| I-43 | 4-({1-[7-(3,4-Dimethoxy-phenylamino)-thiazolo[5,4-d]pyrimidin-5-yl]-piperidine-3-carbonyl}-amino)-2-methoxy-benzoic acid | 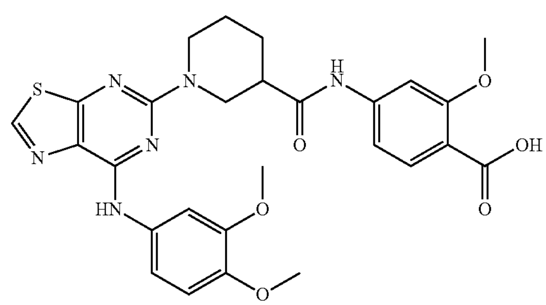 [SMILES: COc1ccc(Nc2nc(N3CCCC(C(=O)Nc4ccc(C(=O)O)c(OC)c4)C3)nc3scnc23)cc1OC] |
| I-44 | 1-(7-(3,4-Dimethoxyphenylamino)thiazolo[5,4-d]pyrimidin-5-yl)-N-(4-(5-oxo-4,5-dihydro-1,2,4-oxadiazol-3-yl)phenyl)piperidine-3-carboxamide | 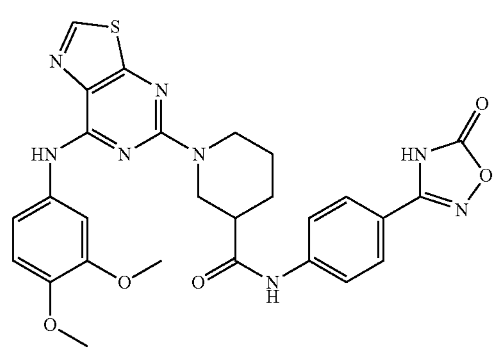 [SMILES: COc1ccc(Nc2nc(N3CCCC(C(=O)Nc4ccc(-c5noc(=O)[nH]5)cc4)C3)nc3scnc23)cc1OC] |

TABLE I-continued

| Compound | Nomenclature | Structure |
|---|---|---|
| I-45 | 1-(7-(3,4-Dimethoxyphenylamino)thiazolo[5,4-d]pyrimidin-5-yl)-N-(1H-indazol-6-yl)piperidine-3-carboxamide | 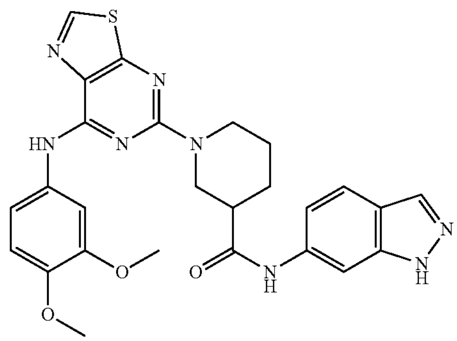 [SMILES: COc1ccc(Nc2nc(N3CCCC(C(=O)Nc4ccc5cn[nH]c5c4)C3)nc3scnc23)cc1OC] |
| I-46 | 1-(7-(3,4-Dimethoxyphenylamino)thiazolo[5,4-d]pyrimidin-5-yl)-N-(1-oxoisoindolin-5-yl)piperidine-3-carboxamide | 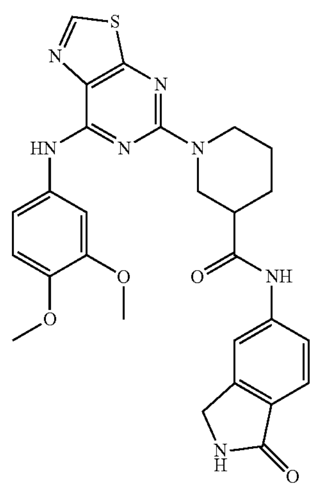 [SMILES: COc1ccc(Nc2nc(N3CCCC(C(=O)Nc4ccc5c(c4)CNC5=O)C3)nc3scnc23)cc1OC] |
| I-47 | 4-(1-(7-(3,4-Dimethoxyphenylamino)thiazolo[5,4-d]pyrimidin-5-yl)piperidine-3-carboxamido)-2-hydroxybenzoic acid | 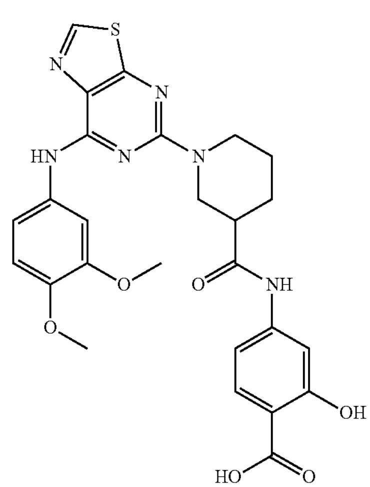 [SMILES: COc1ccc(Nc2nc(N3CCCC(C(=O)Nc4ccc(C(=O)O)c(O)c4)C3)nc3scnc23)cc1OC] |

TABLE I-continued

| Compound | Nomenclature | Structure |
|---|---|---|
| I-48 | 1-(7-(3,4-Dimethoxyphenylamino)thiazolo[5,4-d]pyrimidin-5-yl)-N-(5-oxopyrrolidin-3-yl)piperidine-3-carboxamide | 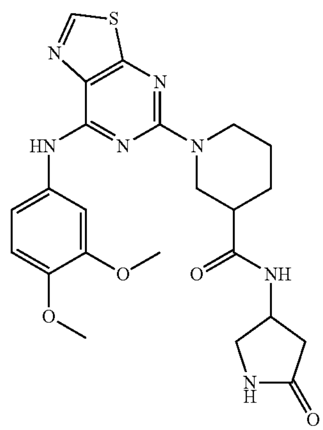 [SMILES: COc1ccc(Nc2nc(N3CCCC(C(=O)NC4CNC(=O)C4)C3)nc3scnc23)cc1OC] |
| I-49 | 1-(7-(3,4-Dimethoxyphenylamino)thiazolo[5,4-d]pyrimidin-5-yl)-N-(pyrazin-2-yl)piperidine-3-carboxamide | 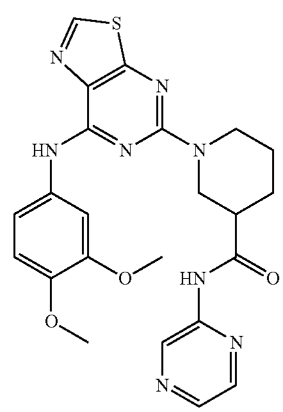 [SMILES: COc1ccc(Nc2nc(N3CCCC(C(=O)Nc4cnccn4)C3)nc3scnc23)cc1OC] |
| I-50 | 1-(7-(3,4-Dimethoxyphenylamino)thiazolo[5,4-d]pyrimidin-5-yl)-N-(1,3-dioxoisoindolin-5-yl)piperidine-3-carboxamide | 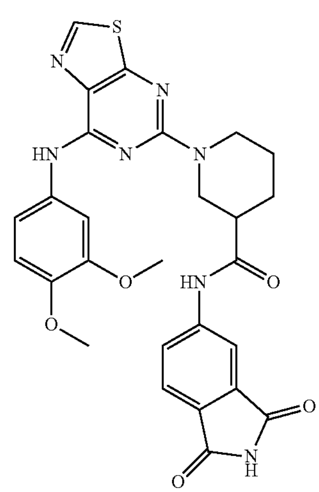 [SMILES: COc1ccc(Nc2nc(N3CCCC(C(=O)Nc4ccc5c(c4)C(=O)NC5=O)C3)nc3scnc23)cc1OC] |

TABLE I-continued

| Compound | Nomenclature | Structure |
|---|---|---|
| I-51 | 1-(7-(3,4-Dimethoxyphenylamino)thiazolo[5,4-d]pyrimidin-5-yl)-N-(4-(5-mercapto-1,3,4-oxadiazol-2-yl)phenyl)piperidine-3-carboxamide | 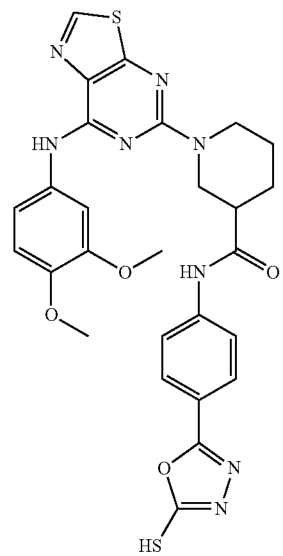 [SMILES: COc1ccc(Nc2nc(N3CCCC(C(=O)Nc4ccc(-c5nnc(S)o5)cc4)C3)nc3scnc23)cc1OC] |
| I-52 | 1-(7-(3,4-Dimethoxyphenylamino)thiazolo[5,4-d]pyrimidin-5-yl)-N-(4-(5-mercapto-4-methyl-4H-1,2,4-triazol-3-yl)phenyl)piperidine-3-carboxamide | 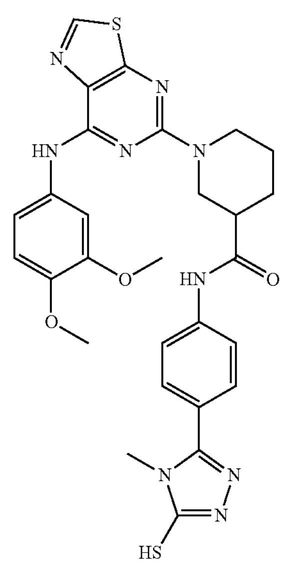 [SMILES: COc1ccc(Nc2nc(N3CCCC(C(=O)Nc4ccc(-c5nnc(S)n5C)cc4)C3)nc3scnc23)cc1OC] |
| I-53 | 3-{7-[3-(2-Oxa-6-aza-spiro[3.3]hept-6-yl)-phenylamino]-thiazolo[5,4-d]pyrimidin-5-yl}-benzoic acid | 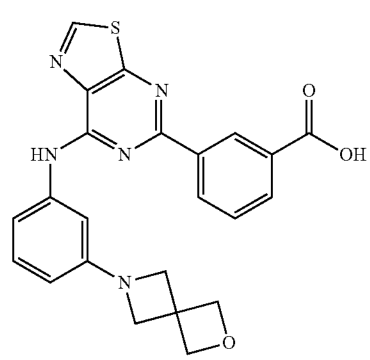 [SMILES: O=C(O)c1cccc(-c2nc(Nc3cccc(N4CC5(COC5)C4)c3)c3ncsc3n2)c1] |

TABLE I-continued

| Compound | Nomenclature | Structure |
|---|---|---|
| I-54 | 4-(1-(7-(3,4-Dimethoxyphenylamino)thiazolo[5,4-d]pyrimidin-5-yl)pyrrolidine-3-carboxamido)benzoic acid | 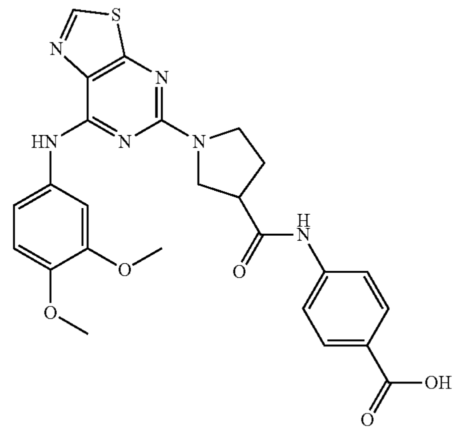 [SMILES: COc1ccc(Nc2nc(N3CCC(C(=O)Nc4ccc(C(=O)O)cc4)C3)nc3scnc23)cc1OC] |
| I-55 | 4-(1-(7-(5,6-Dimethoxypyridin-2-ylamino)thiazolo[5,4-d]pyrimidin-5-yl)pyrrolidin-3-ylcarbamoyl)benzoic acid | 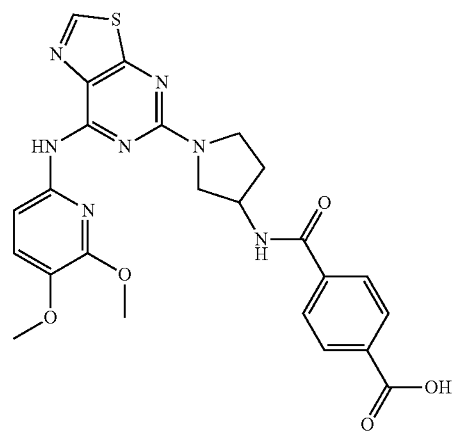 [SMILES: COc1ccc(Nc2nc(N3CCC(NC(=O)c4ccc(C(=O)O)cc4)C3)nc3scnc23)nc1OC] |
| I-56 | Methyl 3-(7-(3-(trifluoromethyl)phenylamino)thiazolo[5,4-d]pyrimidin-5-yl)benzoate | 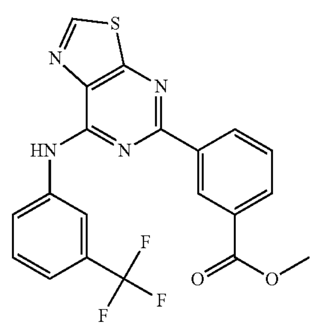 [SMILES: COC(=O)c1cccc(-c2nc(Nc3cccc(C(F)(F)F)c3)c3ncsc3n2)c1] |
| I-57 | 3-[7-(3-Trifluoromethyl-phenylamino)-thiazolo[5,4-d]pyrimidin-5-yl]-benzoic acid | 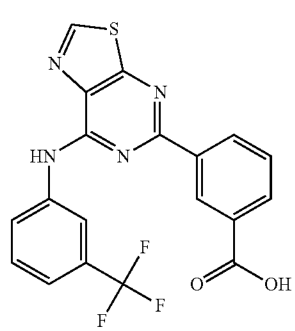 [SMILES: O=C(O)c1cccc(-c2nc(Nc3cccc(C(F)(F)F)c3)c3ncsc3n2)c1] |

TABLE I-continued

| Compound | Nomenclature | Structure |
|---|---|---|
| I-58 | 3-[7-(3,4,5-Trimethoxy-phenylamino)-thiazolo[5,4-d]pyrimidin-5-yl]-benzamide | 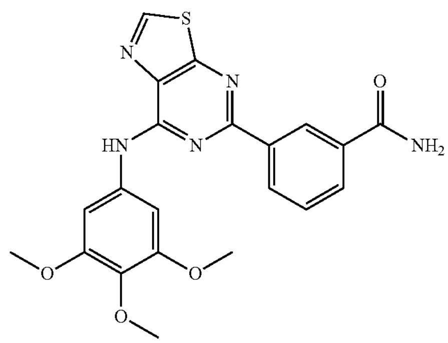 [SMILES: COc1cc(Nc2nc(-c3cccc(C(N)=O)c3)nc3scnc23)cc(OC)c1OC] |
| I-59 | 1-(7-(3-((S)-2-Methylpyrrolidin-1-yl)phenylamino)thiazolo[5,4-d]pyrimidin-5-yl)piperidin-3-ol | 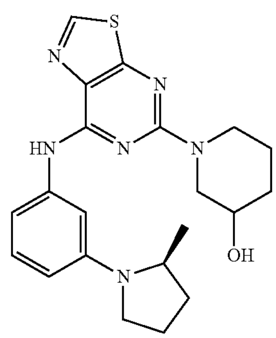 [SMILES: C[C@H]1CCCN1c1cccc(Nc2nc(N3CCCC(O)C3)nc3scnc23)c1] |
| I-60 | 4-{7-[3-Methoxy-5-((S)-2-methyl-pyrrolidin-1-yl)-phenylamino]-thiazolo[5,4-d]pyrimidin-5-yl}-benzamide | 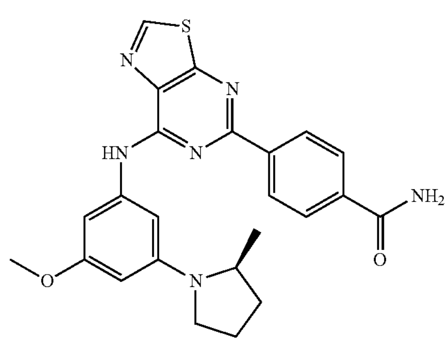 [SMILES: COc1cc(Nc2nc(-c3ccc(C(N)=O)cc3)nc3scnc23)cc(N2CCC[C@@H]2C)c1] |
| I-61 | (S)-5-(6-Methoxypyridin-3-yl)-N-(3-(2-methylpyrrolidin-1-yl)phenyl)thiazolo[5,4-d]pyrimidin-7-amine | 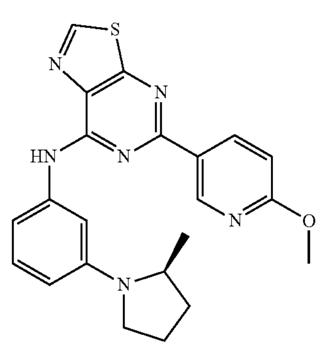 [SMILES: COc1ccc(-c2nc(Nc3cccc(N4CCC[C@@H]4C)c3)c3ncsc3n2)cn1] |

TABLE I-continued

| Compound | Nomenclature | Structure |
|---|---|---|
| I-62 | 4-{7-[3-((S)-2-Methyl-pyrrolidin-1-yl)-phenylamino]-thiazolo[5,4-d]pyrimidin-5-yl}-benzamide | 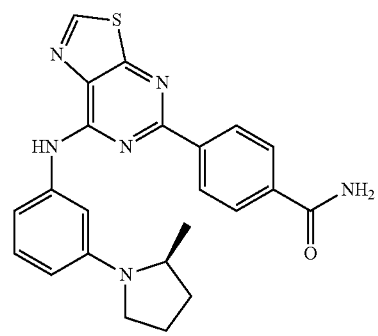 [SMILES: C[C@H]1CCCN1c1cccc(Nc2nc(-c3ccc(C(N)=O)cc3)nc3scnc23)c1] |
| I-63 | 3-[7-(3,4-Dimethoxy-phenylamino)-thiazolo[5,4-d]pyrimidin-5-yl]-N-[4-(2,4-dioxo-thiazolidin-5-yl)-phenyl]-benzamide | 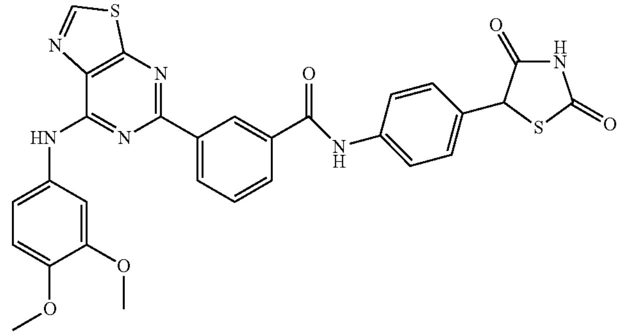 [SMILES: COc1ccc(Nc2nc(-c3cccc(C(=O)Nc4ccc(C5SC(=O)NC5=O)cc4)c3)nc3scnc23)cc1OC] |
| I-64 | 4-[7-(3,4-Dimethoxy-phenylamino)-thiazolo[5,4-d]pyrimidin-5-yl]-benzamide | 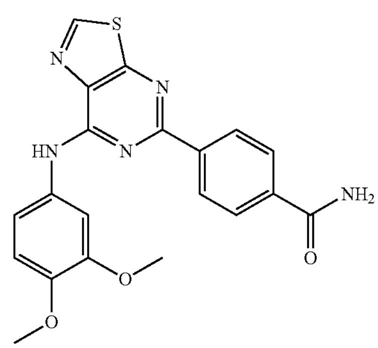 [SMILES: COc1ccc(Nc2nc(-c3ccc(C(N)=O)cc3)nc3scnc23)cc1OC] |
| I-65 | (S)-N-(2-(Dimethylamino)ethyl)-4-(7-(3-(2-methylpyrrolidin-1-yl)phenylamino)thiazolo[5,4-d]pyrimidin-5-yl)benzamide | 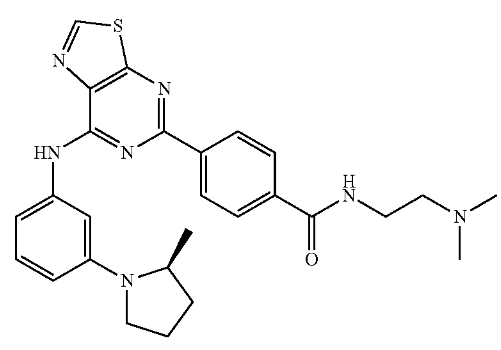 [SMILES: C[C@H]1CCCN1c1cccc(Nc2nc(-c3ccc(C(=O)NCCN(C)C)cc3)nc3scnc23)c1] |

TABLE I-continued

| Compound | Nomenclature | Structure |
|---|---|---|
| I-66 | 4-(7-(3,4-Dimethoxyphenylamino)thiazolo[5,4-d]pyrimidin-5-yl)-N-(2-(dimethylamino)ethyl)benzamide | 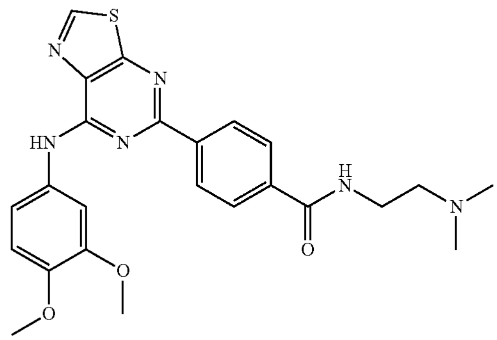 [SMILES: COc1ccc(Nc2nc(-c3ccc(C(=O)NCCN(C)C)cc3)nc3scnc23)cc1OC] |
| I-67 | {3-[7-(3,4-Dimethoxy-phenylamino)-thiazolo[5,4-d]pyrimidin-5-yl]-phenyl}-methanol | 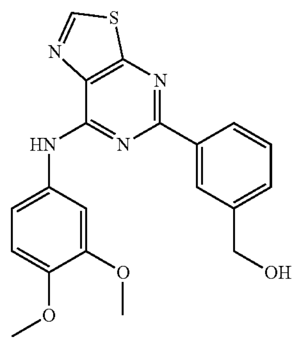 [SMILES: COc1ccc(Nc2nc(-c3cccc(CO)c3)nc3scnc23)cc1OC] |
| I-68 | 3-[7-(3,4-Dimethoxy-phenylamino)-thiazolo[5,4-d]pyrimidin-5-yl]-benzamide | 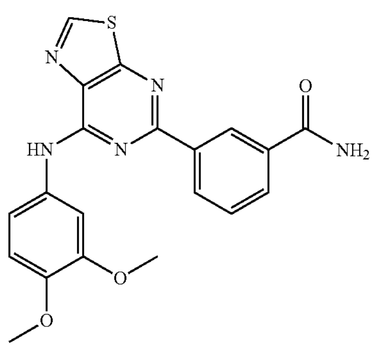 [SMILES: COc1ccc(Nc2nc(-c3cccc(C(N)=O)c3)nc3scnc23)cc1OC] |

Synthesis Schemes

The compounds disclosed herein can be synthesized using general Schemes I-III:

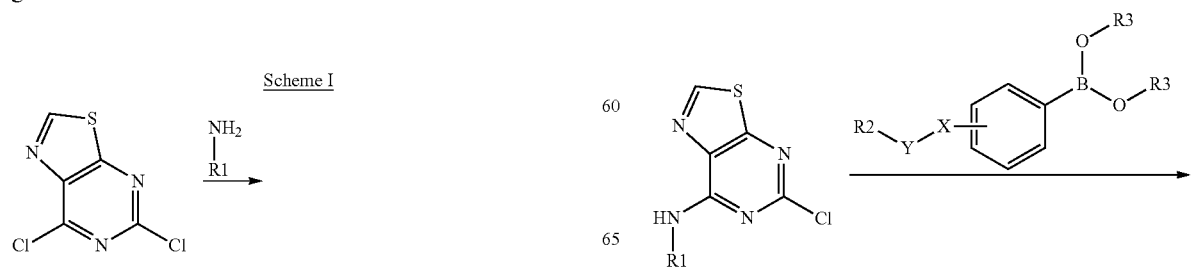

51
-continued
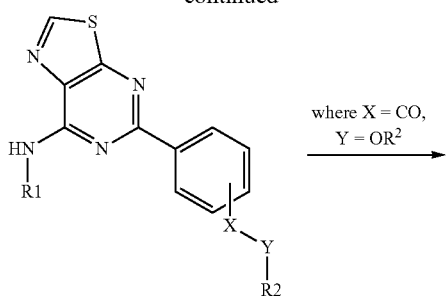
where X = CO, Y = OR²
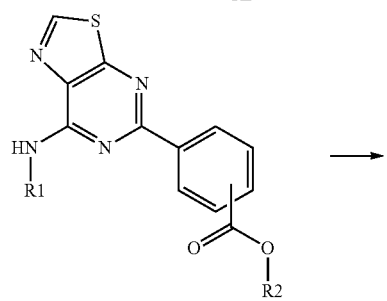
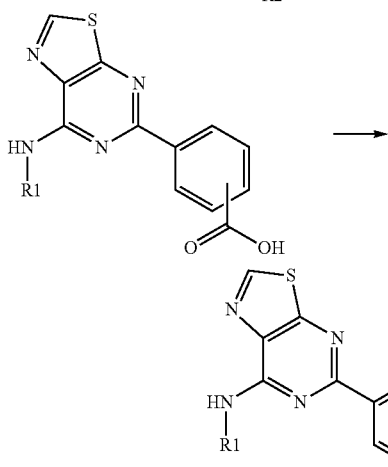
52
-continued
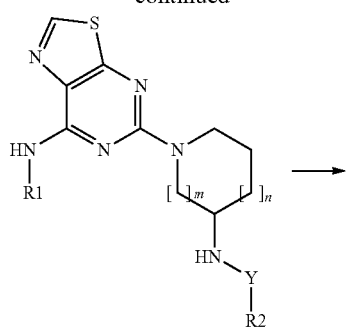
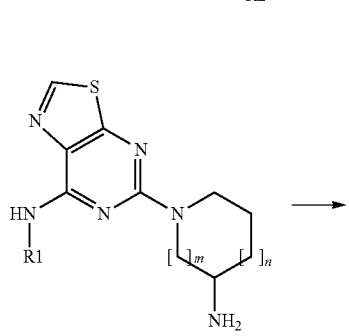
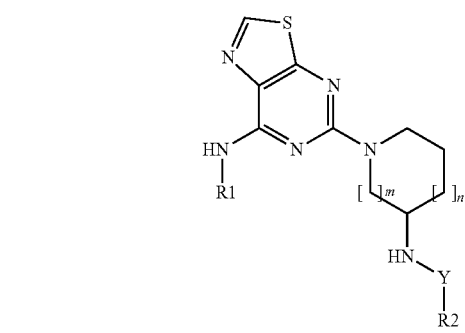
Scheme II
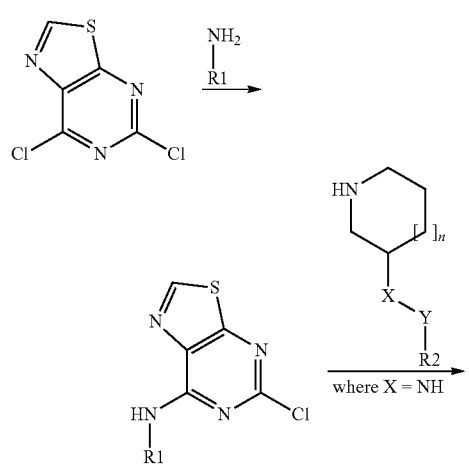
Scheme III
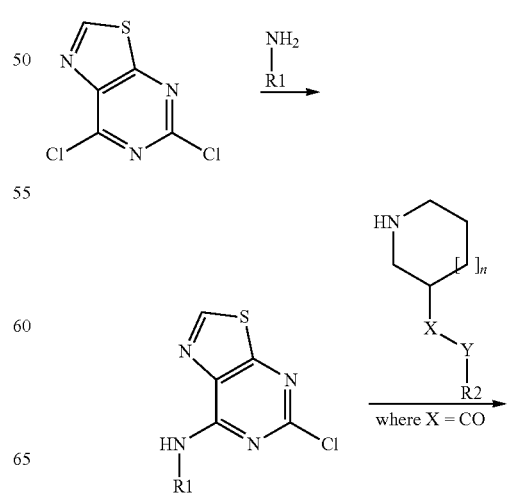

53

-continued

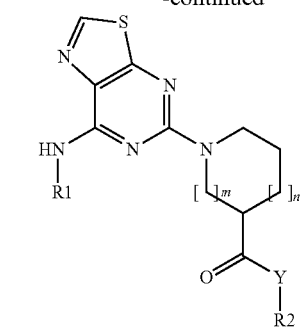

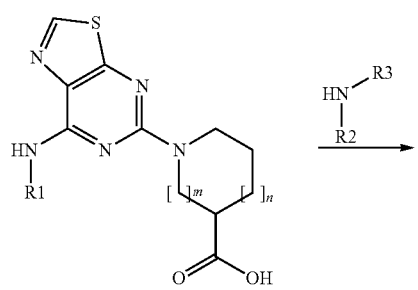

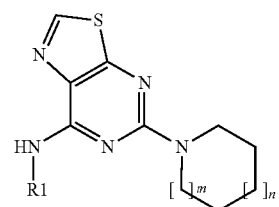

Description of Schemes

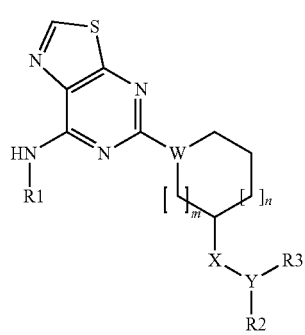

In the above schemes, R¹ can be aryl, optionally substituted with one of more lower alkyl, hydroxyl, hydroxyl lower alkyl, lower alkoxy, halo, nitro, amino, aminoalkyl, amido, cyano, oxo, or halo-lower alkyl, W can be CH or N, n can be 0 or 1, m can be 1 or 2, X can be NH, $CH_2$, C=O, CH, or CF, Y can be O, N, C, or C=O, R² can be H, alkyl, cycloalkyl, heterocyclyl, aryl, or heteroaryl, and R³ can be H, alkyl, cycloalkyl, heterocyclyl, aryl, or heteroaryl. A detailed representative reaction scheme is shown in Schemes IV and V below.

54

Scheme IV

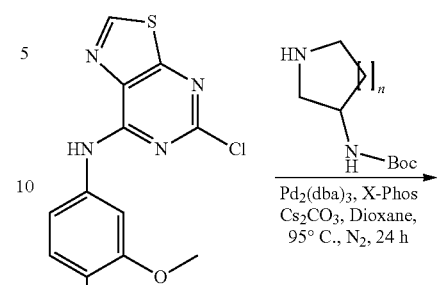

Pd₂(dba)₃, X-Phos
Cs₂CO₃, Dioxane,
95° C., N₂, 24 h

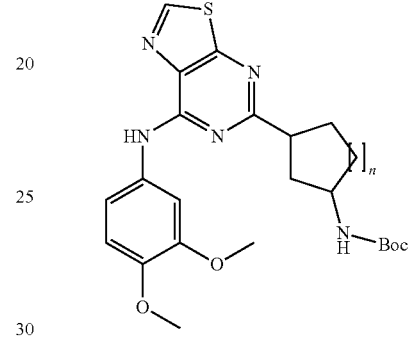

HCl in dioxane
r.t. 24 h

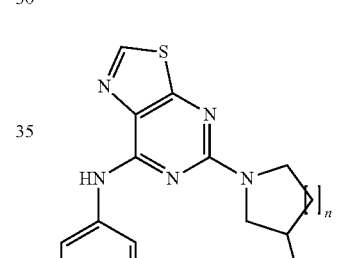

HATU, DIEA, DMF,
EDCl, DMAP, RT, 4 days

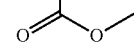

LiOH·H₂O, H₂O
THF, CH₃OH,
RT, 2 h

-continued

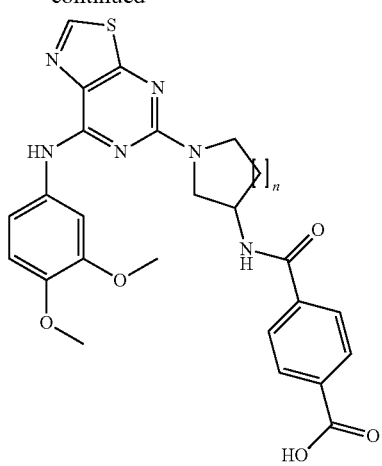

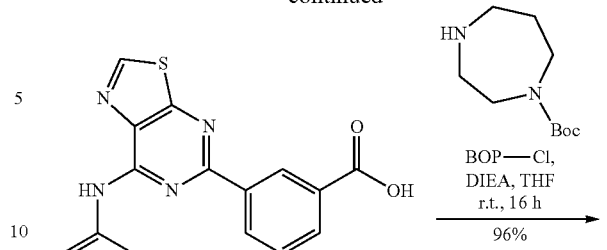

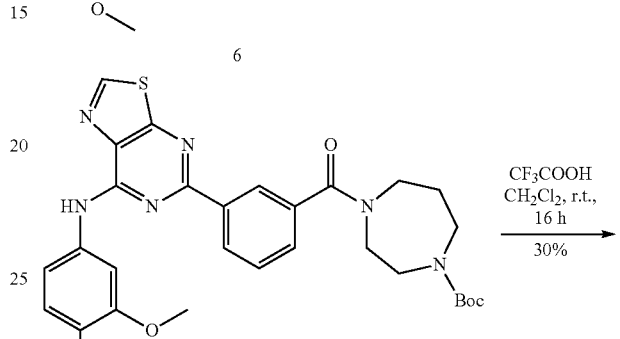

Scheme IV

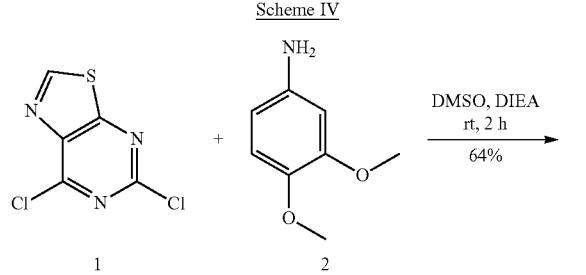

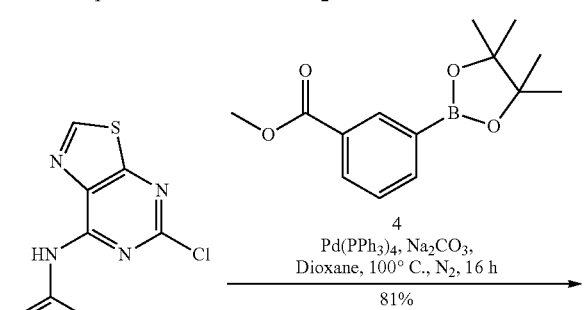

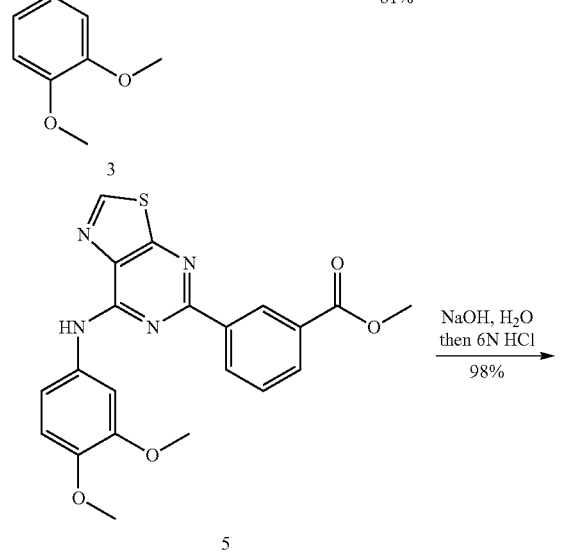

Pharmaceutical Compositions and Administration

The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in Remington: The Science and Practice of Pharmacy 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Formulations

Pharmaceutical preparations for delivery by various routes are formulated as shown in the following Tables. "Active ingredient" or "Active compound" as used in the Tables means one or more of the Compounds of Formula I.

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration

| Ingredient | Amount |
| --- | --- |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Parenteral Formulation

| Ingredient | % wt./wt. |
| --- | --- |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Topical Formulation

| Ingredients | Grams |
| --- | --- |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Indications and Methods of Treatment

The compounds described herein are kinase inhibitors, in particular SYK inhibitors. These inhibitors can be useful for treating one or more diseases responsive to kinase inhibition, including diseases responsive to SYK inhibition and/or inhibition of B-cell proliferation, in mammals. Without wishing to be bound to any particular theory, it is believed that the interaction of the compounds of the invention with SYK results in the inhibition of SYK activity and thus in the pharmaceutical utility of these compounds. Accordingly, the invention includes a method of treating a mammal, for instance a human, having a disease responsive to inhibition of SYK activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to SYK include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

The present application provides a method for treating an inflammatory or autoimmune condition comprising administering to a patient in need thereof a therapeutically effective amount of the compound of Formula I.

The present application provides the above method, further comprising administering an additional therapeutic agent selected from a chemotherapeutic or anti-proliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

The present application provides a method for treating an inflammatory condition comprising administering to a patient in need thereof a therapeutically effective amount of the compound of Formula I.

The present application provides a method for treating rheumatoid arthritis comprising administering to a patient in need thereof a therapeutically effective amount of the compound of Formula I.

The present application provides a method for treating asthma comprising administering to a patient in need thereof a therapeutically effective amount of the compound of Formula I.

The present application provides a method for treating an immune disorder including lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease, and Leukemia, comprising administering to a patient in need thereof a therapeutically effective amount of the compound of Formula I.

The present application provides a method for treating an inflammatory condition comprising co-administering to a patient in need thereof a therapeutically effective amount of an anti-inflammatory compound in combination with the compound of Formula I.

The present application provides a method for treating an immune disorder comprising co-administering to a patient in need thereof a therapeutically effective amount of an immunosuppressant compound in combination with the compound of Formula I.

EXAMPLES

Abbreviations

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether ($Et_2O$), ethyl isopropyl ether (EtOiPr), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgCl), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl)palladium(II) ($Pd(dppf)Cl_2$), palladium(II) acetate ($Pd(OAc)_2$), tris(dibenzylideneacetone)dipalladium(0) ($Pd_2(dba)_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-$BuMe_2Si$ (TBDMS), tetra-n-butylammonium fluoride (TBAF), triethylamine (TEA or $Et_3N$), 2,2,6,6-tetramethylpiperidine 1-oxyl (TEMPO), triflate or $CF_3SO_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or $Me_3Si$ (TMS), p-toluenesulfonic acid monohydrate (TsOH or pTsOH), 4-Me-$C_6H_4SO_2$— or tosyl (Ts), and N-urethane-N-carboxyanhydride (UNCA). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

General Conditions

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Preparations and Examples. All names were generated using Autonom and ChemDraw.

The following preparations and examples are given to enable those skilled in the art to more clearly understand and to practice the present invention. They should not be considered as limiting the scope of the invention, but merely as being illustrative and representative thereof.

Preparative Examples

Preparation 1

(5-Chloro-thiazolo[5,4-d]pyrimidin-7-yl)-(3,4-dimethoxy-phenyl)-amine

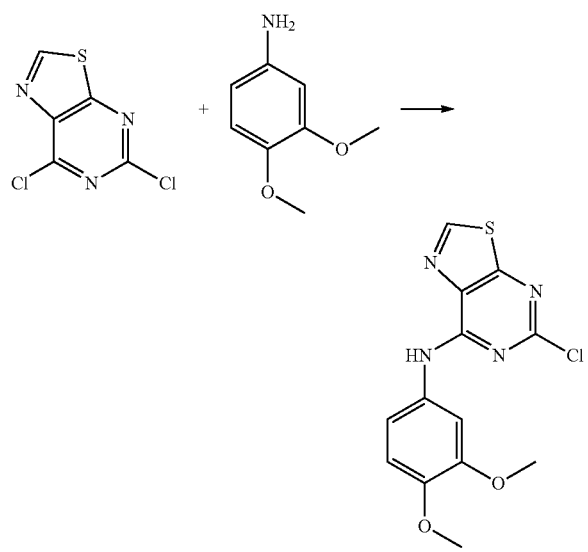

A mixture of 5,7-dichloro-thiazolo[5,4-d]pyrimidine (0.925 g, 4.49 mmol), 3,4-dimethoxy-phenylamine (0.89 g, 5.83 mmol) and DIEA (0.86 g, 6.73 mmol) in 12 mL of DMSO was stirred at room temperature for two hours. The mixture was poured into 50 mL of water and filtered; the solid obtained was washed with water (50 mL) to give a crude product. It was purified by silica gel chromatography (silica gel 200-300 mesh, ethyl acetate as eluent) to give (5-chloro-thiazolo[5,4-d]pyrimidin-7-yl)-(3,4-dimethoxy-phenyl)-amine (0.92 g, 63.8%) as a solid. LC-MS: 323.1 [M+H]$^+$, $t_R$=1.56 min.

Preparation 2

3-[7-(3,4-Dimethoxy-phenylamino)-thiazolo[5,4-d]pyrimidin-5-yl]-benzoic acid methyl ester

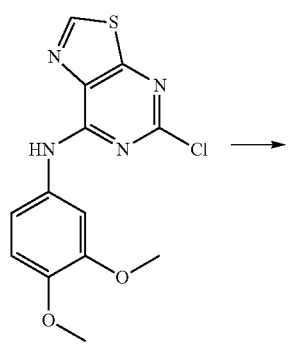

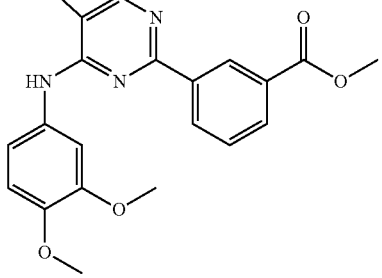

Procedure:

To a stirred solution of (5-chloro-thiazolo[5,4-d]pyrimidin-7-yl)-(3,4-dimethoxy-phenyl)-amine (0.90 g, 2.79 mmol) and 3-(4,4,5,5-tetramethyl-[1,3,2]dioxaborolan-2-yl)-benzoic acid methyl ester (0.95 g, 3.62 mmol) in 100 mL of 1,4-dioxane were added Na$_2$CO$_3$ (0.93 g, 8.8 mmol) and 5 mL of water at room temperature. Then the mixture was degassed with nitrogen for 15 minutes. Pd(PPh$_3$)$_4$ (0.32 g, 0.279 mmol) was added in one portion and the reaction mixture was stirred at 100° C. for 16 hours under nitrogen. The solvent was evaporated and the residue was purified by silica gel chromatography (silica gel 200-300 mesh, CH$_2$Cl$_2$:methanol=100:1) to give 3-[7-(3,4-dimethoxy-phenylamino)-thiazolo[5,4-d]pyrimidin-5-yl]-benzoic acid methyl ester (0.95 g, 81%) as a yellow sold. LC-MS: 423.1 [M+H]$^+$, $t_R$=1.68 min.

Example 1

3-[7-(3,4-Dimethoxy-phenylamino)-thiazolo[5,4-d]pyrimidin-5-yl]-benzoic acid

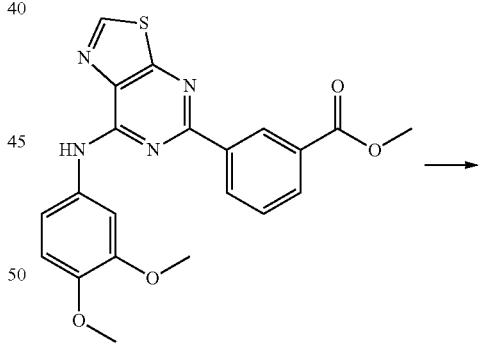

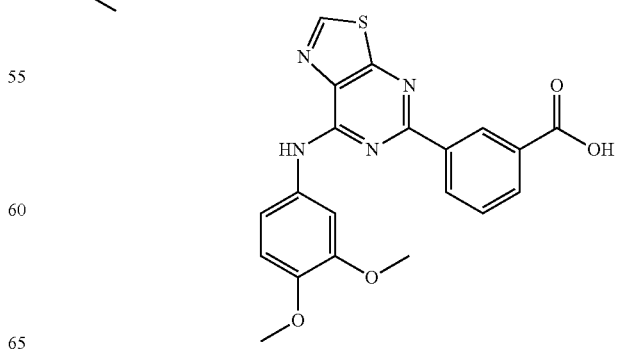

Procedure:

To a stirred solution of 3-[7-(3,4-dimethoxy-phenylamino)-thiazolo[5,4-d]pyrimidin-5-yl]-benzoic acid methyl ester (0.85 g, 2 mmol) in 20 mL of THF and 20 mL of methanol was added a solution of NaOH (0.08 g, 20 mmol) in 2 mL of water at room temperature. Then the reaction was stirred at this temperature for 16 hours. The solvent was evaporated and the residue was suspended in 50 mL of THF, then treated by 6N HCl until pH=3. The solvent was evaporated and then dissolved in 30 mL of THF, filtered. The filtrate was evaporated to give 3-[7-(3,4-dimethoxy-phenylamino)-thiazolo[5,4-d]pyrimidin-5-yl]-benzoic acid (0.8 g, 97.5%) as a yellow solid. $^1$H NMR (300 MHz, DMSO): δ 13.15 (s, 1H), 10.18 (s, 1H), 9.38 (s, 1H), 8.98 (s, 1H), 8.61 (d, 1H, J=8.1 Hz), 8.06 (d, 1H, J=7.5 Hz), 7.84 (d, 1H, J=2.4 Hz), 7.64 (t, 1H, J=7.8 Hz), 7.42 (dd, 1H, $J_1$=8.7 Hz, $J_2$=2.1 Hz), 6.98 (d, 1H, J=8.7 Hz), 3.82 (s, 3H), 3.77 (s, 3H). LC-MS: 409 $[M+H]^+$, 839 $[2M+Na]^+$, $t_R$=1.74 min. HPLC: 98.38% at 214 nm, 97.29% at 254 nm, $t_R$=3.44 min.

Example 2

[1,4]-Diazepan-1-yl-{3-[7-(3,4-dimethoxy-phenylamino)-thiazolo[5,4-d]pyrimidin-5-yl]-phenyl}-methanone Step 1

4-{3-[7-(3,4-Dimethoxy-phenylamino)-thiazolo[5,4-d]pyrimidin-5-yl]-benzoyl}-[1,4]-diazepane-1-carboxylic acid tert-butyl ester

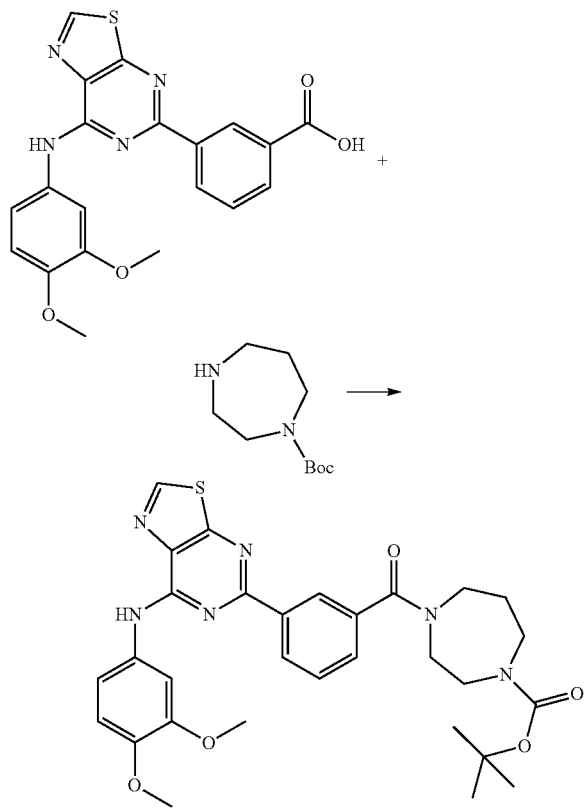

Procedure:

To a stirred solution of 3-[7-(3,4-dimethoxy-phenylamino)-thiazolo[5,4-d]pyrimidin-5-yl]-benzoic acid (95 mg, 0.23 mmol) in 10 mL of THF was added DIEA (30 mg, 0.23 mmol) at room temperature. Then tert-butyl 1,4-diazepane-1-carboxylate (60 mg, 0.3 mmol), BOP-Cl (76 mg, 0.3 mmol) and DIEA (59 mg, 0.46 mmol) were added and the reaction mixture was stirred at room temperature for 16 hours. The solvent was evaporated and the residue was purified by silica gel chromatography (silica gel 200-300 mesh, methanol:$CH_2Cl_2$=1:100) to give 4-{3-[7-(3,4-dimethoxy-phenylamino)-thiazolo[5,4-d]pyrimidin-5-yl]-benzoyl}-[1,4]-diazepane-1-carboxylic acid tert-butyl ester (130 mg, 95.7%) as a yellow solid. LC-MS: 591.2 $[M+H]^+$, $t_R$=1.81 min.

Step 2

[1,4]-Diazepan-1-yl-{3-[7-(3,4-dimethoxy-phenylamino)-thiazolo[5,4-d]pyrimidin-5-yl]-phenyl}-methanone

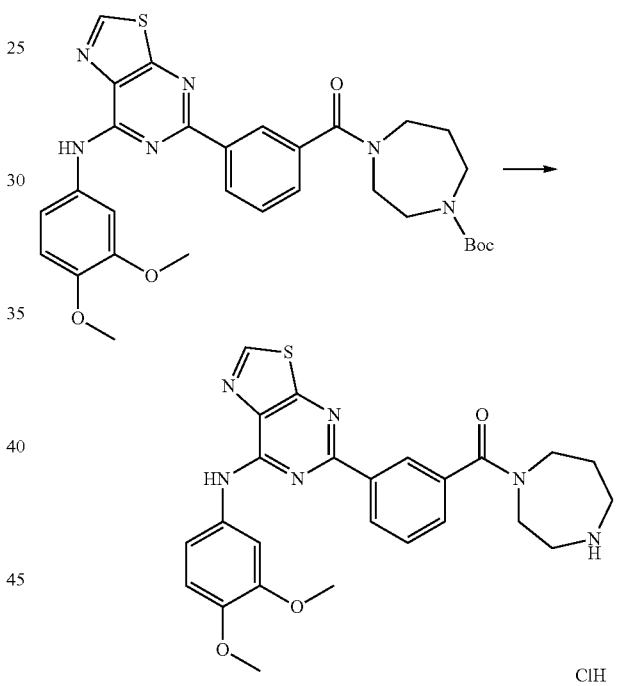

Procedure:

To a stirred solution of 4-{3-[7-(3,4-dimethoxy-phenylamino)-thiazolo[5,4-d]pyrimidin-5-yl]-benzoyl}-[1,4]-diazepane-1-carboxylic acid tert-butyl ester (130 mg, 0.22 mmol) in 10 mL of $CH_2Cl_2$ was added slowly $CF_3COOH$ (4 mL) at room temperature. Then the mixture was stirred at room temperature for 16 hours. The solvent was evaporated and the residue was purified by preparative HPLC (Gemini 5u C18 150×21.2 mm; inject volume: 3 ml/inj, flow rate: 20 ml/min; wavelength: 214 nm and 254 nm; the gradient conditions are: 20% acetonitrile/80% water (0.1% TFA V/V) initially, and then proceed to 45% acetonitrile/55% water (0.1% TFA V/V) in a linear fashion after just 9 min.), then 1M HCl (0.5 mL) was added and stirred, then solvents were removed under reduced pressure to give [1,4]diazepan-1-yl-{3-[7-(3,4-dimethoxy-phenylamino)-thiazolo[5,4-d]pyrimidin-5-yl]-phenyl}-methanone as HCl salt (35 mg, 30.2%) as a yellow solid. ¹H NMR (300 MHz, DMSO): δ 10.18 (s, 1H), 9.38 (s, 1H), 9.05 (brs, 2H), 8.46-8.44 (m, 2H), 7.86 (s, 1H), 7.60-7.59 (m, 2H), 7.42 (dd, 1H, $J_1$=8.7 Hz, $J_2$=2.7 Hz), 6.99 (d, 1H, J=8.7 Hz), 3.85 (brs, 2H), 3.80 (s, 3H), 3.77 (s, 3H), 3.44 (brs, 2H), 3.30 (brs, 2H), 3.20 (brs, 2H), 2.02-1.96 (m, 2H). LC-MS: 491.2 [M+H]⁺, $t_R$=1.51 min. HPLC: 99.24% at 214 nm, 98.23% at 254 nm, $t_R$=4.65 min.

Example 3

3-(7-(3,4-Dimethoxyphenylamino)thiazolo[5,4-d]pyrimidin-5-yl)-N-(4-(methylcarbamoyl)phenyl)benzamide

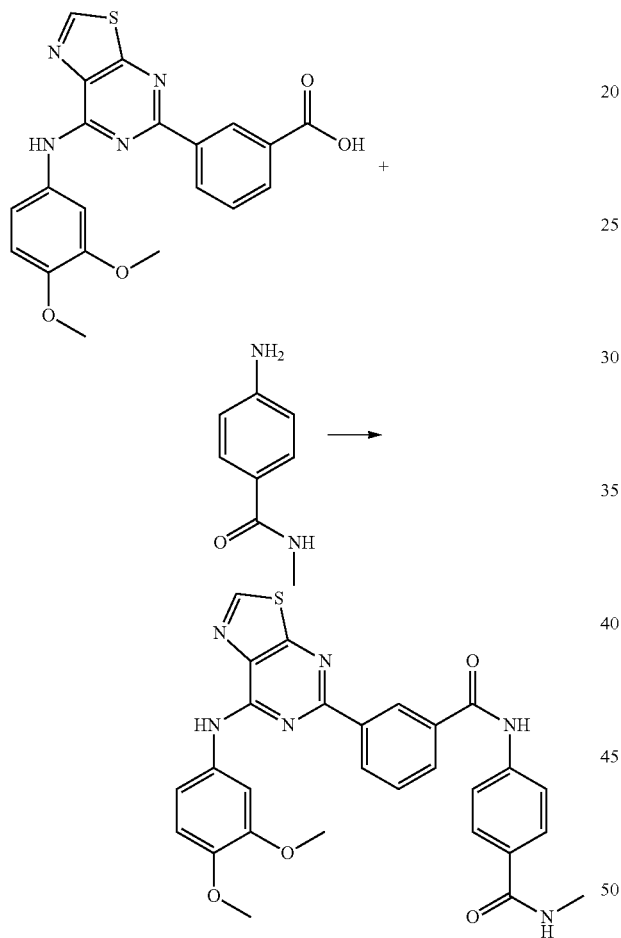

Procedure:

A solution of 3-[7-(3,4-dimethoxy-phenylamino)-thiazolo[5,4-d]pyrimidin-5-yl]-benzoic acid (170 mg, 0.41 mmol) in 10 mL of DMF were added 4-amino-N-methyl-benzamide (81 mg, 0.54 mmol), HATU (205 mg, 0.54 mmol) and DIEA (79 mg, 0.61 mmol) at room temperature. Then the reaction mixture was stirred at room temperature for 16 hours. The solvent was evaporated to give a solid as a crude product. It was purified by preparative HPLC (Gemini 5u C18 150×21.2 mm; inject volume: 3 ml/inj, flow rate: 20 ml/min; wavelength: 214 nm and 254 nm; the gradient conditions are: 40% acetonitrile/60% water (0.1% TFA V/V) initially, and then proceed to 70% acetonitrile/30% water (0.1% TFA V/V) in a linear fashion after just 9 min.) to give 3-(7-(3,4-dimethoxyphenylamino)thiazolo[5,4-d]pyrimidin-5-yl)-N-(4-(methylcarbamoyl)phenyl)benzamide (66 mg, 29.7%) as a yellow solid. ¹H NMR (300 MHz, DMSO): δ 10.66 (s, 1H), 10.21 (s, 1H), 9.39 (s, 1H), 8.93 (s, 1H), 8.59 (d, 1H, J=7.2 Hz), 8.38-8.37 (m, 1H), 8.05 (d, 1H, J=8.7 Hz), 7.89-7.82 (m, 6H), 7.71-7.68 (m, 12H), 7.54-7.50 (m, 1H), 6.97 (d, 1H, J=8.7 Hz), 3.78 (s, 3H), 3.72 (s, 3H), 2.78 (d, 1H, J=3.9 Hz). LC-MS: 541.1 [M+H]⁺, $t_R$=1.72 min. HPLC: 96.60% at 214 nm, 97.75% at 254 nm, $t_R$=6.68 min.

Example 4

4-(3-(7-(3,4-Dimethoxyphenylamino)thiazolo[5,4-d]pyrimidin-5-yl)benzamido)benzoic acid Step 1 tert-Butyl 4-(3-(7-(3,4-dimethoxyphenylamino)thiazolo[5,4-d]pyrimidin-5-yl)benzamido)benzoate

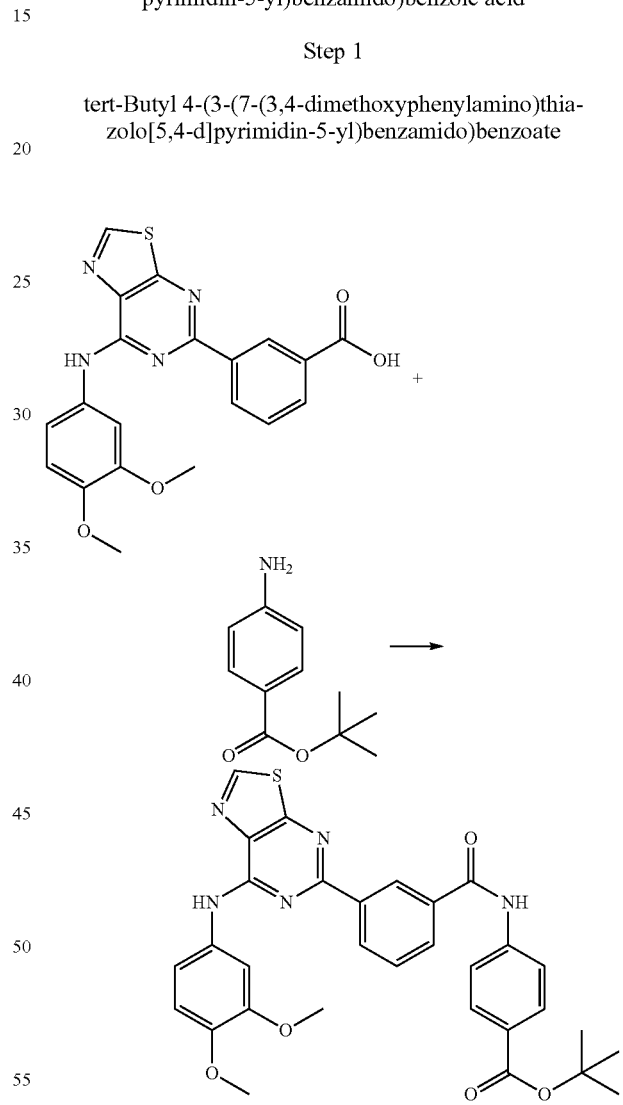

Procedure:

The mixture of 3-(7-(3,4-dimethoxyphenylamino)thiazolo[5,4-d]pyrimidin-5-yl)benzoic acid (130 mg, 0.32 mmol), tert-butyl 4-aminobenzoate (185 mg, 0.96 mmol), EDC (122 mg, 0.64 mmol) and DMAP (78 mg, 0.64 mmol) in 10 mL of DMF was stirred at room temperature for 2 hours. Excess of DMF was removed under reduced pressure and the residue was dissolved in 100 mL of ethyl acetate, washed with brine (2×10 mL), dried over anhydrous sodium sulfate. The crude residue was purified by silica gel chromatography (200-300 mesh, eluting with ethyl acetate) to give tert-butyl 4-(3-(7-(3,4-dimethoxyphenylamino)thiazolo[5,4-d]pyrimidin-5-yl)benzamido)benzoate (130 mg, 70%) as a white solid. $^1$H NMR (300 MHz, DMSO): δ 10.76 (s, 1H), 10.18 (s, 1H), 9.41 (s, 1H), 8.97 (s, 1H), 8.62 (d, 1H, J=8.1 Hz), 8.10 (d, 1H, J=7.8 Hz), 7.95 (s, 4H), 7.85 (s, 1H), 7.71 (t, 1H, J=7.7 Hz), 7.54 (dd, 1H, $J_1$=9.0 Hz, $J_2$=2.4 Hz), 6.99 (d, 1H, J=9.0 Hz), 3.81 (s, 3H), 3.75 (s, 3H), 1.57 (s, 3H). LC-MS: 584 [M+H]$^+$, $t_R$=1.78 min. HPLC: 98.03% at 214 nm, 98.38% at 254 nm, $t_R$=7.05 min.

Step 2

4-(3-(7-(3,4-Dimethoxyphenylamino)thiazolo[5,4-d]pyrimidin-5-yl)benzamido)benzoic acid

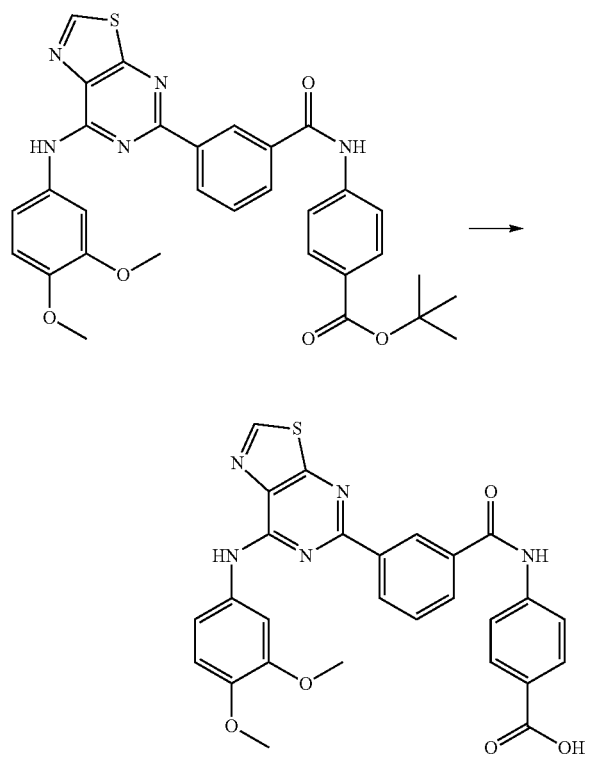

Procedure:

tert-Butyl-4-(3-(7-(3,4-dimethoxyphenylamino)thiazolo[5,4-d]pyrimidin-5-yl)benzamido)benzoate (45 mg, 0.077 mmol) in 10 mL of DCM was treated with TFA (2 mL) dropwise. The resulting yellow solution was stirred at ambient temperature overnight. The excess of solvent was removed under reduced pressure, the residue was triturated with n-hexane decanted, and dried to give 4-(3-(7-(3,4-dimethoxyphenylamino)thiazolo[5,4-d]pyrimidin-5-yl)benzamido)benzoic acid (27 mg, 66.4%). $^1$H NMR (300 MHz, DMSO): δ 12.80 (brs, 1H), 10.76 (s, 1H), 10.19 (s, 1H), 9.41 (s, 1H), 8.96 (s, 1H), 8.62 (d, 1H, J=7.8 Hz), 8.09 (d, 1H, J=7.8 Hz), 7.97 (s, 4H), 7.84 (s, 1H), 7.71 (t, 1H, J=7.7 Hz), 7.54 (dd, 1H, $J_1$=8.7 Hz, $J_2$=2.1 Hz), 6.99 (d, 1H, J=8.7 Hz), 3.81 (s, 3H), 3.74 (s, 3H). LC-MS: 528 [M+H]$^+$, $t_R$=1.54 min. HPLC: 96.02% at 214 nm, 95.94% at 254 nm, $t_R$=6.62 min.

Example 5

Step 1 tert-butyl 1-(7-(3,4-dimethoxyphenylamino)thiazolo[5,4-d]pyrimidin-5-yl)pyrrolidin-3-ylcarbamate

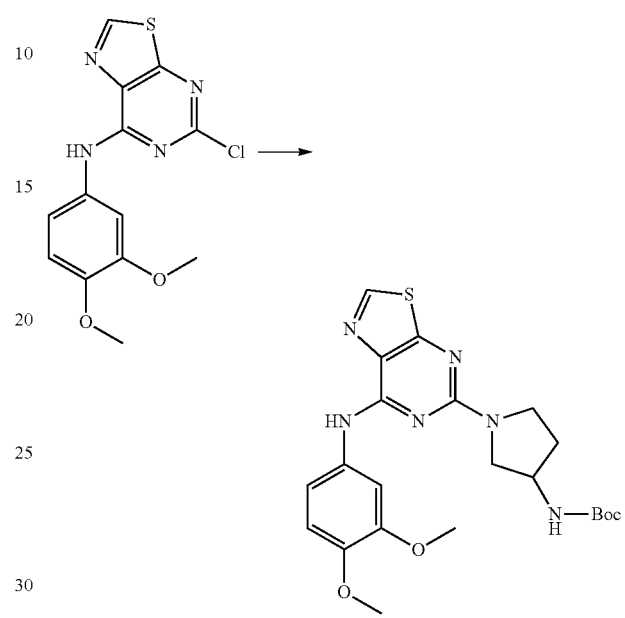

Procedure:

To a stirred solution of (5-chloro-thiazolo[5,4-d]pyrimidin-7-yl)-(3,4-dimethoxy-phenyl)-amine (150 mg, 0.46 mmol), tert-butyl pyrrolidin-3-yl carbamate (130 mg, 0.69 mmol), X-Phos (115 mg, 0.24 mmol) and Cs$_2$CO$_3$ (580 mg, 1.78 mmol) in 60 mL of dry dioxane was added Pd$_2$(dba)$_3$ (60 mg, 0.065 mmol) in one portion at room temperature under nitrogen. Then the reaction mixture was degassed with nitrogen for 15 minutes. The final mixture was stirred at 95° C. under nitrogen for 24 hours. The solvent was evaporated and crude purified by silica gel chromatography (silica gel 200-300 mesh, petroleum ether:ethyl acetate=1:2) to give tert-butyl 1-(7-(3,4-dimethoxyphenylamino)thiazolo[5,4-d]pyrimidin-5-yl)pyrrolidin-3-ylcarbamate (191 mg, 87.8%) as a solid. LC-MS: 473.2 [M+H]$^+$, $t_R$=1.56 min.

Step 2

5-(3-Aminopyrrolidin-1-yl)-N-(3,4-dimethoxyphenyl)thiazolo[5,4-d]pyrimidin-7-amine hydrochloride

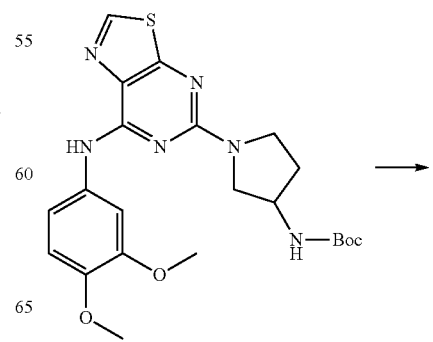

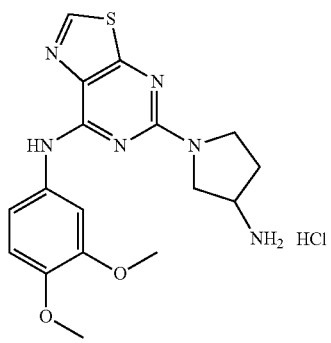

Procedure:

A solution of tert-butyl 1-(7-(3,4-dimethoxyphenylamino) thiazolo[5,4-d]pyrimidin-5-yl)pyrrolidin-3-ylcarbamate (191 mg, 0.40 mmol) in 50 mL of saturated HCl in dioxane was stirred at room temperature for 24 hours. The solvent was evaporated under reduced pressure to give 5-(3-aminopyrrolidin-1-yl)-N-(3,4-dimethoxyphenyl)thiazolo[5,4-d]pyrimidin-7-amine hydrochloride (165 mg, 100%) as a solid. This was used directly in the next step without further purification. LC-MS: 373.1 [M+H]$^+$, $t_R$=1.15 min.

Step 3

Methyl 4-(1-(7-(3,4-dimethoxyphenylamino)thiazolo [5,4-d]pyrimidin-5-yl)pyrrolidin-3-ylcarbamoyl) benzoate

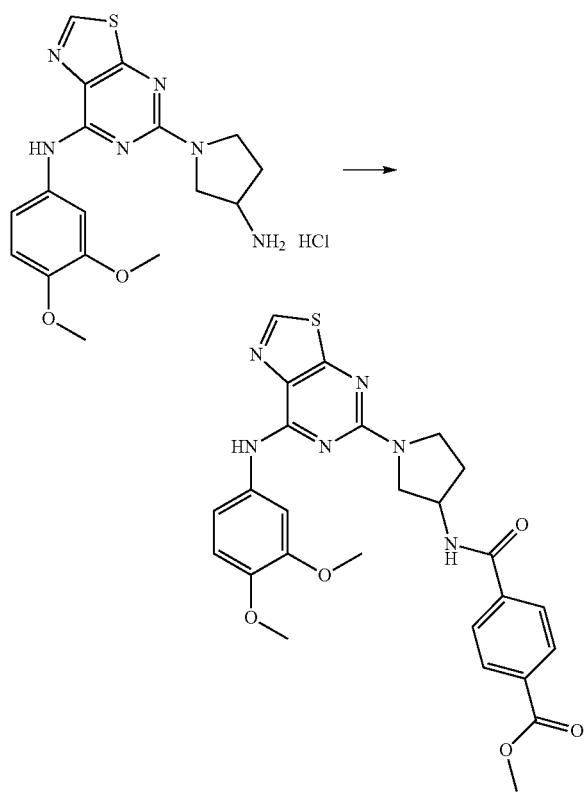

Procedure:

A solution of 5-(3-aminopyrrolidin-1-yl)-N-(3,4-dimethoxyphenyl)thiazolo[5,4-d]pyrimidin-7-amine hydrochloride (165 mg, 0.4 mmol), 4-(methoxycarbonyl)benzoic acid (94 mg, 0.52 mmol), HATU (197 mg, 0.52 mmol) and DIEA (154.8 mg, 1.2 mmol) in 10 mL of DMF was stirred at room temperature for 2 hours. A little of the desired product was detected from LCMS analysis. Then EDCI. HCl (76.4 mg, 0.42 mmol) and DMAP (49 mg, 0.4 mmol) were added in one portion and the solution was stirred at room temperature for additional 4 days. The solvent was evaporated at 80° C. in vacuo and the residue was purified by silica gel chromatography (silica gel 200-300 mesh, dichloromethane:methanol=20:1) to give methyl 4-(1-(7-(3,4-dimethoxyphenylamino)thiazolo[5,4-d]pyrimidin-5-yl)pyrrolidin-3-ylcarbamoyl)benzoate (190 mg, 87.8%) as a yellow solid. LC-MS: 535.1 [M+H]$^+$, $t_R$=1.48 min.

Step 4

4-(1-(7-(3,4-Dimethoxyphenylamino)thiazolo[5,4-d] pyrimidin-5-yl)pyrrolidin-3-ylcarbamoyl)benzoic acid

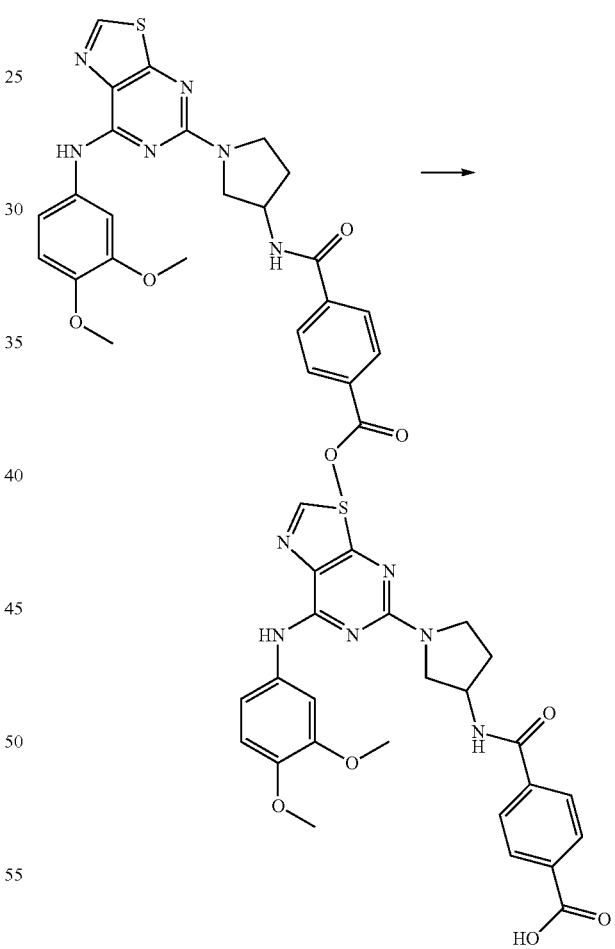

Procedure:

A solution of methyl 4-(1-(7-(3,4-dimethoxyphenylamino)thiazolo[5,4-d]pyrimidin-5-yl)pyrrolidin-3-ylcarbamoyl)benzoate (190 mg, 0.255 mmol) and LiOH.H$_2$O (149 mg, 3.55 mmol) in 2 mL of water, 10 mL of methanol and 15 mL of THF was stirred at room temperature for 2 hours. The solvent was evaporated after the solution was acidified by 2N HCl to pH=2 and the residue was dissolved in 50 mL of THF, filtered to remove the salts. The filtrate was evaporated and the residue was purified by preparative HPLC (Gemini 5u C18 150×21.2 mm; inject volume: 3 ml/inj, flow rate: 20 ml/min; wavelength: 214 nm and 254 nm; the gradient conditions are: 25% acetonitrile/75% water (0.1% TFA V/V) initially, and then proceed to 45% acetonitrile/55% water (0.1% TFA V/V) in a linear fashion after just 9 min.) to give 4-(1-(7-(3,4-dimethoxyphenylamino)thiazolo[5,4-d]pyrimidin-5-yl)pyrrolidin-3-ylcarbamoyl)benzoic acid (86 mg, 46.5%) as a solid. $^1$H NMR (300 MHz, DMSO): δ 9.63 (s, 1H), 8.36-8.79 (m, 2H), 8.02-7.88 (m, 5H), 7.60-7.50 (m, 1H), 6.93 (d, 1H, J=8.7 Hz), 4.61-4.59 (m, 1H), 3.95-3.66 (m, 10H), 2.28-2.10 (m, 2H). LC-MS: 521 [M+H]$^+$; 518.8 [M−H]$^−$, $t_R$=1.36 min. HPLC: 99.85% at 214 nm, 99.84% at 254 nm, $t_R$=4.67 min.

Example 6

Step 1 tert-Butyl 1-(7-(3,4-dimethoxyphenylamino)thiazolo[5,4-d]pyrimidin-5-yl)piperidin-3-ylcarbamate

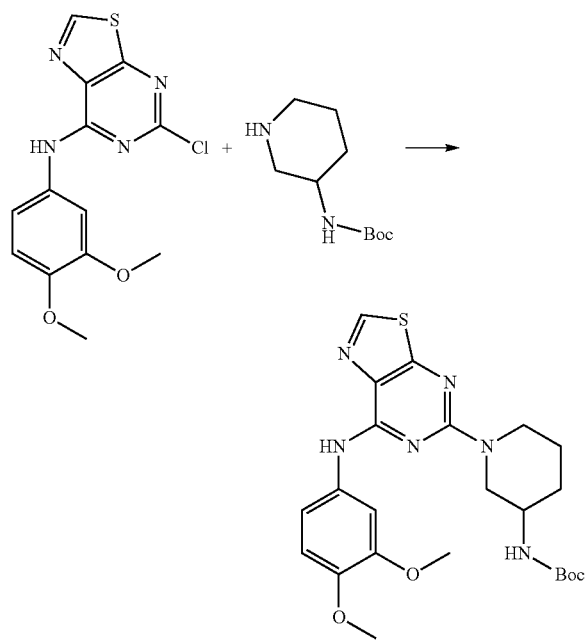

Procedure:

To a stirred solution of tert-butyl 1-(7-(3,4-dimethoxyphenylamino)thiazolo[5,4-d]pyrimidin-5-yl)piperidin-3-ylcarbamate (140 mg, 0.433 mmol), tert-butyl piperidin-3-ylcarbamate (130 mg, 0.649 mmol), X-Phos (115 mg, 0.24 mmol) and Cs$_2$CO$_3$ (580 mg, 1.78 mmol) in 60 mL of dry dioxane was added Pd$_2$(dba)$_3$ (60 mg, 0.065 mmol) in one portion at room temperature under nitrogen. Then the reaction mixture was degassed with nitrogen for 15 minutes. After that, the mixture was stirred at 95° C. under nitrogen for 24 hours. The solvent was evaporated and the residue was purified by silica gel chromatography (silica gel 200-300 mesh, petroleum ether:ethyl acetate=1:2) to give tert-butyl 1-(7-(3,4-dimethoxyphenylamino)thiazolo[5,4-d]pyrimidin-5-yl)piperidin-3-ylcarbamate (195 mg, 92.8%) as a solid. LC-MS: 487.1 [M+H]$^+$, $t_R$=1.67 min.

Step 2

5-(3-Aminopiperidin-1-yl)-N-(3,4-dimethoxyphenyl)thiazolo[5,4-d]pyrimidin-7-amine hydrochloride

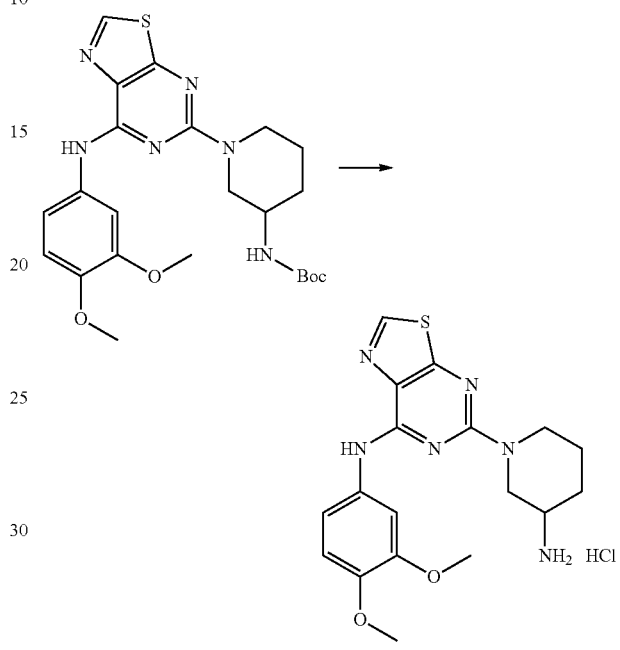

Procedure:

A solution of tert-butyl 1-(7-(3,4-dimethoxyphenylamino)thiazolo[5,4-d]pyrimidin-5-yl)piperidin-3-ylcarbamate (195 mg, 0.4 mmol) in 85 mL of saturated HCl in dioxane was stirred at room temperature for 24 hours. The solvent was evaporated at 40° C. under reduced pressure to give 5-(3-aminopiperidin-1-yl)-N-(3,4-dimethoxyphenyl)thiazolo[5,4-d]pyrimidin-7-amine hydrochloride (200 mg, crude) as a yellow solid. It was used directly in the next step without further purification. LC-MS: 387.0 [M+H]$^+$, $t_R$=1.19 min.

Step 3

Methyl 4-(1-(7-(3,4-dimethoxyphenylamino)thiazolo[5,4-d]pyrimidin-5-yl)piperidin-3-ylcarbamoyl)benzoate

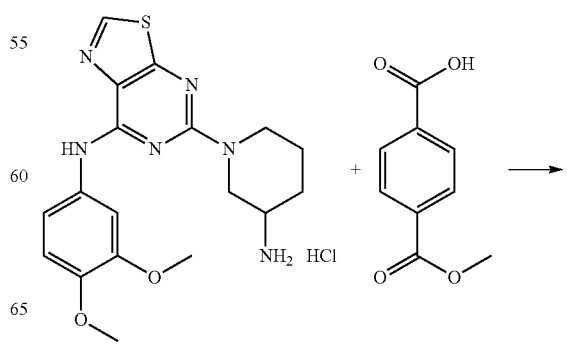

77

-continued

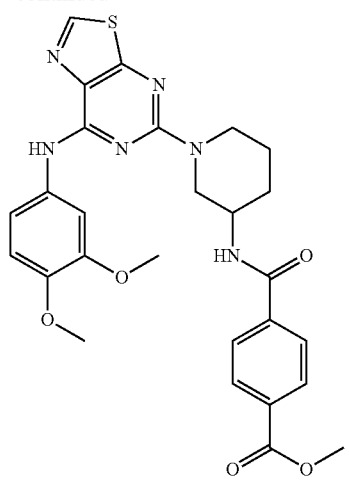

Procedure:

A solution of 5-(3-aminopiperidin-1-yl)-N-(3,4-dimethoxyphenyl)thiazolo[5,4-d]pyrimidin-7-amine hydrochloride (200 mg, 0.47 mmol), 4-(methoxycarbonyl)benzoic acid (111 mg, 0.61 mmol), HATU (231 mg, 0.61 mmol) and DIEA (182 mg, 1.41 mmol) in 10 mL of DMF was stirred at room temperature for 2 hours. Only small amounts of the desired product were detected by LCMS analysis. EDCI.HCl (90 mg, 0.47 mmol) and DMAP (57 mg, 0.47 mmol) were added in one portion and the solution was stirred at room temperature for additional 4 days. The solvent was evaporated at 80° C. on vacuum and the residue was purified by silica gel chromatography (silica gel 200-300 mesh, dichloromethane:methanol=20:1) to give methyl 4-(1-(7-(3,4-dimethoxyphenylamino)thiazolo[5,4-d]pyrimidin-5-yl)piperidin-3-ylcarbamoyl)benzoate (250 mg, 96.1%) as a solid. LC-MS: 549.2 [M+H]$^+$, $t_R$=1.56 min.

Step 4

4-(1-(7-(3,4-Dimethoxyphenylamino)thiazolo[5,4-d]pyrimidin-5-yl)piperidin-3-ylcarbamoyl)benzoic acid

78

-continued

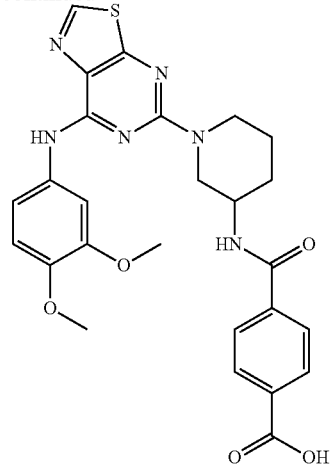

Procedure:

A solution of methyl 4-(1-(7-(3,4-dimethoxyphenylamino)thiazolo[5,4-d]pyrimidin-5-yl)piperidin-3-ylcarbamoyl)benzoate (250 mg, 0.45 mmol) and LiOH.H$_2$O (191 mg, 4.5 mmol) in 2 mL of water, 12 mL of methanol and 30 mL of THF was stirred at room temperature for 1 hour. The solvent was evaporated and the residue was suspended in 30 mL of THF, then treated with 2N HCl to pH=2. The solvent was evaporated and the residue was dissolved in 50 mL of THF, filtered to remove the salts. The filtrate was evaporated and crude purified by preparative HPLC (Gemini 5u C18 150×21.2 mm; inject volume: 3 ml/inj, flow rate: 20 ml/min; wavelength: 214 nm and 254 nm; the gradient conditions are: 28% acetonitrile/72% water (0.1% TFA V/V) initially, and then proceed to 50% acetonitrile/50% water (0.1% TFA V/V) in a linear fashion after just 9 min.) to give 4-(1-(7-(3,4-dimethoxyphenylamino)thiazolo[5,4-d]pyrimidin-5-yl)piperidin-3-ylcarbamoyl)benzoic acid (45 mg, 18.4%) as a solid. $^1$H NMR (300 MHz, DMSO): δ 13.20 (brs, 1H), 9.63 (s, 1H), 8.85 (s, 1H), 8.04-7.95 (m, 4H), 7.63 (s, 1H), 7.41-7.32 (m, 2H), 6.88-6.85 (m, 1H), 5.34-5.31 (m, 1H), 4.71-4.52 (m, 2H), 3.70 (s, 3H), 3.67 (s, 3H), 3.04-2.97 (m, 2H), 2.04-1.96 (m, 4H). LC-MS: 535 [M+H]$^+$; 532.9 [M−H]$^-$, $t_R$=1.43 min. HPLC: 99.26% at 214 nm, 99.79% at 254 nm, $t_R$=5.37 min.

Example 7

Step 1

Methyl 1-(7-(3,4-dimethoxyphenylamino)thiazolo[5,4-d]pyrimidin-5-yl)piperidine-3-carboxylate

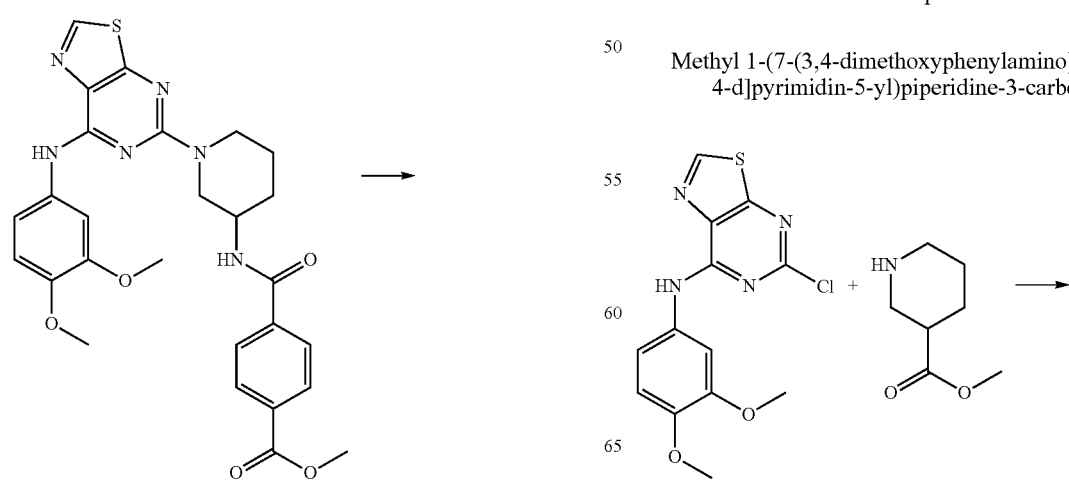

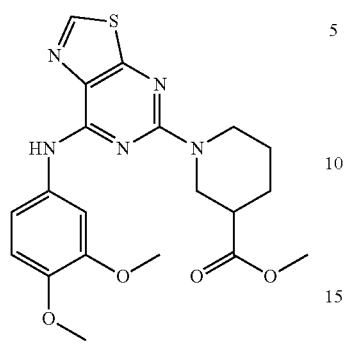

Procedure:

To a solution of (5-chloro-thiazolo[5,4-d]pyrimidin-7-yl)-(3,4-dimethoxy-phenyl)-amine (80 mg, 0.25 mmol) in 10 mL of dioxane, methyl piperidine-3-carboxylate (107 mg, 0.75 mmol), $Cs_2CO_3$ (163 mg, 0.50 mmol), X-Phos (47.6 mg, 0.1 mmol) were added. After degassed three times under nitrogen, $Pd_2(dba)_3$ (28 mg, 0.05 mmol) was added. The resulting mixture was degassed one more time, and stirred at reflux overnight. The excess of dioxane was removed under reduced pressure and the residue was purified by silica gel chromatography (200-300 mesh, petroleum ether:ethyl acetate=1:1) to give methyl 1-(7-(3,4-dimethoxyphenylamino)thiazolo[5,4-d]pyrimidin-5-yl)piperidine-3-carboxylate (60 mg, 56%) as an oil, which was solidified after standing overnight. $^1$H NMR (300 MHz, $CDCl_3$): δ 8.41 (s, 1H), 7.77 (s, 1H), 7.64 (s, 1H), 7.08 (d, 1H, J=9.0 Hz), 6.88 (d, 1H, J=8.7 Hz), 4.92-4.87 (m, 1H), 4.68-4.64 (m, 1H), 3.93 (s, 3H), 3.91 (s, 3H), 3.71 (s, 3H), 3.30-3.22 (m, 1H), 3.10-3.09 (m, 1H), 2.60-2.59 (m, 1H), 2.11-2.06 (m, 1H), 1.85-1.60 (m, 3H). LC-MS: 430.1 [M+H]$^+$, 452.1 [M+Na]$^+$, $t_R$=1.63 min.

Step 2

1-(7-(3,4-Dimethoxyphenylamino)thiazolo[5,4-d]pyrimidin-5-yl)piperidine-3-carboxylic acid

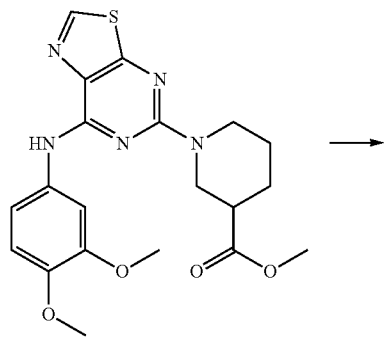

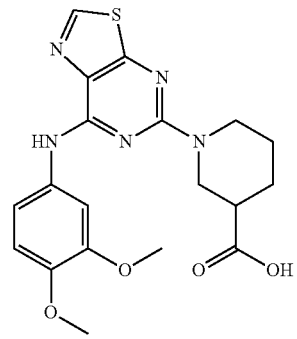

Procedure:

To a stirred solution of methyl 1-(7-(3,4-dimethoxyphenylamino)thiazolo[5,4-d]pyrimidin-5-yl)piperidine-3-carboxylate (0.06 g, 0.139 mmol) in 5 mL of THF and 5 mL of methanol was added a solution of NaOH (0.056 g, 1.39 mmol) in 1 mL of water at room temperature. After the addition, the reaction was stirred at this temperature for 24 hours. The solvent was evaporated and the residue was suspended in 10 mL of THF, then treated by HCl until pH=2. The solvent was evaporated and then dissolved in 30 mL of THF, filtered. The filtrate was evaporated to give 1-(7-(3,4-dimethoxyphenylamino)thiazolo[5,4-d]pyrimidin-5-yl)piperidine-3-carboxylic acid (0.057 g, 98%) as a solid. LC-MS: 416.1 [M+H]$^+$, $t_R$=1.57 min.

Step 3 tert-Butyl 4-(1-(7-(3,4-dimethoxyphenylamino)thiazolo[5,4-d]pyrimidin-5-yl)piperidine-3-carboxamido)benzoate

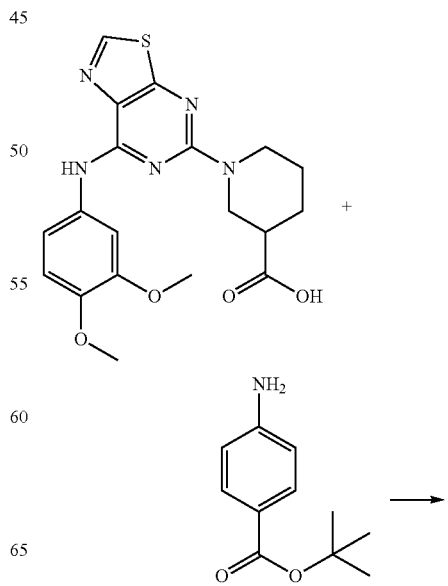

-continued

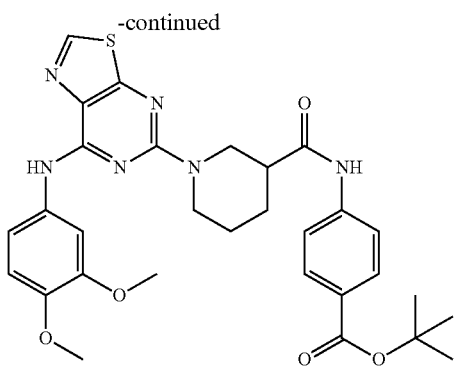

Procedure:

A mixture of 1-(7-(3,4-dimethoxyphenylamino)thiazolo[5,4-d]pyrimidin-5-yl)piperidine-3-carboxylic acid (57 mg, 0.137 mmol), tert-butyl-4-aminobenzoate (34.4 mg, 0.178 mmol), HATU (67.6 mg, 0.178 mmol) and DIEA (53 mg, 0.411 mmol) in 10 mL of DMF was stirred at room temperature for 72 hours. The solvent was evaporated and the residue was purified by silica gel chromatography (silica gel 200-300 mesh, ethyl acetate:petroleum ether=1:1) to give tert-butyl 4-(1-(7-(3,4-dimethoxyphenylamino)thiazolo[5,4-d]pyrimidin-5-yl)piperidine-3-carboxamido)benzoate (75 mg, 92%) as a solid. LC-MS: 591.2 [M+H]$^+$, $t_R$=1.77 min.

Step 4

4-(1-(7-(3,4-Dimethoxyphenylamino)thiazolo[5,4-d]pyrimidin-5-yl)piperidine-3-carboxamido)benzoic acid

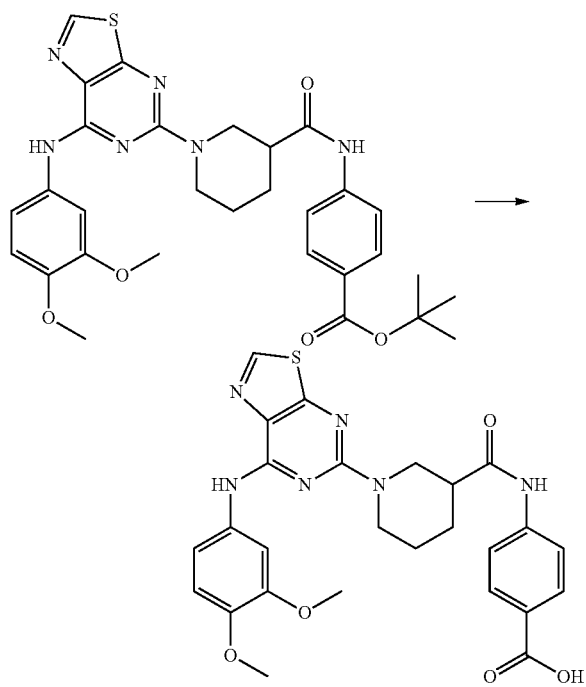

Procedure

To a stirred solution of tert-butyl 4-(1-(7-(3,4-dimethoxyphenylamino)thiazolo[5,4-d]pyrimidin-5-yl)piperidine-3-carboxamido)benzoate (75 mg, 0.127 mmol) in 5 mL of DCM was added TFA (2 mL) dropwise at room temperature. Then the reaction mixture was stirred at room temperature for 24 hours. The solvent was evaporated at 40° C. at reduced pressure and the residue was purified by preparative HPLC (Gemini 5u C18 150×21.2 mm; inject volume: 3 ml/inj, flow rate: 20 ml/min; wavelength: 214 nm and 254 nm; the gradient conditions are: 30% acetonitrile/70% water (0.1% TFA V/V) initially, and then proceed to 55% acetonitrile/45% water (0.1% TFA V/V) in a linear fashion after just 9 min.) to give 4-(1-(7-(3,4-dimethoxyphenylamino)thiazolo[5,4-d]pyrimidin-5-yl)piperidine-3-carboxamido)benzoic acid (25 mg, 36.8%) as a white solid. $^1$H NMR (300 MHz, CD$_3$OD): δ 8.71 (s, 1H), 7.99-7.96 (m, 2H), 7.68-7.65 (m, 2H), 7.51 (s, 1H), 7.27-7.23 (m, 1H), 6.86 (d, 1H, J=8.4 Hz), 3.79 (s, 3H), 3.70 (s, 3H), 2.67 (brs, 3H), 2.19-1.87 (m, 6H). LC-MS: 535 [M+H]$^+$; 533 [M−H]$^−$, $t_R$=1.47 min. HPLC: 96.74% at 214 nm, 97.85% at 254 nm, $t_R$=5.46 min.

Example 8

N-(1-(7-(3,4-Dimethoxyphenylamino)thiazolo[5,4-d]pyrimidin-5-yl)pyrrolidin-3-yl)-2-oxoindoline-6-carboxamide

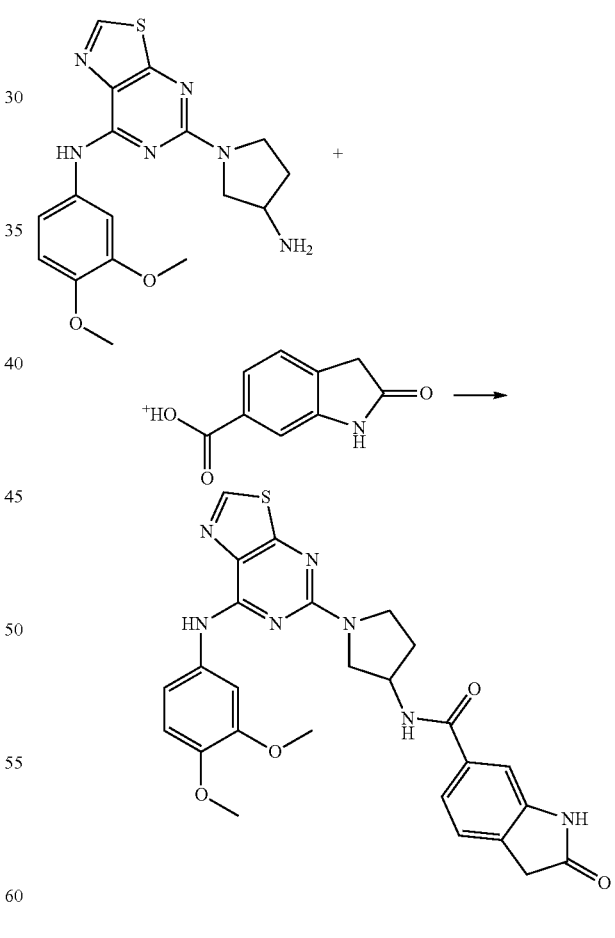

Procedure:

A mixture of 5-(3-aminopyrrolidin-1-yl)-N-(3,4-dimethoxyphenyl)thiazolo[5,4-d]pyrimidin-7-amine hydrochloride (82 mg, 0.2 mmol), 2-oxoindoline-6-carboxylic acid (36 mg, 0.2 mmol), EDCI (76 mg, 0.4 mmol) and N-methylimidazole (50 mg, 0.6 mmol) in 5 mL of DCM was stirred at room temperature for 16 hours. The mixture was washed with water (4 mL), The organic layer was dried over $Na_2SO_4$. After filtration and concentration, the residue was purified by preparative TLC (Silica gel, 20 cm×20 cm, separated by EtOAc, eluted by DCM:MeOH=1:20, v/v) to give N-(1-(7-(3,4-dimethoxyphenylamino)thiazolo[5,4-d]pyrimidin-5-yl)pyrrolidin-3-yl)-2-oxoindoline-6-carboxamide (25 mg, 23.5%). $^1$H NMR (300 MHz, DMSO): δ 10.52 (s, 1H), 9.56 (s, 1H), 8.81 (s, 1H), 8.61 (d, 1H, J=6.3 Hz), 7.90 (brs, 1H), 7.48-7.46 (m, 2H), 7.28-7.25 (m, 2H), 6.93-6.90 (m, 1H), 4.54 (brs, 1H), 3.77-3.34 (m, 11H), 2.50-2.34 (m, 1H), 2.07-1.99 (m, 2H). LC-MS: 532 $[M+H]^+$, 530 $[M-H]^-$, $t_R$=1.35 min. HPLC: 97.39% at 214 nm, 97.05% at 254 nm, $t_R$=4.54 min.

Example 9

Step 1

Methyl 4-(1-(7-(3,4-dimethoxyphenylamino)thiazolo[5,4-d]pyrimidin-5-yl)pyrrolidin-3-ylcarbamoyl)-2-hydroxybenzoate

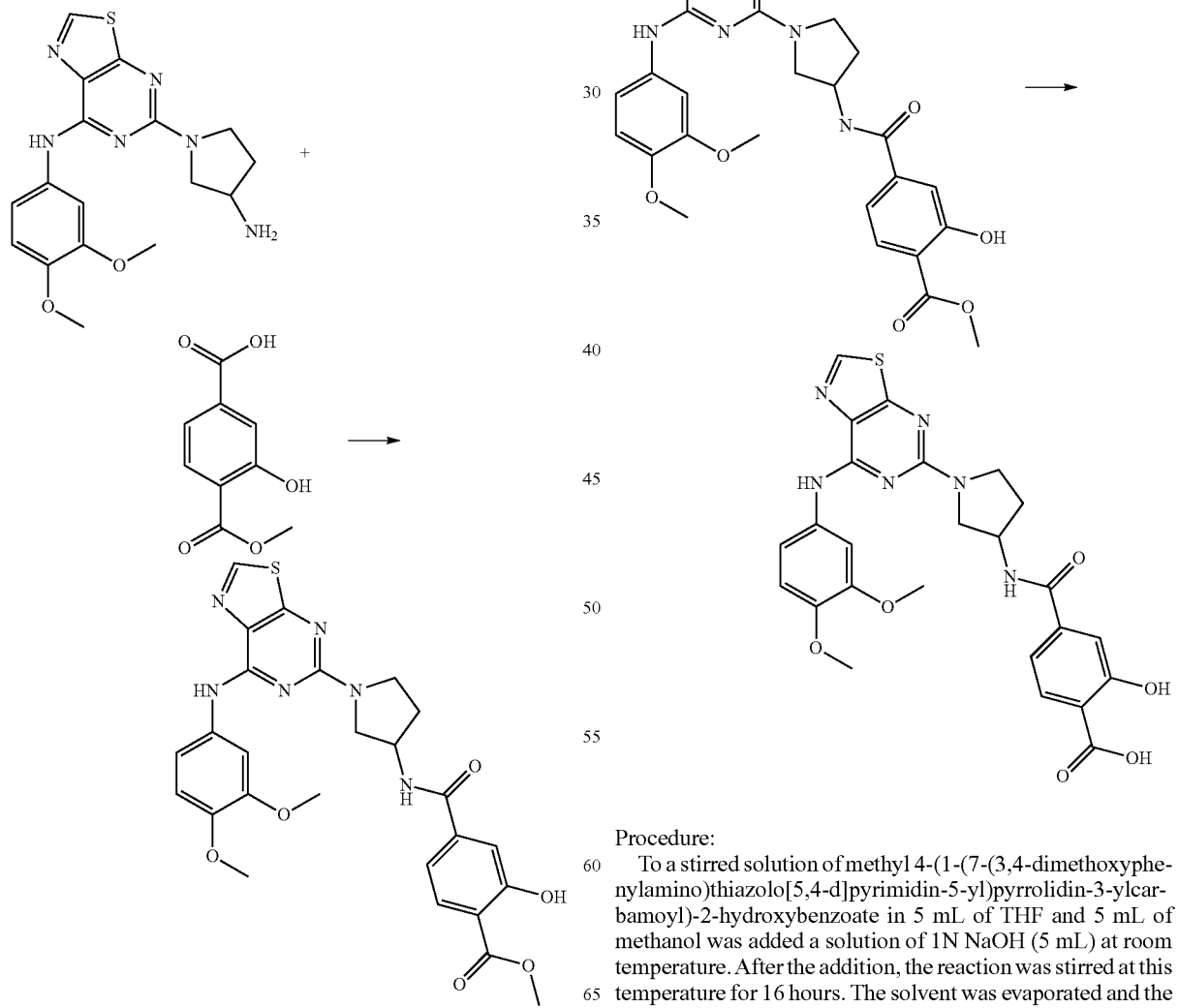

Procedure:

A mixture of 5-(3-aminopyrrolidin-1-yl)-N-(3,4-dimethoxyphenyl)thiazolo[5,4-d]pyrimidin-7-amine hydrochloride (164 mg, 0.4 mmol), 3-hydroxy-4-(methoxycarbonyl)benzoic acid (78 mg, 0.4 mmol), EDCI (153 mg, 0.8 mmol) and N-methylimidazole (100 mg, 1.2 mmol) in 5 mL of DCM was stirred at room temperature for 16 hours. The mixture was washed with water (4 mL), The organic layer was dried over $Na_2SO_4$. After filtration and concentration, the residue was purified by column chromatography (silica gel, 100% DCM to DCM:MeOH=50:1) to give methyl 4-(1-(7-(3,4-dimethoxyphenylamino)thiazolo[5,4-d]pyrimidin-5-yl)pyrrolidin-3-ylcarbamoyl)-2-hydroxybenzoate (100 mg, yield 45%). LC-MS: 551 $[M+H]^+$, $t_R$=1.61 min.

Step 2

4-(1-(7-(3,4-Dimethoxyphenylamino)thiazolo[5,4-d]pyrimidin-5-yl)pyrrolidin-3-ylcarbamoyl)-2-hydroxybenzoic acid

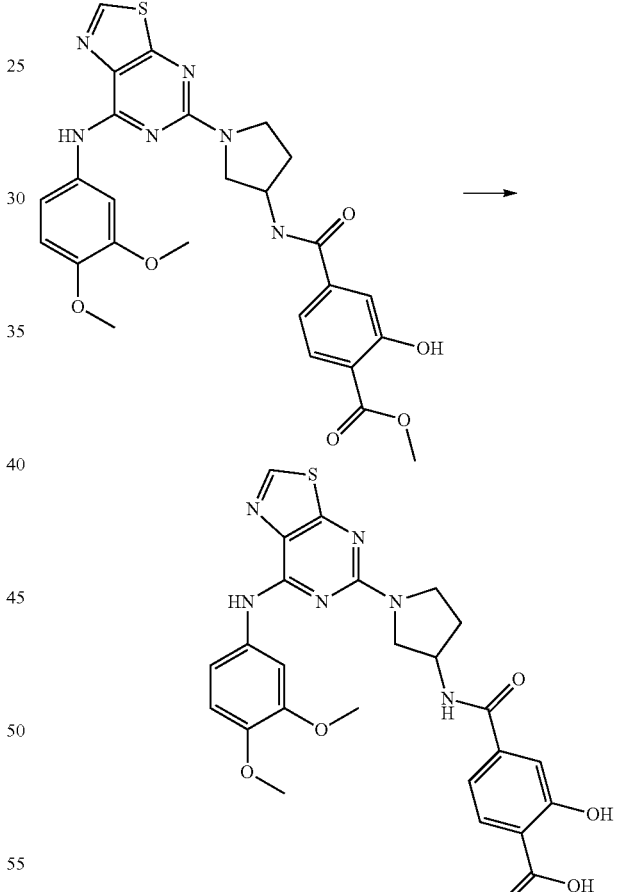

Procedure:

To a stirred solution of methyl 4-(1-(7-(3,4-dimethoxyphenylamino)thiazolo[5,4-d]pyrimidin-5-yl)pyrrolidin-3-ylcarbamoyl)-2-hydroxybenzoate in 5 mL of THF and 5 mL of methanol was added a solution of 1N NaOH (5 mL) at room temperature. After the addition, the reaction was stirred at this temperature for 16 hours. The solvent was evaporated and the residue was diluted with water and adjusted to pH=2 by HCl (aq.). The suspension was filtered and dried. The crude was purified by preparative HPLC (Gemini 5u C18 150×21.2 mm; inject volume: 3 ml/inj, flow rate: 20 ml/min; wavelength: 214 nm and 254 nm; the gradient conditions are: 20% acetonitrile/80% water (0.1% TFA V/V) initially, and then proceed to 45% acetonitrile/55% water (0.1% TFA V/V) in a linear fashion after just 9 min.) to give 4-(1-(7-(3,4-dimethoxyphenylamino)thiazolo[5,4-d]pyrimidin-5-yl)pyrrolidin-3-ylcarbamoyl)-2-hydroxybenzoic acid (15 mg, 14% over two steps). $^1$H NMR (300 MHz, DMSO): δ 9.72 (s, 1H), 8.85 (s, 1H), 8.76 (d, 1H, J=6.0 Hz), 7.86 (s, 1H), 7.84 (s, 1H), 7.43-7.37 (m, 3H), 6.92 (d, 1H, J=8.4 Hz), 4.56 (brs, 1H), 3.77-3.73 (m, 11H), 2.27-2.23 (m, 1H), 2.09-2.07 (m, 1H). LC-MS: 537 [M+H]$^+$, $t_R$=1.37 min. HPLC: 99.62% at 214 nm, 99.22% at 254 nm, $t_R$=3.53 min.

Example 10

Step 1

Methyl 4-(1-(7-(3,4-dimethoxyphenylamino)thiazolo[5,4-d]pyrimidin-5-yl)pyrrolidin-3-ylcarbamoyl)-2-methoxybenzoate

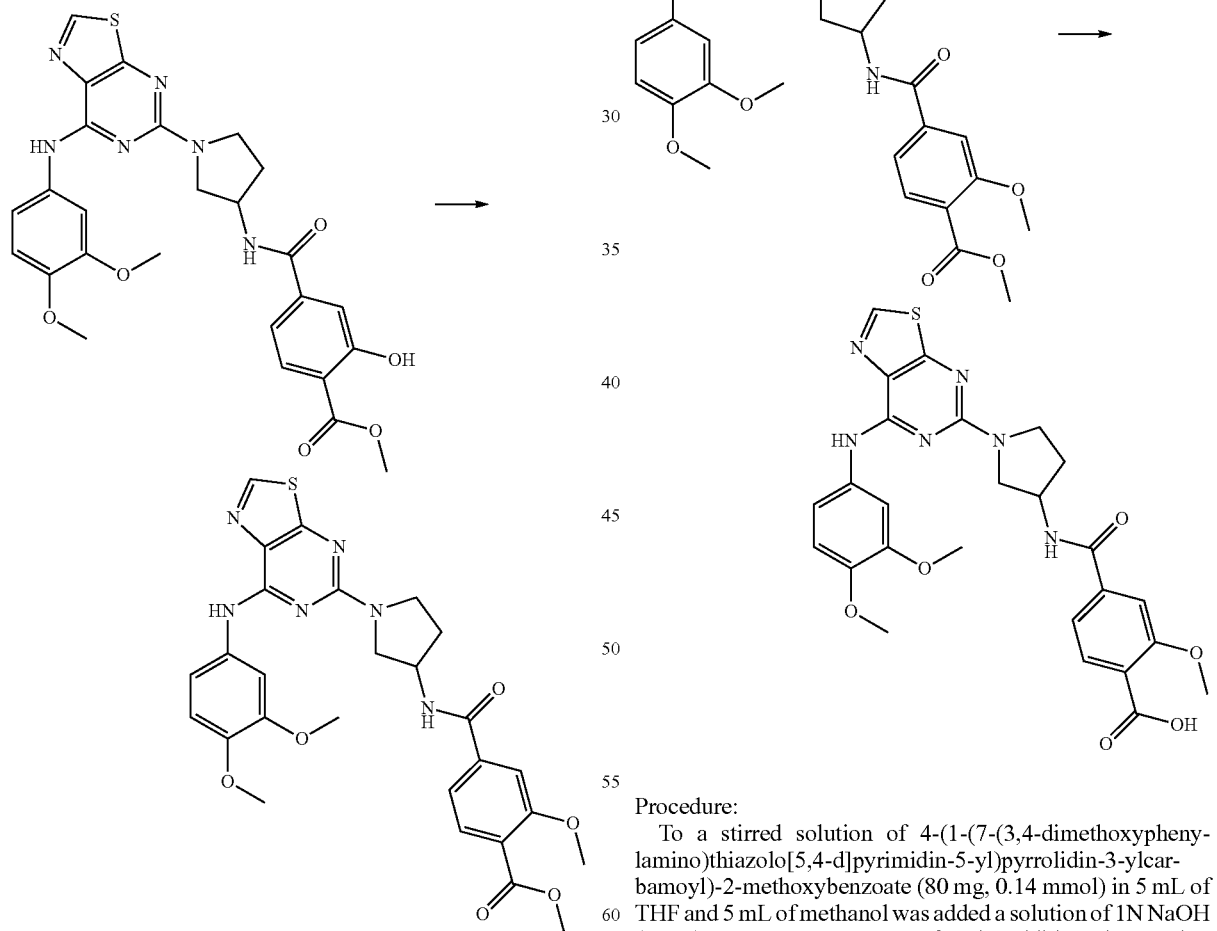

Procedure:

To a mixture of methyl 4-(1-(7-(3,4-dimethoxyphenylamino)thiazolo[5,4-d]pyrimidin-5-yl)pyrrolidin-3-ylcarbamoyl)-2-hydroxybenzoate (100 mg, 0.18 mmol) in 2 mL of DMF were added MeI (38 mg, 0.27 mmol) and K$_2$CO$_3$ (37 mg, 0.27 mmol) at room temperature, and then the mixture was stirred for 16 hours. The mixture was poured into water and extracted with EtOAc (3×5 mL). The organic layer was washed with 0.1 N HCl (5 mL) and brine. The organic layer was dried over Na$_2$SO$_4$. After filtration and concentration, the crude methyl 4-(1-(7-(3,4-dimethoxyphenylamino)thiazolo[5,4-d]pyrimidin-5-yl)pyrrolidin-3-ylcarbamoyl)-2-methoxybenzoate was obtained and used the next step without purification (80 mg, 78%). LC-MS: 565 [M+H]$^+$, $t_R$=1.48 min.

Step 2

4-(1-(7-(3,4-Dimethoxyphenylamino)thiazolo[5,4-d]pyrimidin-5-yl)pyrrolidin-3-ylcarbamoyl)-2-methoxybenzoic acid

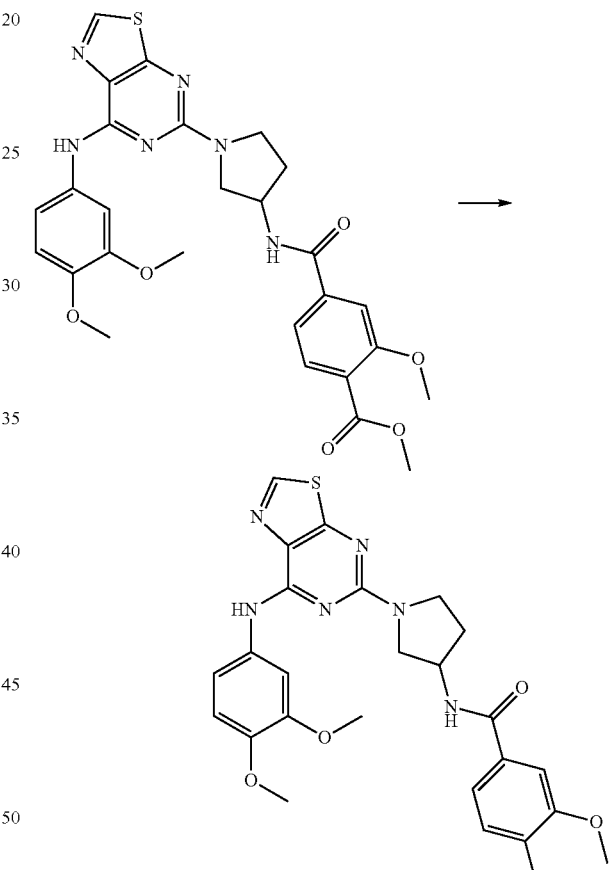

Procedure:

To a stirred solution of 4-(1-(7-(3,4-dimethoxyphenylamino)thiazolo[5,4-d]pyrimidin-5-yl)pyrrolidin-3-ylcarbamoyl)-2-methoxybenzoate (80 mg, 0.14 mmol) in 5 mL of THF and 5 mL of methanol was added a solution of 1N NaOH (5 mL) at room temperature. After the addition, the reaction was stirred at this temperature for 16 hours. The solvent was evaporated and the residue was diluted with water and adjusted to pH=2 by HCl (aq.). The suspension was filtered and dried. The crude was purified by preparative HPLC (Gemini 5u C18 150×21.2 mm; inject volume: 3 ml/inj, wavelength: 214 nm and 254 nm; the gradient conditions are: 20% acetonitrile/80% water (0.1% TFA V/V) initially, and then proceed to 55% acetonitrile/45% water (0.1% TFA V/V) in a linear fashion after just 9 min) to give 4-(1-(7-(3,4-dimethoxyphenylamino)thiazolo[5,4-d]pyrimidin-5-yl)pyrrolidin-3-ylcarbamoyl)-2-methoxybenzoic acid (30 mg, 39%) as white solid. $^1$H NMR (300 MHz, DMSO): δ 9.66 (s, 1H), 8.83 (s, 1H), 8.74-8.72 (m, 1H), 7.88 (brs, 1H), 7.66 (d, 1H, J=7.8 Hz), 7.50-7.46 (m, 3H), 6.91 (d, 1H, J=8.7 Hz), 4.59 (brs, 1H), 3.87 (s, 4H), 3.76-3.72 (m, 8H), 2.27 (brs, 1H), 2.09 (brs, 1H). LC-MS: 550.8 [M+H]$^+$, $t_R$=1.38 min. HPLC: 98.09% at 214 nm, 96.40% at 254 nm, $t_R$=4.64 min.

Example 11

N-(1-(7-(3,4-Dimethoxyphenylamino)thiazolo[5,4-d]pyrimidin-5-yl)pyrrolidin-3-yl)-1H-indazole-6-carboxamide

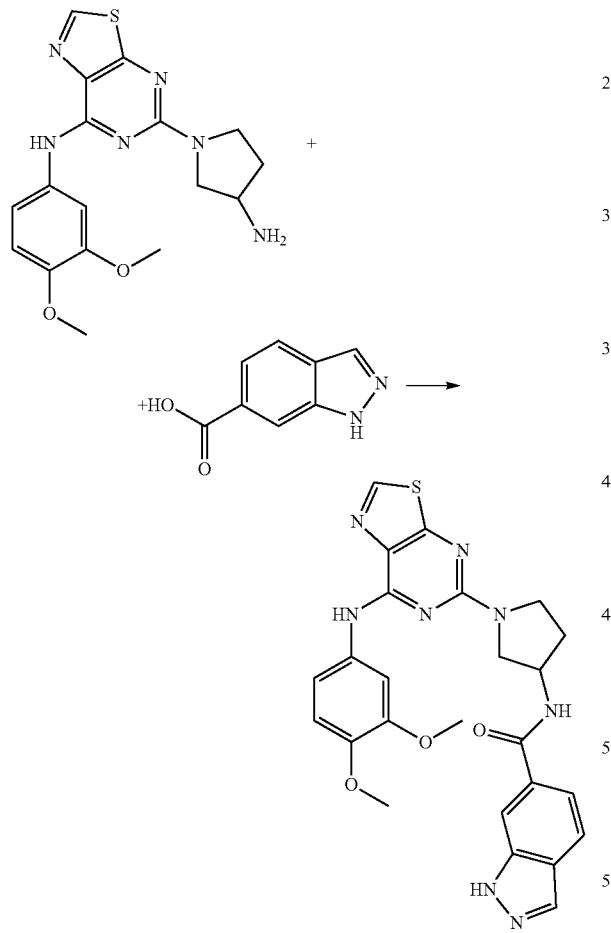

Procedure:

A mixture of 5-(3-aminopyrrolidin-1-yl)-N-(3,4-dimethoxyphenyl)thiazolo[5,4-d]pyrimidin-7-amine hydrochloride (100 mg, 0.245 mmol), 1H-indazole-6-carboxylic acid (40 mg, 0.245 mmol), EDCI (97 mg, 0.49 mmol) and N-methylimidazole (60 mg, 0.735 mmol) in 10 mL of DCM was stirred at room temperature for 16 hours. The mixture was washed with water (5 mL), The organic layer was dried over Na$_2$SO$_4$. After filtration and concentration, the residue was purified by preparative HPLC (Gemini 5u C18 150×21.2 mm; inject volume: 3 ml/inj, flow rate: 20 ml/min; wavelength: 214 nm and 254 nm; the gradient conditions are: 25% acetonitrile/75% water (0.1% TFA V/V) initially, and then proceed to 50% acetonitrile/50% water (0.1% TFA V/V) in a linear fashion after just 9 min.) to give N-(1-(7-(3,4-dimethoxyphenylamino)thiazolo[5,4-d]pyrimidin-5-yl)pyrrolidin-3-yl)-1H-indazole-6-carboxamide (45 mg, 36%) as white solid. $^1$H NMR (300 MHz, DMSO): δ 9.69 (s, 1H), 8.84 (s, 1H), 8.74 (d, 1H, J=6.3 Hz), 8.14 (s, 1H), 8.06 (s, 1H), 7.89 (s, 1H), 7.81 (d, 1H, J=8.4 Hz), 7.63-7.44 (m, 2H), 6.92 (d, 1H, J=9.0 Hz), 4.62-4.25 (m, 2H), 3.96-3.66 (m, 10H), 2.35-2.11 (m, 3H). LC-MS: 516.9 [M+H]$^+$, $t_R$=1.38 min. HPLC: 100% at 214 nm, 100% at 254 nm, $t_R$=5.76 min.

Example 12

N-(1-(7-(3,4-Dimethoxyphenylamino)thiazolo[5,4-d]pyrimidin-5-yl)pyrrolidin-3-yl)pyrazine-2-carboxamide

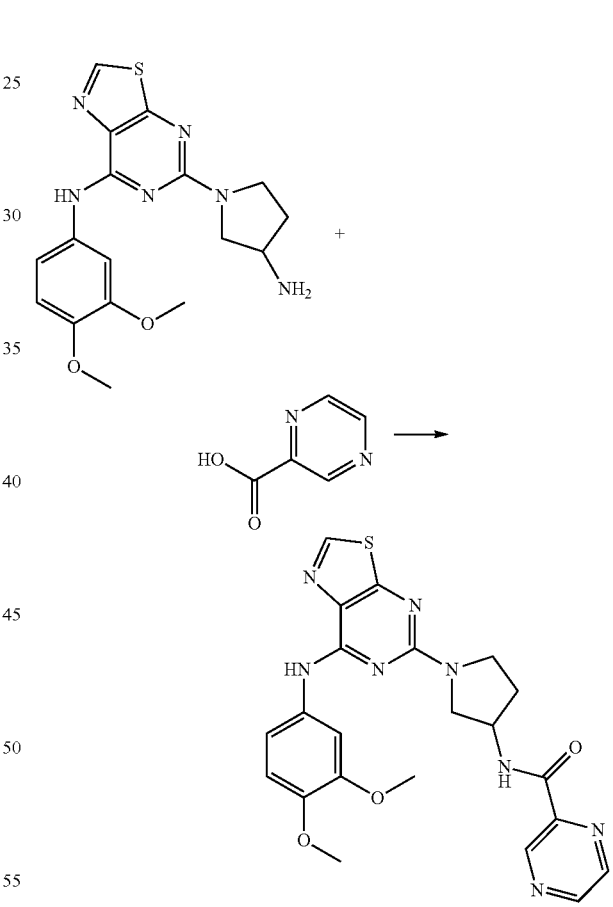

Procedure:

A mixture of 5-(3-aminopyrrolidin-1-yl)-N-(3,4-dimethoxyphenyl)thiazolo[5,4-d]pyrimidin-7-amine hydrochloride (40 mg, 0.1 mmol), pyrazine-2-carboxylic acid (14 mg, 0.11 mmol), EDCI (38 mg, 0.2 mmol) and N-methylimidazole (25 mg, 0.3 mmol) in 3 mL of DCM was stirred at room temperature for 15 hours. The mixture was washed with water (5 mL), the organic layer was dried over Na$_2$SO$_4$. After filtration and concentration, the residue was purified by preparative TLC (Silica gel, 20 cm×20 cm, separated by EtOAc, eluted by DCM:MeOH=1:20, v/v) to give N-(1-(7-(3,4-dimethoxyphenylamino)thiazolo[5,4-d]pyrimidin-5-yl)pyrrolidin-3-yl)pyrazine-2-carboxamide (35 mg, 73%) as white solid. ¹H NMR (300 MHz, DMSO): δ 9.56 (s, 1H), 9.18 (s, 1H), 9.12 (d, 1H, J=7.8 Hz), 8.86 (d, 1H, J=2.4 Hz), 8.80 (s, 1H), 8.71 (s, 1H), 7.85 (s, 1H), 7.50-7.27 (m, 1H), 6.90 (d, 1H, J=8.4 Hz), 4.64-4.62 (m, 1H), 3.75-3.64 (m, 10H), 2.27-2.16 (m, 2H). LC-MS: 479 [M+H]$^+$, 477 [M-H]$^-$, $t_R$=1.39 min. HPLC: 97.06% at 214 nm, 96.92% at 254 nm, $t_R$=4.63 min.

Example 13

6-Amino-N-(1-(7-(3,4-dimethoxyphenylamino)thiazolo[5,4-d]pyrimidin-5-yl)pyrrolidin-3-yl)nicotinamide

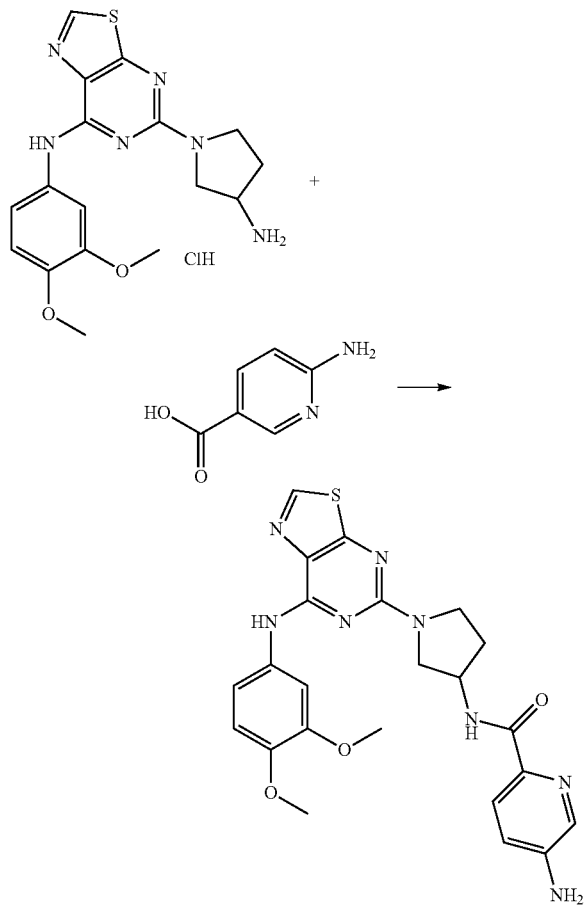

Procedure:

A mixture of 5-(3-aminopyrrolidin-1-yl)-N-(3,4-dimethoxyphenyl)thiazolo[5,4-d]pyrimidin-7-amine hydrochloride (100 mg, 0.245 mmol), 6-aminonicotinic acid (40 mg, 0.27 mmol), EDCI (97 mg, 0.49 mmol) and N-methylimidazole (60 mg, 0.735 mmol) in 5 mL of DCM was stirred at room temperature for 16 hours. The mixture was washed with water (5 mL), The organic layer was dried over Na$_2$SO$_4$. After filtration and concentration, the residue was purified by column chromatography on silica gel eluting with a mixture of CH$_2$Cl$_2$ and methanol (100:1→15:1) to give 6-amino-N-(1-(7-(3,4-dimethoxyphenylamino)thiazolo[5,4-d]pyrimidin-5-yl)pyrrolidin-3-yl)nicotinamide (40 mg, 33%). ¹H NMR (300 MHz, DMSO): δ 9.57 (s, 1H), 8.81 (s, 1H), 8.475-8.46 (m, 1H), 8.27-8.25 (m, 2H), 7.60-7.25 (m, 2H), 6.92 (d, 1H, J=8.7 Hz), 6.47-6.39 (m, 3H), 4.54-4.52 (m, 1H), 3.76-3.58 (m, 10H), 2.34-2.04 (m, 2H). LC-MS: 247 [M/2+H]$^+$, 493 [M+H]$^+$, 491 [M-H]$^-$, $t_R$=1.22 min. HPLC: 95.20% at 214 nm, 95.06% at 254 nm, $t_R$=5.64 min.

Example 14

N-(1-(7-(3,4-Dimethoxyphenylamino)thiazolo[5,4-d]pyrimidin-5-yl)pyrrolidin-3-yl)-2-oxo-2,3-dihydro-1H-benzo[d]imidazole-5-carboxamide

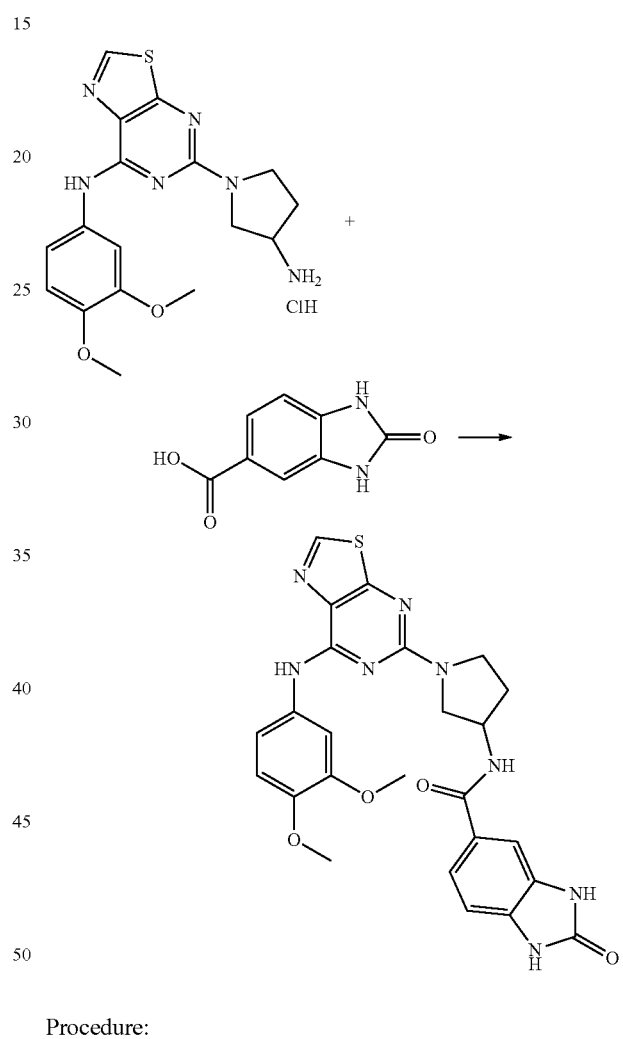

Procedure:

A mixture of 5-(3-aminopyrrolidin-1-yl)-N-(3,4-dimethoxyphenyl)thiazolo[5,4-d]pyrimidin-7-amine hydrochloride (100 mg, 0.245 mmol), 2-oxo-2,3-dihydro-1H-benzo[d]imidazole-5-carboxylic acid (48 mg, 0.27 mmol), EDCI (97 mg, 0.49 mmol) and N-methylimidazole (60 mg, 0.735 mmol) in 10 mL of DCM was stirred at room temperature for 16 hours. The mixture was washed with water (5 mL), The organic layer was dried over Na$_2$SO$_4$. After filtration and concentration, the residue was purified by column chromatography on silica gel eluting with a mixture of CH$_2$Cl$_2$ and methanol (100:1: to 20:1, V/V) to give N-(1-(7-(3,4-dimethoxyphenylamino)thiazolo[5,4-d]pyrimidin-5-yl)pyrrolidin-3-yl)-2-oxo-2,3-dihydro-1H-benzo[d]imidazole-5-carboxamide (25 mg, 19%) as white solid. ¹H NMR (300

MHz, DMSO): δ 9.57 (s, 1H), 8.81 (s, 1H), 8.475-8.46 (m, 1H), 8.27-8.25 (m, 2H), 7.60-7.25 (m, 2H), 6.92 (d, 1H, J=8.7 Hz), 6.47-6.39 (m, 3H), 4.54-4.52 (m, 1H), 3.76-3.58 (m, 10H), 2.27-2.05 (m, 2H). LC-MS: 247 [M/2+H]$^+$, 493 [M+H]$^+$, 491 [M−H]$^−$, $t_R$=1.22 min. HPLC: 95.20% at 214 nm, 95.06% at 254 nm, $t_R$=5.64 min.

Example 15

3-(7-(3,4-Dimethoxyphenylamino)thiazolo[5,4-d]pyrimidin-5-yl)-N-(4-(5-mercapto-1,3,4-oxadiazol-2-yl)phenyl)benzamide

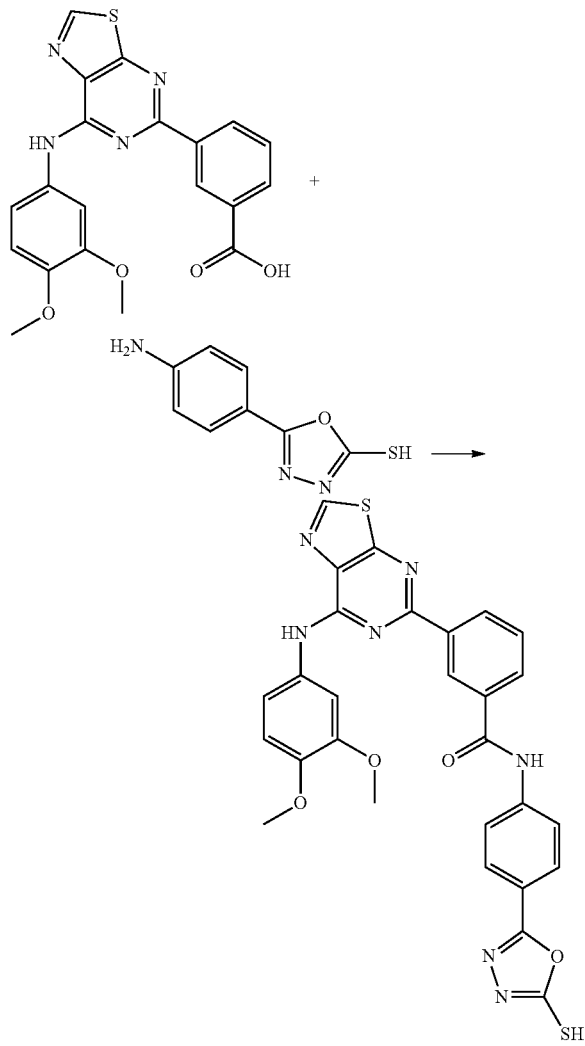

Procedure:

A mixture of 3-(7-(3,4-dimethoxyphenylamino)thiazolo[5,4-d]pyrimidin-5-yl)benzoic acid (100 mg, 0.245 mmol), 5-(4-aminophenyl)-1,3,4-oxadiazole-2-thiol (53 mg, 0.27 mmol), EDCI (94 mg, 0.49 mmol) and DMAP (90 mg, 0.735 mmol) in 5 mL of DMF was stirred at room temperature for 40 hours. The mixture was poured into water and extracted with EtOAc (3×10 mL). The water layer was allowed to stand overnight then filtered to give 3-(7-(3,4-dimethoxyphenylamino)thiazolo[5,4-d]pyrimidin-5-yl)-N-(4-(5-mercapto-1,3,4-oxadiazol-2-yl)phenyl)benzamide (28 mg, 19.5%) as white solid. $^1$H NMR (300 MHz, DMSO): δ 10.67 (s, 1H), 10.20 (s, 1H), 9.41 (s, 1H), 8.96 (s, 1H), 9.61 (d, 1H, J=7.8 Hz), 8.10 (d, 1H, J=8.1 Hz), 7.96-7.93 (m, 3H), 7.83-7.68 (m, 4H), 7.55 (d, 1H, J=6.6 Hz), 6.99 (d, 1H, J=9.0 Hz), 3.81 (s, 3H), 3.74 (s, 3H). LC-MS: 584 [M+H]$^+$, 582 [M−H]$^−$, $t_R$=1.61 min. HPLC: 96.43% at 214 nm, 96.83% at 254 nm, $t_R$=4.60 min.

Example 16

4-(3-(7-(3,4-Dimethoxyphenylamino)thiazolo[5,4-d]pyrimidin-5-yl)benzamido)-2-methoxybenzoic acid

Step 1

Methyl 2-methoxy-4-(3-(4,4,5,5-tetramethyl-1,3,2-dioxaborolan-2-yl)benzamido)benzoate

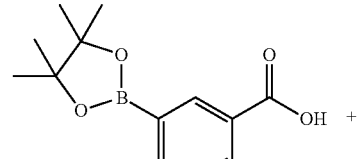

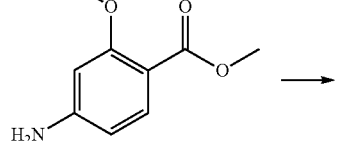

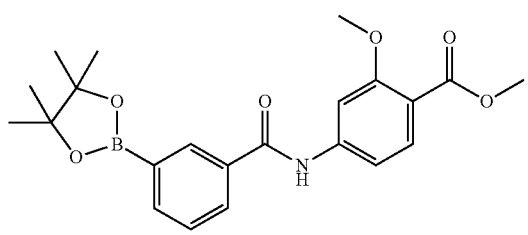

Procedure:

A mixture of 3-(4,4,5,5-tetramethyl-1,3,2-dioxaborolan-2-yl)benzoic acid (600 mg, 2.4 mmol), methyl 4-amino-2-methoxybenzoate (362 mg, 2 mmol), EDCI (764 mg, 4 mmol) and DMAP (488 mg, 4 mmol) in 10 mL of DMF was stirred at room temperature for 38 hours. The mixture was poured into water and extracted with EtOAc (3×15 mL). The organic layer was washed with brine and dried over Na$_2$SO$_4$. After filtration and concentration, the residue was purified by column chromatography on silica gel eluting with (petroleum ether:EtOAc=4:1) to give methyl 2-methoxy-4-(3-(4,4,5,5-tetramethyl-1,3,2-dioxaborolan-2-yl)benzamido)benzoate (180 mg, 22%) as solid. $^1$H NMR (300 MHz, CD$_3$OD): δ 8.31 (s, 1H), 8.05-8.01 (m, 1H), 7.97-7.94 (m, 1H), 7.81 (d, 1H, J=8.7 Hz), 7.71 (d, 1H, J=1.8 Hz), 7.53 (d, 1H, J=7.5 Hz), 7.37 (dd, 1H, J$_1$=8.7 Hz, J$_2$=2.1 Hz), 3.91 (s, 3H), 3.85 (s, 3H).

Step 2

Methyl 4-(3-(7-(3,4-dimethoxyphenylamino)thiazolo[5,4-d]pyrimidin-5-yl)benzamido)-2-methoxybenzoate

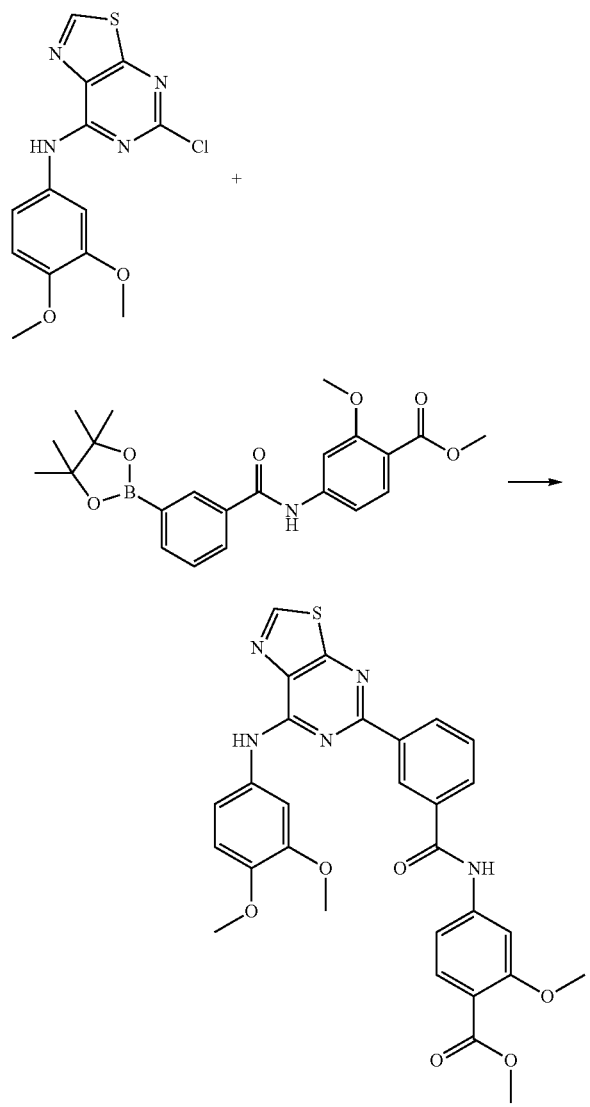

Procedure:

To a solution of 5-chloro-N-(3,4-dimethoxyphenyl)thiazolo[5,4-d]pyrimidin-7-amine (155 mg, 0.48 mmol) and methyl 2-methoxy-4-(3-(4,4,5,5-tetramethyl-1,3,2-dioxaborolan-2-yl)benzoate (180 mg, 0.44 mmol) in 10 mL of 1,4-dioxane and 1 mL of water was added $Na_2CO_3$ (140 mg, 1.32 mmol) followed by $Pd(PPh_3)_4$ (26 mg) under nitrogen with stirring. The mixture was refluxed for 15 hours under nitrogen. After cooled, the solvent was evaporated by rotary evaporation. The residue was purified by column chromatography on silica gel eluting with (petroleum ether:EtOAc=1:1) to give methyl 4-(3-(7-(3,4-dimethoxyphenylamino)thiazolo[5,4-d]pyrimidin-5-yl)benzamido)-2-methoxybenzoate (160 mg, 64%) as solid. LC-MS: 572 $[M+H]^+$, $t_R$=1.62 min.

Step 3

4-(3-(7-(3,4-Dimethoxyphenylamino)thiazolo[5,4-d]pyrimidin-5-yl)benzamido)-2-methoxybenzoic acid

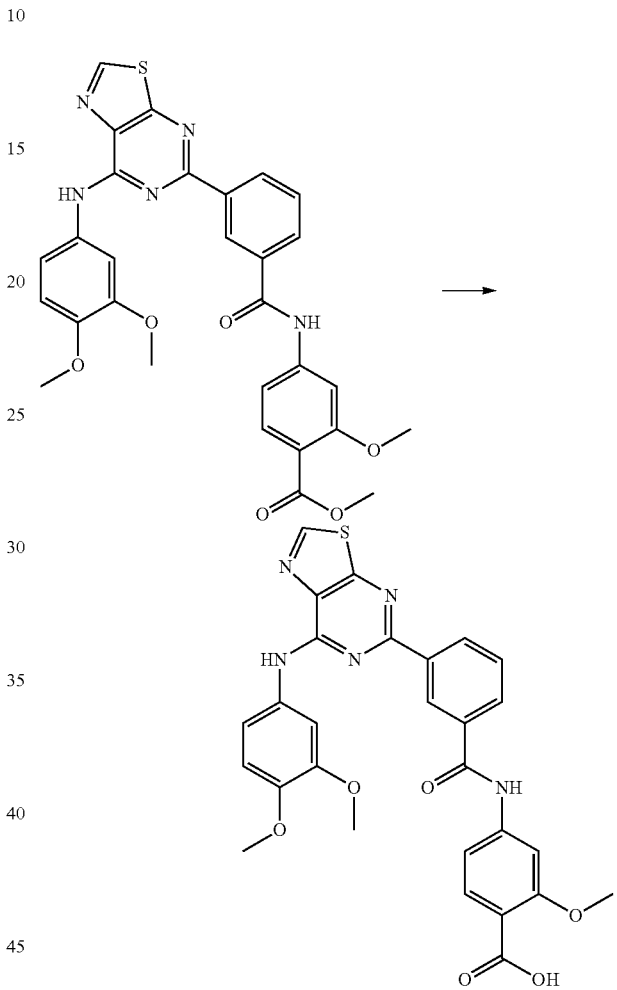

Procedure:

To a stirred solution of methyl 4-(3-(7-(3,4-dimethoxyphenylamino)thiazolo[5,4-d]pyrimidin-5-yl)benzamido)-2-methoxybenzoate (100 mg, 0.175 mmol) in 20 mL of THF and 5 mL of methanol was added a solution of 1N NaOH (2 mL) at room temperature. After the addition, the reaction was stirred at this temperature for 16 hours. The solvent was evaporated and the residue was diluted with water and adjusted to pH=2 by HCl (aq.). The mixture was concentrated by rotary evaporation. The residue was purified by preparative HPLC (Gemini 5u C18 150×21.2 mm; inject volume: 3 ml/inj, flow rate: 20 ml/min; wavelength: 214 nm and 254 nm; the gradient conditions are: 20% acetonitrile/80% water (0.1% TFA V/V) initially, and then proceed to 70% acetonitrile/30% water (0.1% TFA V/V) in a linear fashion after just 9 min.) to give 4-(3-(7-(3,4-dimethoxyphenylamino)thiazolo[5,4-d]pyrimidin-5-yl)benzamido)-2-methoxybenzoic acid (30 mg, 31%). $^1$H NMR (300 MHz, DMSO): δ 10.70 (s, 1H), 10.21 (s, 1H), 9.41 (s, 1H), 8.96 (s, 1H), 8.62 (d, 1H, J=7.5

Hz), 8.09 (d, 1H, J=7.8 Hz), 7.84 (s, 1H), 7.77-7.70 (m, 3H), 7.54 (d, 1H, J=8.4 Hz), 6.99 (d, 1H, J=9.0 Hz), 3.84 (s, 3H), 3.81 (s, 3H), 3.74 (s, 3H). LC-MS: 558 [M+H]$^+$, $t_R$=1.54 min. HPLC: 100% at 214 nm, 100% at 254 nm, $t_R$=6.02 min.

Example 17

3-(7-(3,4-Dimethoxyphenylamino)thiazolo[5,4-d]pyrimidin-5-yl)-N-(4-(5-oxo-4,5-dihydro-1,2,4-oxadiazol-3-yl)phenyl)benzamide

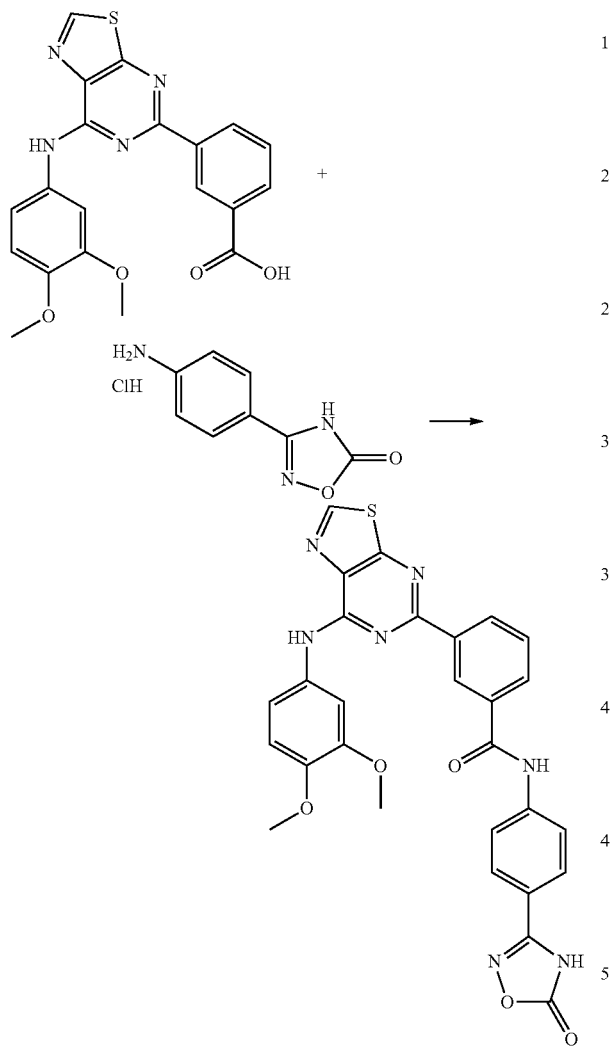

Procedure:

To a mixture of 3-(7-(3,4-dimethoxyphenylamino)thiazolo[5,4-d]pyrimidin-5-yl)benzoic acid (40 mg, 0.1 mmol) and 3-(4-aminophenyl)-1,2,4-oxadiazol-5(4H)-one hydrochloride (22 mg, 0.1 mmol) in 3 mL of DCM was added EDCI (58 mg, 0.3 mmol) followed by N-methylimidazole (25 mg, 0.3 mmol). The mixture was stirred at room temperature for 16 hours. The solvent was removed under reduced pressure. The residue was purified by column chromatography on silica gel eluting with EtOAc to give 3-(7-(3,4-dimethoxyphenylamino)thiazolo[5,4-d]pyrimidin-5-yl)-N-(4-(5-oxo-4,5-dihydro-1,2,4-oxadiazol-3-yl)phenyl)benzamide (15 mg, 26%) as white solid. $^1$H NMR (300 MHz, DMSO): δ 10.82 (s, 1H), 10.22 (s, 1H), 9.43 (s, 1H), 8.98 (s, 1H), 8.64 (d, 1H, J=8.1 Hz), 8.12-8.02 (m, 3H), 7.87-7.54 (m, 5H), 7.01 (d, 1H, J=9.0 Hz), 3.82 (s, 3H), 3.76 (s, 3H). LC-MS: 568 [M+H]$^+$, $t_R$=1.54 min. HPLC: 97.16% at 214 nm, 96.94% at 254 nm, $t_R$=2.86 min.

Example 18

3-(7-(3,4-Dimethoxyphenylamino)thiazolo[5,4-d]pyrimidin-5-yl)-N-(1H-indazol-5-yl)benzamide

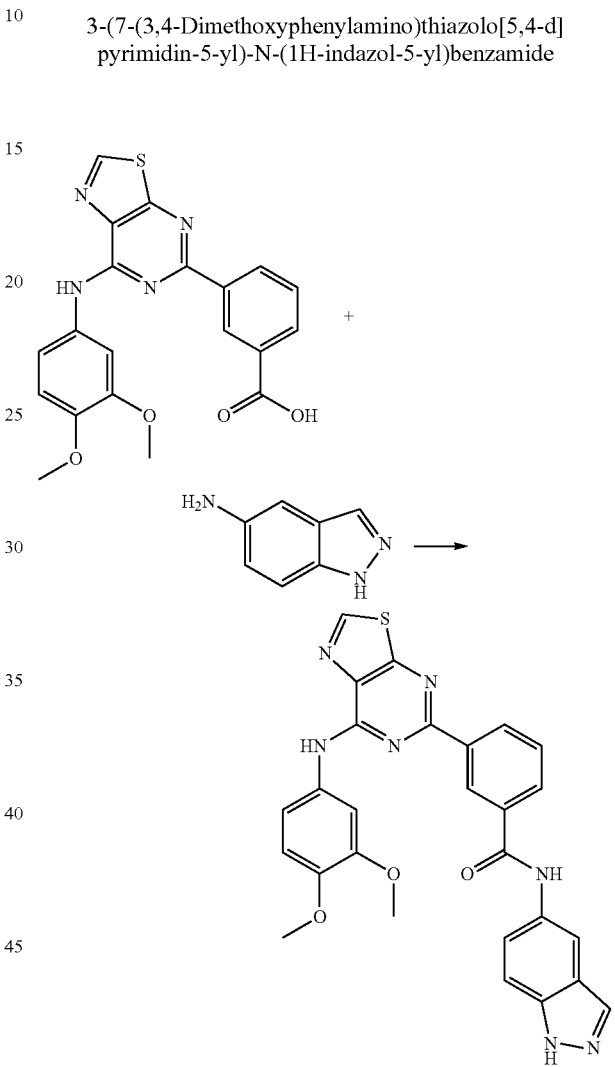

Procedure:

To a mixture of 3-(7-(3,4-dimethoxyphenylamino)thiazolo[5,4-d]pyrimidin-5-yl)benzoic acid (82 mg, 0.2 mmol) and 1H-indazol-5-amine (27 mg, 0.2 mmol) in 5 mL of DCM was added EDCI (80 mg, 0.6 mmol) followed by N-methylimidazole (50 mg, 0.6 mmol). The mixture was stirred at room temperature for 16 hours. The solvent was removed under reduced pressure. The residue was purified by column chromatography on silica gel eluting with EtOAc to give 3-(7-(3,4-dimethoxyphenylamino)thiazolo[5,4-d]pyrimidin-5-yl)-N-(1H-indazol-5-yl)benzamide (20 mg, 19%) as white solid. $^1$H NMR (300 MHz, DMSO): δ 13.01 (s, 1H), 10.46 (s, 1H), 10.14 (s, 1H), 9.42 (s, 1H), 8.99 (s, 1H), 8.62 (d, 1H, J=7.8 Hz), 8.29 (s, 1H), 8.13-8.10 (m, 2H), 7.88 (s, 1H), 7.74-7.69 (m, 2H), 7.58-7.55 (m, 2H), 7.01 (d, 1H, J=8.7 Hz), 3.84 (s, 3H), 3.75 (s, 3H). LC-MS: 524 [M+H]+, $t_R$=1.50 min. HPLC: 95.85% at 214 nm, 95.63% at 254 nm, $t_R$=4.60 min.

Example 19

3-(7-(3,4-Dimethoxyphenylamino)thiazolo[5,4-d]pyrimidin-5-yl)-N-(1H-indazol-6-yl)benzamide

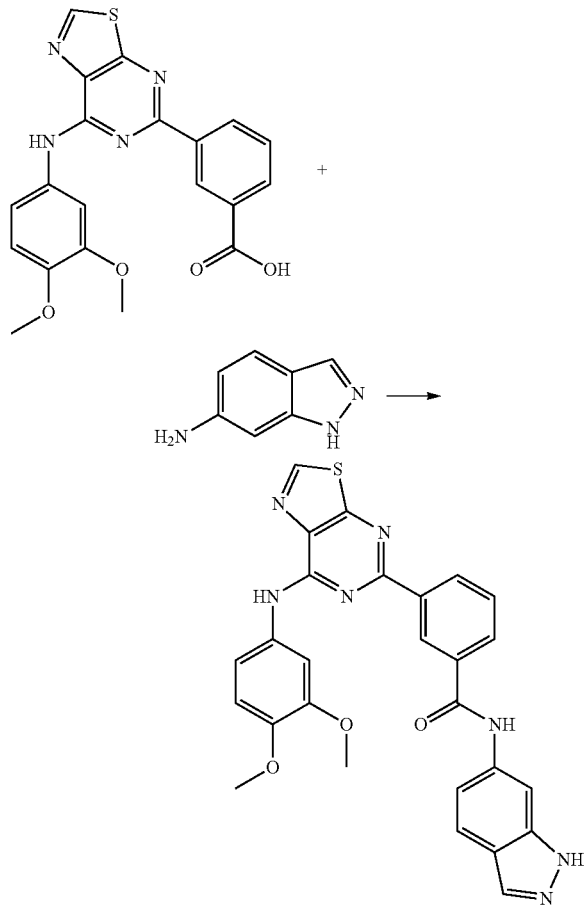

Procedure:

To a mixture of 3-(7-(3,4-dimethoxyphenylamino)thiazolo[5,4-d]pyrimidin-5-yl)benzoic acid (82 mg, 0.2 mmol) and 1H-indazol-6-amine (27 mg, 0.2 mmol) in 5 mL of DCM was added EDCI (80 mg, 0.6 mmol) followed by N-methylimidazole (50 mg, 0.6 mmol). The mixture was stirred at room temperature for 16 hours. The solvent was removed under reduced pressure. The residue was purified by column chromatography on silica gel eluting with EtOAc to give 3-(7-(3,4-dimethoxyphenylamino)thiazolo[5,4-d]pyrimidin-5-yl)-N-(1H-indazol-6-yl)benzamide (30 mg, 28%) as white solid. $^1$H NMR (300 MHz, DMSO): δ 12.96 (s, 1H), 10.57 (s, 1H), 10.15 (s, 1H), 9.42 (s, 1H), 8.99 (s, 1H), 8.63 (d, 1H, J=8.1 Hz), 8.33 (s, 1H), 8.12 (d, 1H, J=7.8 Hz), 8.03 (s, 1H), 7.87 (s, 1H), 7.76-7.70 (m, 2H), 7.57 (dd, 1H, $J_1$=8.7 Hz, $J_2$=2.4 Hz), 7.45 (dd, 1H, $J_1$=8.7 Hz, $J_2$=1.5 Hz), 7.01 (d, 1H, J=9.0 Hz), 3.84 (s, 3H), 3.74 (s, 3H). LC-MS: 524 [M+H]+, $t_R$=1.52 min. HPLC: 97.61% at 214 nm, 97.19% at 254 nm, $t_R$=4.75 min.

Example 20

4-(7-(3,4-Dimethoxyphenylamino)thiazolo[5,4-d]pyrimidin-5-yl)-N-(2-(pyridin-4-yl)ethyl)benzamide Step 1

N-(2-(Pyridin-4-yl)ethyl)-4-(4,4,5,5-tetramethyl-1,3,2-dioxaborolan-2-yl)benzamide Procedure:

A solution of 4-(4,4,5,5-tetramethyl-1,3,2-dioxaborolan-2-yl)benzoic acid (150 mg, 0.60 mmol) in 30 mL of DCM were added 2-(pyridin-4-yl)ethanamine (110 mg, 0.9 mmol), HATU (274 mg, 0.72 mmol) and DIEA (232 mg, 1.80 mmol) at room temperature. Then the reaction mixture was stirred at room temperature overnight. The solution was washed with sat NaHCO$_3$ (2×20 mL), brine (20 mL), then dried over anhydrous sodium sulfate, concentrated under reduce pressure to give crude N-(2-(pyridin-4-yl)ethyl)-4-(4,4,5,5-tetramethyl-1,3,2-dioxaborolan-2-yl)benzamide (250 mg) and used without further purification. LC-MS: 353 [M+H]+, $t_R$=1.22 min Step 2

4-(7-(3,4-Dimethoxyphenylamino)thiazolo[5,4-d]pyrimidin-5-yl)-N-(2-(pyridin-4-yl)ethyl)benzamide

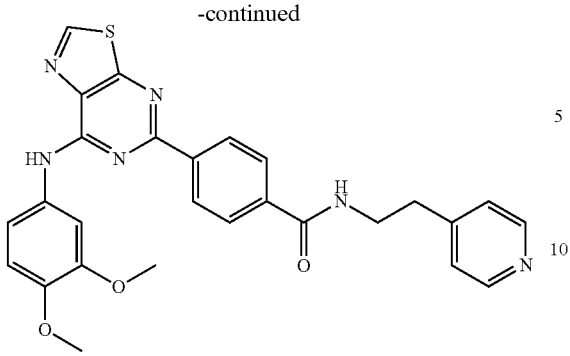

Procedure:

To a stirred solution of 5-chloro-N-(3,4-dimethoxyphenyl)thiazolo[5,4-d]pyrimidin-7-amine (100 mg, 0.31 mmol) and N-(2-(pyridin-4-yl)ethyl)-4-(4,4,5,5-tetramethyl-1,3,2-dioxaborolan-2-yl)benzamide (140 mg, 0.4 mmol) in 25 mL of 1,4-dioxane were added $Na_2CO_3$ (64 mg, 0.6 mmol) and 3 mL of water at room temperature. Then the mixture was degassed with nitrogen for 15 minutes. $Pd(PPh_3)_4$ (20 mg, 0.017 mmol) was added in one portion and the reaction mixture was stirred at reflux for 16 hours under nitrogen. The solvent was evaporated and the residue was purified by silica gel chromatography (200-300 mesh, eluting with EtOAc) to give 4-(7-(3,4-dimethoxyphenylamino)thiazolo[5,4-d]pyrimidin-5-yl)-N-(2-(pyridin-4-yl)ethyl)benzamide (50 mg, 31%) as a yellow sold. $^1$H NMR (300 MHz, DMSO): δ 10.15 (s, 1H), 9.37 (s, 1H), 8.68 (t, 1H, J=5.3 Hz), 8.46-8.42 (m, 4H), 7.94-7.91 (m, 2H), 7.81 (d, 1H, J=2.7 Hz), 7.52-7.47 (m, 1H), 7.27-7.26 (m, 2H), 7.00 (d, 1H, J=8.7 Hz), 4.02 (s, 3H), 4.00 (s, 3H), 3.58-3.52 (m, 2H), 2.89 (t, 2H, J=7.0 Hz). LC-MS: 513 $[M+H]^+$, 511 $[M-H]^-$, $t_R$=1.32 min. HPLC: 97.72% at 214 nm, 96.31% at 254 nm, $t_R$=4.19 min.

Example 21

1-(7-(3,4-Dimethoxyphenylamino)thiazolo[5,4-d]pyrimidin-5-yl)-N-(2-(pyridin-4-yl)ethyl)piperidine-4-carboxamide Step 1

Methyl 1-(7-(3,4-dimethoxyphenylamino)thiazolo[5,4-d]pyrimidin-5-yl)piperidine-4-carboxylate

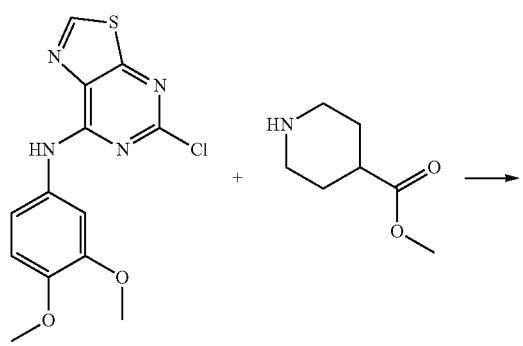

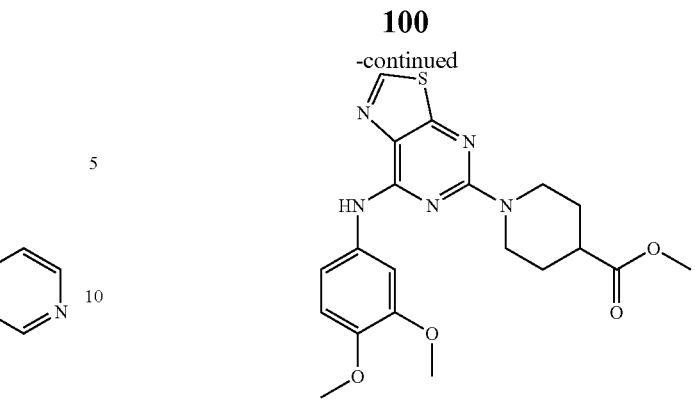

Procedure

To a mixture of 5-chloro-N-(3,4-dimethoxyphenyl)thiazolo[5,4-d]pyrimidin-7-amine (200 mg, 0.62 mmol), methyl piperidine-4-carboxylate (177 mg, 1.24 mmol), $Cs_2CO_3$ (404 mg, 1.24 mmol), X-Phos (20 mg, 0.042 mmol), $Pd(dba)_2$ (20 mg, 0.035 mmol) in 30 mL of dioxane were stirred at 100° for 18 hours under $N_2$ atmosphere. The excess of dioxane was removed under reduced pressure and the residue was purified by silica gel chromatography (eluting with a mixture of petroleum ether and ethyl acetate=3:1) to give methyl 1-(7-(3,4-dimethoxyphenylamino)thiazolo[5,4-d]pyrimidin-5-yl)piperidine-4-carboxylate (150 mg, 56%) as a yellow solid. LC-MS: 430 $[M+H]^+$, $t_R$=1.63 min Step 2

1-(7-(3,4-Dimethoxyphenylamino)thiazolo[5,4-d]pyrimidin-5-yl)piperidine-4-carboxylic acid

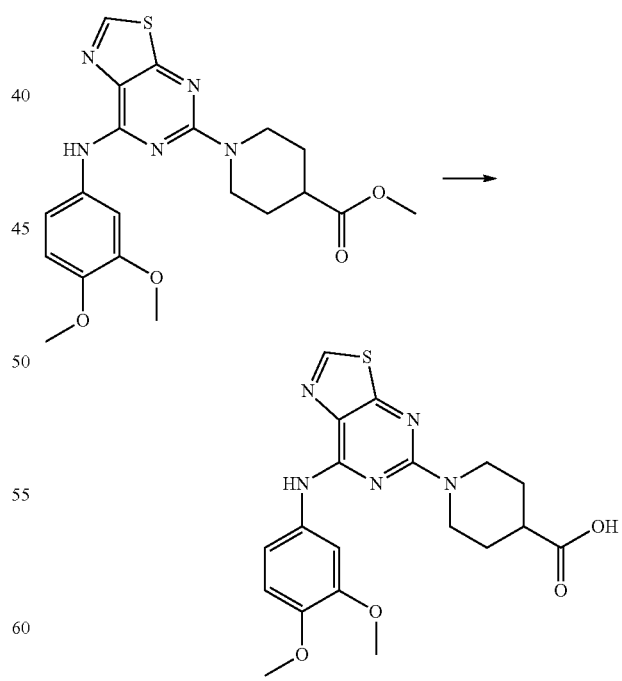

Procedure:

To a stirred solution of methyl 1-(7-(3,4-dimethoxyphenylamino)thiazolo[5,4-d]pyrimidin-5-yl)piperidine-4-carboxylate (150 mg, 0.35 mmol) in 7.5 mL of 1,4-dioxane and 7.5 mL of H$_2$O was added NaOH (140 mg, 3.5 mmol) at room temperature. Then the reaction was stirred at 60° C. for 3 hours. The solvent was evaporated and the residue was suspended in 50 mL of H$_2$O, then treated by 1N HCl until pH=5. The white solid was appeared and then filtered the solid was dried to give 1-(7-(3,4-dimethoxyphenylamino)thiazolo[5,4-d]pyrimidin-5-yl)piperidine-4-carboxylic acid (130 mg, 90%) as a yellow solid

Step 3

1-(7-(3,4-Dimethoxyphenylamino)thiazolo[5,4-d]pyrimidin-5-yl)-N-(2-(pyridin-4-yl)ethyl)piperidine-4-carboxamide

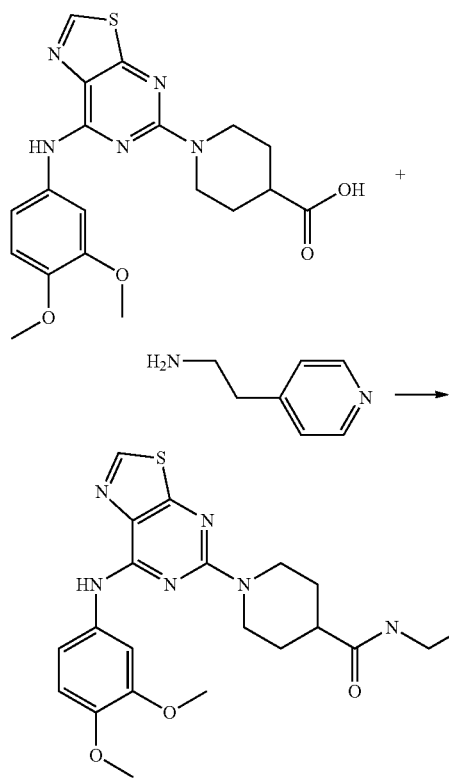

Procedure:

The mixture of 1-(7-(3,4-dimethoxyphenylamino)thiazolo[5,4-d]pyrimidin-5-yl)piperidine-4-carboxylic acid (50 mg, 0.12 mmol), 2-(pyridin-4-yl)ethanamine (22 mg, 0.18 mmol), EDCI (69 mg, 0.36 mmol) and 1-methyl-1H-imidazole (50 mg, 0.60 mmol) in 25 mL of DCM was stirred at room temperature for 16 hours. Excess of DCM was removed under reduced pressure and the residue was washed with H$_2$O (30 mL) and EtOAc (20 mL) dried under reduced pressure to give 1-(7-(3,4-dimethoxyphenylamino)thiazolo[5,4-d]pyrimidin-5-yl)-N-(2-(pyridin-4-yl)ethyl)piperidine-4-carboxamide (30 mg, 48%) as a yellow solid. $^1$H NMR (300 MHz, CD$_3$OD): δ 8.62 (s, 1H), 8.44-8.42 (m, 2H), 7.61 (d, 1H, J=2.4 Hz), 7.31-7.18 (m, 3H), 6.95 (d, 1H, J=8.7 Hz), 4.82-4.77 (m, 2H), 3.86 (s, 3H), 3.84 (s, 3H), 3.47 (t, 2H, J=6.9 Hz), 2.95-2.92 (m, 2H), 2.86 (t, 2H, J=6.9 Hz), 2.44 (brs, 1H), 1.74-1.62 (m, 4H). LC-MS: 520 [M+H]$^+$, 260 [M/2+H]$^+$, 518 [M−H]$^−$, t$_R$=1.29 min. HPLC: 97.06% at 214 nm, 97.32% at 254 nm, t$_R$=3.47 min.

Example 22

1-(7-(3,4-Dimethoxyphenylamino)thiazolo[5,4-d]pyrimidin-5-yl)-N-(2-(2-oxo-1,2-dihydropyridin-4-yl)ethyl)piperidine-4-carboxamide

Step 1

2-Methoxy-4-methylpyridine

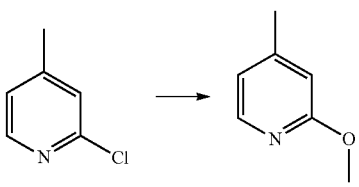

Procedure:

A mixture of 2-chloro-4-methylpyridine (20 g, 0.156 mol) and NaOCH$_3$ (9.3 g, 0.172 mol) in DMSO (200 mL) was stirred at 100° C. for 4 hours. The solution was added to H$_2$O and then extracted with ethyl acetate (50 mL×2). The organic layer was washed with H$_2$O (300 mL) brine (300 mL) and dried concentrated to give 2-methoxy-4-methylpyridine (9 g, 46%). LC-MS: 124 [M+H]$^+$, t$_R$=1.21 min.

Step 2

3-(2-Methoxypyridin-4-yl)propanoic acid

Procedure:

Sodamide (4 g, 103 mmol) and 2-methoxy-4-methylpyridine (9 g, 73 mmol) in liquid ammonia (150 mL) was stirred for 30 min at −50° C. The dark orange mixture was carefully treated with sodium 2-chloroacetate (9 g, 78 mmol). After 1.5 hours a second portion of sodium 2-chloroacetate (8 g, 69 mmol) was added. After a total reaction time of 3.5 hours, the reaction mixture was treated with ammonium chloride (13 g, 245 mmol). Ammonia was allowed to evaporate and the solid residue was treated with water (200 mL) and extracted with DCM (50 mL×3). The aqueous layer was acidified to pH=1 with concentrated hydrochloric acid and then extracted with ethyl acetate (3×50 mL). The aqueous layer was basified to pH 4.5 with 40% w/v aqueous sodium hydroxide, then cooled to 0-5° C., and stirred at this temperature for 2 hours. The mixture was filtered under reduced pressure and the filter cake was washed with water (5 mL), and dried to give 3-(2-methoxypyridin-4-yl)propanoic acid (3.2 g, 24%) as a white solid. LC-MS: 182 [M+H]$^+$, $t_R$=1.10 min.

Step 3

2-(2-Methoxypyridin-4-yl)ethanamine hydrochloride

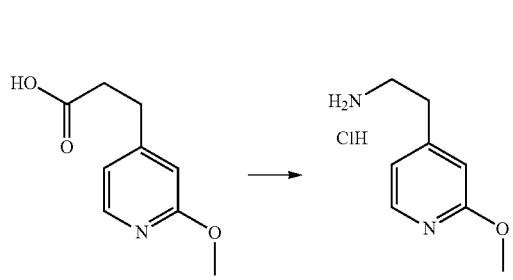

Procedure:

3-(2-Methoxypyridin-4-yl)propanoic acid (2.5 g, 18.3 mmol) was added to concentrated H$_2$SO$_4$ (10 ml) and stirred at 70° C. When the solution became clear, sodium azide (1.8 g, 27.6 mmol) was slowly added over a period of 2 hours. The mixture was stirred for 2 hours at 70° C. and then for 16 hours at room temperature, and then poured onto ice. The solution was basified with sat. NaHCO$_3$ and extracted with DCM (3×100 mL). The combined organic layers were dried over anhydrous Na$_2$SO$_4$, and evaporated under reduced pressure. The oily residue was dissolved in anhydrous EtOH and HCl in dioxane was added to the solution. The solvent was evaporated under reduce pressure to give 2-(2-methoxypyridin-4-yl)ethanamine hydrochloride (1.3 g, 50%) as a yellow solid. LC-MS: 153 [M+H]$^+$, $t_R$=0.36 min.

Step 4

4-(2-Aminoethyl)pyridin-2(1H)-one hydrobromide

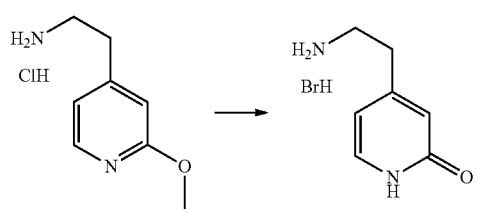

Procedure:

A solution of 2-(2-methoxypyridin-4-yl)ethanamine hydrochloride (0.8 g, 4.23 mmol) was dissolved in 45% HBr (7 mL) and HOAc (7 mL). The mixture was heated to reflux for 4 hours and then the solvent was removed under reduce pressure. The residue was washed with THF (20 mL) and dried to give 4-(2-aminoethyl)pyridin-2(1H)-one hydrobromide (0.8 g 86%) as a grey solid. LC-MS: 139 [M+H]$^+$, $t_R$=0.28 min.

Step 5

1-(7-(3,4-Dimethoxyphenylamino)thiazolo[5,4-d]pyrimidin-5-yl)-N-(2-(2-oxo-1,2-dihydropyridin-4-yl)ethyl)piperidine-4-carboxamide

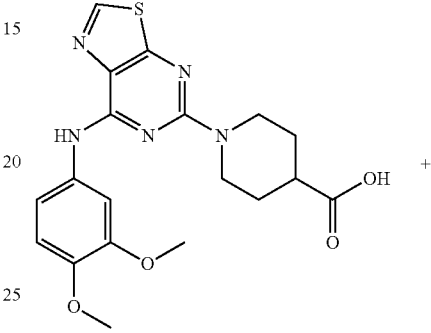

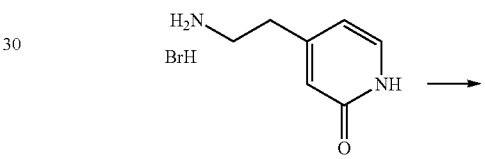

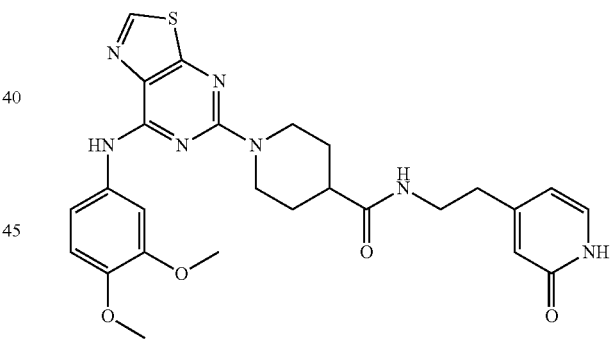

Procedure:

The mixture of 1-(7-(3,4-dimethoxyphenylamino)thiazolo[5,4-d]pyrimidin-5-yl)piperidine-4-carboxylic acid (70 mg, 0.22 mmol), 4-(2-aminoethyl)pyridin-2(1H)-one hydrobromide (70 mg, 0.32 mmol), EDC (170 mg, 0.89 mmol) and 1-methyl-1H-imidazole (108 mg, 1.32 mmol) in 20 mL of DCM was stirred at room temperature overnight. Excess of DCM was removed under reduced pressure and the residue was triturated with H$_2$O (30 mL) and EtOAc (20 mL) then dried under reduce pressure to give 1-(7-(3,4-dimethoxyphenylamino)thiazolo[5,4-d]pyrimidin-5-yl)-N-(2-(2-oxo-1,2-dihydropyridin-4-yl)ethyl)piperidine-4-carboxamide (25 mg, 40%) as a yellow solid. $^1$H NMR (300 MHz, CD$_3$OD): δ

8.62 (s, 1H), 7.61 (d, 1H, J=2.4 Hz), 7.35 (d, 1H, J=7.2 Hz), 7.20 (dd, 1H, J$_1$=8.7 Hz, J$_2$=2.4 Hz), 6.95 (d, 1H, J=8.7 Hz), 6.36-6.32 (m, 2H), 4.83-4.79 (m, 2H), 3.86 (s, 3H), 3.84 (s, 3H), 3.44 (t, 2H, J=6.8 Hz), 3.00-2.92 (m, 2H), 2.70 (t, 2H, J=6.8 Hz), 2.45 (brs, 1H), 1.80-1.64 (m, 4H). LC-MS: 536 [M+H]$^+$, 534 [M–H]$^-$, t$_R$=1.38 min. HPLC: 95.70% at 214 nm, 96.10% at 254 nm, t$_R$=3.65 min.

Example 23

4-(7-(3,4-Dimethoxyphenylamino)thiazolo[5,4-d]pyrimidin-5-yl)-N-(2-(2-oxo-1,2-dihydropyridin-4-yl)ethyl)benzamide Step 1

N-(2-(2-Oxo-1,2-dihydropyridin-4-yl)ethyl)-4-(4,4,5,5-tetramethyl-1,3,2-dioxaborolan-2-yl)benzamide

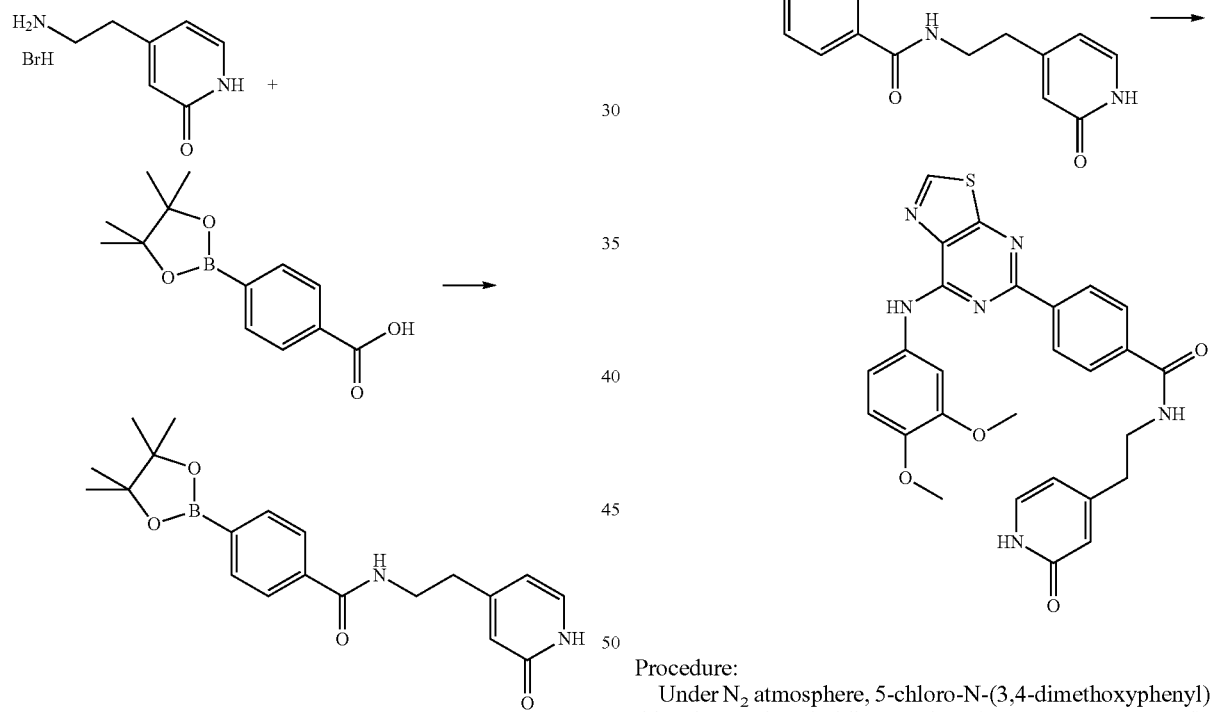

Procedure:

A mixture of 4-(4,4,5,5-tetramethyl-1,3,2-dioxaborolan-2-yl)benzoic acid (100 mg, 0.4 mmol), 4-(2-aminoethyl)pyridin-2(1H)-one hydrobromide (96 mg, 0.44 mmol), HATU (182 mg, 0.48 mmol) and DIEA (155 mg, 1.20 mmol) in 30 mL of DCM was stirred at room temperature overnight. The solution was washed with sat NaHCO$_3$ (2×30 mL), brine (30 mL), dried over anhydrous sodium sulfate, concentrated under reduce pressure to give crude N-(2-(2-oxo-1,2-dihydropyridin-4-yl)ethyl)-4-(4,4,5,5-tetramethyl-1,3,2-dioxaborolan-2-yl)benzamide (160 mg) and used without further purification. LC-MS: 369 [M+H]$^+$, t$_R$=1.35 min.

Step 2

4-(7-(3,4-Dimethoxyphenylamino)thiazolo[5,4-d]pyrimidin-5-yl)-N-(2-(2-oxo-1,2-dihydropyridin-4-yl)ethyl)benzamide

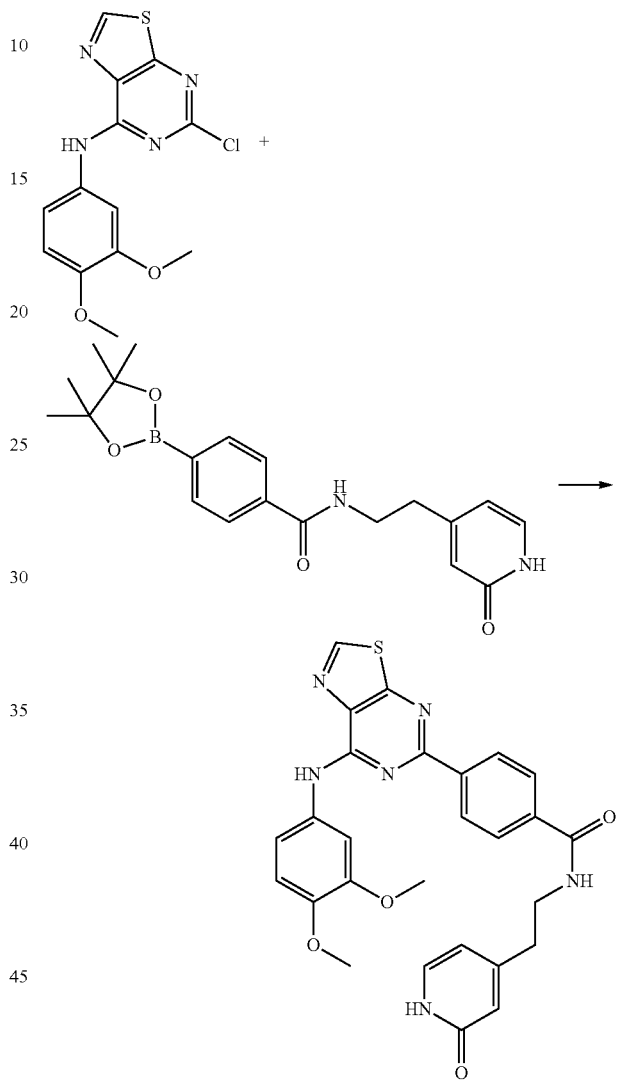

Procedure:

Under N$_2$ atmosphere, 5-chloro-N-(3,4-dimethoxyphenyl)thiazolo[5,4-d]pyrimidin-7-amine (100 mg, 0.31 mmol), N-(2-(2-oxo-1,2-dihydropyridin-4-yl)ethyl)-4-(4,4,5,5-tetramethyl-1,3,2-dioxaborolan-2-yl)benzamide (140 mg, 0.38 mmol), Pd(PPh$_3$)$_4$ (20 mg, 0.017 mmol) was added in 20 mL of 1,4-dioxane. Na$_2$CO$_3$ (100 mg, 0.94 mmol) in 3 mL of water was added and then the mixture was stirred at reflux for 18 hours. The solvent was removed under reduce pressure and the residue was purified by silica gel chromatography, eluting with DCM/MeOH (20/1) to give 4-(7-(3,4-dimethoxyphenylamino)thiazolo[5,4-d]pyrimidin-5-yl)-N-(2-(2-oxo-1,2-dihydropyridin-4-yl)ethyl)benzamide (15 mg, 9%) as a yellow sold. $^1$H NMR (300 MHz, DMSO): δ 11.34 (s, 1H), 10.15 (s, 1H), 9.38 (s, 1H), 8.67-8.65 (m, 1H), 8.45 (s, 1H), 8.43 (s, 1H), 7.95-7.81 (m, 3H), 7.51-7.47 (m, 1H), 7.26 (d, 1H, J=6.6 Hz), 7.01 (d, 1H, J=8.7 Hz), 6.15 (s, 1H), 6.08 (d, 1H, J=6.6

Hz), 3.83 (s, 3H), 3.78 (s, 3H), 3.50-3.48 (m, 2H), 2.72-2.65 (m, 2H). LC-MS: 528.9 [M+H]$^+$, $t_R$=1.35 min. HPLC: 98.40% at 214 nm, 99.86% at 254 nm, $t_R$=5.18 min.

Example 24

4-(7-(3,4-Dimethoxyphenylamino)thiazolo[5,4-d]pyrimidin-5-yl)-N-(2-(1-methyl-2-oxo-1,2-dihydropyridin-4-yl)ethyl)benzamide Step 1

2-(2-(2-Oxo-1,2-dihydropyridin-4-yl)ethyl)isoindoline-1,3-dione

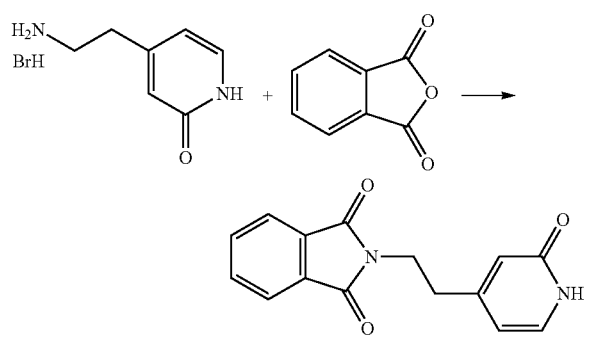

Procedure:

A mixture of 4-(2-aminoethyl)pyridin-2(1H)-one hydrobromide (400 mg, 1.83 mmol), isobenzofuran-1,3-dione (271 mg, 1.83 mmol) and DIEA (472 mg, 3.66 mmol) in 30 mL of xylene was stirred at 140° C. for 6 hours. The solvent was removed under reduce pressure. The residue was purified by silica gel chromatography, eluting with DCM/MeOH (30/1) to give 2-(2-(2-oxo-1,2-dihydropyridin-4-yl)ethyl)isoindoline-1,3-dione (370 mg, 76%) as a white sold. LC-MS: 269 [M+H]$^+$, $t_R$=1.23 min.

Step 2

2-(2-(1-Methyl-2-oxo-1,2-dihydropyridin-4-yl)ethyl)isoindoline-1,3-dione

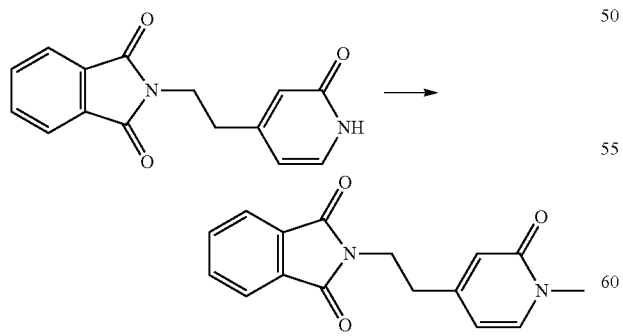

Procedure:

A mixture of 2-(2-(2-oxo-1,2-dihydropyridin-4-yl)ethyl)isoindoline-1,3-dione (300 mg, 1.1 mmol) CH$_3$I (1.0 g, 7 mmol) and K$_2$CO$_3$ (700 mg, 5 mmol) in 30 mL of DCM and 10 mL of DMF was stirred at room temperature for 3 days. 30 mL of DCM was added. The mixture was washed with H$_2$O (3×30 mL), dried over anhydrous sodium sulfate, concentrated under reduce pressure to give 2-(2-(1-methyl-2-oxo-1,2-dihydropyridin-4-yl)ethyl)isoindoline-1,3-dione (230 mg, 73%) as a white solid. LC-MS: 283 [M+H]$^+$, $t_R$=1.29 min.

Step 3

4-(2-Aminoethyl)-1-methylpyridin-2(1H)-one hydrochloride

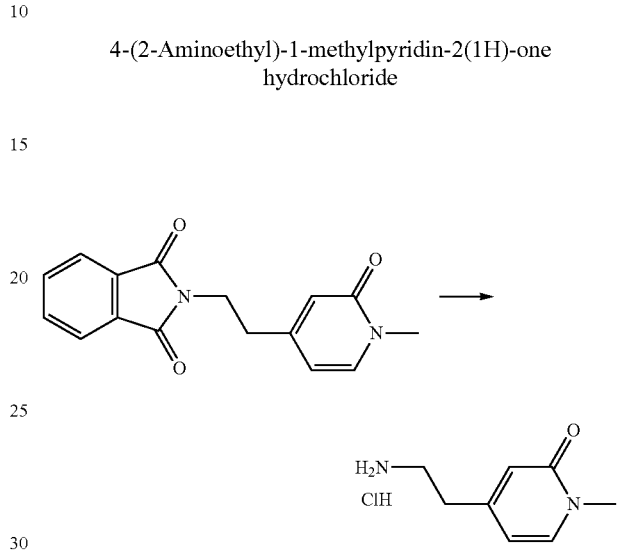

Procedure:

2-(2-(1-Methyl-2-oxo-1,2-dihydropyridin-4-yl)ethyl)isoindoline-1,3-dione (230 mg, 0.8 mmol) in conc. HCl (25 mL) was stirred at 95° C. for 18 hours. H$_2$O (20 mL) was added and then extracted with ethyl acetate (3×30 mL). The aqueous was concentrated under reduce pressure to give 4-(2-aminoethyl)-1-methylpyridin-2(1H)-one hydrochloride (130 mg, 85%). LC-MS: 153 [M+H]$^+$, $t_R$=0.42 min.

Step 4

N-(2-(1-Methyl-2-oxo-1,2-dihydropyridin-4-yl)ethyl)-4-(4,4,5,5-tetramethyl-1,3,2-dioxaborolan-2-yl)benzamide

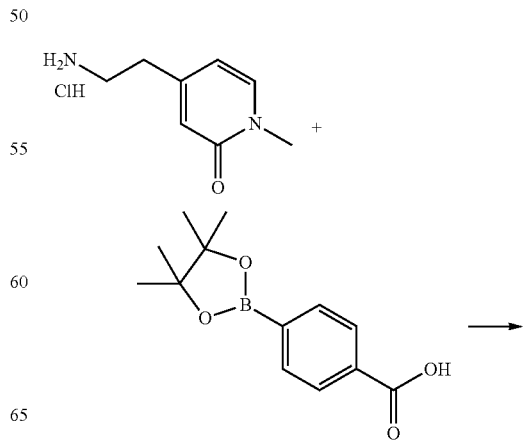

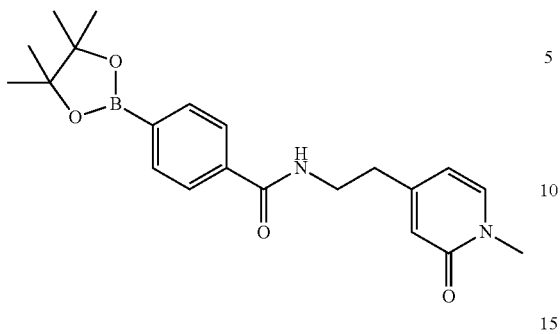

Procedure:

A mixture of 4-(2-aminoethyl)-1-methylpyridin-2(1H)-one hydrochloride (76 mg, 0.4 mmol), 4-(4,4,5,5-tetramethyl-1,3,2-dioxaborolan-2-yl)benzoic acid (100 mg, 0.4 mmol), HATU (190 mg, 0.5 mmol) and DIEA (260 mg, 2 mmol) in 25 mL of DCM and 5 mL of DMF was stirred at room temperature overnight. The solution was washed with sat NaHCO₃ (2×20 mL), brine (2×20 mL), dried over anhydrous sodium sulfate, concentrated under reduce pressure to give crude N-(2-(1-methyl-2-oxo-1,2-dihydropyridin-4-yl)ethyl)-4-(4,4,5,5-tetramethyl-1,3,2-dioxaborolan-2-yl)benzamide (230 mg) and used for next step without further purification. LC-MS: 383 [M+H]⁺, t_R=1.41 min.

Step 5

4-(7-(3,4-Dimethoxyphenylamino)thiazolo[5,4-d]pyrimidin-5-yl)-N-(2-(1-methyl-2-oxo-1,2-dihydropyridin-4-yl)ethyl)benzamide

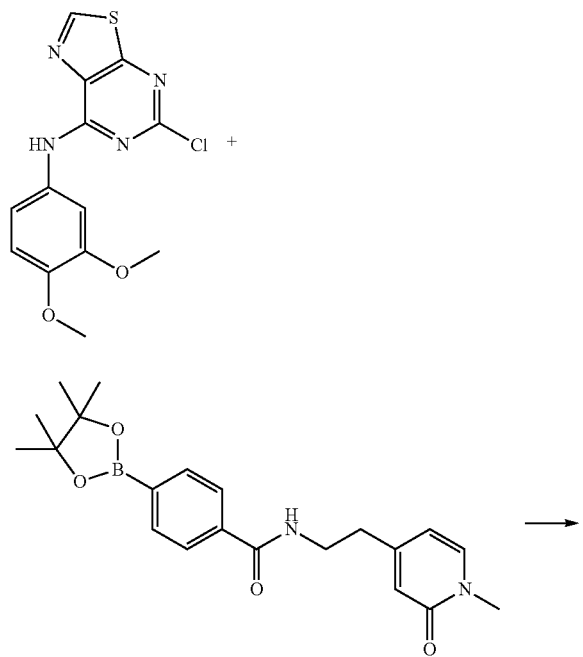

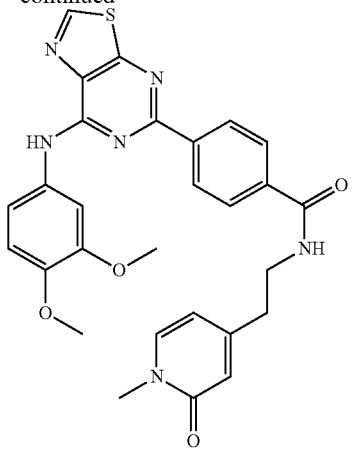

Procedure:

Under N₂ atmosphere, 5-chloro-N-(3,4-dimethoxyphenyl)thiazolo[5,4-d]pyrimidin-7-amine (150 mg, 0.47 mmol), N-(2-(1-methyl-2-oxo-1,2-dihydropyridin-4-yl)ethyl)-4-(4,4,5,5-tetramethyl-1,3,2-dioxaborolan-2-yl)benzamide (220 mg, crude), Pd(PPh₃)₄ (40 mg, 0.035 mmol) and Na₂CO₃ (100 mg, 0.94 mmol) in 3 mL of water was added in 30 mL of 1,4-dioxane. The mixture was stirred at reflux for 18 hours. The solvent was removed under reduce pressure and the residue was purified by silica gel chromatography, eluting with DCM/MeOH (20/1, v/v) to give 4-(7-(3,4-dimethoxyphenylamino)thiazolo[5,4-d]pyrimidin-5-yl)-N-(2-(1-methyl-2-oxo-1,2-dihydropyridin-4-yl)ethyl)benzamide (30 mg, 12%) as a yellow sold. ¹H NMR (300 MHz, CD₃OD): δ 9.13 (s, 1H), 8.52-8.50 (m, 2H), 7.89-7.80 (m, 3H), 7.58 (d, 1H, J=6.9 Hz), 7.40 (dd, 1H, J₁=8.4 Hz, J₂=2.4 Hz), 7.03 (d, 1H, J=8.7 Hz), 6.46 (s, 1H), 6.38 (dd, 1H, J₁=6.6 Hz, J₂=1.8 Hz), 3.94 (s, 3H), 3.88 (s, 3H), 3.66 (t, 2H, J=7.0 Hz), 3.54 (s, 3H), 2.84 (t, 2H, J=7.0 Hz). LC-MS: 543 [M+H]⁺, 541 [M−H]⁻, t_R=1.37 min. HPLC: 100% at 214 nm, 100% at 254 nm, t_R=5.36 min.

Example 25

1-(7-(3,4-Dimethoxyphenylamino)thiazolo[5,4-d]pyrimidin-5-yl)-N-(2-(pyridin-4-yl)ethyl)piperidine-3-carboxamide

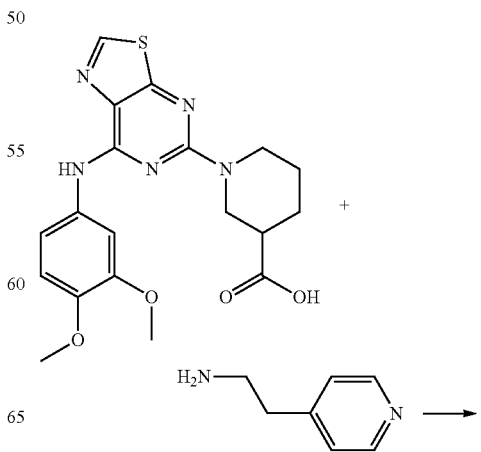

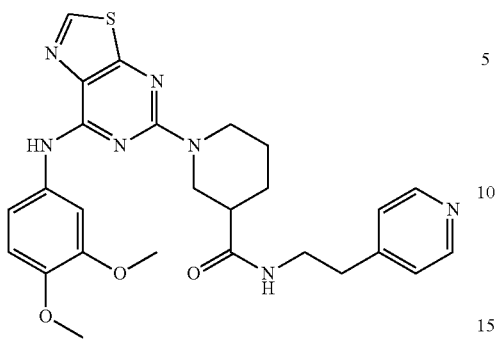

lp;1pProcedure:

The mixture of 1-(7-(3,4-dimethoxyphenylamino)thiazolo[5,4-d]pyrimidin-5-yl)piperidine-3-carboxylic acid (50 mg, 0.12 mmol), 2-(pyridin-4-yl)ethanamine (50 mg, 0.41 mmol), EDC (50 mg, 0.26 mmol) and 1-methyl-1H-imidazole (50 mg, 0.61 mmol) in 25 mL of DCM was stirred at room temperature overnight. Excess of DCM was removed under reduced pressure and the residue was purified by silica gel chromatography, eluting with petroleum ether and ethyl acetate (3:1) to give 1-(7-(3,4-dimethoxyphenylamino)thiazolo[5,4-d]pyrimidin-5-yl)-N-(2-(pyridin-4-yl)ethyl)piperidine-3-carboxamide (25 mg, 39%) as a yellow sold. $^1$H NMR (300 MHz, DMSO): δ 9.64 (s, 1H), 8.85 (s, 1H), 8.46-8.44 (m, 2H), 8.02-8.01 (m, 1H), 7.71-7.69 (m, 1H), 7.33-7.21 (m, 3H), 6.92 (d, 1H, J=9.0 Hz), 4.64-4.63 (m, 2H), 3.75 (s, 3H), 3.73 (s, 3H), 3.35-3.30 (m, 2H), 2.98-2.91 (m, 2H), 2.77-2.75 (m, 2H), 2.51 (brs, 1H), 1.82-1.42 (m, 4H). LC-MS: 520 [M+H]$^+$, 260 [M/2+H]$^+$, 518 [M−H]$^−$, $t_R$=1.29 min. HPLC: 97.55% at 214 nm, 97.72% at 254 nm, $t_R$=3.51 min.

Example 26

3-(7-(3-(Methylsulfonyl)phenylamino)thiazolo[5,4-d]pyrimidin-5-yl)benzoic acid

Step 1

5-Chloro-N-(3-(methylsulfonyl)phenyl)thiazolo[5,4-d]pyrimidin-7-amine

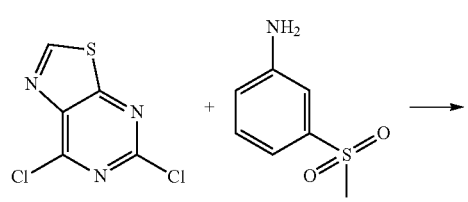

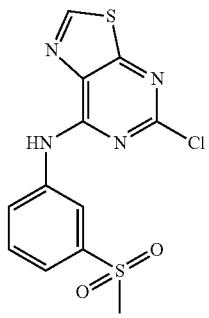

Procedure:

A mixture of 5,7-dichlorothiazolo[5,4-d]pyrimidine (200 mg, 0.97 mmol), 3-(methylsulfonyl)aniline (182 mg, 1.07 mmol) and DIEA (375 g, 2.91 mmol) in 20 mL of DMSO was stirred at room temperature overnight. The mixture was poured into 150 mL of water and filtered, the solid obtained was washed with petroleum ether dried to give crude product which was purified by silica gel chromatography, silica gel 200-300 mesh, eluting with ethyl acetate to give 5-chloro-N-(3-(methylsulfonyl)phenyl)thiazolo[5,4-d]pyrimidin-7-amine (220 mg, 66%) as a yellow solid. LC-MS: 341 [M+H]$^+$, 3621 [M+Na]$^+$, $t_R$=1.48 min.

Step 2

Methyl 3-(7-(3-(methylsulfonyl)phenylamino)thiazolo[5,4-d]pyrimidin-5-yl)benzoate

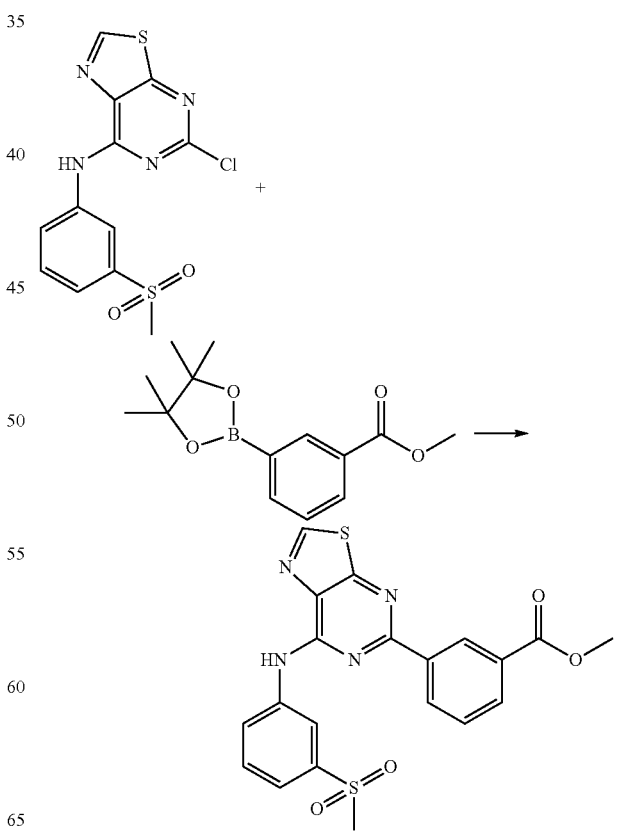

Procedure:

Under N$_2$ atmosphere, 5-chloro-N-(3-(methylsulfonyl)phenyl)thiazolo[5,4-d]pyrimidin-7-amine (200 mg, 0.59 mmol), methyl 3-(4,4,5,5-tetramethyl-1,3,2-dioxaborolan-2-yl)benzoate (183 mg, 0.7 mmol), Pd(PPh$_3$)$_4$ (30 mg, 0.026 mmol) and Na$_2$CO$_3$ (127 mg, 1.2 mmol) in 5 mL of water was added into the mixture solvent of 5 mL of water and 50 mL of 1,4-dioxane. The mixture was stirred at reflux for 18 hours. The solvent was removed under reduce pressure and the residue was purified by silica gel chromatography, eluting with petroleum ether and ethyl acetate (3:1) to give methyl 3-(7-(3-(methylsulfonyl)phenylamino)thiazolo[5,4-d]pyrimidin-5-yl)benzoate (150 mg, 58%) as a yellow sold. $^1$H NMR (300 MHz, DMSO): δ 10.76 (s, 1H), 9.45 (s, 1H), 8.99-8.98 (m, 1H), 8.93 (s, 1H), 8.73 (d, 1H, J=7.8 Hz), 8.21-8.18 (m, 1H), 8.09 (d, 1H, J=7.8 Hz), 7.69-7.65 (m, 3H), 3.91 (s, 3H), 3.26 (s, 3H). LC-MS: 441 [M+H]$^+$, 903 [2M+Na]$^+$, 439 [M−H]$^−$, t$_R$=1.61 min. HPLC: 98.78% at 214 nm, 97.72% at 254 nm, t$_R$=8.14 min.

Example 27

3-(7-(3-(Methylsulfonyl)phenylamino)thiazolo[5,4-d]pyrimidin-5-yl)benzoic acid

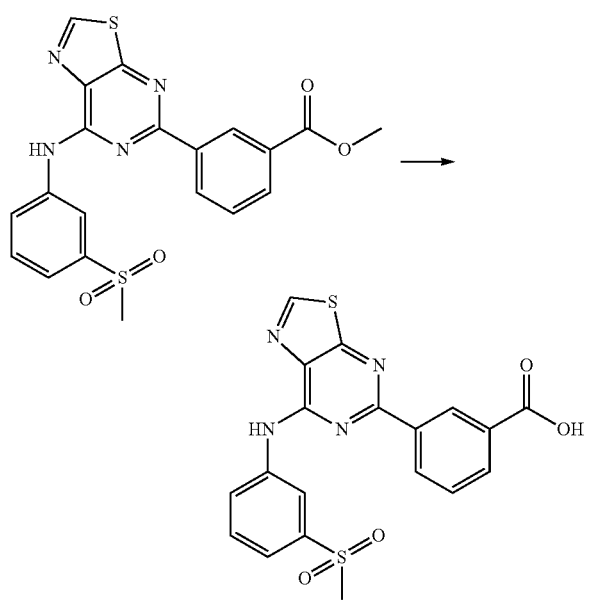

Procedure:

Methyl 3-(7-(3-(methylsulfonyl)phenylamino)thiazolo[5,4-d]pyrimidin-5-yl)benzoate (130 mg, 0.29 mmol) and NaOH (130 mg, 3.25 mmol) in 3 mL of 1,4-dioxane and 3 mL of H$_2$O were stirred at room temperature for 3 hours and then treated by conc. HCl until pH=3-4. The solvent was removed under reduce pressure the residue was purified by preparative HPLC (Gemini 5u C18 150×21.2 mm; inject volume: 3 ml/inj, flow rate: 20 ml/min; wavelength: 214 nm and 254 nm; the gradient conditions are: 40% acetonitrile/60% water (0.1% TFA V/V) initially, and then proceed to 55% acetonitrile/45% water (0.1% TFA V/V) in a linear fashion after just 9 min.) to give 3-(7-(3-(methylsulfonyl)phenylamino)thiazolo[5,4-d]pyrimidin-5-yl)benzoic acid (50 mg, 40%) as a yellow solid. $^1$H NMR (300 MHz, DMSO): δ 13.18 (brs, 1H), 10.76 (s, 1H), 9.45 (s, 1H), 8.99-8.95 (m, 2H), 8.72 (dt, 1H, J$_1$=7.8 Hz, J$_2$=1.5 Hz), 8.22-8.18 (m, 1H), 8.08 (dt, 1H, J$_2$=8.1 Hz, J$_2$=1.4 Hz), 7.69-7.61 (m, 3H), 3.24 (s, 3H). LC-MS: 427 [M+H]$^+$, t$_R$=1.48 min. HPLC: 98.42% at 214 nm, 99.23% at 254 nm, t$_R$=5.75 min.

Example 28

3-(7-(3-(2-(Methoxymethyl)pyrrolidin-1-yl)phenylamino)thiazolo[5,4-d]pyrimidin-5-yl)benzoic acid hydrochloride Step 1

2-(Methoxymethyl)-1-(3-nitrophenyl)pyrrolidine

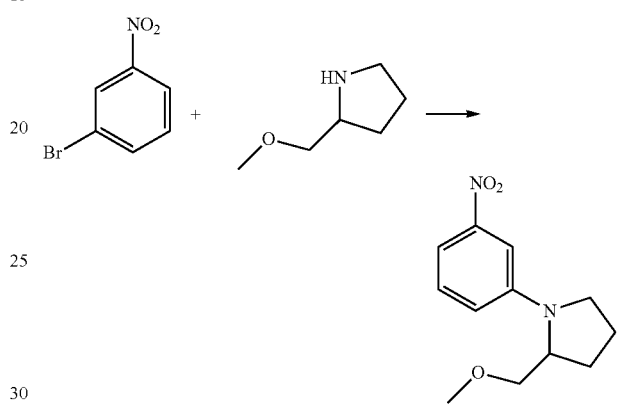

Procedure:

To a mixture of 1-bromo-3-nitrobenzene (300 mg, 1.48 mmol), 2-(methoxymethyl)pyrrolidine (187 mg, 1.63 mmol), Cs$_2$CO$_3$ (800 mg, 2.45 mmol), X-Phos (50 mg, 0.1 mmol), Pd(dba)$_2$ (50 mg, 0.087 mmol) in 50 mL of dioxane were stirred at reflux overnight under N$_2$ atmosphere. The excess of dioxane was removed under reduced pressure and the residue was purified by silica gel chromatography, eluting with a mixture of petroleum ether and ethyl acetate (5:1) to give 2-(methoxymethyl)-1-(3-nitrophenyl)pyrrolidine (250 mg, 72%) as a yellow solid. LC-MS: 237 [M+H]$^+$, t$_R$=1.71 min.

Step 2

3-(2-(Methoxymethyl)pyrrolidin-1-yl)aniline

Procedure:

The mixture of 2-(methoxymethyl)-1-(3-nitrophenyl)pyrrolidine (200 mg, 0.85 mmol), Pd/C (50 mg, 10%) in 50 mL of MeOH was stirred at room temperature for 18 hours under H$_2$ atmosphere. Pd/C was filtrated off and the filtrate was concentrated under reduce pressure to give crude 3-(2-(methoxymethyl)pyrrolidin-1-yl)aniline (170 mg) as an oil. LC-MS: 207 [M+H]$^+$, t$_R$=1.15 min.

Step 3

5-Chloro-N-(3-(2-(methoxymethyl)pyrrolidin-1-yl)phenyl)thiazolo[5,4-d]pyrimidin-7-amine

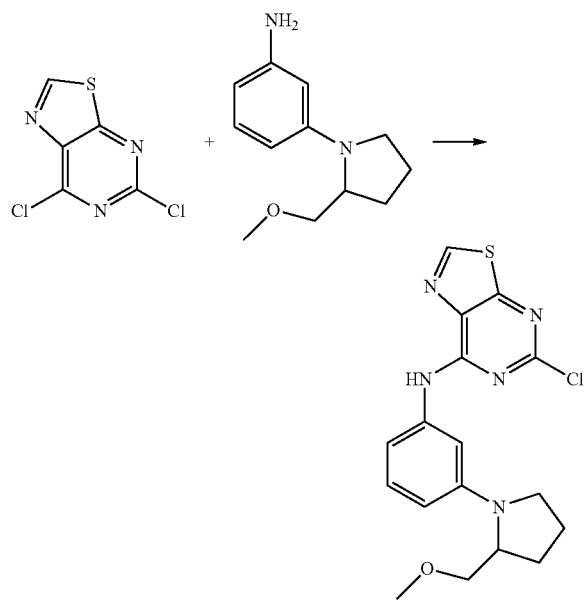

Procedure:

A mixture of 5,7-dichlorothiazolo[5,4-d]pyrimidine (170 mg, 0.83 mmol), 3-(2-(methoxymethyl)pyrrolidin-1-yl)aniline (170 mg, 0.83 mmol) and DIEA (214 g, 1.66 mmol) in 15 mL of DMSO was stirred at room temperature overnight. 100 mL of water were added, the mixture was extracted with ethyl acetate (3×30 mL). The organic layer was washed with water (2×30 mL) and brine (30 mL), concentrated under reduced pressure to give 5-chloro-N-(3-(2-(methoxymethyl)pyrrolidin-1-yl)phenyl)thiazolo[5,4-d]pyrimidin-7-amine (200 mg, 64%) as a yellow solid. LC-MS: 376 [M+H]$^+$, $t_R$=1.75 min.

Step 4

Methyl 3-(7-(3-(2-(methoxymethyl)pyrrolidin-1-yl)phenylamino)thiazolo[5,4-d]pyrimidin-5-yl)benzoate

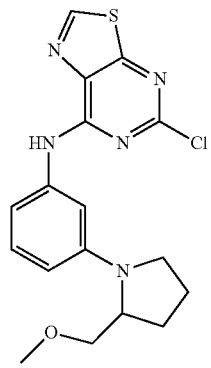

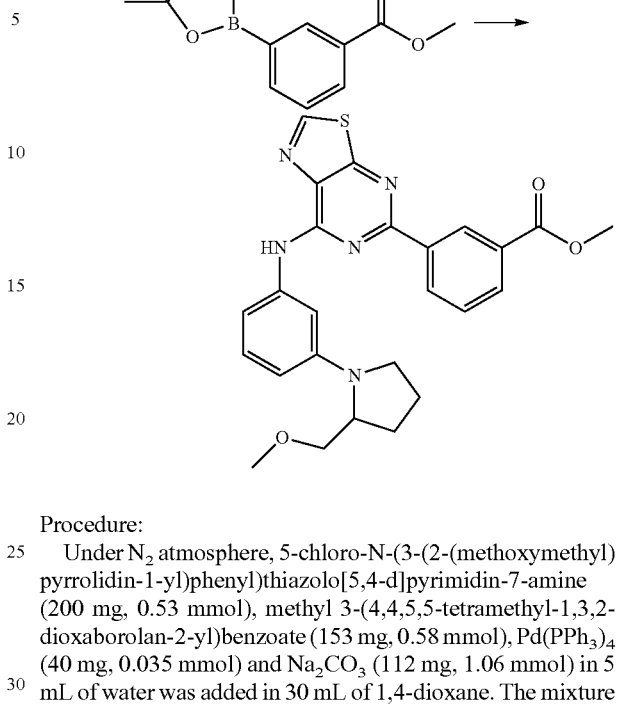

Procedure:

Under N$_2$ atmosphere, 5-chloro-N-(3-(2-(methoxymethyl)pyrrolidin-1-yl)phenyl)thiazolo[5,4-d]pyrimidin-7-amine (200 mg, 0.53 mmol), methyl 3-(4,4,5,5-tetramethyl-1,3,2-dioxaborolan-2-yl)benzoate (153 mg, 0.58 mmol), Pd(PPh$_3$)$_4$ (40 mg, 0.035 mmol) and Na$_2$CO$_3$ (112 mg, 1.06 mmol) in 5 mL of water was added in 30 mL of 1,4-dioxane. The mixture was stirred at reflux for 18 hours. The solvent was removed under reduce pressure and the residue was purified by silica gel chromatography, eluting with petroleum ether and ethyl acetate (3:1) to give methyl 3-(7-(3-(2-(methoxymethyl)pyrrolidin-1-yl)phenylamino)thiazolo[5,4-d]pyrimidin-5-yl)benzoate (150 mg, 59%) as a yellow solid. $^1$H NMR (300 MHz, CDCl$_3$): δ 9.13 (s, 1H), 8.82 (s, 1H), 8.68 (d, 1H, J=7.8 Hz), 8.14 (d, 1H, J=7.8 Hz), 8.06 (s, 1H), 7.54 (t, 1H, J=7.8 Hz), 7.35 (s, 1H), 7.28 (t, 1H, J=7.2 Hz), 7.16 (d, 1H, J=7.8 Hz), 6.49 (d, 1H, J=7.5 Hz), 3.96 (brs, 4H), 3.57-3.50 (brs, 2H), 3.32 (s, 3H), 3.25-3.19 (m, 2H), 2.11-2.02 (m, 5H). LC-MS: 476 [M+H]$^+$, $t_R$=1.93 min. HPLC: 98.15% at 214 nm, 97.85% at 254 nm, $t_R$=5.24 min.

Step 5

3-(7-(3-(2-(Methoxymethyl)pyrrolidin-1-yl)phenylamino)thiazolo[5,4-d]pyrimidin-5-yl)benzoic acid hydrochloride

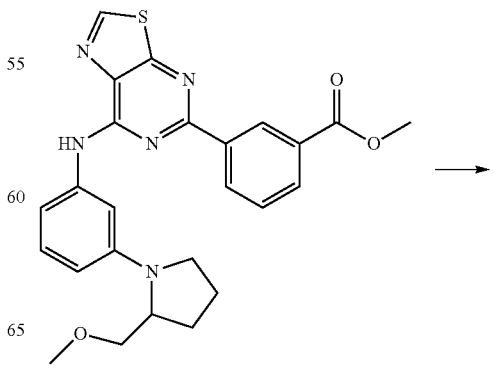

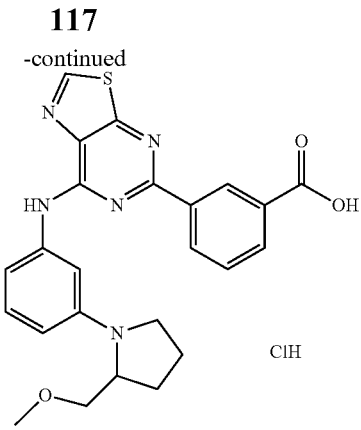

Procedure:

Methyl 3-(7-(3-(2-(methoxymethyl)pyrrolidin-1-yl)phenylamino)thiazolo[5,4-d]pyrimidin-5-yl)benzoate (100 mg, 0.21 mmol) and NaOH (100 mg, 2.5 mmol) in 3 mL of 1,4-dioxane and 3 mL of H₂O was stirred at room temperature for 3 hours and then treated by conc. HCl until pH=3-4. The solvent was removed under reduce pressure the residue was purified by preparative HPLC (Gemini 5u C18 150×21.2 mm; inject volume: 3 ml/inj, flow rate: 20 ml/min; wavelength: 214 nm and 254 nm; the gradient conditions are: 50% acetonitrile/50% water (0.1% TFA V/V) initially, and then proceed to 80% acetonitrile/20% water (0.1% TFA V/V) in a linear fashion after just 9 min.) to give 3-(7-(3-(2-(methoxymethyl)pyrrolidin-1-yl)phenylamino)thiazolo[5,4-d]pyrimidin-5-yl)benzoic acid hydrochloride (30 mg, 31%) as a yellow solid. ¹H NMR (300 MHz, DMSO): δ 10.28 (s, 1H), 9.41 (s, 1H), 8.98 (s, 1H), 6.62 (d, 1H, J=7.5 Hz), 8.08 (d, 1H, J=7.5 Hz), 7.66-7.62 (m, 2H), 7.47 (brs, 1H), 7.28 (brs, 1H), 3.95 (brs, 1H), 3.54-3.51 (m, 2H), 3.32-3.27 (m, 2H), 3.19 (s, 3H), 2.03-1.19 (m, 4H). LC-MS: 462 [M+H]⁺, $t_R$=1.66 min. HPLC: 96.12% at 214 nm, 96.76% at 254 nm, $t_R$=6.84 min.

Example 29

4-(3-(7-(3,4-Dimethoxyphenylamino)thiazolo[5,4-d]pyrimidin-5-yl)benzylamino)benzoic acid hydrochloride Step 1 tert-Butyl 4-(3-(4,4,5,5-tetramethyl-1,3,2-dioxaborolan-2-yl)benzylamino)benzoate

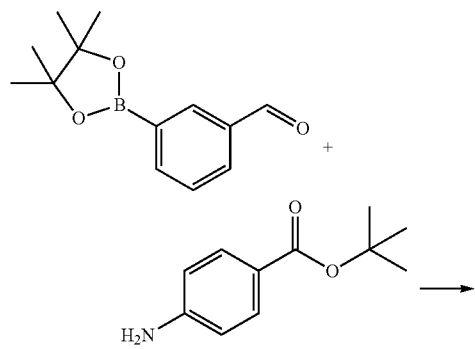

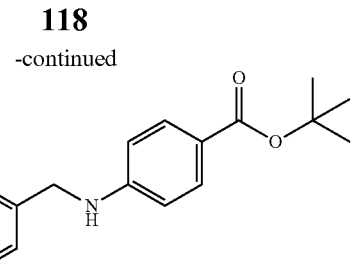

Procedure:

A mixture of 3-(4,4,5,5-tetramethyl-1,3,2-dioxaborolan-2-yl)benzaldehyde (100 mg, 0.43 mmol), tert-butyl 4-aminobenzoate (83 mg, 0.43 mmol), NaHB(OAc)₃ (273 g, 1.29 mmol) and AcOH (2 drops) in 30 mL of DCM was stirred at room temperature overnight. The mixture was washed with sat NaHCO₃ (30 mL), water (2×30 mL), and brine (30 mL) dried over Na₂SO₄ concentrated under reduce pressure to give a crude tert-butyl 4-(3-(4,4,5,5-tetramethyl-1,3,2-dioxaborolan-2-yl)benzylamino)benzoate (130 mg) as a black oil. LC-MS: 410 [M+H]⁺, $t_R$=1.92 min.

Step 2 tert-Butyl 4-(3-(7-(3,4-dimethoxyphenylamino)thiazolo[5,4-d]pyrimidin-5-yl)benzylamino)benzoate

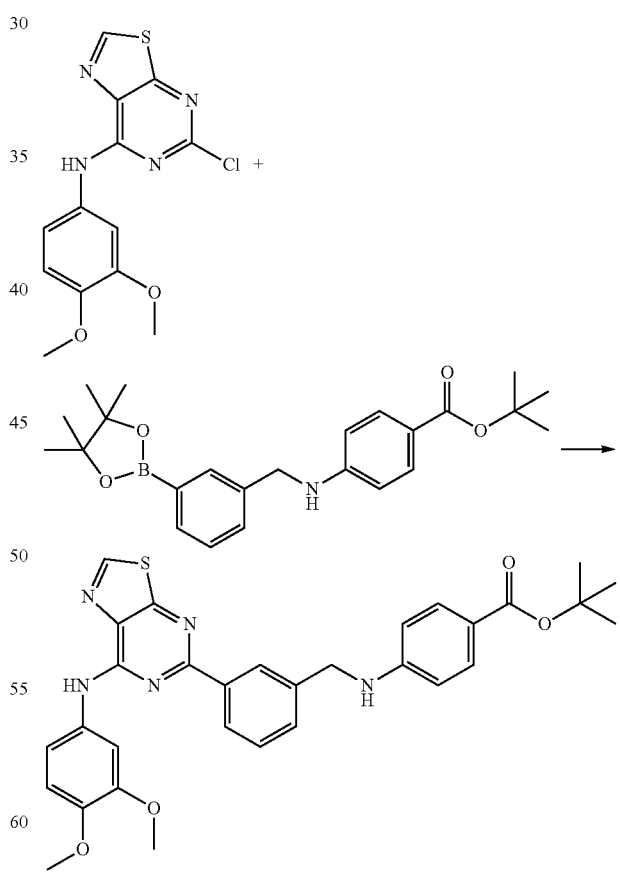

Procedure:

Under N₂ atmosphere, 5-chloro-N-(3,4-dimethoxyphenyl)thiazolo[5,4-d]pyrimidin-7-amine (100 mg, 0.31 mmol), tert-butyl 4-(3-(4,4,5,5-tetramethyl-1,3,2-dioxaborolan-2-yl)

benzylamino)benzoate (150 mg, crude), Pd(PPh$_3$)$_4$ (30 mg, 0.026 mmol) and Na$_2$CO$_3$ (150 mg, 1.41 mmol) in 5 mL of water was added in 30 mL of 1,4-dioxane. The mixture was stirred at reflux for 18 hours. The solvent was removed under reduce pressure and the residue was purified by silica gel chromatography, eluting with petroleum ether and ethyl acetate (5:1) to give tert-butyl 4-(3-(7-(3,4-dimethoxyphenylamino)thiazolo[5,4-d]pyrimidin-5-yl)benzylamino)benzoate (72 mg, 41%) as a yellow sold. $^1$H NMR (300 MHz, DMSO): δ 8.87 (s, 1H), 8.54-8.47 (m, 2H), 7.86-7.82 (m, 3H), 7.49-7.28 (m, 2H), 7.27-7.23 (m, 1H), 6.94 (d, 1H, J=8.7 Hz), 6.65-6.62 (m, 2H), 4.49 (s, 2H), 4.16 (s, 3H), 4.13 (s, 3H). LC-MS: 570 [M+H]$^+$, t$_R$=1.83 min. HPLC: 98.31% at 214 nm, 98.91% at 254 nm, t$_R$=8.06 min.

Example 30

4-(3-(7-(3,4-Dimethoxyphenylamino)thiazolo[5,4-d]pyrimidin-5-yl)benzylamino)benzoic acid hydrochloride

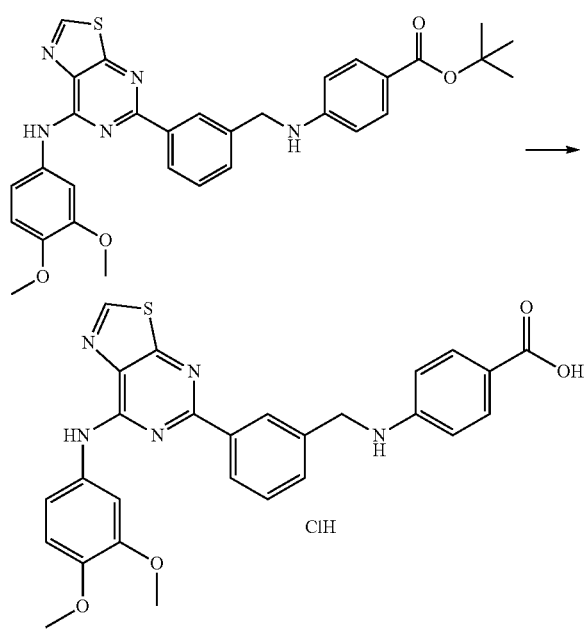

Procedure:

To a stirred solution of tert-butyl 4-(3-(7-(3,4-dimethoxyphenylamino)thiazolo[5,4-d]pyrimidin-5-yl)benzylamino)benzoate (45 mg, 0.08 mmol) in 10 mL of CH$_2$Cl$_2$ was added CF$_3$COOH (4 mL) at room temperature. Then the mixture was stirred at room temperature for 16 hours. The solvent was evaporated and the residue was purified by preparative HPLC (Gemini 5u C18 150×21.2 mm; inject volume: 3 ml/inj, flow rate: 20 ml/min; wavelength: 214 nm and 254 nm; the gradient conditions are: 20% acetonitrile/80% water (0.1% TFA V/V) initially, and then proceed to 50% acetonitrile/50% water (0.1% TFA V/V) in a linear fashion after just 9 min.) to give the corresponding trifluoroacetate salt. The salt was suspended in MeOH (10 mL) and conc. HCl (0.5 mL) was added dropwise, the mixture was stirred for 10 min. Then the mixture was concentrated under reduced pressure to give 4-(3-(7-(3,4-dimethoxyphenylamino)thiazolo[5,4-d]pyrimidin-5-yl)benzylamino)benzoic acid hydrochloride (25 mg, 57%) as a yellow solid. $^1$H NMR (300 MHz, DMSO): δ 10.05 (s, 1H), 9.36 (s, 1H), 8.43 (s, 1H), 8.36 (brs, 1H), 7.81 (s, 1H), 7.67-7.48 (m, 5H), 7.00 (d, 1H, J=8.7 Hz), 6.65 (d, 1H, J=9.0 Hz), 4.44 (s, 2H), 3.82 (s, 3H), 3.78 (s, 3H). LC-MS: 514 [M+H]$^+$, t$_R$=1.53 min. HPLC: 96.98% at 214 nm, 96.99% at 254 nm, t$_R$=4.45 min.

Example 31

(Z)-4-(2-(3-(7-(3,4-Dimethoxyphenylamino)thiazolo[5,4-d]pyrimidin-5-yl)phenyl)-2-fluorovinyl)benzoic acid Step 1

Diethyl(3-bromophenyl)(hydroxy)methylphosphonate

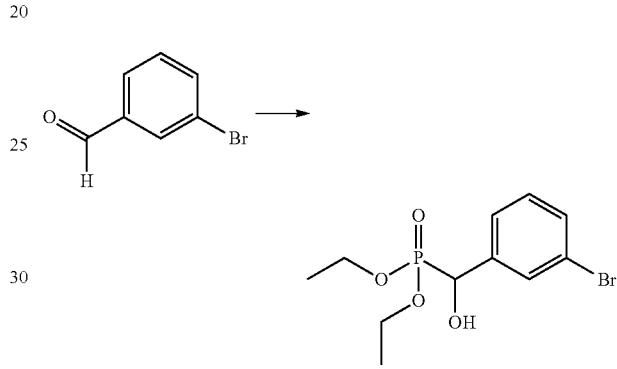

Procedure:

The mixture of 3-bromobenzaldehyde (22.2 g, 0.12 mol) and diethyl phosphonate (13.8 g, 0.1 mol) was stirred at 100-110° C. for 15 hours under N$_2$ atmosphere. The mixture was purified by silica gel chromatography (eluting with a mixture of petroleum ether and ethyl acetate=10-0:1) to give diethyl(3-bromophenyl)(hydroxy)methylphosphonate (22 g, 68%) as a colorless oil. LC-MS: 323 [M+H]$^+$, 347 [M+Na]$^+$, 669 [2M+Na]$^+$, t$_R$=1.41 min.

Step 2

Diethyl(3-bromophenyl)fluoromethylphosphonate

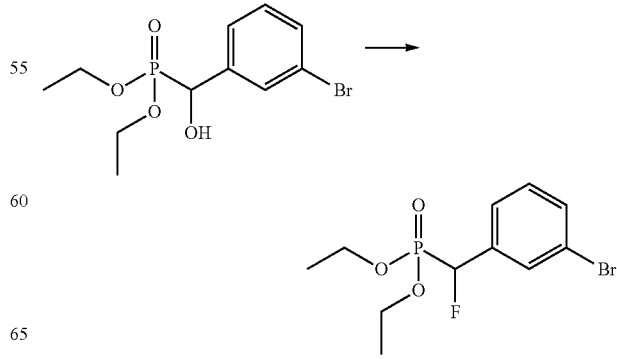

121

Procedure:

A solution of diethyl(3-bromophenyl)(hydroxy)methylphosphonate (5 g, 15 mmol) in 40 mL of DCM was added dropwise via syringe to a solution of DAST (2.9 g, 18 mmol) in 20 mL of DCM at −78° C. under $N_2$ atmosphere. The mixture was allowed to warm to room temperature and stirred further for 2 hours and then it was carefully quenched by pouring into a solution of EtOH (50 mL) and pyridine (3 mL). The solvent was removed under reduce pressure and the residue was purified by silica gel chromatography (eluting with a mixture of petroleum ether and ethyl acetate=3:1 to 1:1) to give diethyl(3-bromophenyl)fluoromethylphosphonate (4.7 g, 94%) as a colorless oil. LC-MS: 327 $[M+H]^+$, 349 $[M+Na]^+$, 673 $[2M+Na]^+$, $t_R$=1.62 min.

Step 3

(Z)-Methyl 4-(2-(3-bromophenyl)-2-fluorovinyl)benzoate

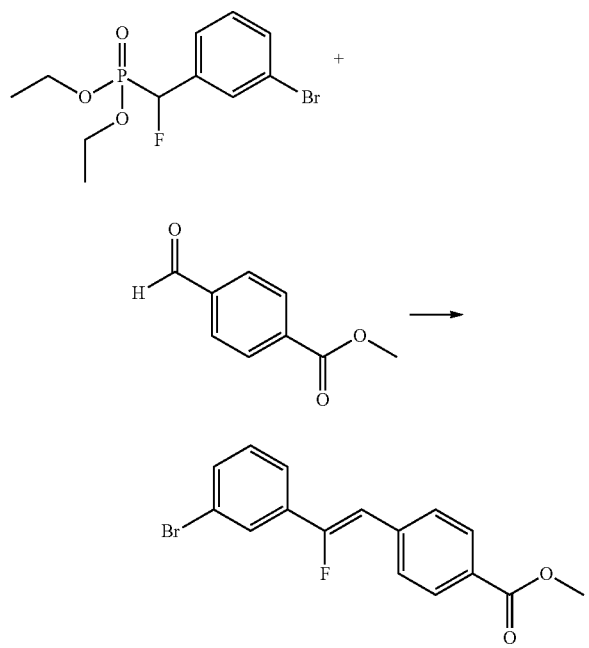 [SMILES: CCOP(=O)(OCC)C(F)c1cccc(Br)c1 ; COC(=O)c1ccc(C=O)cc1 ; COC(=O)c1ccc(/C=C(\F)c2cccc(Br)c2)cc1]

Procedure:

A solution of diethyl(3-bromophenyl)fluoromethylphosphonate (2.1 g, 6.5 mmol) in 50 mL of THF was added dropwise via syringe to a solution of LDA (5 mL, 10 mmol) in THF at −78° C. under $N_2$ atmosphere. After 30 min at this temperature methyl 4-formylbenzoate (1.1 g, 6.5 mmol) in 50 mL of THF was added dropwise via syringe and then stirred at this temperature for 30 min and then allow warm to room temperature over 4 hours, and stirred overnight. The mixture was poured into $H_2O$ (300 mL) and then extracted with ethyl acetate (3×100 mL). The combined organic layer was concentrated and purified by silica gel chromatography (eluting with a mixture of petroleum ether and ethyl acetate=50:1) to give (Z)-methyl 4-(2-(3-bromophenyl)-2-fluorovinyl)benzoate (0.73 g, 33.6%) as a yellow oil.

Step 4

(Z)-Methyl 4-(2-fluoro-2-(3-(4,4,5,5-tetramethyl-1,3,2-dioxaborolan-2-yl)phenyl)vinyl)benzoate

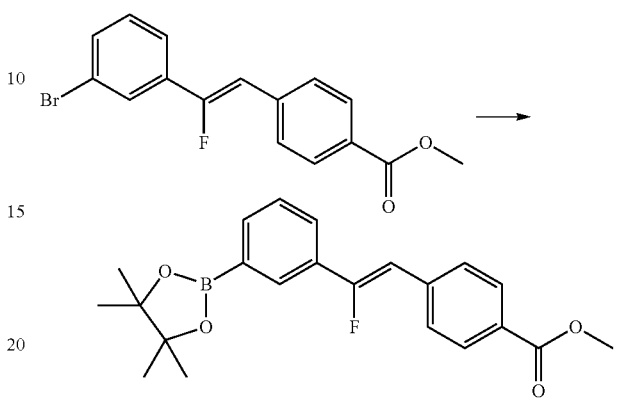

Procedure:

A mixture of (Z)-methyl 4-(2-(3-bromophenyl)-2-fluorovinyl)benzoate (700 mg, 2.1 mmol), bis(pinacolato)diboron (600 mg, 2.4 mmol), Pd(dppf)Cl$_2$ (150 mg, 0.2 mmol) and KOAc (620 mg, 6.3 mmol) in 30 mL of DMSO was stirred at 80° C. overnight under $N_2$ atmosphere. The mixture was added 200 mL of ethyl acetate, washed with water, dried over anhydrous $Na_2SO_4$, concentrated under reduce pressure to give (Z)-methyl 4-(2-fluoro-2-(3-(4,4,5,5-tetramethyl-1,3,2-dioxaborolan-2-yl)phenyl)vinyl)benzoate (500 mg, crude) as an oil which was used for nest step without further purification.

Step 5

(Z)-Methyl 4-(2-(3-(7-(3,4-dimethoxyphenylamino)thiazolo[5,4-d]pyrimidin-5-yl)phenyl)-2-fluorovinyl)benzoate

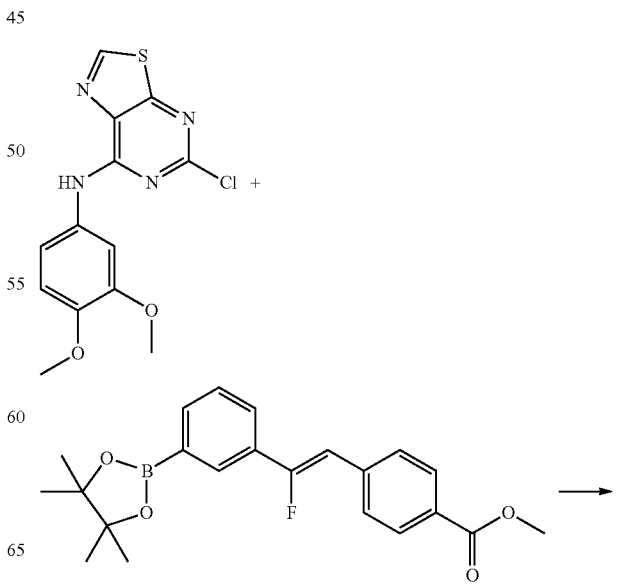

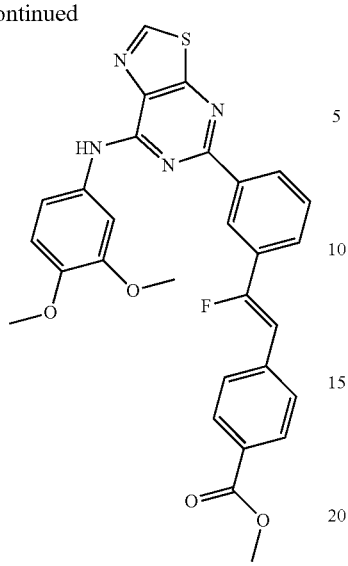

Procedure:

To a stirred solution of 5-chloro-N-(3,4-dimethoxyphenyl)thiazolo[5,4-d]pyrimidin-7-amine (100 mg, 0.31 mmol) and (Z)-methyl 4-(2-fluoro-2-(3-(4,4,5,5-tetramethyl-1,3,2-dioxaborolan-2-yl)phenyl)vinyl)benzoate (150 mg, 0.39 mmol) in 25 mL of 1,4-dioxane were added $Na_2CO_3$ (64 mg, 0.6 mmol) and 3 mL of water at room temperature. Then the mixture was degassed with nitrogen for 15 minutes. $Pd(PPh_3)_4$ (20 mg, 0.017 mmol) was added in one portion and the reaction mixture was stirred at reflux for 18 hours under nitrogen. The solvent was evaporated and the residue was purified by silica gel chromatography (200-300 mesh, eluting with a mixture of petroleum ether and ethyl acetate=1:1) to give (Z)-methyl 4-(2-(3-(7-(3,4-dimethoxyphenylamino)thiazolo[5,4-d]pyrimidin-5-yl)phenyl)-2-fluorovinyl)benzoate (70 mg, 42%) as a yellow sold. 543 [M+H]$^+$, $t_R$=1.88 min.

Step 6

(Z)-4-(2-(3-(7-(3,4-Dimethoxyphenylamino)thiazolo[5,4-d]pyrimidin-5-yl)phenyl)-2-fluorovinyl)benzoic acid

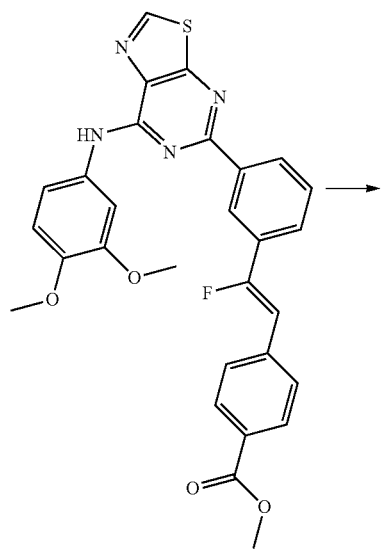

Procedure:

To a stirred solution of (Z)-methyl 4-(2-(3-(7-(3,4-dimethoxyphenylamino)thiazolo[5,4-d]pyrimidin-5-yl)phenyl)-2-fluorovinyl)benzoate (50 mg, 0.09 mmol) in 3 mL of 1,4-dioxane and 3 mL of $H_2O$ was added NaOH (140 mg, 3.5 mmol) at room temperature. Then the reaction was stirred at room temperature overnight and then treated by conc. HCl until pH=3-4. The solvent was removed under reduce pressure the residue was purified by preparative HPLC (Gemini 5u C18 150×21.2 mm; inject volume: 3 ml/inj, flow rate: 20 ml/min; wavelength: 214 nm and 254 nm; the gradient conditions are: 40% acetonitrile/60% water (0.1% TFA V/V) initially, and then proceed to 55% acetonitrile/45% water (0.1% TFA V/V) in a linear fashion after just 9 min.) to give (Z)-4-(2-(3-(7-(3,4-dimethoxyphenylamino)thiazolo[5,4-d]pyrimidin-5-yl)phenyl)-2-fluorovinyl)benzoic acid (25 mg, 51%) as a yellow solid. $^1$H NMR (300 MHz, DMSO): δ 12.94 (brs, 1H, exchangeable by $D_2O$), 10.18 (s, 1H, exchangeable by $D_2O$), 9.40 (s, 1H), 8.54-8.49 (m, 2H), 7.82-7.74 (m, 3H), 7.41-7.31 (m, 5H), 6.90-6.78 (m, 2H), 3.80 (s, 6H). LC-MS: 529 [M+H]$^+$, 527 [M−H]$^-$, $t_R$=1.71 min. HPLC: 96.85% at 214 nm, 95.49% at 254 nm, $t_R$=5.08 min.

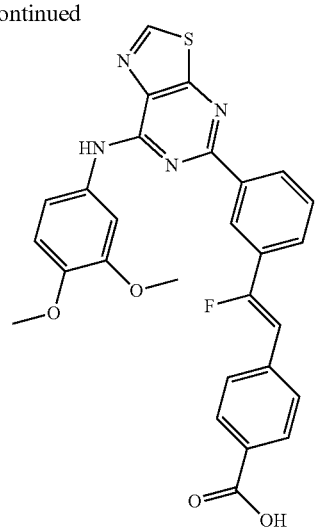

Example 32

(E)-4-(3-(7-(3,4-Dimethoxyphenylamino)thiazolo[5,4-d]pyrimidin-5-yl)styryl)benzoic acid Step 1

(4-(Methoxycarbonyl)benzyl)triphenylphosphonium bromide

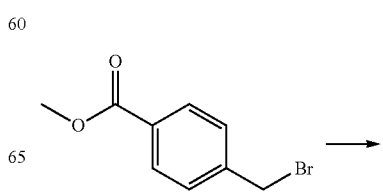

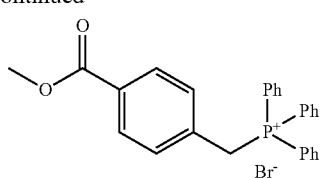

Procedure:

A mixture of methyl 4-(bromomethyl)benzoate (5 g, 22 mmol) and PPh₃ (5.77 g, 22 mmol) in 150 mL of toluene were stirred at 120° C. for 5 hours. The mixture was cooled to room temperature and filtered dried to give (4-(methoxycarbonyl)benzyl)triphenylphosphonium bromide (8.8 g, 82%) as a white solid ¹H NMR (300 MHz, DMSO): δ 7.92-7.63 (m, 17H), 7.11-7.08 (m, 2H), 5.32-5.26 (m, 2H), 3.32 (s, 3H).

Step 2

(E)-Methyl 4-(3-(4,4,5,5-tetramethyl-1,3,2-dioxaborolan-2-yl)styryl)benzoate

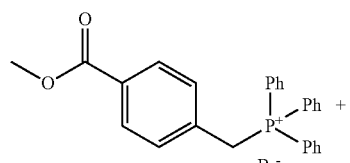

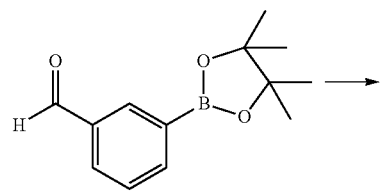

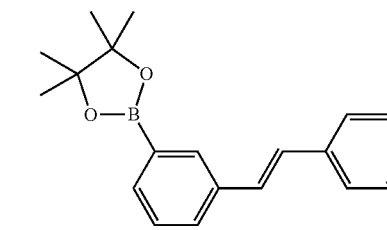

Procedure:

A solution of (4-(methoxycarbonyl)benzyl)triphenylphosphonium bromide (2.9 g, 6 mmol) in 50 mL of THF was added dropwise via syringe to a solution of LDA (5 mL, 10 mmol) in THF at −78° C. under N₂ atmosphere. After 30 min at this temperature 3-(4,4,5,5-tetramethyl-1,3,2-dioxaborolan-2-yl)benzaldehyde (1.4 g, 6 mmol) in 50 mL of THF was added dropwise via syringe and then stirred at this temperature for 30 min and then allow warm to room temperature over 4 hours, and stirred overnight. The mixture was poured into H₂O (300 mL) and then extracted with ethyl acetate (3×100 mL). The combined organic layer was concentrated and purified by silica gel chromatography (eluting with a mixture of petroleum ether and ethyl acetate=50:1) to give (E)-methyl 4-(3-(4,4,5,5-tetramethyl-1,3,2-dioxaborolan-2-yl)styryl)benzoate (0.9 g, 41%) as a colorless oil. LC-MS: 365 [M+H]⁺, $t_R$=1.98 min.

Step 3

(E)-Methyl 4-(3-(7-(3,4-dimethoxyphenylamino)thiazolo[5,4-d]pyrimidin-5-yl)styryl)benzoate

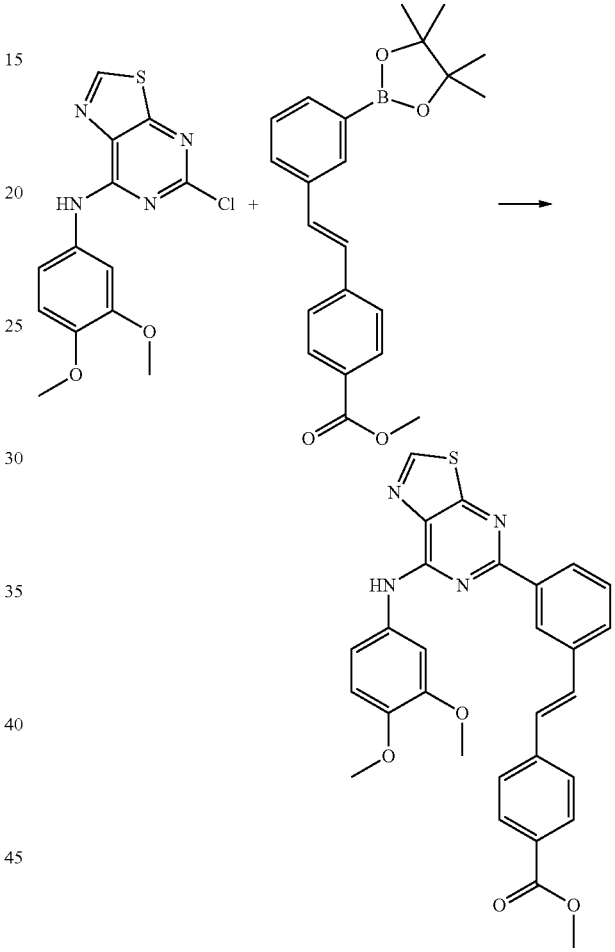

Procedure:

To a stirred solution of 5-chloro-N-(3,4-dimethoxyphenyl)thiazolo[5,4-d]pyrimidin-7-amine (150 mg, 0.46 mmol) and (E)-methyl 4-(3-(4,4,5,5-tetramethyl-1,3,2-dioxaborolan-2-yl)styryl)benzoate (200 mg, 0.55 mmol) in 25 mL of 1,4-dioxane were added Na₂CO₃ (100 mg, 0.94 mmol) and 3 mL of water at room temperature. Then the mixture was degassed with nitrogen for 15 minutes. Pd(PPh₃)₄ (40 mg, 0.035 mmol) was added in one portion and the reaction mixture was stirred at reflux for 18 hours under nitrogen. The solvent was evaporated and the residue was purified by silica gel chromatography (200-300 mesh, eluting with a mixture of petroleum ether and ethyl acetate=1:1) to give (E)-methyl 4-(3-(7-(3,4-dimethoxyphenylamino)thiazolo[5,4-d]pyrimidin-5-yl)styryl)benzoate (90 mg, 37%) as a yellow sold. LC-MS: 525 [M+H]⁺, $t_R$=1.89 min.

127

Step 4

(E)-4-(3-(7-(3,4-Dimethoxyphenylamino)thiazolo[5,4-d]pyrimidin-5-yl)styryl)benzoic acid

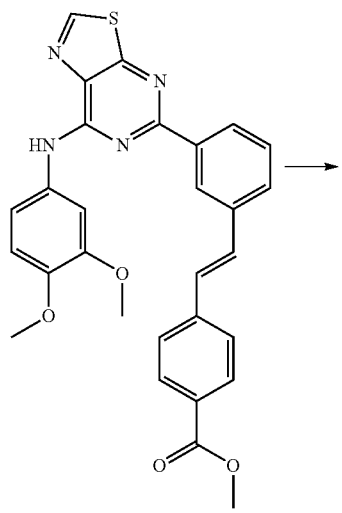

Procedure:

To a stirred solution of (E)-methyl 4-(3-(7-(3,4-dimethoxyphenylamino)thiazolo[5,4-d]pyrimidin-5-yl)styryl)benzoate (90 mg, 0.17 mmol) in 3 mL of 1,4-dioxane and 3 mL of $H_2O$ was added NaOH (140 mg, 3.5 mmol) at room temperature. Then the reaction was stirred at room temperature overnight and then treated by conc. HCl until pH=3-4. The solvent was removed under reduce pressure the residue was purified by preparative HPLC to give (E)-4-(3-(7-(3,4-dimethoxyphenylamino)thiazolo[5,4-d]pyrimidin-5-yl)styryl)benzoic acid (33 mg, 38%) as a yellow solid. $^1$H NMR (300 MHz, DMSO): δ 12.95 (brs, 1H), 10.09 (s, 1H), 9.38 (s, 1H), 8.37-8.30 (m, 2H), 7.82-7.78 (m, 3H), 7.47-7.32 (m, 5H), 6.92-6.78 (m, 3H), 3.81 (s, 3H), 3.80 (s, 3H). LC-MS: 511 [M+H]$^+$, 509 [M-H]$^-$, $t_R$=1.71 min. HPLC: 99.30% at 214 nm, 99.65 at 254 nm, $t_R$=4.98 min.

128

Example 33

4-(3-(7-(3,4-Dimethoxyphenylamino)thiazolo[5,4-d]pyrimidin-5-yl)phenethyl)benzoic acid Step 1

Methyl 4-(3-(4,4,5,5-tetramethyl-1,3,2-dioxaborolan-2-yl)phenethyl)benzoate

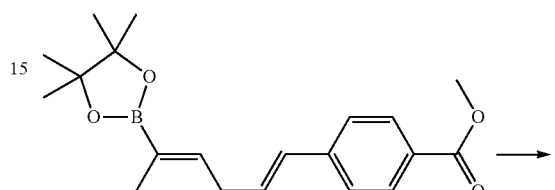

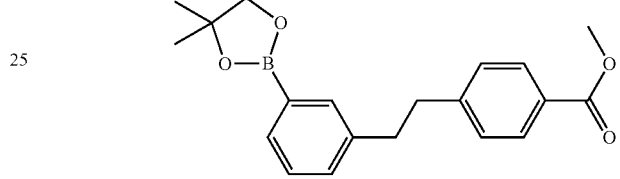

Procedure:

A mixture of (E)-methyl 4-(3-(4,4,5,5-tetramethyl-1,3,2-dioxaborolan-2-yl)styryl)benzoate (200 mg, 0.55 mmol) and $PtO_2$ (50 mg, 0.22 mmol) in 30 mL of MeOH was stirred at room temperature for 18 hours under $H_2$ atmosphere. The solvent was evaporated and the residue was purified by silica gel chromatography (200-300 mesh, eluting with a mixture of petroleum ether and ethyl acetate=50:1) to give methyl 4-(3-(4,4,5,5-tetramethyl-1,3,2-dioxaborolan-2-yl)phenethyl)benzoate (90 mg, 50%) as a colorless oil Step 2

Methyl 4-(3-(7-(3,4-dimethoxyphenylamino)thiazolo[5,4-d]pyrimidin-5-yl)phenethyl)benzoate

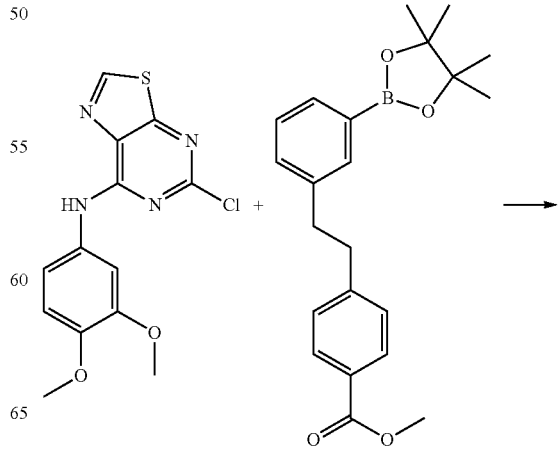

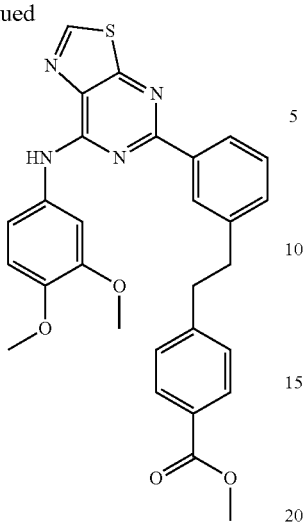

Procedure:

To a stirred solution of 5-chloro-N-(3,4-dimethoxyphenyl)thiazolo[5,4-d]pyrimidin-7-amine (88 mg, 0.27 mmol) and methyl 4-(3-(4,4,5,5-tetramethyl-1,3,2-dioxaborolan-2-yl)phenethyl)benzoate (100 mg, 0.27 mmol) in 25 mL of 1,4-dioxane were added Na₂CO₃ (100 mg, 0.94 mmol) and 3 mL of water at room temperature. Then the mixture was degassed with nitrogen for 15 minutes. Pd(PPh₃)₄ (20 mg, 0.017 mmol) was added in one portion and the reaction mixture was stirred at reflux for 18 hours under nitrogen. The solvent was evaporated and the residue was purified by silica gel chromatography (200-300 mesh, eluting with a mixture of petroleum ether and ethyl acetate=1:1) to give methyl 4-(3-(7-(3,4-dimethoxyphenylamino)thiazolo[5,4-d]pyrimidin-5-yl)phenethyl)benzoate (80 mg, 56%) as a yellow sold. LC-MS: 527 [M+H]$^+$, $t_R$=1.87 min.

Step 3

4-(3-(7-(3,4-Dimethoxyphenylamino)thiazolo[5,4-d]pyrimidin-5-yl)phenethyl)benzoic acid

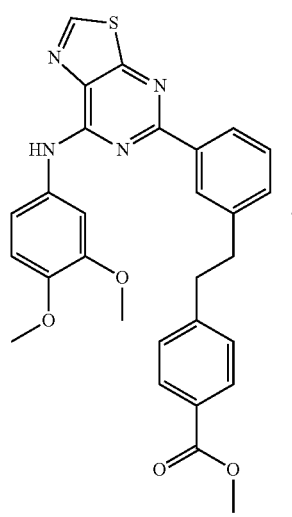

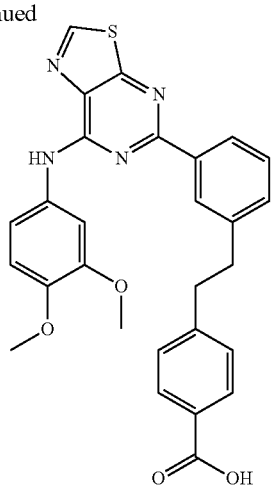

Procedure:

To a stirred solution of methyl 4-(3-(7-(3,4-dimethoxyphenylamino)thiazolo[5,4-d]pyrimidin-5-yl)phenethyl)benzoate (70 mg, 0.13 mmol) in 3 mL of 1,4-dioxane and 3 mL of H₂O was added NaOH (140 mg, 3.5 mmol) at room temperature. Then the reaction was stirred at room temperature overnight and then treated with conc. HCl until pH=3-4. The solvent was removed under reduced pressure, the residue was triturated with H₂O (3×10 mL) and ethyl acetate (3×10 mL) then dried to give 4-(3-(7-(3,4-dimethoxyphenylamino)thiazolo[5,4-d]pyrimidin-5-yl)phenethyl)benzoic acid (35 mg, 51%) as a yellow solid. $^1$H NMR (300 MHz, DMSO): δ 10.13 (s, 1H), 9.39 (s, 1H), 8.32-8.24 (m, 2H), 7.89-7.84 (m, 3H), 7.52-7.40 (m, 5H), 7.03 (d, 1H, J=8.7 Hz), 3.84 (s, 3H), 3.79 (s, 3H), 3.37 (brs, 4H). LC-MS: 513 [M+H]$^+$, $t_R$=1.67 min. HPLC: 97.30% at 214 nm, 97.09% at 254 nm, $t_R$=5.16 min.

Example 34

3-(7-(3-((1R,5S)-8-Oxa-3-azabicyclo[3.2.1]octan-3-yl)phenylamino)thiazolo[5,4-d]pyrimidin-5-yl)benzoic acid Step 1

(1R,5S)-3-(3-Nitrophenyl)-8-oxa-3-azabicyclo[3.2.1]octane

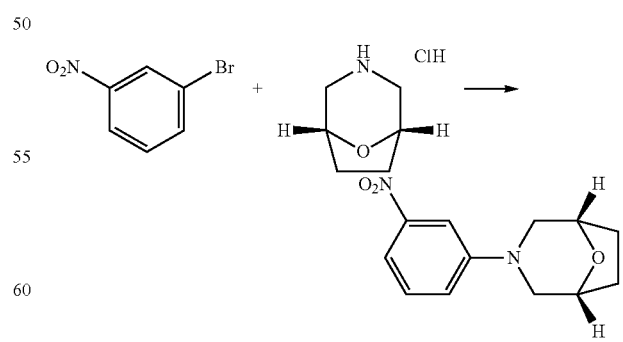

Procedure:

The mixture of 1-bromo-3-nitrobenzene (0.15 g, 0.743 mmol), (1R,5S)-8-oxa-3-azabicyclo[3.2.1]octane hydrochloride (0.122 g, 0.82 mmol), Pd₂(dba)₃ (0.043 g, 0.074 mmol), X-Phos (0.071 g, 0.15 mmol) and Cs₂CO₃ (0.727 g, 2.23 mmol) in dioxane (30 mL) was heated to 100° C. for 16 h under N₂ atmosphere. Then it was concentrated to dryness. The residue was purified by column chromatography (silica gel, 200~300 mesh, eluting with ethyl acetate:petroleum ether=1:8) to afford (1R,5S)-3-(3-nitrophenyl)-8-oxa-3-azabicyclo[3.2.1]octane (0.12 g, 69%) as a brown solid. LC-MS: 235 [M+H]⁺, t$_R$=1.57 min.

Step 2

3-((1R,5S)-8-Oxa-3-azabicyclo[3.2.1]octan-3-yl)aniline

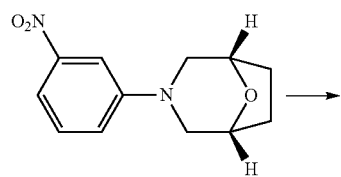

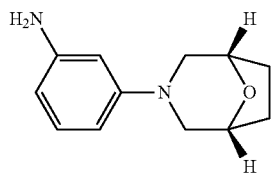

Procedure:

To a stirred solution of (1R,5S)-3-(3-nitrophenyl)-8-oxa-3-azabicyclo[3.2.1]octane (0.08 g, 0.341 mmol) and Zn (0.223 g, 3.41 mmol) in dioxane (10 mL) and H₂O (2 mL) was added dropwise conc. HCl (0.34 mL, 3.41 mmol) at 25° C. for 2 h. It was adjusted to pH=8 by the addition of solid NaHCO₃. It was filtered and the filtration was extracted with ethyl acetate (2×10 mL) and the extraction was concentrated to dryness. The residue was purified by column chromatography (silica gel, 200~300 mesh, eluting with ethyl acetate:petroleum ether=1:2) to afford 3-((1R,5S)-8-oxa-3-azabicyclo[3.2.1]octan-3-yl)aniline (0.061 g, 88%) as a yellow oil. LC-MS: 205 [M+H]⁺, t$_R$=1.09 min.

Step 3

N-(3-((1R,5S)-8-Oxa-3-azabicyclo[3.2.1]octan-3-yl)phenyl)-5-chlorothiazolo[5,4-d]pyrimidin-7-amine

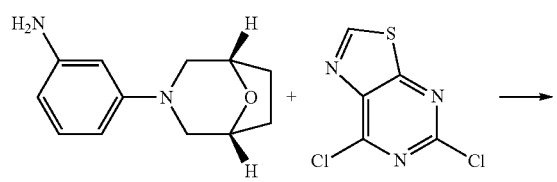

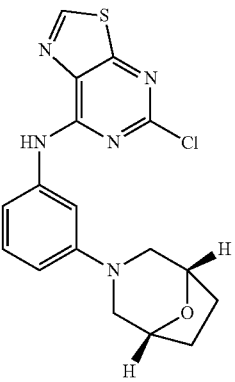

Procedure:

The mixture of 3-((1R,5S)-8-oxa-3-azabicyclo[3.2.1]octan-3-yl)aniline (0.061 g, 0.3 mmol), 5,7-dichlorothiazolo[5,4-d]pyrimidine (0.061 g, 0.3 mmol) and DIPEA (0.046 g, 0.36 mmol) in DMSO (10 mL) was heated to 30° C. for 2 h. Then it was diluted with water and extracted with ethyl acetate (3×10 mL), the organics were dried and concentrated. The residue was purified by column chromatography (silica gel, 200~300 mesh, eluting with MeOH:DCM=1:80) to afford N-(3-((1R,5S)-8-oxa-3-azabicyclo[3.2.1]octan-3-yl)phenyl)-5-chlorothiazolo[5,4-d]pyrimidin-7-amine (0.095 g, 86%) as a yellow solid. LC-MS: 374 [M+H]⁺, t$_R$=1.66 min.

Step 4

Methyl 3-(7-(3-((1R,5S)-8-oxa-3-azabicyclo[3.2.1]octan-3-yl)phenylamino)thiazolo[5,4-d]pyrimidin-5-yl)benzoate

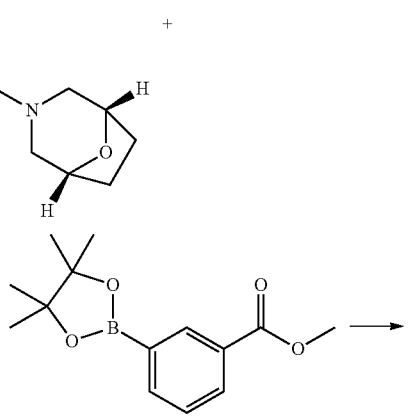

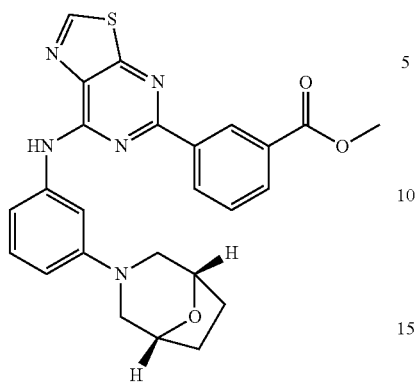

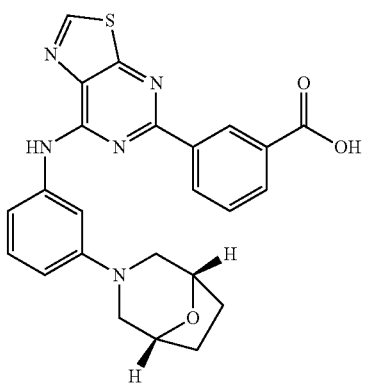

Procedure:

The mixture of N-(3-((1R,5S)-8-oxa-3-azabicyclo[3.2.1]octan-3-yl)phenyl)-5-chlorothiazolo[5,4-d]pyrimidin-7-amine (0.095 g, 0.254 mmol), methyl 3-(4,4,5,5-tetramethyl-1,3,2-dioxaborolan-2-yl)benzoate (0.073 g, 0.28 mmol), Pd(PPh$_3$)$_4$ (0.015 g, 0.013 mmol) and Na$_2$CO$_3$ (0.081 g, 0.762 mmol) in dioxane (20 mL) and H$_2$O (5 mL) was heated to 100° C. for 16 h under N$_2$ atmosphere. Then it was concentrated to dryness. The residue was purified by column chromatography (silica gel, 200~300 mesh, eluting with ethyl acetate:petroleum ether=1:2) to afford methyl 3-(7-(3-((1R,5S)-8-oxa-3-azabicyclo[3.2.1]octan-3-yl)phenylamino)thiazolo[5,4-d]pyrimidin-5-yl)benzoate (0.094 g, 78%) as a yellow solid. LC-MS: 474 [M+H]$^+$, t$_R$=1.84 min.

Procedure:

The mixture of methyl 3-(7-(3-((1R,5S)-8-oxa-3-azabicyclo[3.2.1]octan-3-yl)phenylamino)thiazolo[5,4-d]pyrimidin-5-yl)benzoate (0.094 g, 0.2 mmol) and NaOH (0.079 g, 2.0 mmol) in dioxane (10 mL) and H$_2$O (5 mL) was stirred at 30° C. for 2 h. It was concentrated, residue diluted with water, washed with ether (2×5 mL) and the aqueous layer was adjusted to pH=4 by the addition of conc. HCl, then the solid formed was filtered and purified by recrystallization (15 mL, MeOH:EtOAc:ether=5:20:100, v/v/v) to afford 3-(7-(3-((1R,5S)-8-oxa-3-azabicyclo[3.2.1]octan-3-yl)phenylamino)thiazolo[5,4-d]pyrimidin-5-yl)benzoic acid (0.042 g, 46%) as a yellow solid. $^1$H NMR (300 MHz, DMSO): δ 13.23 (s, 1H), 10.15 (s, 1H), 9.42 (s, 1H), 8.98 (s, 1H), 8.61 (d, 1H, J=7.8 Hz), 8.09 (d, 1H, J=7.8 Hz), 7.68-7.62 (m, 2H), 7.41 (d, 1H, J=8.1 Hz), 7.23 (t, 1H, J=8.4 Hz), 6.65 (d, 1H, J=8.4 Hz), 4.44 (s, 2H), 3.43-3.36 (m, 2H), 2.89 (d, 1H, J=9.3 Hz), 1.86 (s, 4H). LC-MS: 460 [M+H]$^+$, t$_R$=1.64 min. HPLC: 95.36% at 214 nm, 96.48% at 254 nm, t$_R$=5.20 min.

Step 5

3-(7-(3-((1R,5S)-8-Oxa-3-azabicyclo[3.2.1]octan-3-yl)phenylamino)thiazolo[5,4-d]pyrimidin-5-yl)benzoic acid Example 35

N-(1-(7-(3,4-Dimethoxyphenylamino)thiazolo[5,4-d]pyrimidin-5-yl)pyrrolidin-3-yl)-1H-indazole-5-carboxamide

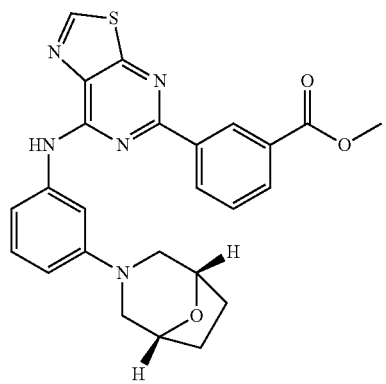

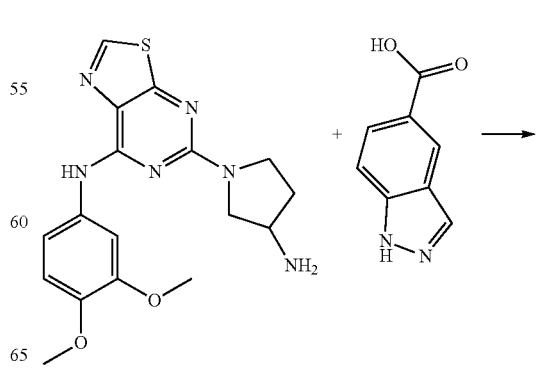

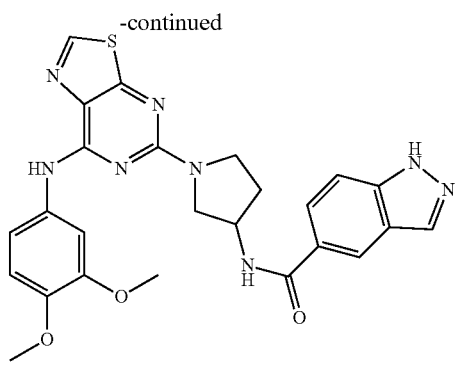

Procedure:

To a solution of 5-(3-aminopyrrolidin-1-yl)-N-(3,4-dimethoxyphenyl)thiazolo[5,4-d]pyrimidin-7-amine (100 mg, 0.27 mmol) and 1H-indazole-5-carboxylic acid (44 mg, 0.27 mmol) in dichloromethane (20 mL) were added the solution of 1-methyl-1H-imidazole (88 mg, 1.1 mmol) and EDCI (206 mg, 1.1 mmol) in dichloromethane (10 mL). The reaction mixture was stirred at room temperature for 15 hours, the solid formed during the reaction was collected by filtration and washed with MeOH to afford N-(1-(7-(3,4-dimethoxyphenylamino)thiazolo[5,4-d]pyrimidin-5-yl)pyrrolidin-3-yl)-1H-indazole-5-carboxamide (78 mg, 56.1%) as a off-white solid. $^1$H NMR (300 MHz, DMSO): δ 13.25 (s, 1H), 9.58 (s, 1H), 8.81 (s, 1H), 8.61 (d, 1H, J=6.3 Hz), 8.36 (s, 1H), 8.19 (s, 1H), 7.88-7.86 (m, 2H), 7.56 (d, 1H, J=8.7 Hz), 7.50 (s, 1H), 6.91 (d, 1H, J=8.4 Hz), 4.61-4.59 (m, 1H), 3.73 (s, 3H), 3.65 (s, 3H), 3.62 (brs, 3H), 2.28-2.09 (m, 2H). LC-MS: 517 [M+H]$^+$, $t_R$=1.34 min. HPLC: 95.89% at 214 nm, 97.39% at 254 nm, $t_R$=4.52 min Example 36

(S)—N-(3-(2-Methylpyrrolidin-1-yl)phenyl)-5-(3-((piperidin-4-ylamino)methyl)phenyl)thiazolo[5,4-d]pyrimidin-7-amine 2,2,2-trifluoroacetate Step 1

(S)-2-methyl-1-(3-nitrophenyl)pyrrolidine

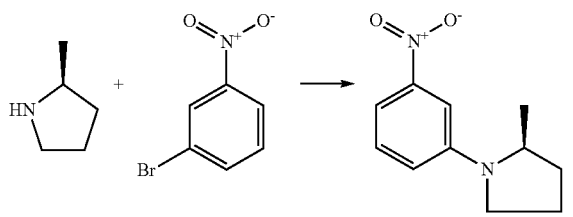

Procedure:

To a solution of 1-bromo-3-nitrobenzene (2.02 g, 0.01 mol) and (S)-2-methylpyrrolidine (1.02 g, 0.012 mol) in 20 mL of 1,4-dioxane was added Cs$_2$CO$_3$ (6.5 g, 0.02 mol) followed by Pd(dba)$_2$ (1.15 g, 0.002 mmol) and X-Phos (476 mg, 0.001 mol) under nitrogen with stirring. The mixture was refluxed for 16 hours under nitrogen. After cooled, the mixture was filtered, and then the filtrate was evaporated by rotary evaporation. The residue was diluted with water and extracted with EtOAc (3×30 mL). The organic layer was washed with brine and dried over Na$_2$SO$_4$. After filtration and concentration, the residue was purified by column chromatography on silica gel eluting with (petroleum ether:EtOAc=10:1) to give (S)-2-methyl-1-(3-nitrophenyl)pyrrolidine (1.2 g, 57%) as an oil. $^1$H NMR (300 MHz, CDCl$_3$) δ 7.47-7.44 (m, 1H), 7.37-7.35 (m, 1H), 7.32-7.27 (m, 1H), 6.86-6.83 (m, 1H), 3.95-3.91 (m, 1H), 3.50-3.44 (m, 1H), 3.26-3.18 (m, 1H), 2.18-1.99 (m, 3H), 1.80-1.72 (m, 1H), 1.21 (d, 2H, J=6.3 Hz). LC-MS: 207 [M+H]$^+$, $t_R$=1.75 min.

Step 2

(S)-3-(2-Methylpyrrolidin-1-yl)benzenamine

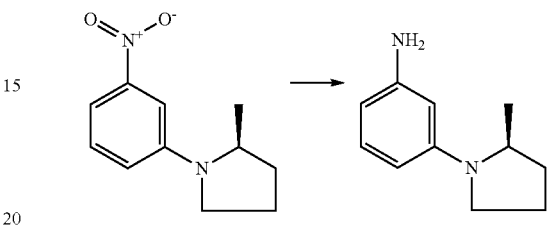

Procedure:

To a solution of (S)-2-methyl-1-(3-nitrophenyl)pyrrolidine (1.2 g, 5.83 mmol) and Zn dust (5.68 g, 87.4 mmol) in 20 mL of 1,4-dioxane was added dropwise HCl (aq.) (5 ml), the mixture was stirred for 1 hour at room temperature. The solvent was removed under reduced pressure. The residue was diluted with water and extracted with EtOAc (3×15 mL). The organic layer was washed with brine and dried over Na$_2$SO$_4$. After filtration and concentration, the residue was used for the next step without purification. LC-MS: 177 [M+H]$^+$, $t_R$=1.10 min.

Step 3

(S)-5-Chloro-N-(3-(2-methylpyrrolidin-1-yl)phenyl)thiazolo[5,4-d]pyrimidin-7-amine

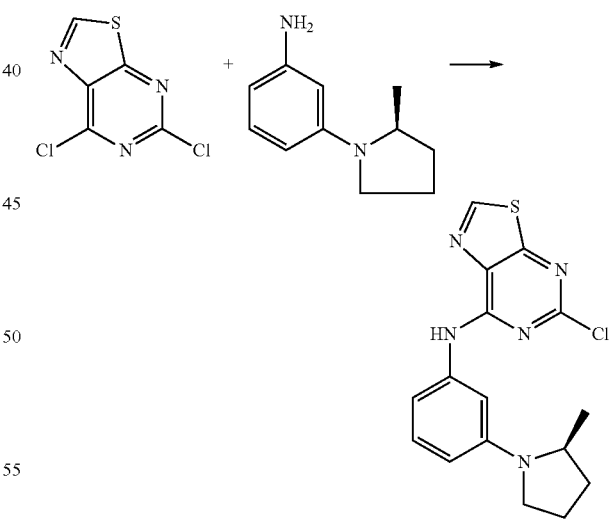

Procedure:

A mixture of 5,7-dichlorothiazolo[5,4-d]pyrimidine (1 g, 4.85 mmol), (S)-3-(2-methylpyrrolidin-1-yl)benzenamine and DIEA (1.25 g, 9.7 mmol) in 15 mL of DMSO was stirred at room temperature for 2 hours. The mixture was poured into water and extracted with EtOAc (3×20 mL). The organic layer was washed with brine and dried over Na$_2$SO$_4$. After filtration and concentration, the residue was used the next step without purification. LC-MS: 346 [M+H]$^+$, $t_R$=1.79 min.

137

Step 4 tert-Butyl-4-oxopiperidine-1-carboxylate

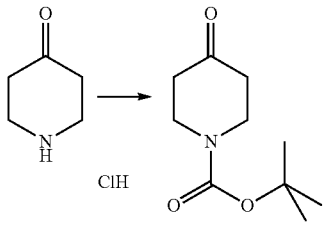

Procedure:

To a solution of piperidin-4-one hydrochloride (1.53 g, 0.01 mol) in 20 mL of MeOH was added di-tert-butyl dicarbonate (2.62 g, 0.012 mol) and triethylamine (2.02 g, 0.02 mol), the mixture was stirred for 2 hours at room temperature. The solvent was removed under reduced pressure. The residue was diluted with water and extracted with EtOAc (3×15 mL). The organic layer was washed with brine and dried over $Na_2SO_4$. After filtration and concentration, the residue (1.5 g, 75%) was used the next step without purification. $^1$H NMR (300 MHz, $CDCl_3$) δ 3.71 (t, 4H, J=6.3 Hz), 2.44 (t, 4H, J=6.3 Hz), 1.49 (s, 9H).

Step 5 tert-Butyl 4-(3-bromobenzylamino)piperidine-1-carboxylate

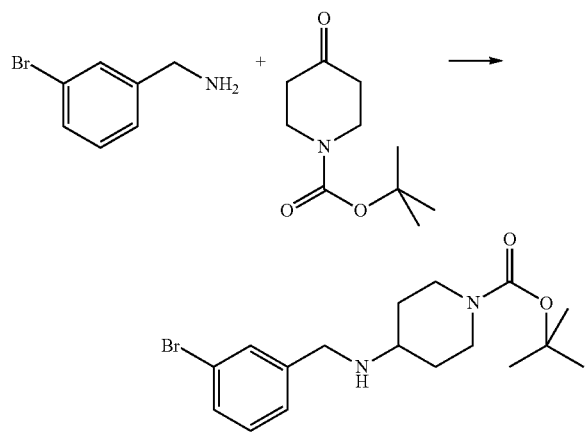

Procedure:

To a solution of (3-bromophenyl)methanamine (670 mg, 3.6 mmol), tert-butyl 4-oxopiperidine-1-carboxylate (600 mg, 3 mmol) and sodium triacetoxyborohydride (1.27 g, 6 mmol) in 10 mL of dichloromethane was added acetic acid (360 mg, 6 mmol). The mixture was stirred at room temperature overnight. The solvent was removed under reduced pressure. The residue was purified by column chromatography (silica gel, eluting with petroleum ether:EtOAc=3:1) to give tert-butyl 4-(3-bromobenzylamino)piperidine-1-carboxylate (0.9 g, 68%) as an oil. $^1$H NMR (300 MHz, $CDCl_3$) δ 7.48-7.47 (m, 1H), 7.38-7.35 (m, 1H), 7.25-7.17 (m, 2H), 4.10 (brs, 1H), 3.79 (s, 2H), 2.85-2.76 (m, 2H), 2.67-2.61 (m, 1H), 1.87-1.82 (m, 2H), 1.45 (s, 9H), 1.37-1.29 (m, 2H).

138

Step 6 tert-Butyl-4-(3-(4,4,5,5-tetramethyl-1,3,2-dioxaborolan-2-yl)benzylamino)piperidine-1-carboxylate

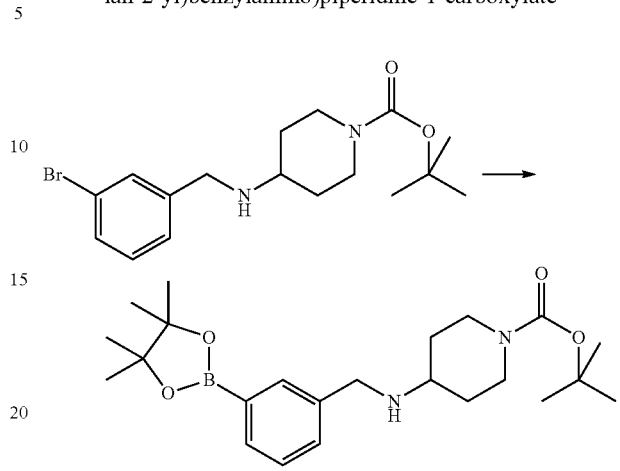

Procedure:

To a solution of tert-butyl 4-(3-bromobenzylamino)piperidine-1-carboxylate (500 mg, 1.36 mmol), 4,4,4',4',5,5,5',5'-octamethyl-2,2'-bis(1,3,2-dioxaborolane) (413 mg, 1.63 mmol) and KOAc (266 mg, 2.71 mmol) in 10 mL of DMSO was added Pd(dppf)$Cl_2$ (43 mg, 0.04 mmol) under nitrogen with stirring. The mixture was heated at 80° C. for 15 hours under nitrogen. After cooled, the mixture was poured into water and extracted with EtOAc (3×10 mL). The organic layer was washed with brine (2×10 mL) and dried over $MgSO_4$. After filtration and concentration, the residue was filtered through a plug of silica gel to give the crude product which was used for next step without further purification. LC-MS: 417 [M+H]$^+$, $t_R$=1.38 min.

Step 7

(S)-tert-Butyl-4-(3-(7-(3-(2-methylpyrrolidin-1-yl)phenylamino)thiazolo[5,4-d]pyrimidin-5-yl)benzylamino)piperidine-1-carboxylate

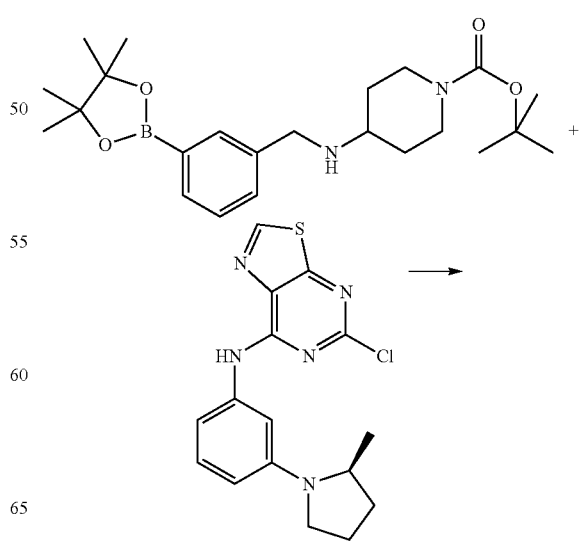

-continued

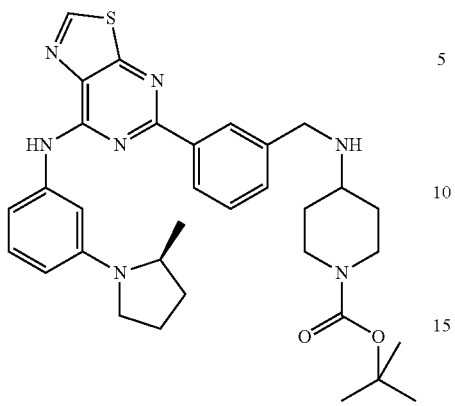

Procedure:

To a solution of (S)-5-chloro-N-(3-(2-methylpyrrolidin-1-yl)phenyl)thiazolo[5,4-d]pyrimidin-7-amine (200 mg, 0.58 mmol) and crude tert-butyl 4-(3-(4,4,5,5-tetramethyl-1,3,2-dioxaborolan-2-yl)benzylamino)piperidine-1-carboxylate in 10 mL of 1,4-dioxane and 2 mL of water was added $Na_2CO_3$ (184 mg, 1.74 mmol) followed by $Pd(PPh_3)_4$ (184 mg, 0.03 mmol) under nitrogen with stirring. The mixture was refluxed for 15 hours under nitrogen. After cooled, the solvent was evaporated by rotary evaporation under reduced pressure. The residue was poured into water and extracted with EtOAc (3×15 mL). The organic layer was washed with brine and dried over $Na_2SO_4$. After filtration and concentration, the residue was purified by column chromatography (silica gel, eluting with EtOAc) to give (S)-tert-butyl 4-(3-(7-(3-(2-methylpyrrolidin-1-yl)phenylamino)thiazolo[5,4-d]pyrimidin-5-yl)benzylamino)piperidine-1-carboxylate (110 mg, 32% for the two steps). LC-MS: 250.6 $[M/2+H]^+$, 600 $[M+H]^+$, $t_R$=1.57 min.

Step 8

(S)—N-(3-(2-Methylpyrrolidin-1-yl)phenyl)-5-(3-((piperidin-4-ylamino)methyl)phenyl)thiazolo[5,4-d]pyrimidin-7-amine 2,2,2-trifluoroacetate

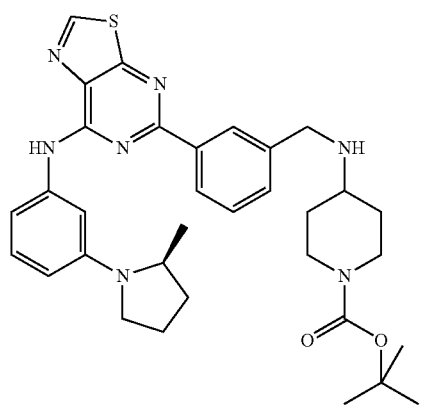

-continued

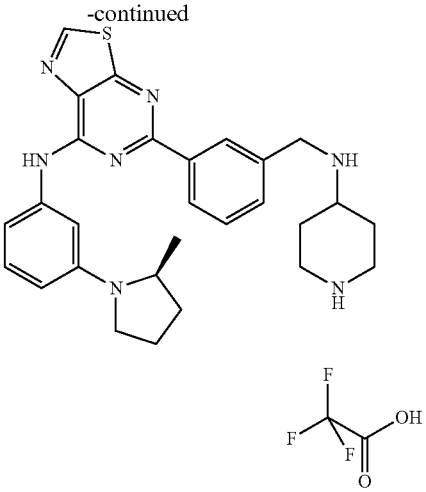

Procedure:

To a stirred solution of (S)-tert-butyl 4-(3-(7-(3-(2-methylpyrrolidin-1-yl)phenylamino)thiazolo[5,4-d]pyrimidin-5-yl)benzylamino)piperidine-1-carboxylate (110 mg, 0.184 mmol) in 2 mL of DCM was added 2 mL of 2,2,2-trifluoroacetic acid. The solution was stirred at room temperature overnight. The mixture was washed with $NaHCO_3$(aq.), the organic layer was concentrated. The residue was purified by preparative HPLC (Gemini 5u C18 150×21.2 mm; inject volume: 3 ml/inj, flow rate: 20 ml/min; wavelength: 214 nm and 254 nm; the gradient conditions are: 40% acetonitrile/60% water (0.1% TFA V/V) initially, and then proceed to 55% acetonitrile/45% water (0.1% TFA V/V) in a linear fashion after just 9 min.) to give (S)—N-(3-(2-methylpyrrolidin-1-yl)phenyl)-5-(3-((piperidin-4-ylamino)methyl)phenyl)thiazolo[5,4-d]pyrimidin-7-amine 2,2,2-trifluoroacetate (40 mg, 43%) as an oil. $^1$H NMR (300 MHz, DMSO): δ 9.18 (s, 1H), 8.60 (s, 1H), 8.51 (dd, 1H, $J_1$=7.5 Hz, $J_2$=1.2 Hz), 7.92 (s, 1H), 7.84 (brs, 1H), 7.68-7.52 (m, 3H), 7.15 (brs, 1H), 4.40 (s, 2H), 4.08-4.01 (m, 2H), 3.87-3.85 (m, 1H), 3.64-3.55 (m, 4H), 3.17-3.08 (m, 2H), 2.48-2.21 (m, 5H), 2.03-1.87 (m, 3 h), 1.34 (d, 3H, J=6.3 Hz). LC-MS: 250 $[M/2+H]^+$, 500 $[M+H]^+$, $t_R$=1.20 min. HPLC: 100% at 214 nm, 100% at 254 nm, $t_R$=4.59 min.

Example 37

N5-(1-(7-(3,4-Dimethoxyphenylamino)thiazolo[5,4-d]pyrimidin-5-yl)pyrrolidin-3-yl)pyridine-2,5-dicarboxamide hydrochloride

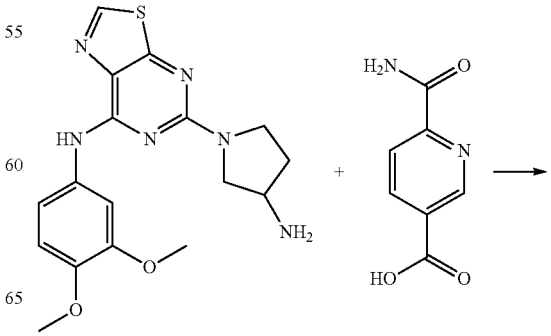

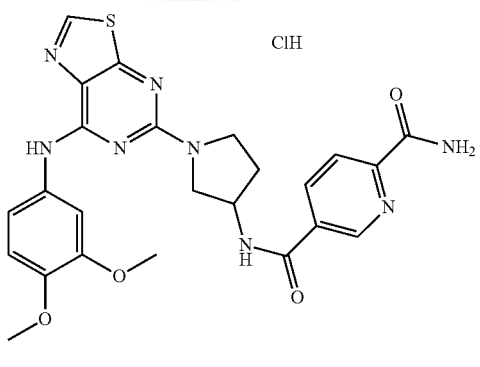

Procedure:

To a solution of 5-(3-aminopyrrolidin-1-yl)-N-(3,4-dimethoxyphenyl)thiazolo[5,4-d]pyrimidin-7-amine (95 mg, 0.26 mmol) and 6-carbamoylnicotinic acid (42 mg, 0.26 mmol) in dichloromethane (15 mL) were added the solution of 1-methyl-1H-imidazole (85 mg, 1.04 mol) and EDCI (199 mg, 1.04 mol) in dichloromethane (15 mL), the reaction mixture was stirred at room temperature for 15 hours, the solvent was removed on vacuum and the residue was washed with MeOH and then purified by preparative HPLC (Gemini 5u C18 150×21.2 mm; inject volume: 3 ml/inj, flow rate: 20 ml/min; wavelength: 214 nm and 254 nm; the gradient conditions are: 20% acetonitrile/80% water (0.1% TFA V/V) initially, and then proceed to 40% acetonitrile/60% water (0.1% TFA V/V) in a linear fashion after just 9 min.) to get the corresponding trifluoroacetate salt which was exchanged with conc. HCl to obtain N5-(1-(7-(3,4-dimethoxyphenylamino)thiazolo[5,4-d]pyrimidin-5-yl)pyrrolidin-3-yl)pyridine-2,5-dicarboxamide hydrochloride (25 mg, 16.2%) as HCL salt and as an orange solid. $^1$H NMR (300 MHz, DMSO): δ 9.00-8.93 (m, 2H), 8.36-8.33 (m, 1H), 8.10 (d, 1H, J=8.1 Hz), 7.73 (s, 1H), 7.45-7.38 (m, 1H), 6.95 (d, 1H, J=8.7 Hz), 4.63 (s, 1H), 3.93-3.75 (m, 10H), 2.31-2.17 (m, 2H). LC-MS: 520.9 [M+H]$^+$, $t_R$=1.33 min. HPLC: 98.94% at 214 nm, 98.61% at 254 nm, $t_R$=3.64 min.

Example 38

Methyl 5-(1-(7-(3,4-dimethoxyphenylamino)thiazolo[5,4-d]pyrimidin-5-yl)pyrrolidin-3-ylcarbamoyl)picolinate

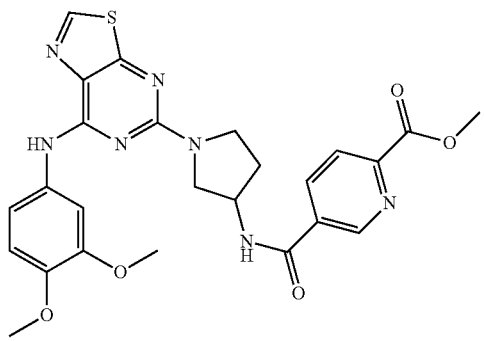

Procedure:

To a solution of 5-(3-aminopyrrolidin-1-yl)-N-(3,4-dimethoxyphenyl)thiazolo[5,4-d]pyrimidin-7-amine (80 mg, 0.22 mmol) and 6-(methoxycarbonyl)nicotinic acid (39 mg, 0.22 mmol) in dichloromethane (15 mL) was added the solution of 1-methyl-1H-imidazole (71 mg, 0.88 mmol) and EDCI (164 mg, 0.88 mmol) in dichloromethane (5 mL). The reaction mixture was stirred at room temperature for 15 hours, the solid was collected by filtration and washed with MeOH to afford methyl 5-(1-(7-(3,4-dimethoxyphenylamino)thiazolo[5,4-d]pyrimidin-5-yl)pyrrolidin-3-ylcarbamoyl)picolinate (90 mg, 80.3%) as a off-white solid. $^1$H NMR (300 MHz, DMSO): δ 9.57 (s, 1H), 9.07 (s, 1H), 8.99 (d, 1H, J=6.3 Hz), 8.79 (s, 1H), 8.36 (dd, 1H, $J_1$=8.1 Hz, $J_2$=2.1 Hz), 8.11 (d, 1H, J=8.1 Hz), 7.86 (s, 1H), 7.45 (s, 1H), 6.90 (d, 1H, J=8.7 Hz), 4.60-4.58 (m, 1H), 3.89 (s, 3H), 3.75 (s, 3H), 3.71 (s, 3H), 3.64 (brs, 4H), 2.28-2.24 (m, 1H), 2.11-2.06 (m, 1H). LC-MS: 536 [M+H]$^+$, $t_R$=1.37 min. HPLC: 95.95% at 214 nm, 96.44% at 254 nm, $t_R$=4.85 min.

Example 39

5-(1-(7-(3,4-Dimethoxyphenylamino)thiazolo[5,4-d]pyrimidin-5-yl)pyrrolidin-3-ylcarbamoyl)picolinic acid

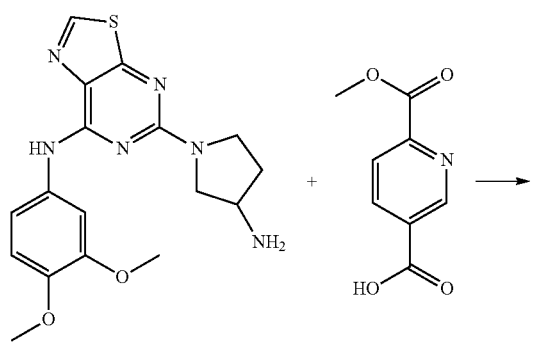

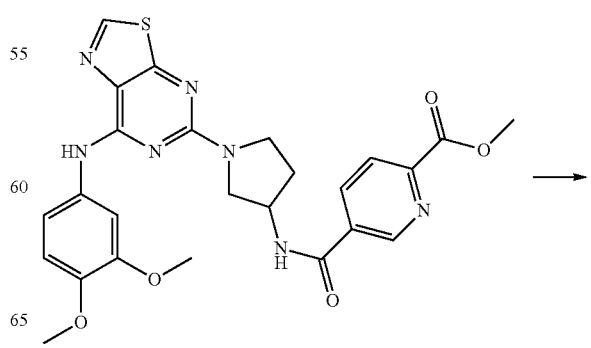

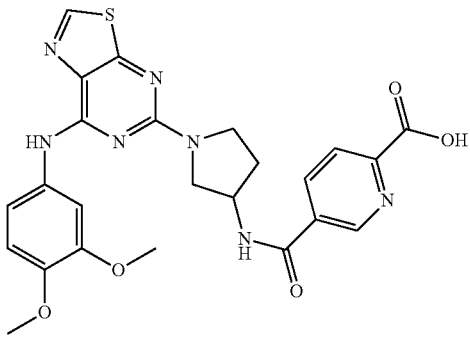

Procedure:

To a solution of methyl 5-(1-(7-(3,4-dimethoxyphenylamino)thiazolo[5,4-d]pyrimidin-5-yl)pyrrolidin-3-ylcarbamoyl)picolinate (80 mg, 0.15 mmol) in dioxane/H$_2$O (60 mL/6 mL) was added NaOH (60 mg, 1.5 mol), the reaction mixture was heated to 35° C. with stirring for 1 hour, then dioxane was removed in vacuo, and the aqueous layer was adjusted to pH~4-5 with conc. HCl, the precipitate was collected by filtration and washed with water (5 mL) and dried to afford 5-(1-(7-(3,4-dimethoxyphenylamino)thiazolo[5,4-d]pyrimidin-5-yl)pyrrolidin-3-ylcarbamoyl)picolinic acid as brown solid (67 mg, 84.8%). $^1$H NMR (300 MHz, DMSO): δ 9.56 (s, 1H), 9.06 (s, 1H), 8.96 (d, 1H, J=6.3 Hz), 8.79 (s, 1H), 8.33 (dd, 1H, J$_1$=8.1 Hz, J$_2$=1.8 Hz), 8.07 (d, 1H, J=8.1 Hz), 7.86 (s, 1H), 7.50 (brs, 1H), 6.90 (d, 1H, J=8.7 Hz), 4.60-4.58 (brs, 1H), 3.76-3.52 (m, 10H), 2.30-2.24 (m, 1H), 2.11-2.07 (m, 1H). LC-MS: 522 [M+H]$^+$, t$_R$=1.31 min. HPLC: 98.03% at 214 nm, 97.82% at 254 nm, t$_R$=3.20 min.

Procedure:

To a solution of 1-(7-(3,4-dimethoxyphenylamino)thiazolo[5,4-d]pyrimidin-5-yl)piperidine-3-carboxylic acid (100 mg, 0.24 mmol) and 5-aminoindolin-2-one (36 mg, 0.24 mmol) in dichloromethane (20 mL) were added 1-methyl-1H-imidazole (79 mg, 0.96 mmol) and EDCI (183 mg, 0.96 mmol) in dichloromethane (10 mL). The reaction mixture was stirred at room temperature for 15 hours, the solid was collected by filtration and washed with methanol (4 mL) to afford 1-(7-(3,4-dimethoxyphenylamino)thiazolo[5,4-d]pyrimidin-5-yl)-N-(2-oxoindolin-5-yl)piperidine-3-carboxamide as a orange solid (68 mg, 51.8%). $^1$H NMR (300 MHz, DMSO): δ 10.31 (s, 1H), 9.87 (s, 1H), 9.67 (s, 1H), 8.86 (s, 1H), 7.68 (d, 1H, J=2.4 Hz), 7.53 (s, 1H), 7.37 (s, 1H), 7.35 (s, 1H), 6.83-6.81 (m, 1H), 6.75 (d, 1H, J=8.4 Hz), 4.82-4.67 (m, 2H), 3.71-3.65 (m, 6H), 3.48 (s, 2H), 3.12-2.95 (m, 2H), 1.98-1.74 (m, 5H). LC-MS: 546 [M+H]$^+$, t$_R$=1.493 min. HPLC: 98.74% at 214 nm, 98.67% at 25 4 nm, t$_R$=3.60 min.

Example 41

1-(7-(3,4-Dimethoxyphenylamino)thiazolo[5,4-d]pyrimidin-5-yl)-N-(1H-indazol-5-yl)piperidine-3-carboxamide hydrochloride Example 40

1-(7-(3,4-Dimethoxyphenylamino)thiazolo[5,4-d]pyrimidin-5-yl)-N-(2-oxoindolin-5-yl)piperidine-3-carboxamide

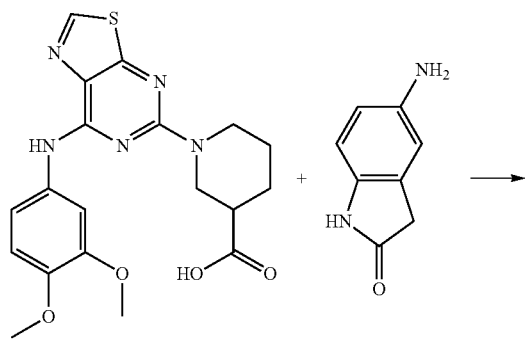

-continued

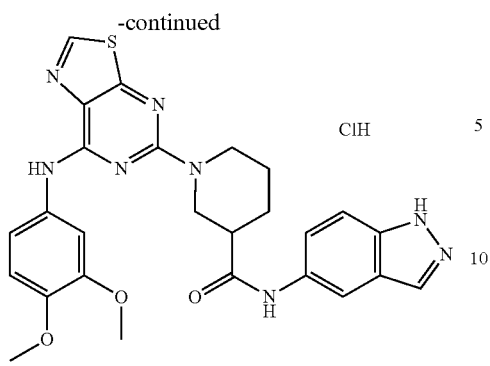

Procedure:

To a solution of 1-(7-(3,4-dimethoxyphenylamino)thiazolo[5,4-d]pyrimidin-5-yl)piperidine-3-carboxylic acid (110 mg, 0.27 mmol) and 1H-indazol-5-amine (36 mg, 0.27 mmol) in dichloromethane (20 mL) were added the solution of 1-methyl-1H-imidazole (87 mg, 1.08 mol) and EDCI (203 mg, 1.08 mol) in dichloromethane (5 mL), the reaction mixture was stirred at room temperature for 15 hours, the precipitate was collected by filtration and washed with methanol, and then purified by preparative HPLC (Gemini 5u C18 150×21.2 mm; inject volume: 3 ml/inj, flow rate: 20 ml/min; wavelength: 214 nm and 254 nm; the gradient conditions are: 30% acetonitrile/70% water (0.1% TFA V/V) initially, and then proceed to 50% acetonitrile/50% water (0.1% TFA V/V) in a linear fashion after just 9 min.) to get the corresponding trifluoroacetate salt. The salt was suspended in dichloromethane (8 mL) and conc. HCl (0.5 mL) was added dropwise, the mixture was stirred for 10 minutes and concentrated to give 1-(7-(3,4-dimethoxyphenylamino)thiazolo[5,4-d]pyrimidin-5-yl)-N-(1H-indazol-5-yl)piperidine-3-carboxamide hydrochloride (45 mg, 29.4%) as an orange solid with HCl salt. $^1$H NMR (300 MHz, DMSO+H$_2$O): δ 8.85 (d, 1H, J=3.0 Hz), 8.07 (s, 1H), 7.99 (s, 1H), 7.52-7.38 (m, 3H), 7.26 (d, 1H, J=8.7 Hz), 6.79 (brs, 1H), 4.66-4.47 (m, 2H), 3.66-3.54 (m, 6H), 3.20 (t, 1H, J=12.6 Hz), 3.09-3.01 (m, 1H), 2.60-2.53 (m, 1H), 2.02-1.99 (m, 1H), 1.82-1.70 (m, 2H), 1.51-1.47 (m, 1H). LC-MS: 531 [M+H]$^+$, $t_R$=1.44 min. HPLC: 95.98% at 214 nm, 95.22% at 254 nm, $t_R$=4.55 min.

Example 42

5-(1-(7-(3,4-Dimethoxyphenylamino)thiazolo[5,4-d]pyrimidin-5-yl)piperidine-3-carboxamido)picolinic acid Step 1

Methyl 5-(1-(7-(3,4-dimethoxyphenylamino)thiazolo[5,4-d]pyrimidin-5-yl)piperidine-3-carboxamido)picolinate

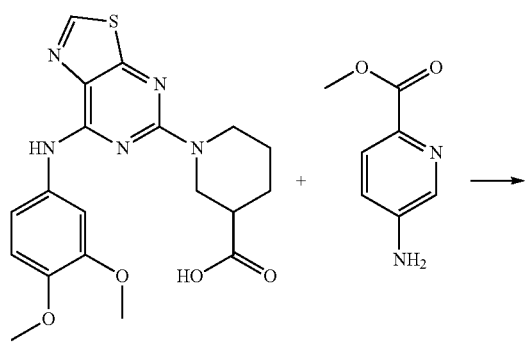

-continued

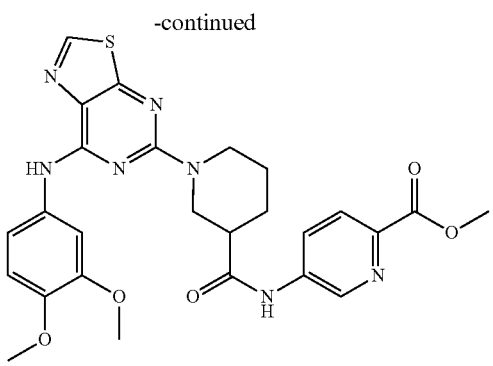

Procedure:

To a solution of 1-(7-(3,4-dimethoxyphenylamino)thiazolo[5,4-d]pyrimidin-5-yl)piperidine-3-carboxylic acid (200 mg, 0.48 mmol) and methyl 5-aminopicolinate (73 mg, 0.48 mmol) in dichloromethane (30 mL) were added the solution of 1-methyl-1H-imidazole (158 mg, 1.92 mmol) and EDCI (368 mg, 1.92 mmol) in dichloromethane (10 mL), the reaction mixture was stirred at room temperature for 15 hours, the solvent was removed in vacuo and methanol (6 mL) was added and stirred for 30 minutes, the solid was collected by filtration and washed with methanol to afford methyl 5-(1-(7-(3,4-dimethoxyphenylamino)thiazolo[5,4-d]pyrimidin-5-yl)piperidine-3-carboxamido)picolinate (230 mg, 87.1%) as an orange solid. LC-MS: 550 [M+H]$^+$, $t_R$=1.58 min.

Step 2

5-(1-(7-(3,4-Dimethoxyphenylamino)thiazolo[5,4-d]pyrimidin-5-yl)piperidine-3-carboxamido)picolinic acid

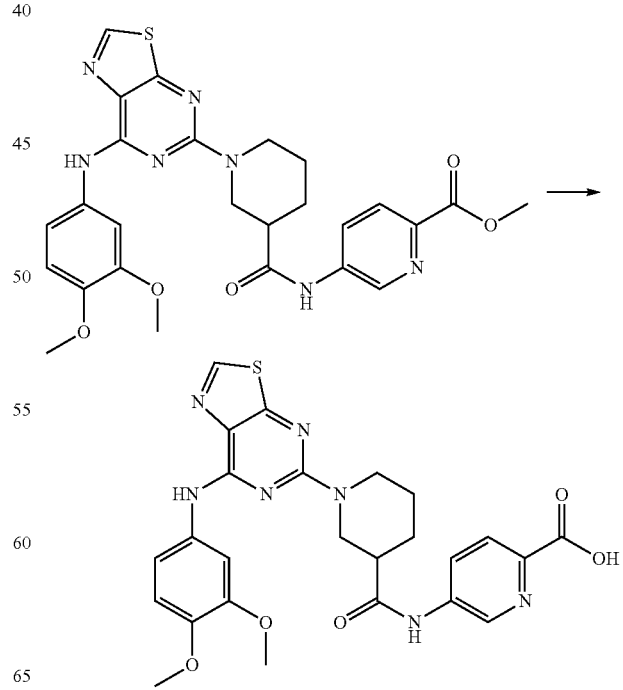

Procedure:

To a solution of methyl 5-(1-(7-(3,4-dimethoxyphenylamino)thiazolo[5,4-d]pyrimidin-5-yl)piperidine-3-carboxamido)picolinate (130 mg, 0.24 mmol) in dioxane/H$_2$O (8 mL/8 mL) was added NaOH (70 mg, 1.75 mmol), the reaction mixture was heated to 35° C. with stirring for 30 minutes, the dioxane was removed in vacuo, and the aqueous layer was adjusted to pH=4-5 with conc. HCl, the precipitate was collected by filtration and washed with methanol (5 mL) to afford 5-(1-(7-(3,4-dimethoxyphenylamino)thiazolo[5,4-d]pyrimidin-5-yl)piperidine-3-carboxamido)picolinic acid (98 mg, 76.2%) as an orange solid. $^1$H NMR (300 MHz, DMSO): δ 10.58 (s, 1H), 9.68 (s, 1H), 8.87 (s, 2H), 8.24 (dd, 1H, J$_1$=8.7 Hz, J$_2$=2.4 Hz), 8.03 (d, 1H, J=8.7 Hz), 7.67 (d, 1H, J=2.1 Hz), 7.35 (dd, 1H, J$_1$=8.7 Hz, J$_2$=2.1 Hz), 6.82 (brs, 1H), 4.84-4.65 (m, 2H), 3.77-3.65 (m, 6H), 3.18-3.00 (m, 2H), 2.67-2.64 (m, 1H), 2.05-1.75 (m, 4H). LC-MS: 536 [M+H]$^+$, t$_R$=1.50 min. HPLC: 97.47% at 214 nm, 97.48% at 254 nm, t$_R$=4.096 min.

Example 43

4-(1-(7-(3,4-Dimethoxyphenylamino)thiazolo[5,4-d]pyrimidin-5-yl)piperidine-3-carboxamido)-2-methoxybenzoic acid Step 1

Methyl 4-(1-(7-(3,4-dimethoxyphenylamino)thiazolo[5,4-d]pyrimidin-5-yl)piperidine-3-carboxamido)-2-methoxybenzoate

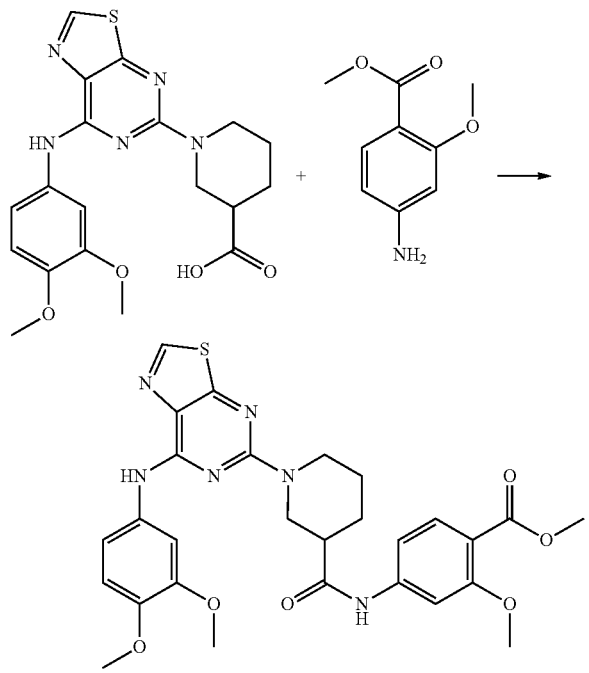

Procedure:

To a solution of 1-(7-(3,4-dimethoxyphenylamino)thiazolo[5,4-d]pyrimidin-5-yl)piperidine-3-carboxylic acid (110 mg, 0.27 mmol) and methyl 4-amino-2-methoxybenzoate (48 mg, 0.27 mmol) in dichloromethane (15 mL) were added the solution of 1-methyl-1H-imidazole (87 mg, 1.1 mmol) and EDCI (203 mg, 1.1 mmol) in dichloromethane (5 mL), the reaction mixture was stirred at room temperature for 15 hours, the solvent was removed in vacuo, then methanol (5 mL) was added, the precipitate was collected by filtration and washed with methanol (5 mL) to afford methyl 4-(1-(7-(3,4-dimethoxyphenylamino)thiazolo[5,4-d]pyrimidin-5-yl)piperidine-3-carboxamido)-2-methoxybenzoate (126 mg, 80.8%) as an orange solid. LC-MS: 579 [M+H]$^+$, t$_R$=1.58 min.

Step 2

4-(1-(7-(3,4-Dimethoxyphenylamino)thiazolo[5,4-d]pyrimidin-5-yl)piperidine-3-carboxamido)-2-methoxybenzoic acid

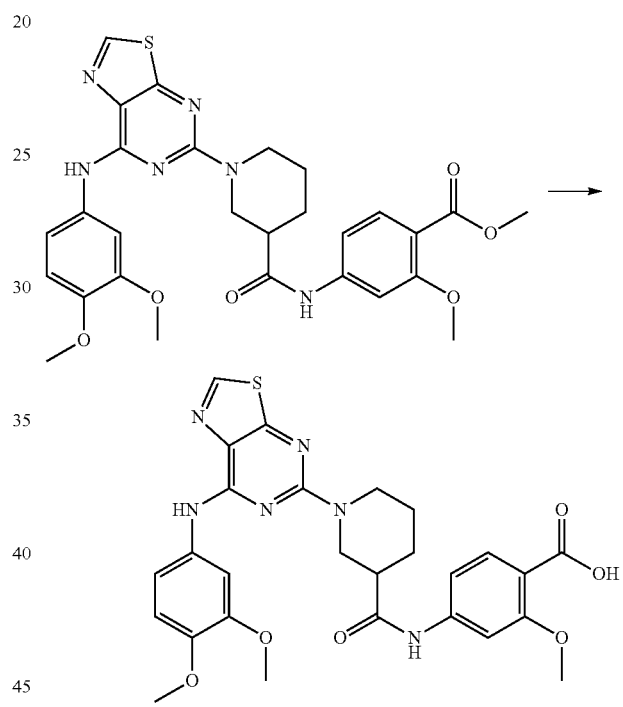

To a solution of methyl 4-(1-(7-(3,4-dimethoxyphenylamino)thiazolo[5,4-d]pyrimidin-5-yl)piperidine-3-carboxamido)-2-methoxybenzoate (126 mg, 0.22 mmol) in dioxane/H$_2$O (8 mL/8 mL) was added NaOH (75 mg, 1.9 mmol), the reaction mixture was heated to 35° C. with stirring for 1 hour, the dioxane was removed in vacuo, and the aqueous layer was adjusted to pH=4-5 with conc. HCl, the precipitate was collected by filtration and washed with methanol (5 mL) to afford 4-(1-(7-(3,4-dimethoxyphenylamino)thiazolo[5,4-d]pyrimidin-5-yl)piperidine-3-carboxamido)-2-methoxybenzoic acid (68 mg, 54.8%) as a off-white solid. $^1$H NMR (300 MHz, DMSO): δ 10.23 (s, 1H), 9.63 (s, 1H), 8.83 (s, 1H), 7.63 (d, 1H, J=2.1 Hz), 7.58 (d, 1H, J=8.4 Hz), 7.46 (s, 1H), 7.33 (dd, 1H, J$_1$=8.7 Hz, J$_2$=2.4 Hz), 7.14 (dd, 1H, J$_1$=8.4 Hz, J$_2$=1.5 Hz), 6.80-6.78 (m, 1H), 4.79 (d, 1H, J=11.7 Hz), 4.65 (d, 1H, J=12.6 Hz), 3.68-3.61 (m, 9H), 3.10-2.89 (m, 2H), 2.58-2.54 (m, 1H), 2.03-1.99 (m, 1H), 1.78-1.71 (m, 2H), 1.48-1.44 (m, 1H). LC-MS: 585 [M+H]$^+$, t$_R$=1.48 min. HPLC: 96.06% at 214 nm, 97.26% at 254 nm, t$_R$=5.66 min.

Example 44

1-(7-(3,4-Dimethoxyphenylamino)thiazolo[5,4-d]pyrimidin-5-yl)-N-(4-(5-oxo-4,5-dihydro-1,2,4-oxadiazol-3-yl)phenyl)piperidine-3-carboxamide hydrochloride

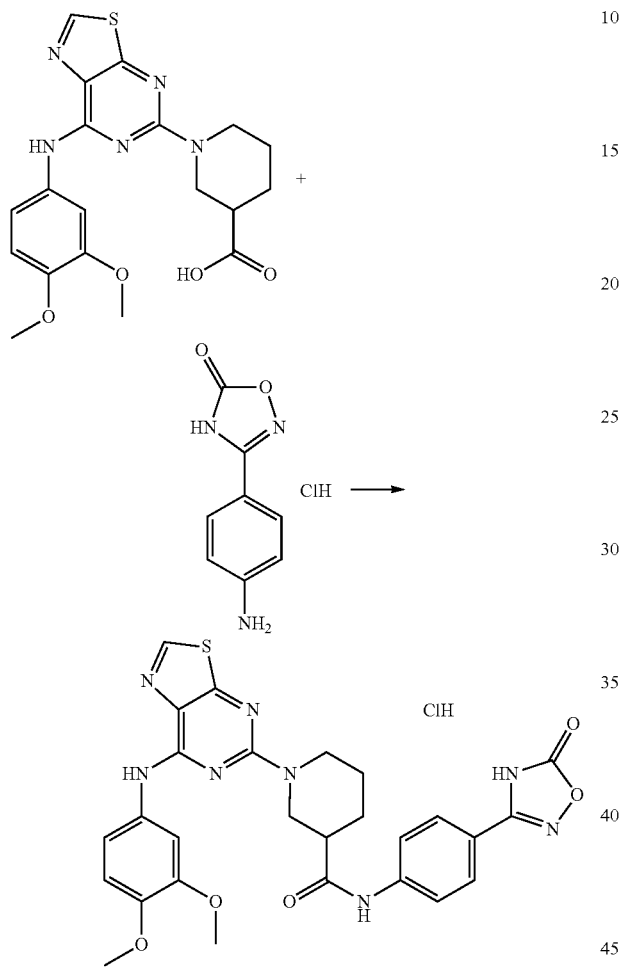

Procedure:

To a solution of 1-(7-(3,4-dimethoxyphenylamino)thiazolo[5,4-d]pyrimidin-5-yl)piperidine-3-carboxylic acid (50 mg, 0.12 mmol) and 3-(4-aminophenyl)-1,2,4-oxadiazol-5 (4H)-one hydrochloride (26 mg, 0.12 mmol) in dichloromethane (15 mL) were added the solution of 1-methyl-1H-imidazole (40 mg, 0.48 mmol) and EDCI (92 mg, 0.48 mmol) in dichloromethane (5 mL), the reaction mixture was stirred at room temperature for 24 hours, the solvent was removed in vacuo, methanol (5 mL) was added, the precipitate was collected by filtration and then purified by preparative HPLC (Gemini 5u C18 150×21.2 mm; inject volume: 3 ml/inj, flow rate: 20 ml/min; wavelength: 214 nm and 254 nm; the gradient conditions are: 35% acetonitrile/65% water (0.1% TFA V/V) initially, and then proceed to 50% acetonitrile/50% water (0.1% TFA V/V) in a linear fashion after just 9 min.) to afford the corresponding trifluoroacetate salt. The salt was suspended in dichloromethane (8 mL) and conc. HCl (0.5 mL) was added dropwise. The mixture was stirred for 15 minutes at room temperature and then concentrated under reduced pressure to give 1-(7-(3,4-dimethoxyphenylamino)thiazolo[5,4-d]pyrimidin-5-yl)-N-(4-(5-oxo-4,5-dihydro-1,2,4-oxadiazol-3-yl)phenyl)piperidine-3-carboxamide hydrochloride (53 mg, 68.8%) as an orange solid. $^1$H NMR (300 MHz, DMSO): δ 12.88 (s, 1H), 10.45 (s, 1H), 9.84 (s, 1H), 8.88 (s, 1H), 7.81-7.74 (m, 4H), 7.61 (d, 1H, J=2.1 Hz), 7.32 (dd, 1H, $J_1$=8.7 Hz, $J_2$=2.1 Hz), 6.80 (brs, 1H), 4.77-4.59 (m, 2H), 3.68 (s, 3H), 3.62 (s, 3H), 3.18-2.97 (m, 2H), 2.72-2.64 (m, 1H), 2.05-2.02 (m, 1H), 1.90-1.69 (m, 2H), 1.22-1.18 (m, 1H). LC-MS: 575 [M+H]$^+$, $t_R$=1.64 min. HPLC: 99.98% at 214 nm, 98.99% at 254 nm, $t_R$=6.29 min.

Example 45

1-(7-(3,4-Dimethoxyphenylamino)thiazolo[5,4-d]pyrimidin-5-yl)-N-(1H-indazol-6-yl)piperidine-3-carboxamide hydrochloride

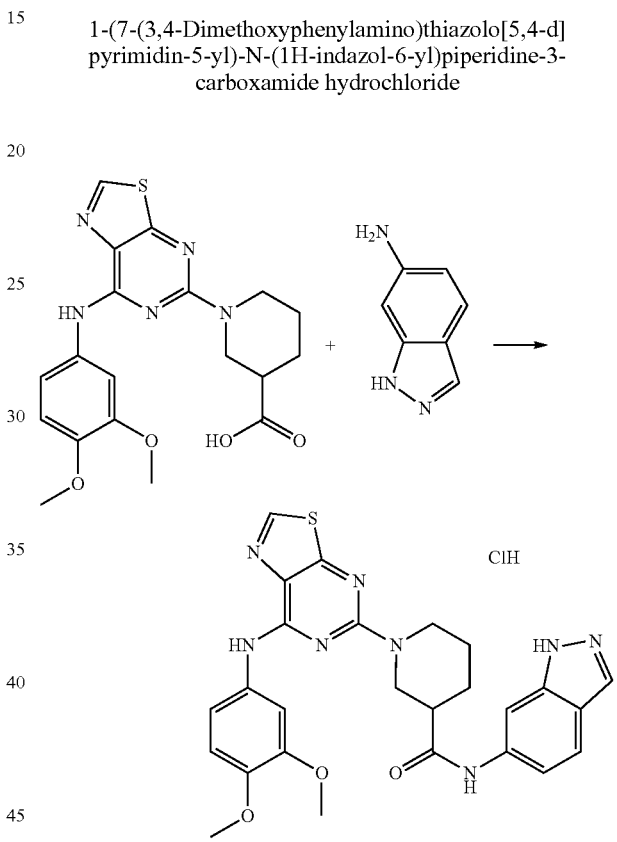

Procedure:

To a solution of 1-(7-(3,4-dimethoxyphenylamino)thiazolo[5,4-d]pyrimidin-5-yl)piperidine-3-carboxylic acid (80 mg, 0.19 mmol) and 1H-indazol-6-amine (26 mg, 0.19 mmol) in dichloromethane (15 mL) was added the solution of 1-methyl-1H-imidazole (63 mg, 0.76 mmol) and EDCI (147 mg, 0.76 mmol) in dichloromethane (5 mL), the reaction mixture was stirred at room temperature for 24 hours, the solvent was removed in vacuo, then methanol (5 mL) was added, the precipitate was collected by filtration and purified by preparative HPLC (Gemini 5u C18 150×21.2 mm; inject volume: 3 ml/inj, flow rate: 20 ml/min; wavelength: 214 nm and 254 nm; the gradient conditions are: 30% acetonitrile/70% water (0.1% TFA V/V) initially, and then proceed to 55% acetonitrile/45% water (0.1% TFA V/V) in a linear fashion after just 9 min.), to give the corresponding trifluoroacetate salt. The salt was suspended in dichloromethane (8 mL) and conc. HCl (0.5 mL) was added dropwise. The mixture was stirred for 10 minutes at room temperature and then concentrated under reduced pressure to afford 1-(7-(3,4-dimethoxyphenylamino)thiazolo[5,4-d]pyrimidin-5-yl)-N-(1H-indazol-6-yl)piperidine-3-carboxamide hydrochloride (25 mg, 21.9%) as a orange solid. $^1$H NMR (300 MHz, DMSO): δ 10.19 (s, 1H), 9.81 (s, 1H), 8.87 (s, 1H), 8.16 (s, 1H), 7.96 (s, 1H), 7.66-7.60 (m, 2H), 7.34 (dd, 1H, $J_1$=8.7 Hz, $J_2$=2.1 Hz), 7.11 (dd, 1H, $J_1$=8.4 Hz, $J_2$=1.5 Hz), 6.80 (brs, 1H), 4.81-4.63 (m, 2H), 3.68 (s, 3H), 3.55 (s, 3H), 3.16-2.95 (m, 2H), 2.72-2.59 (m, 1H), 2.04-2.02 (m, 1H), 1.82-1.51 (m, 2H), 1.25-1.20 (m, 1H). LC-MS: 531 [M+H]$^+$, $t_R$=1.60 min. HPLC: 99.21% at 214 nm, 98.92% at 254 nm, $t_R$=5.94 min.

Example 46

1-(7-(3,4-Dimethoxyphenylamino)thiazolo[5,4-d]pyrimidin-5-yl)-N-(1-oxoisoindolin-5-yl)piperidine-3-carboxamide

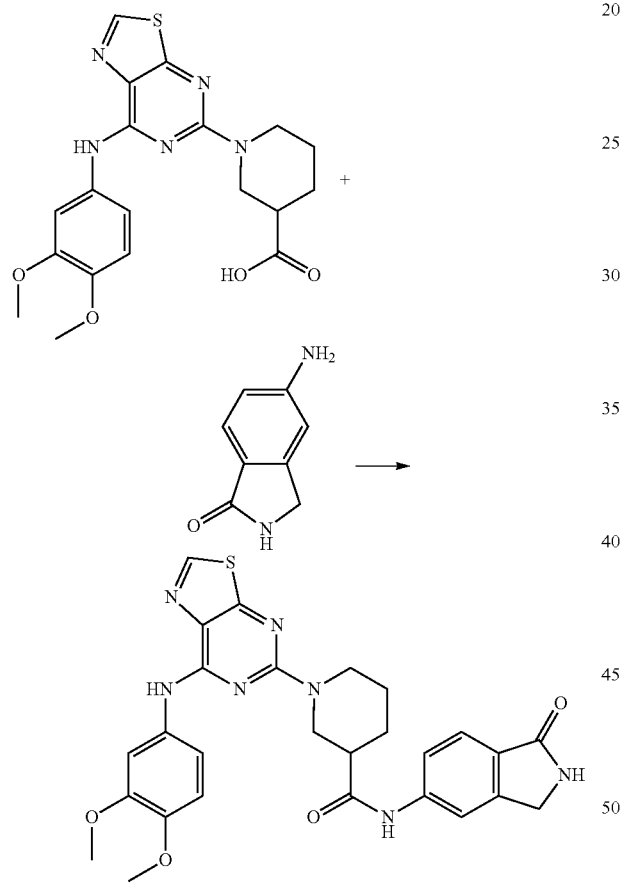

Procedure:

To a solution of 1-(7-(3,4-dimethoxyphenylamino)thiazolo[5,4-d]pyrimidin-5-yl)piperidine-3-carboxylic acid (70 mg, 0.17 mmol) and 5-aminoisoindolin-1-one (25 mg, 0.17 mmol) in dichloromethane (15 mL) were added the solution of 1-methyl-1H-imidazole (55 mg, 0.68 mmol) and EDCI (129 mg, 0.68 mmol) in dichloromethane (5 mL), the reaction mixture was stirred at room temperature for 24 hours, the solvent was removed in vacuo, then methanol (5 mL) was added, the precipitate was collected by filtration and washed with methanol (3 mL) to afford 1-(7-(3,4-dimethoxyphenylamino)thiazolo[5,4-d]pyrimidin-5-yl)-N-(1-oxoisoindolin-5-yl)piperidine-3-carboxamide (48 mg, 51.8%) as a brown solid. $^1$H NMR (300 MHz, DMSO): δ 10.29 (s, 1H), 9.64 (s, 1H), 8.84 (s, 1H), 8.38 (s, 1H), 7.96 (s, 1H), 7.64-7.53 (m, 3H), 7.33 (dd, 1H, $J_1$=8.4 Hz, $J_2$=1.8 Hz), 6.80 (brs, 1H), 4.81-4.63 (m, 2H), 4.33 (s, 2H), 3.68 (s, 3H), 3.59 (s, 3H), 3.14-2.92 (m, 2H), 2.65-2.60 (m, 1H), 2.04-2.00 (m, 1H), 1.81-1.69 (m, 2H), 1.49-1.45 (m, 1H). LC-MS: 545.9 [M+H]$^+$, $t_R$=1.42 min. HPLC: 99.69% at 214 nm, 99.44% at 254 nm, $t_R$=4.87 min.

Example 47

4-(1-(7-(3,4-Dimethoxyphenylamino)thiazolo[5,4-d]pyrimidin-5-yl)piperidine-3-carboxamido)-2-hydroxybenzoic acid hydrochloride Step 1

Methyl 4-(1-(7-(3,4-dimethoxyphenylamino)thiazolo[5,4-d]pyrimidin-5-yl)piperidine-3-carboxamido)-2-hydroxybenzoate

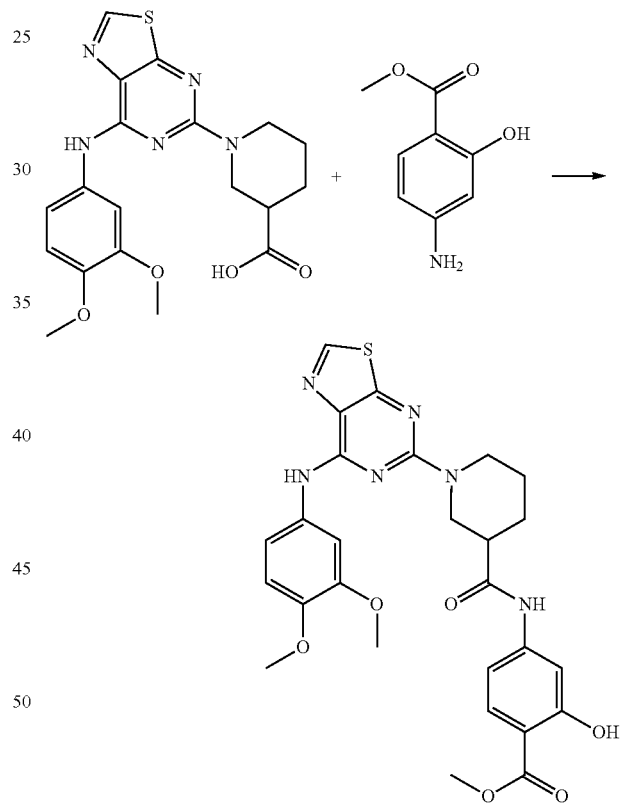

Procedure:

To a solution of 1-(7-(3,4-dimethoxyphenylamino)thiazolo[5,4-d]pyrimidin-5-yl)piperidine-3-carboxylic acid (80 mg, 0.19 mmol) and methyl 4-amino-2-hydroxybenzoate (32 mg, 0.19 mmol) in dichloromethane (15 mL) were added the solution of 1-methyl-1H-imidazole (63 mg, 0.76 mmol) and EDCI (147 mg, 0.76 mmol) in dichloromethane (5 mL), the reaction mixture was stirred at room temperature for 24 hours, the solvent was removed in vacuo, methanol (5 mL) was added, the precipitate was collected by filtration to afford methyl4-(1-(7-(3,4-dimethoxyphenylamino)thiazolo[5,4-d]pyrimidin-5-yl)piperidine-3-carboxamido)-2-hydroxyben-

Step 2

4-(1-(7-(3,4-Dimethoxyphenylamino)thiazolo[5,4-d]pyrimidin-5-yl)piperidine-3-carboxamido)-2-hydroxybenzoic acid hydrochloride

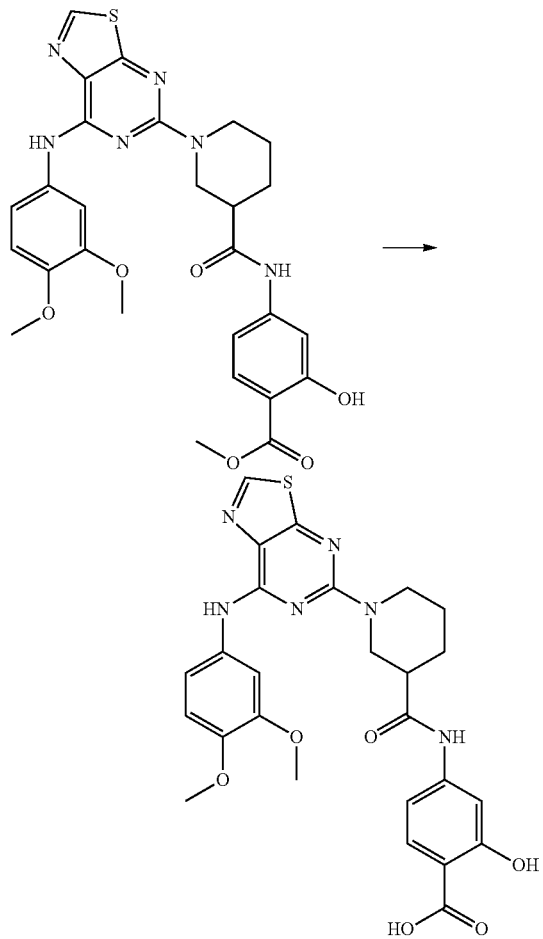

Procedure:

To a solution of methyl 4-(1-(7-(3,4-dimethoxyphenylamino)thiazolo[5,4-d]pyrimidin-5-yl)piperidine-3-carboxamido)-2-hydroxybenzoate (110 mg, 0.20 mmol) in dioxane/$H_2O$ (8 mL/8 mL) was added NaOH (100 mg, 2.5 mmol), the reaction mixture was heated to 40° C. with stirring for 5 hours, the dioxane was removed in vacuo, and the aqueous layer was adjusted to pH=4-5 with conc. HCl and the precipitate was collected by filtration and purified by preparative HPLC (Gemini 5u C18 150×21.2 mm; inject volume: 3 ml/inj, flow rate: 20 ml/min; wavelength: 214 nm and 254 nm; the gradient conditions are: 10% acetonitrile/90% water (0.1% TFA V/V) initially, and then proceed to 60% acetonitrile/40% water (0.1% TFA V/V) in a linear fashion after just 9 min.) to give the corresponding trifluoroacetate salt. The salt was suspended in dichloromethane (8 mL) and conc. HCl (0.5 mL) was added dropwise. The mixture was stirred for 10 minutes and concentrated under reduced pressure to afford 4-(1-(7-(3,4-dimethoxyphenylamino)thiazolo[5,4-d]pyrimidin-5-yl)piperidine-3-carboxamido)-2-hydroxybenzoic acid hydrochloride (25 mg, 21.9%) as an orange solid. $^1$H NMR (300 MHz, DMSO+$D_2O$): δ 8.81 (s, 1H), 7.71 (d, 1H, J=8.7 Hz), 7.54 (s, 1H), 7.33 (d, 1H, J=2.1 Hz), 7.27 (d, 1H, J=8.4 Hz), 7.05 (dd, $J_1$=8.7 Hz, $J_2$=2.1 Hz), 6.80 (brs, 1H), 4.65 (d, 1H, J=13.2 Hz), 4.52 (d, 1H, J=12.6 Hz), 3.66 (s, 3H), 3.60 (s, 3H), 3.15 (t, 1H, J=11.7 Hz), 3.01 (t, 1H, J=12.6 Hz), 2.58-2.54 (m, 1H), 2.00-1.69 (m, 3H), 1.48-1.43 (m, 1H). LC-MS: 551 [M+H]$^+$, $t_R$=1.532 min. HPLC: 99.65% at 214 nm, 99.71% at 254 nm, $t_R$=5.77 min.

Example 48

1-(7-(3,4-Dimethoxyphenylamino)thiazolo[5,4-d]pyrimidin-5-yl)-N-(5-oxopyrrolidin-3-yl)piperidine-3-carboxamide hydrochloride

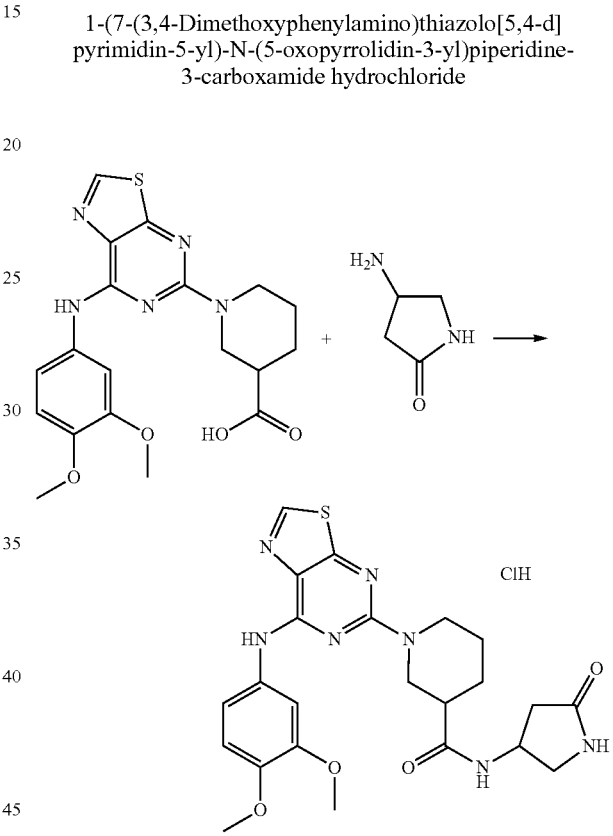

Procedure:

To a solution of 1-(7-(3,4-dimethoxyphenylamino)thiazolo[5,4-d]pyrimidin-5-yl)piperidine-3-carboxylic acid (80 mg, 0.19 mmol) and 4-aminopyrrolidin-2-one (19 mg, 0.19 mmol) in dichloromethane (15 mL) were added the solution of 1-methyl-1H-imidazole (63 mg, 0.76 mmol) and EDCI (151 mg, 0.76 mmol) in dichloromethane (5 mL), the reaction mixture was stirred at room temperature for 24 hours, the solvent was removed in vacuo, then methanol (5 mL) was added, the precipitate was collected by filtration and purified by preparative HPLC (Gemini 5u C18 150×21.2 mm; inject volume: 3 ml/inj, flow rate: 20 ml/min; wavelength: 214 nm and 254 nm; the gradient conditions are: 30% acetonitrile/70% water (0.1% TFA V/V) initially, and then proceed to 55% acetonitrile/45% water (0.1% TFA V/V) in a linear fashion after just 9 min.) to give the corresponding trifluoroacetate salt. The salt was suspended in dichloromethane (8 mL) and conc. HCl (0.5 mL) was added dropwise. The mixture was stirred for 10 minutes at room temperature and then concentrated under reduced pressure to afford 1-(7-(3,4-dimethoxyphenylamino)thiazolo[5,4-d]pyrimidin-5-yl)-N-(5-oxopyrrolidin-3-yl)piperidine-3-carboxamide hydrochloride (33 mg, 28.2%) as an orange solid. $^1$H NMR (300 MHz, DMSO+D$_2$O): δ 8.86 (d, 1H, J=3.0 Hz), 7.57 (s, 1H), 7.27-7.24 (m, 1H), 6.89 (d, 1H, J=8.1 Hz), 4.58-4.48 (m, 2H), 4.33 (brs, 1H), 3.73 (s, 3H), 3.71 (s, 3H), 3.59-3.46 (m, 1H), 3.11-2.94 (m, 3H), 2.45-2.33 (m, 2H), 2.04-1.97 (m, 1H), 1.89-1.84 (m, 1H), 1.76-1.60 (m, 2H), 1.44-1.21 (m, 1H). LC-MS: 498 [M+H]$^+$, $t_R$=1.35 min. HPLC: 98.69% at 214 nm, 99.23% at 254 nm, $t_R$=4.27 min.

Example 49

1-(7-(3,4-Dimethoxyphenylamino)thiazolo[5,4-d]pyrimidin-5-yl)-N-(pyrazin-2-yl)piperidine-3-carboxamide

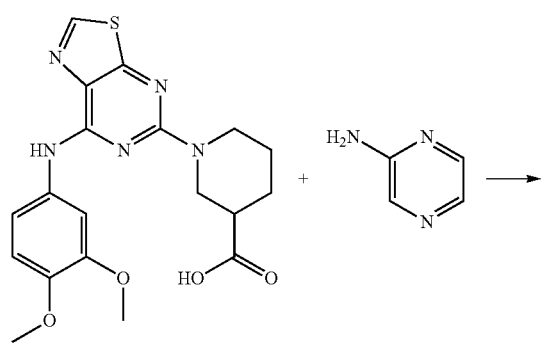

Procedure:

To a solution of 1-(7-(3,4-dimethoxyphenylamino)thiazolo[5,4-d]pyrimidin-5-yl)piperidine-3-carboxylic acid (30 mg, 0.07 mmol) and pyrazin-2-amine (7 mg, 0.07 mmol) in pyridine (6 mL) was added POCl$_3$ (0.2 mL, 2.19 mmol) at 0° C., the reaction mixture was stirred at room temperature for 15 hours, a sat. NaHCO$_3$ solution was added slowly, the solvent was removed in vacuo, and water (5 mL) and methanol (3 mL) were added. The precipitate was collected by filtration and washed with water (3 mL) and methanol (3 mL) to afford 1-(7-(3,4-dimethoxyphenylamino)thiazolo[5,4-d]pyrimidin-5-yl)-N-(pyrazin-2-yl)piperidine-3-carboxamide (30 mg, 87.2%) as a brown solid. $^1$H NMR (300 MHz, DMSO): δ 10.87 (s, 1H), 9.62 (s, 1H), 9.30 (s, 1H), 8.83 (s, 1H), 8.39-8.33 (m, 2H), 7.61 (d, 1H, J=2.1 Hz), 7.31 (dd, 1H, J$_1$=8.7 Hz, J$_2$=2.4 Hz), 6.82 (d, 1H, J=8.4 Hz), 4.76 (d, 1H, J=11.4 Hz), 4.60 (d, 1H, J=12.3 Hz), 3.68 (s, 3H), 3.64 (s, 3H), 3.13 (t, 1H, J=10.8 Hz), 3.01-2.93 (m, 1H), 2.79-2.71 (m, 1H), 2.04-2.00 (m, 1H), 1.81-1.67 (m, 2H), 1.46-1.42 (m, 1H). LC-MS: 493 [M+H]$^+$, $t_R$=1.50 min. HPLC: 95.75% at 214 nm, 96.29% at 254 nm, $t_R$=5.38 min.

Example 50

1-(7-(3,4-Dimethoxyphenylamino)thiazolo[5,4-d]pyrimidin-5-yl)-N-(1,3-dioxoisoindolin-5-yl)piperidine-3-carboxamide

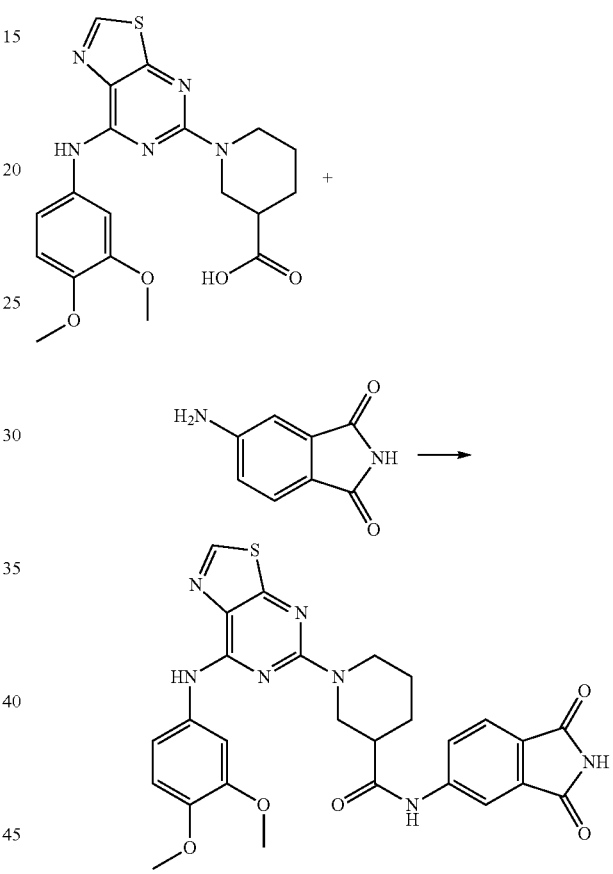

Procedure:

To a solution of 1-(7-(3,4-dimethoxyphenylamino)thiazolo[5,4-d]pyrimidin-5-yl)piperidine-3-carboxylic acid (50 mg, 0.12 mmol) and 5-aminoisoindoline-1,3-dione (19 mg, 0.12 mmol) in pyridine (8 mL) was added POCl$_3$ (0.3 mL, 3.23 mmol) at 0° C., the reaction mixture was stirred at room temperature for 4 hours, a sat. NaHCO$_3$ solution was added slowly, the solvent was removed in vacuo, water (5 mL) and methanol (2 mL) were added. The precipitate was collected by filtration and washed with water (5 mL) and methanol (5 mL) to afford 1-(7-(3,4-dimethoxyphenylamino)thiazolo[5,4-d]pyrimidin-5-yl)-N-(1,3-dioxoisoindolin-5-yl)piperidine-3-carboxamide (27 mg, 40.0%) as an orange solid. $^1$H NMR (300 MHz, DMSO): δ 11.20 (s, 1H), 10.59 (s, 1H), 9.64 (s, 1H), 8.83 (s, 1H), 8.13 (s, 1H), 7.86-7.73 (m, 2H), 7.63 (s, 1H), 7.38-7.29 (m, 1H), 6.78 (s, 1H), 4.77 (d, 1H, J=12.0 Hz), 4.62 (d, 1H, J=12.3 Hz), 3.66 (s, 3H), 3.61 (s, 3H), 3.16-2.94 (m, 2H), 2.60-2.55 (m, 1H), 2.04-2.01 (m, 1H), 1.76-1.72 (m, 2H), 1.52-1.41 (m, 1H). LC-MS: 560 [M+H]$^+$, $t_R$=1.49 min. HPLC: 99.49% at 214 nm, 99.47% at 254 nm, $t_R$=5.33 min.

Example 51

1-(7-(3,4-Dimethoxyphenylamino)thiazolo[5,4-d]pyrimidin-5-yl)-N-(4-(5-mercapto-1,3,4-oxadiazol-2-yl)phenyl)piperidine-3-carboxamide 1H). LC-MS: 591 [M+H]$^+$, $t_R$=1.56 min. HPLC: 97.80% at 214 nm, 97.26% at 254 nm, $t_R$=5.91 min Example 52

1-(7-(3,4-Dimethoxyphenylamino)thiazolo[5,4-d]pyrimidin-5-yl)-N-(4-(5-mercapto-4-methyl-4H-1,2,4-triazol-3-yl)phenyl)piperidine-3-carboxamide

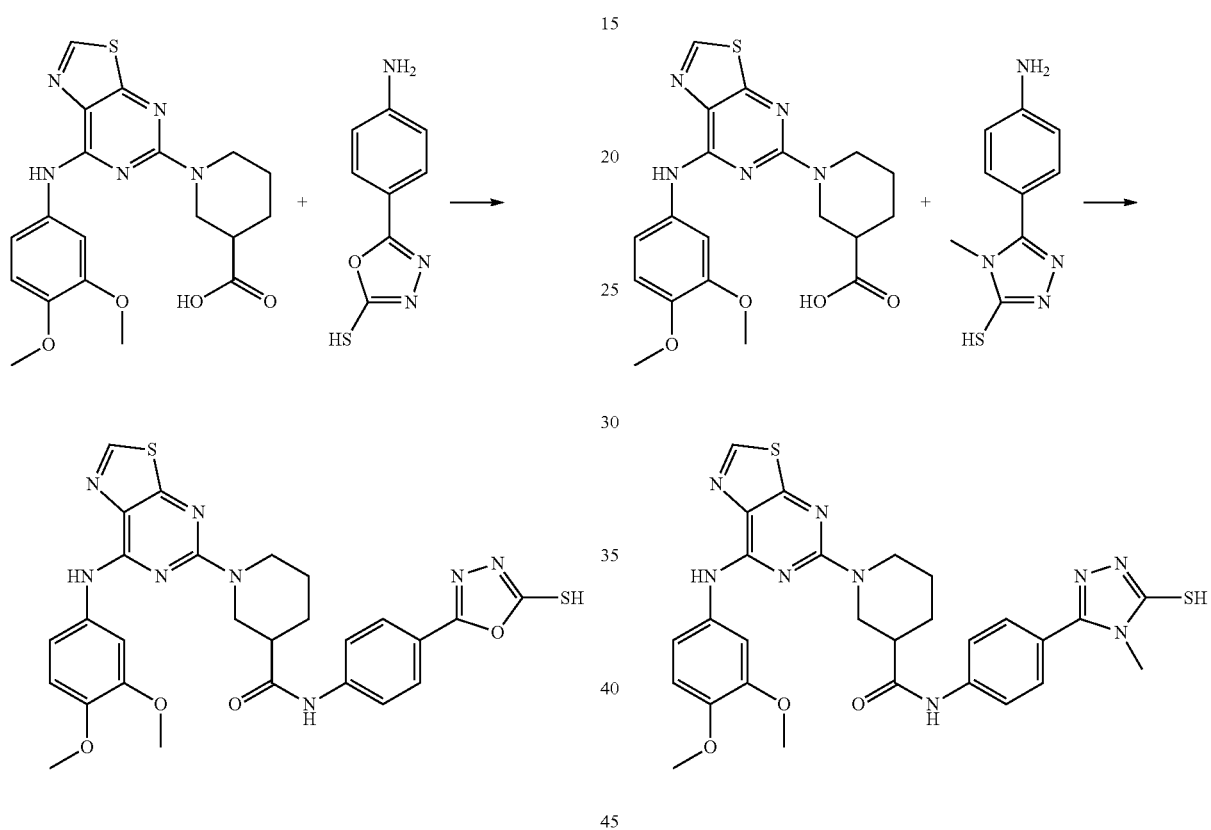

Procedure:

To a solution of 1-(7-(3,4-dimethoxyphenylamino)thiazolo[5,4-d]pyrimidin-5-yl)piperidine-3-carboxylic acid (50 mg, 0.12 mmol) and 5-(4-aminophenyl)-1,3,4-oxadiazole-2-thiol (23 mg, 0.12 mmol) in pyridine (10 mL) was added POCl$_3$ (0.3 mL, 3.29 mmol) at 0° C., the reaction mixture was stirred at room temperature for 6 hours, a sat. NaHCO$_3$ solution was added slowly, the solvent was removed in vacuo, methanol (20 mL) were added and filtrated. The filtrate was collected, concentrated and purified by a silica column chromatography (silica gel 200-300 mesh, eluting with dichloromethane:methanol=40:1) to afford 1-(7-(3,4-dimethoxyphenylamino)thiazolo[5,4-d]pyrimidin-5-yl)-N-(4-(5-mercapto-1,3,4-oxadiazol-2-yl)phenyl)piperidine-3-carboxamide (8.0 mg, 11.3%) as a white solid. $^1$H NMR (300 MHz, DMSO): δ 10.42 (s, 1H), 9.67 (s, 1H), 8.86 (s, 1H), 7.86-7.78 (m, 4H), 7.66 (s, 1H), 7.35 (d, 1H, J=8.7 Hz), 6.81 (brs, 1H), 4.81 (d, 1H, J=11.7 Hz), 4.66 (d, 1H, J=13.2 Hz), 3.69 (s, 3H), 3.63 (s, 3H), 3.15-3.07 (m, 1H), 3.01-2.93 (m, 1H), 2.73-2.61 (m, 1H), 2.07-1.74 (m, 3H), 1.78-1.74 (m, Procedure:

To a solution of 1-(7-(3,4-dimethoxyphenylamino)thiazolo[5,4-d]pyrimidin-5-yl)piperidine-3-carboxylic acid (50 mg, 0.12 mmol) and 5-(4-aminophenyl)-4-methyl-4H-1,2,4-triazole-3-thiol (25 mg, 0.12 mmol) in pyridine (10 mL) was added POCl$_3$ (0.3 mL, 3.29 mmol) at 0° C., the reaction mixture was stirred at room temperature for 8 hours, a sat. NaHCO$_3$ solution (15 mL) was added slowly, the solvent was removed in vacuo, dichloromethane (40 mL) was added and filtrated, the filtrate was collected, concentrated and purified by a silica column chromatography (silica gel 200-300 mesh, eluting with dichloromethane:methanol=50:1) to afford 1-(7-(3,4-dimethoxyphenylamino)thiazolo[5,4-d]pyrimidin-5-yl)-N-(4-(5-mercapto-4-methyl-4H-1,2,4-triazol-3-yl)phenyl)piperidine-3-carboxamide (24.0 mg, 33.1%) as a white solid. $^1$H NMR (300 MHz, DMSO): δ 13.88 (s, 1H), 10.34 (s, 1H), 9.68 (s, 1H), 8.87 (s, 1H), 7.82-7.66 (m, 5H), 7.38-7.35 (m, 1H), 6.83 (brs, 1H), 4.83 (d, 1H, J=12.0 Hz), 4.68 (d, 1H, J=11.7 Hz), 3.71 (s, 3H), 3.63 (s, 3H), 3.58 (s, 3H), 3.15-3.07 (m, 1H), 3.00-2.93 (m, 1H), 2.62-2.58 (m, 1H), 2.07-2.03 (m, 1H), 1.83-1.71 (m, 2H), 1.51-1.47 (m, 1H). LC-MS: 604 [M+H]+, $t_R$=1.50 min. HPLC: 99.39% at 214 nm, 99.39% at 254 nm, $t_R$=5.36 min.

Example 53

3-(7-(3-(2-Oxa-6-azaspiro[3.3]heptan-6-yl)phenylamino)thiazolo[5,4-d]pyrimidin-5-yl)benzoic acid Step 1

6-(Toluene-4-sulfonyl)-2-oxa-6-azaspiro[3.3]heptane

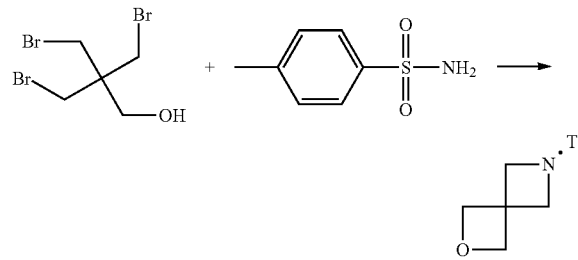

Procedure:

To a solution of KOH (4.98 g, 0.089 mol) and 4-methylbenzenesulfonamide (5.7 g, 0.033 mol) in 90 ml of ethanol, 3-bromo-2,2-bis(bromomethyl)propan-1-ol (9 g, 0.0277 mol) was added at room temperature and the reaction mixture was heated to reflux for 45 h. The solvent was removed by evaporation, 75 ml of 1 M KOH were added and the white suspension was left to stir for another 2 h at room temperature. The mixture was filtered and the white filter cake was rinsed with water until the washing water was neutral. The filter cake was dried under high vacuum to give 4.87 g 6-toluene-4-sulfonyl-2-oxa-6-azaspiro[3.3]heptane (69%) as a white solid. $^1$H NMR (300 MHz, CDCl$_3$) δ 7.70-7.68 (m, 2H), 7.36-7.34 (m, 2H), 4.58 (s, 4H), 3.90 (s, 4H), 2.45 (s, 3H).

Step 2

2-Oxa-6-azaspiro[3.3]heptane hemioxalate

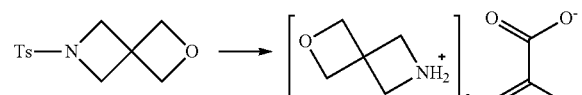

Procedure:

6-(Toluene-4-sulfonyl)-2-oxa-6-azaspiro[3.3]heptane (510 mg, 2 mmol) and magnesium granular (336 mg, 14 mmol) were sonicated for one hour in methanol (100 ml). Almost all solvent was removed from the grey reaction mixture on a rotary evaporator to give a viscous grey residue. Diethyl ether (10 ml) and sodium sulfate decahydrate (1 g) were added and the resulting light grey mixture was stirred vigorously for 30 minutes before filtration. The filtrate was dried over anhydrous sodium sulfate and anhydrous oxalic acid (90 mg, 1 mmol) dissolved in Ethanol (~0.5 mL) was added to the organic phase. A thick white precipitate formed instantly. It was filtered off and dried under vacuum to give 2-oxa-6-azaspiro[3.3]heptane hemioxalate (140 mg, 37%) off-white solid. $^1$H NMR (300 MHz, CDCl$_3$) δ 4.64 (s, 4H), 4.11 (s, 4H).

Step 3

6-(3-Nitrophenyl)-2-oxa-6-azaspiro[3.3]heptane

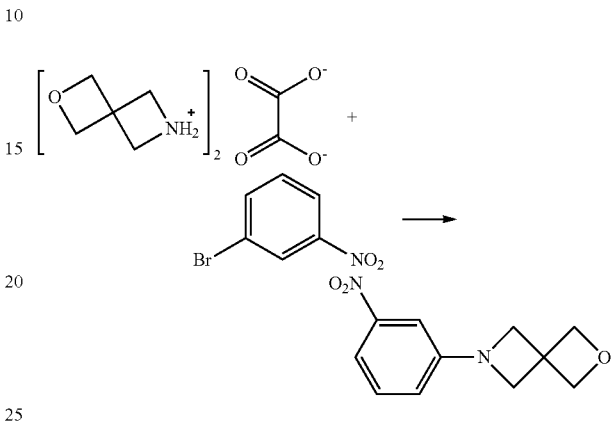

Procedure:

To a solution of 2-oxa-6-azaspiro[3.3]heptane hemioxalate (144 mg, 0.766 mmol) and 1-bromo-3-nitrobenzene (170 mg, 0.84 mmol) in 10 mL of 1,4-dioxane was added Cs$_2$CO$_3$ (500 mg, 1.5 mmol) followed by Pd(dba)$_2$ (88 mg, 0.15 mmol) and X-Phos (37 mg, 0.076 mmol) under nitrogen with stirring. The mixture was refluxed for 16 hours under nitrogen. After cooled, the mixture was filtered, and then the filtrate was evaporated by rotary evaporation. The residue was purified by column chromatography on silica gel eluting with (petroleum ether:EtOAc=2:1) to give 6-(3-nitrophenyl)-2-oxa-6-azaspiro[3.3]heptane (130 mg, 77%) as a yellow solid. $^1$H NMR (300 MHz, CDCl$_3$) δ 7.56 (dq, 1H, J$_1$=8.1 Hz, J$_2$=1.0 Hz), 7.31 (t, 1H, J=8.0 Hz), 7.20 (t, 1H, J=2.2 Hz), 6.68 (dq, 1H, J$_1$=8.0 Hz), 4.85 (s, 4H), 4.10 (s, 4H).

Step 4

3-(2-Oxa-6-azaspiro[3.3]heptan-6-yl)aniline

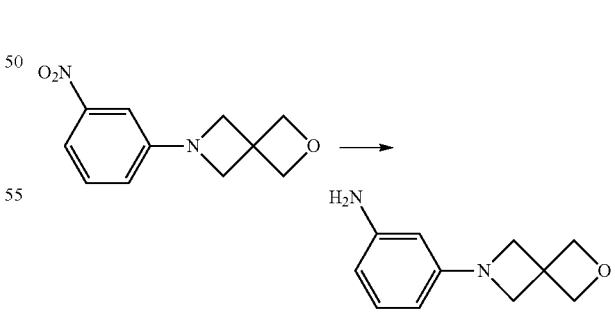

Procedure:

To a solution of 6-(3-nitrophenyl)-2-oxa-6-azaspiro[3.3] heptane (130 mg, 0.59 mmol) in 5 mL of EtOH was added 10% Pd/C (20 mg), the mixture was stirred for 15 hours at room temperature in a hydrogen atmosphere. Insoluble matters were removed and the filtrate was concentrated in vacuo to give 3-(2-oxa-6-azaspiro[3.3]heptan-6-yl)aniline (100 mg, 98%). LC-MS: 191 [M+H]⁺, $t_R$=0.99 min.

Step 5

N-(3-(2-Oxa-6-azaspiro[3.3]heptan-6-yl)phenyl)-5-chlorothiazolo[5,4-d]pyrimidin-7-amine

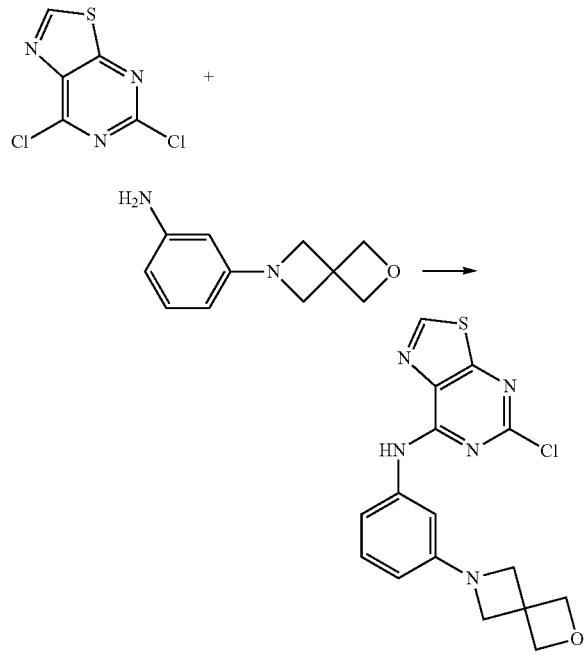

Procedure:

A mixture of 5,7-dichlorothiazolo[5,4-d]pyrimidine (108 mg, 0.526 mmol), 3-(2-oxa-6-azaspiro[3.3]heptan-6-yl)aniline (100 mg, 0.526 mmol) and DIEA (102 mg, 0.789 mmol) in 5 mL of DMSO was stirred at room temperature for 16 hours. The mixture was poured into water and the precipitate was filtered. The crude N-(3-(2-oxa-6-azaspiro[3.3]heptan-6-yl)phenyl)-5-chlorothiazolo[5,4-d]pyrimidin-7-amine (160 mg, 85%) was used into the next step without purification. LC-MS: 360 [M+H]⁺, $t_R$=1.53 min.

Step 6

Methyl 3-(7-(3-(2-oxa-6-azaspiro[3.3]heptan-6-yl)phenylamino)thiazolo[5,4-d]pyrimidin-5-yl)benzoate

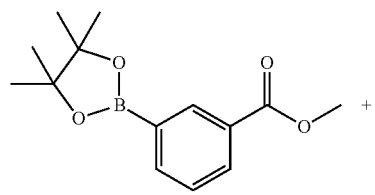

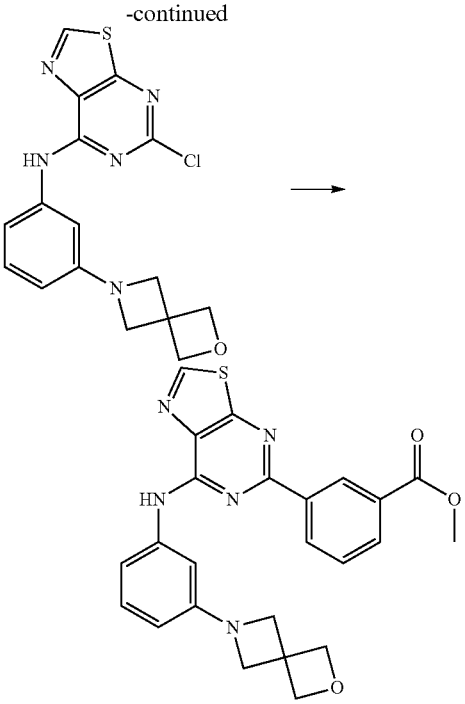

Procedure:

To a solution of N-(3-(2-oxa-6-azaspiro[3.3]heptan-6-yl)phenyl)-5-chlorothiazolo[5,4-d]pyrimidin-7-amine (160 mg, 0.5 mmol) and methyl 3-(4,4,5,5-tetramethyl-1,3,2-dioxaborolan-2-yl)benzoate (145 mg, 0.55 mmol) in 9 mL of 1,4-dioxane and 1 mL of water was added Na₂CO₃ (159 mg, 1.5 mmol) followed by Pd(PPh₃)₄ (58 mg) under nitrogen with stirring. The mixture was refluxed for 15 hours under nitrogen. After cooled, the solvent was evaporated by rotary evaporation. The residue was poured into water and extracted with EtOAc (3×10 mL). The organic layer was washed with brine and dried over Na₂SO₄. After filtration and concentration, the residue was purified by column chromatography on silica gel eluting with (petroleum ether EtOAc=1:1) to give methyl 3-(7-(3-(2-oxa-6-azaspiro[3.3]heptan-6-yl)phenylamino)thiazolo[5,4-d]pyrimidin-5-yl)benzoate (70 mg, 30%). LC-MS: 460 [M+H]⁺, $t_R$=1.74 min.

Step 7

3-(7-(3-(2-Oxa-6-azaspiro[3.3]heptan-6-yl)phenylamino)thiazolo[5,4-d]pyrimidin-5-yl)benzoic acid -continued

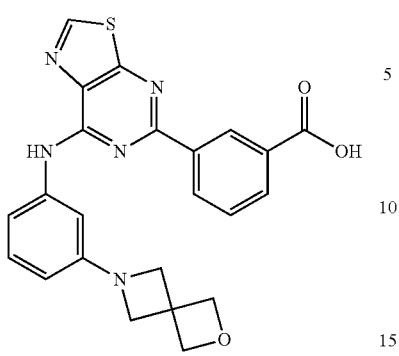

Procedure:

To a stirred solution of methyl 3-(7-(3-(2-oxa-6-azaspiro[3.3]heptan-6-yl)phenylamino)thiazolo[5,4-d]pyrimidin-5-yl)benzoate (70 mg, 0.15 mmol) in 5 mL of THF and 5 mL of methanol was added a solution of 1N NaOH (2 mL) at room temperature. After the addition, the reaction was stirred at this temperature for 15 hours. The solvent was evaporated and the residue was diluted with water and adjusted to pH=2 by HCl (aq.). The precipitate was filtered, the cake was purified by preparative HPLC (Gemini 5u C18 150×21.2 mm; inject volume: 3 ml/inj, flow rate: 20 ml/min; wavelength: 214 nm and 254 nm; the gradient conditions are: 40% acetonitrile/60% water (0.1% TFA V/V) initially, and then proceed to 70% acetonitrile/30% water (0.1% TFA V/V) in a linear fashion after just 9 min.) to give 3-(7-(3-(2-oxa-6-azaspiro[3.3]heptan-6-yl)phenylamino)thiazolo[5,4-d]pyrimidin-5-yl)benzoic acid (10 mg, 15%). $^1$H NMR (300 MHz, DMSO): δ 10.13 (s, 1H), 9.41 (s, 1H), 9.00 (s, 1H), 8.66 (d, 1H, J=8.1 Hz), 8.12-8.10 (m, 1H), 7.70 (t, 1H, J=7.9 Hz), 7.45 (s, 1H), 7.24-7.18 (m, 2H), 6.23 (d, 1H, J=7.5 Hz), 4.75 (s, 4H), 4.03 (s, 4H). LC-MS: 446 [M+H]$^+$, $t_R$=1.59 min. HPLC: 97.95% at 214 nm, 100% at 254 nm, $t_R$=7.31 min.

Example 54

4-(1-(7-(3,4-Dimethoxyphenylamino)thiazolo[5,4-d]pyrimidin-5-yl)pyrrolidine-3-carboxamido)benzoic acid Step 1

5-Chloro-N-(3,4-dimethoxyphenyl)thiazolo[5,4-d]pyrimidin-7-amine

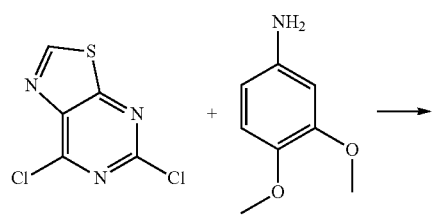

-continued

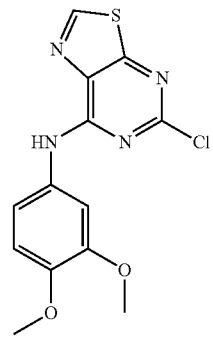

Procedure:

A mixture of 5,7-dichlorothiazolo[5,4-d]pyrimidine (0.925 g, 4.49 mmol), 3,4-dimethoxybenzenamine (0.89 g, 5.8 mmol) and DIEA (0.86 g, 6.66 mmol) in 12 mL of DMSO was stirred at room temperature for 24 hours. Then the reaction mixture was poured into 50 mL of water, the solid was filtered and washed with water (50 mL) to give a crude product as a solid. It was purified by silica gel chromatography (silica gel 200-300 mesh, eluting with ethyl acetate) to give 5-chloro-N-(3,4-dimethoxyphenyl)thiazolo[5,4-d]pyrimidin-7-amine (1.2 g, 82.8%) as a grey solid. LC-MS: 322.9 [M+H]$^+$, $t_R$=1.51 min.

Step 2

Methyl 1-(7-(3,4-dimethoxyphenylamino)thiazolo[5,4-d]pyrimidin-5-yl)pyrrolidine-3-carboxylate

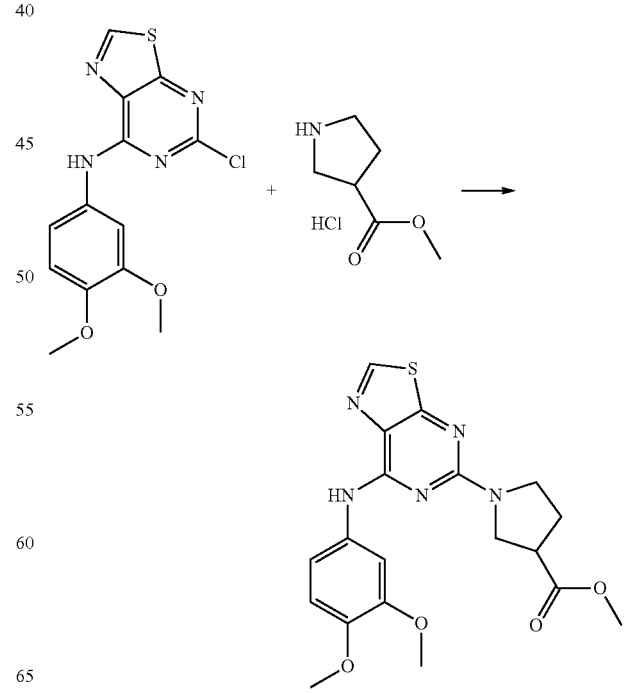

Procedure:

To a solution of 5-chloro-N-(3,4-dimethoxyphenyl)thiazolo[5,4-d]pyrimidin-7-amine (140 mg, 0.433 mmol), methylpyrrolidine-3-carboxylate hydrochloride (107.7 mg, 0.65 mmol), X-Phos (115 mg, 0.24 mmol) and $Cs_2CO_3$ (580 mg, 1.78 mmol) in 60 mL of dry dioxane was added $Pd_2(dba)_3$ (60 mg, 0.065 mmol) in one portion at room temperature under nitrogen. Then the reaction mixture was degassed by nitrogen for 15 minutes. The mixture was then stirred at 95° C. under nitrogen for 24 hours. The solvent was evaporated at 40° C. at reduced pressure and the residue was purified by silica gel chromatography (silica gel 200-300 mesh, eluting a mixture of ethyl acetate and petroleum ether (2:1)) to give methyl 1-(7-(3,4-dimethoxyphenylamino)thiazolo[5,4-d]pyrimidin-5-yl)pyrrolidine-3-carboxylate (160 mg, 88.7%) as a yellow solid. LC-MS: 416.1 $[M+H]^+$, $t_R$=1.60 min.

Step 3

1-(7-(3,4-Dimethoxyphenylamino)thiazolo[5,4-d]pyrimidin-5-yl)pyrrolidine-3-carboxylic acid Procedure:

To a stirred solution of methyl 1-(7-(3,4-dimethoxyphenylamino)thiazolo[5,4-d]pyrimidin-5-yl)pyrrolidine-3-carboxylate (160 mg, 0.38 mmol) in 10 mL of methanol was added a solution of sodium hydroxide (154 mg, 3.8 mmol) in 2 mL of water at room temperature. Then the reaction mixture was stirred at this temperature for 24 hours. Then solvent was evaporated at 40° C. at reduced pressure and the residue was suspended in 30 mL of THF, then treated with 2N HCl to pH=2. The solvent was evaporated and the residue was dissolved in 50 mL of THF, then filtered and the filtrate was evaporated to give 1-(7-(3,4-dimethoxyphenylamino)thiazolo[5,4-d]pyrimidin-5-yl)pyrrolidine-3-carboxylic acid (95 mg, 61.4%) as a yellow solid. LC-MS: 402.1 $[M+H]^+$, $t_R$=1.33 min.

Step 4 tert-Butyl 4-(1-(7-(3,4-dimethoxyphenylamino)thiazolo[5,4-d]pyrimidin-5-yl)pyrrolidine-3-carboxamido)benzoate

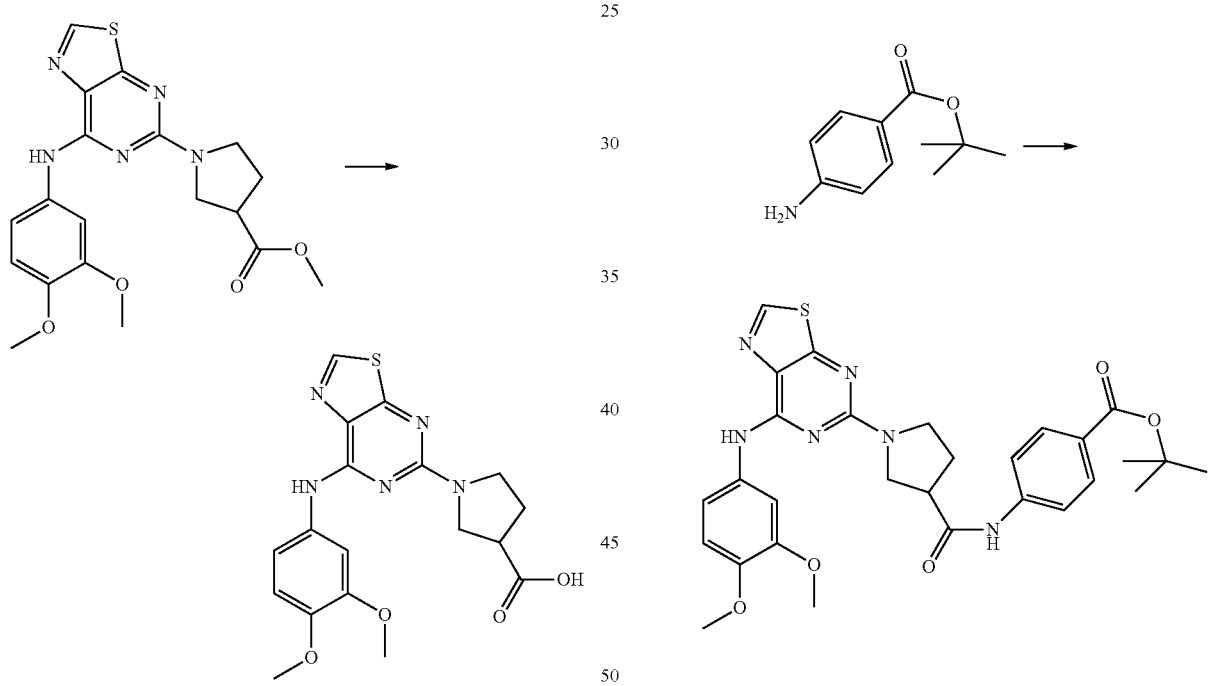

Procedure:

A mixture of 1-(7-(3,4-dimethoxyphenylamino)thiazolo[5,4-d]pyrimidin-5-yl)pyrrolidine-3-carboxylic acid (95 mg, 0.236 mmol), tert-butyl 4-aminobenzoate (59 mg, 0.306 mmol), HATU (116 mg, 0.306 mmol) and DIEA (91 mg, 0.708 mmol) in 10 mL of DMF was stirred at room temperature for 72 hours. The solvent was evaporated at 80° C. at reduced pressure and the residue was purified by silica gel chromatography (silica gel 200-300 mesh, eluting with a mixture of ethyl acetate and petroleum ether (1:1)) to give tert-butyl 4-(1-(7-(3,4-dimethoxyphenylamino)thiazolo[5,4-d]pyrimidin-5-yl)pyrrolidine-3-carboxamido)benzoate (105 mg, 77%) as a solid. LC-MS: 577.2 $[M+H]^+$, $t_R$=1.69 min

167
Step 5

4-(1-(7-(3,4-Dimethoxyphenylamino)thiazolo[5,4-d]pyrimidin-5-yl)pyrrolidine-3-carboxamido)benzoic acid

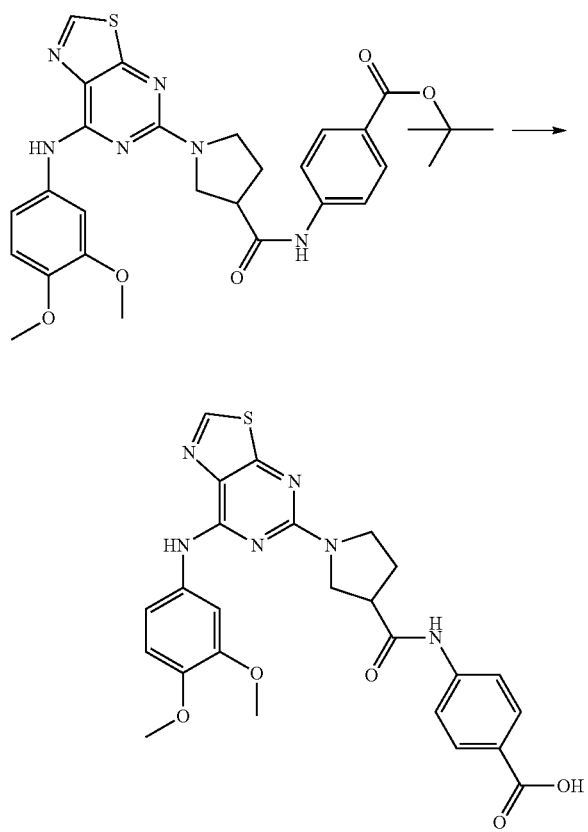

Procedure:

To a stirred solution of tert-butyl 4-(1-(7-(3,4-dimethoxyphenylamino)thiazolo[5,4-d]pyrimidin-5-yl)pyrrolidine-3-carboxamido)benzoate (105 mg, 0.18 mmol) in 10 mL of dichloromethane was added trifluoroacetic acid (5 mL) in one portion at room temperature. Then the reaction mixture was stirred at this temperature for 24 hours. The solvent was evaporated at 37° C. at reduced pressure and the residue was purified by preparative HPLC (Gemini 5u C18 150×21.2 mm; inject volume: 3 ml/inj, flow rate: 20 ml/min; wavelength: 214 nm and 254 nm; the gradient conditions are: 30% acetonitrile/70% water (0.1% TFA V/V) initially, and then proceed to 60% acetonitrile/40% water (0.1% TFA V/V) in a linear fashion after just 9 min.) to give 4-(1-(7-(3,4-dimethoxyphenylamino)thiazolo[5,4-d]pyrimidin-5-yl)pyrrolidine-3-carboxamido)benzoic acid (56 mg, 59%) as a white solid. $^1$H NMR (300 MHz, DMSO): δ 10.42 (s, 1H), 9.64 (s, 1H), 8.84 (s, 1H), 7.92-7.73 (m, 6H), 7.48 (brs, 1H), 6.93 (d, 1H, J=9.0 Hz), 3.92-3.36 (m, 11H), 2.29-2.21 (m, 2H). LC-MS: 521 [M+H]$^+$, $t_R$=1.38 min. HPLC: 99.34% at 214 nm, 99.25% at 254 nm, $t_R$=4.75 min.

168
Example 55

4-(1-(7-(5,6-Dimethoxypyridin-2-ylamino)thiazolo[5,4-d]pyrimidin-5-yl)pyrrolidine-3-ylcarbamoyl)benzoic acid

Step 1
5-Chloro-N-(5,6-dimethoxypyridin-2-yl)thiazolo[5,4-d]pyrimidin-7-amine

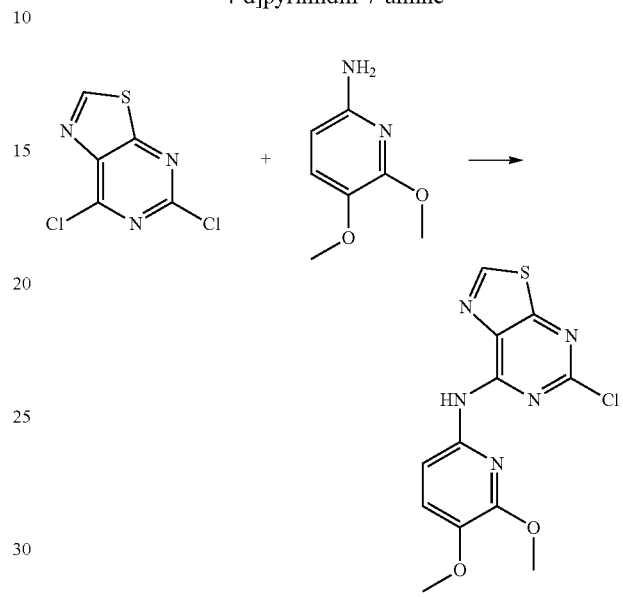

Procedure:

A solution of 5,7-dichlorothiazolo[5,4-d]pyrimidine (300 mg, 1.45 mmol), 5,6-dimethoxypyridin-2-amine (269 mg, 1.74 mmol) and DIEA (281 mg, 2.17 mmol) in 5 mL of DMSO was stirred at room temperature for 24 hours. Then the mixture was poured into 30 mL of water, and the formed solid was filtered and washed with water. The obtained crude product was purified by silica gel chromatography (silica gel 200-300 mesh, eluting with ethyl acetate) to give 5-chloro-N-(5,6-dimethoxypyridin-2-yl)thiazolo[5,4-d]pyrimidin-7-amine (344 mg, 73%) as an off-white solid. LC-MS: 324.1 [M+H]$^+$, $t_R$=1.69 min.

Step 2 tert-Butyl 1-(7-(5,6-dimethoxypyridin-2-ylamino)thiazolo[5,4-d]pyrimidin-5-yl)pyrrolidin-3-ylcarbamate

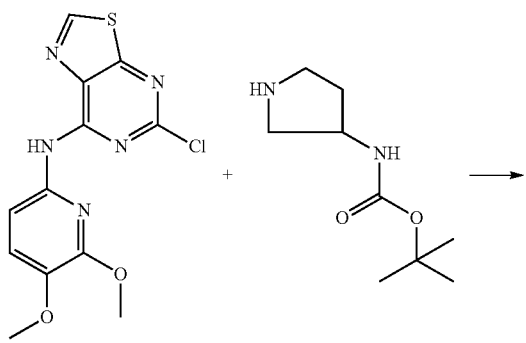

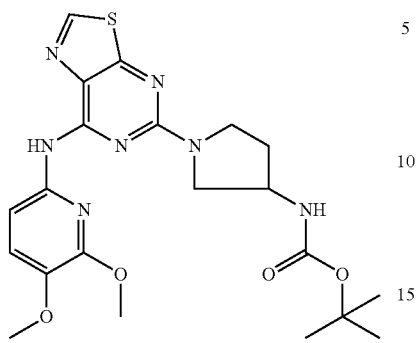

Procedure:

To a stirred solution of 5-chloro-N-(5,6-dimethoxypyridin-2-yl)thiazolo[5,4-d]pyrimidin-7-amine (344 mg, 1.06 mmol), tert-butyl pyrrolidin-3-ylcarbamate (289 mg, 1.55 mmol), X-Phos (256 mg, 0.53 mmol) and Cs$_2$CO$_3$ (1.3 g, 3.9 mmol) in 120 mL of dioxane at room temperature under nitrogen was added Pd$_2$(dba)$_3$ (138 mg, 0.24 mmol) in one portion. Then the reaction was stirred at 95° C. under nitrogen for 24 hours. The solvent was evaporated and the residue was purified by silica gel chromatography (silica gel 200-300 mesh, eluting with a mixture of ethyl acetate and petroleum ether (2:1)) to give tert-butyl 1-(7-(5,6-dimethoxypyridin-2-ylamino)thiazolo[5,4-d]pyrimidin-5-yl)pyrrolidin-3-ylcarbamate (260 mg, 51.7%) as an oil. LC-MS: 474.2 [M+H]$^+$, t$_R$=1.67 min.

Step 3

5-(3-Aminopyrrolidin-1-yl)-N-(5,6-dimethoxypyridin-2-yl)thiazolo[5,4-d]pyrimidin-7-amine hydrochloride

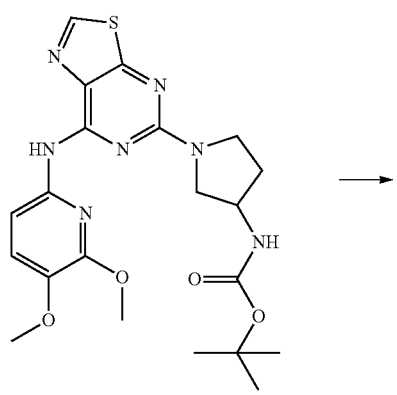

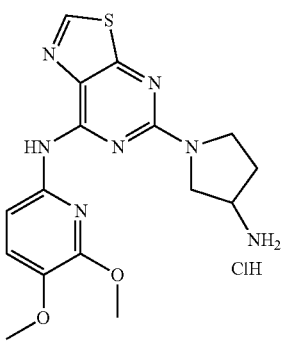

Procedure:

A solution of tert-butyl 1-(7-(5,6-dimethoxypyridin-2-ylamino)thiazolo[5,4-d]pyrimidin-5-yl)pyrrolidin-3-ylcarbamate (260 mg, 0.549 mmol) in 20 mL of saturated HCl in dioxane was stirred at room temperature for 24 hours. The solvent was evaporated to give 5-(3-aminopyrrolidin-1-yl)-N-(5,6-dimethoxypyridin-2-yl)thiazolo[5,4-d]pyrimidin-7-amine hydrochloride (283 mg, crude) as a yellow solid. It was used directly in the next step without further purification. LC-MS: 187.6 [M/2+H]$^+$, 374.0 [M+H]$^+$, t$_R$=1.18 min.

Step 4

Methyl 4-(1-(7-(5,6-dimethoxypyridin-2-ylamino)thiazolo[5,4-d]pyrimidin-5-yl)pyrrolidin-3-ylcarbamoyl)benzoate

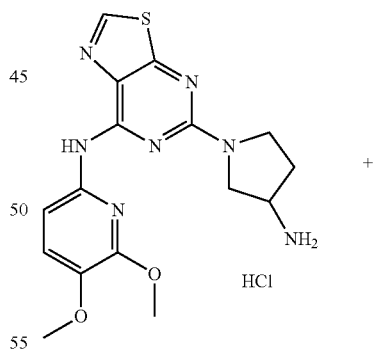

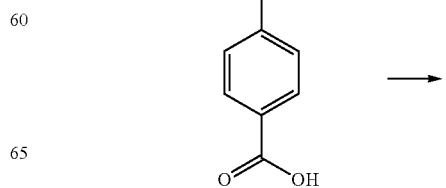

-continued

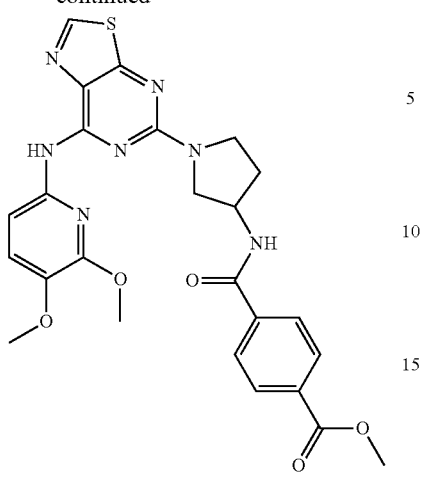

Procedure:

To a stirred solution of 5-(3-aminopyrrolidin-1-yl)-N-(5,6-dimethoxypyridin-2-yl)thiazolo[5,4-d]pyrimidin-7-amine hydrochloride (283 mg, 0.69 mmol), 4-(methoxycarbonyl)benzoic acid (161 mg, 0.89 mmol) in 10 mL of DMF were added HATU (340 mg, 0.89 mmol), DIEA (267 mg, 2.07 mmol), EDCI (145 mg, 0.759 mmol) and DMAP (93 mg, 0.76 mmol) at room temperature. Then the reaction mixture was stirred at room temperature for 24 hours. The solvent was evaporated at 80° C. at reduced pressure and the residue was purified by silica gel chromatography (silica gel 200-300 mesh, eluting with a mixture of dichloromethane and methanol (20:1)) to give methyl 4-(1-(7-(5,6-dimethoxypyridin-2-ylamino)thiazolo[5,4-d]pyrimidin-5-yl)pyrrolidin-3-ylcarbamoyl)benzoate (350 mg, 94%) as a yellow solid. LC-MS: 536.1 [M+H]+, $t_R$=1.68 min.

Step 5

4-(1-(7-(5,6-Dimethoxypyridin-2-ylamino)thiazolo[5,4-d]pyrimidin-5-yl)pyrrolidin-3-ylcarbamoyl)benzoic acid

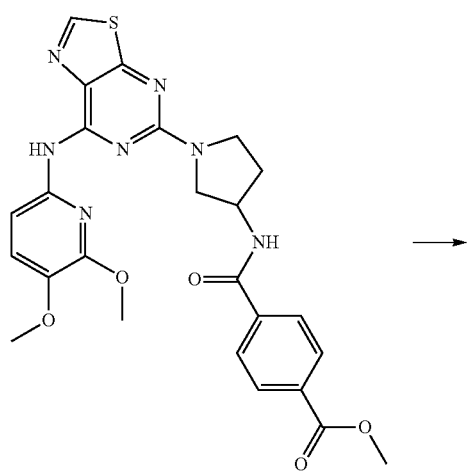

-continued

Procedure:

To a stirred solution of methyl 4-(1-(7-(5,6-dimethoxypyridin-2-ylamino)thiazolo[5,4-d]pyrimidin-5-yl)pyrrolidin-3-ylcarbamoyl)benzoate (350 mg, 0.65 mmol) in 20 mL of methanol and 40 mL of THF was added a solution of LiOH.H₂O (274 mg, 6.5 mmol) in one portion at room temperature. Then the solution was stirred at room temperature for 24 hours. The solution was acidified with 1N HCl to pH=4. The solvent was evaporated and the residue was purified by preparative HPLC (Gemini 5u C18 150×21.2 mm; inject volume: 3 ml/inj, flow rate: 20 ml/min; wavelength: 214 nm and 254 nm; the gradient conditions are: 30% acetonitrile/70% water (0.1% TFA V/V) initially, and then proceed to 55% acetonitrile/45% water (0.1% TFA V/V) in a linear fashion after just 9 min.) to give 4-(1-(7-(5,6-dimethoxypyridin-2-ylamino)thiazolo[5,4-d]pyrimidin-5-yl)pyrrolidin-3-ylcarbamoyl)benzoic acid (70 mg, 20.5%) as a pale yellow solid. ¹H NMR (300 MHz, DMSO): δ 8.87-8.18 (m, 2H), 8.67 (s, 1H), 8.03-7.96 (m, 5H), 7.44 (d, 1H, J=8.7 Hz), 4.66 (brs, 1H), 4.11 (brs, 2H), 3.90 (s, 3H), 3.78 (s, 3H), 3.68 (brs, 2H), 2.27 (brs, 1H), 2.08 (brs, 1H). LC-MS: 522 [M+H]+, $t_R$=1.44 min. HPLC: 99.68% at 214 nm, 99.31% at 254 nm, $t_R$=6.98 min.

Example 56

Methyl 3-(7-(3-(trifluoromethyl)phenylamino)thiazolo[5,4-d]pyrimidin-5-yl)benzoate Step 1

5-Chloro-N-(3-(trifluoromethyl)phenyl)thiazolo[5,4-d]pyrimidin-7-amine

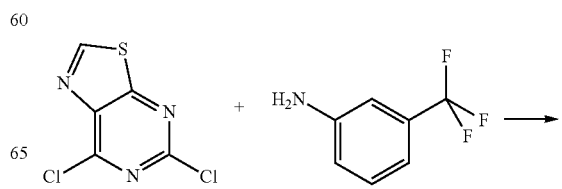

-continued

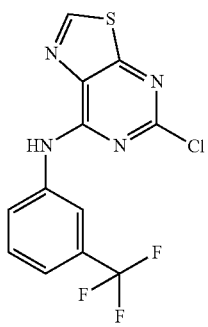

Procedure:

To a stirred solution of 5,7-dichlorothiazolo[5,4-d]pyrimidine (300 mg, 1.45 mmol) and 3-(trifluoromethyl)benzenamine (304.8 mg, 1.89 mmol) in 10 mL of DMSO was added DIEA (282 mg, 2.18 mmol) in one portion at room temperature. Then the reaction mixture was stirred at room temperature for 5 hours. The reaction mixture was poured into 40 mL of water, and the solid obtained was filtered, rinsed with water, and dried. The desired product 5-chloro-N-(3-(trifluoromethyl)phenyl)thiazolo[5,4-d]pyrimidin-7-amine was obtained (356 mg, 74%) as a yellow solid. LC-MS: 331.0 [M+H]$^+$, $t_R$=1.70 min.

Step 2

Methyl 3-(7-(3-(trifluoromethyl)phenylamino)thiazolo[5,4-d]pyrimidin-5-yl)benzoate

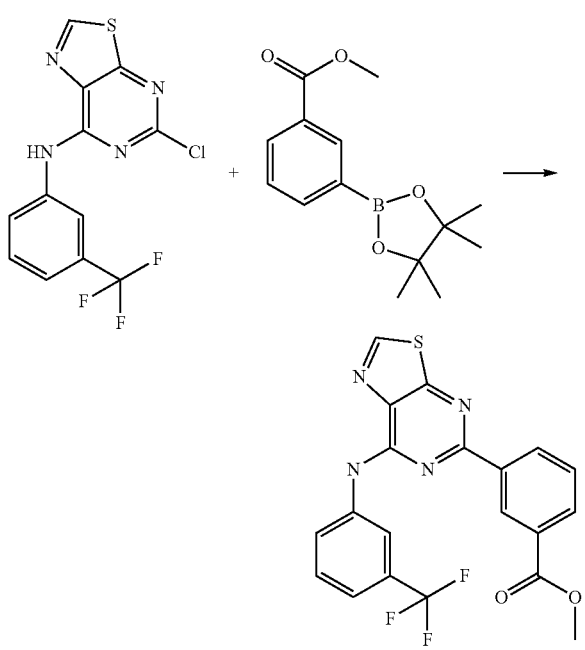

Procedure:

To a stirred solution of 5-chloro-N-(3-(trifluoromethyl)phenyl)thiazolo[5,4-d]pyrimidin-7-amine (330 mg, 1 mmol), methyl 3-(4,4,5,5-tetramethyl-1,3,2-dioxaborolan-2-yl)benzoate (314 mg, 1.2 mmol) and Na$_2$CO$_3$ (498 mg, 4.7 mmol) in 2 mL of water and 20 mL of dioxane was added Pd(PPh$_3$)$_4$ (93 mg, 0.075 mmol) in one portion at room temperature under nitrogen. Then the mixture was stirred at 95° C. for 16 hours under nitrogen. The solvent was evaporated at 40° C. at reduced pressure and the residue was purified by silica gel chromatography (silica gel 200-300 mesh, eluting with a mixture of petroleum ether and ethyl acetate (4:1)) to give methyl 3-(7-(3-(trifluoromethyl)phenylamino)thiazolo[5,4-d]pyrimidin-5-yl)benzoate (365 mg, 84.8%) as a yellow solid. $^1$H NMR (300 MHz, DMSO): δ 9.18 (s, 1H), 8.93 (s, 1H), 8.74 (d, 1H, J=7.8 Hz), 8.61 (s, 1H), 8.21 (brs, 2H), 7.94 (d, 1H, J=7.8 Hz), 7.65-7.60 (m, 2H), 7.48-7.46 (m, 1H), 4.01 (s, 3H). LC-MS: 431 [M+H]$^+$, 429 [M–H]$^-$, $t_R$=1.92 min. HPLC: 95.92% at 214 nm, 97.01% at 254 nm, $t_R$=5.14 min.

Example 57

3-(7-(3-(Trifluoromethyl)phenylamino)thiazolo[5,4-d]pyrimidin-5-yl)benzoic acid

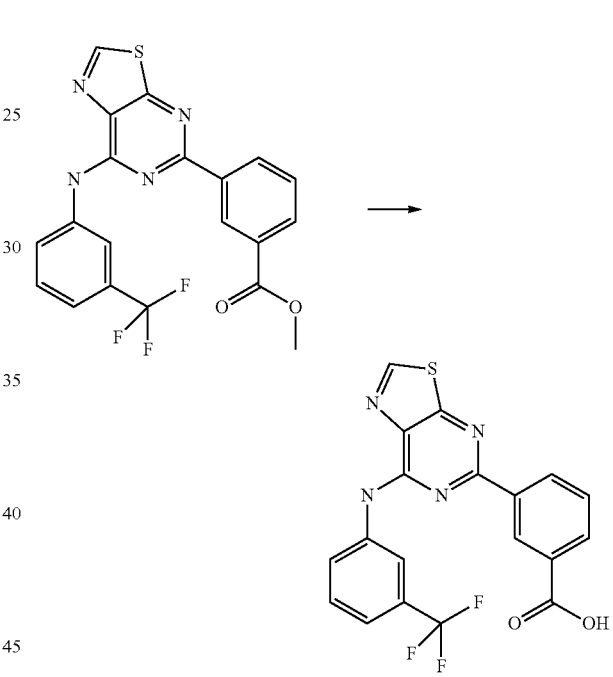

Procedure:

To a stirred solution of methyl 3-(7-(3-(trifluoromethyl)phenylamino)thiazolo[5,4-d]pyrimidin-5-yl)benzoate (100 mg, 0.23 mmol) in 3 mL of THF and 3 mL of methanol was added a solution of sodium hydroxide (46.5 mg, 1.16 mmol) in 1 mL of water at room temperature. Then the reaction mixture was stirred at room temperature for 16 hours. HCl was added until pH=4. The solvent was evaporated at 40° C. at reduced pressure and the residue was purified by silica gel chromatography (silica gel 200-300 mesh, eluting with a mixture of petroleum ether and ethyl acetate (1:1)) to give 3-(7-(3-(trifluoromethyl)phenylamino)thiazolo[5,4-d]pyrimidin-5-yl)benzoic acid (65 mg, 67.2%) as a pale yellow solid. $^1$H NMR (300 MHz, DMSO): δ 13.15 (brs, 1H), 10.65 (s, 1H), 9.46 (s, 1H), 9.00 (s, 1H), 8.67 (s, 1H), 8.60 (d, 1H, J=7.8 Hz), 8.26 (d, 1H, J=7.8 Hz), 8.10 (d, 1H, J=7.5 Hz), 7.68-7.63 (m, 2H), 7.49 (d, 1H, J=7.8 Hz). LC-MS: 417 [M+H]$^+$, 415 [M–H]$^-$, $t_R$=1.65 min. HPLC: 95.14% at 214 nm, 95.28% at 254 nm, $t_R$=7.71 min.

Example 58

3-(7-(3,4,5-Trimethoxyphenylamino)thiazolo[5,4-d]pyrimidin-5-yl)benzamide

Step 1

5-Chloro-N-(3,4,5-trimethoxyphenyl)thiazolo[5,4-d]pyrimidin-7-amine

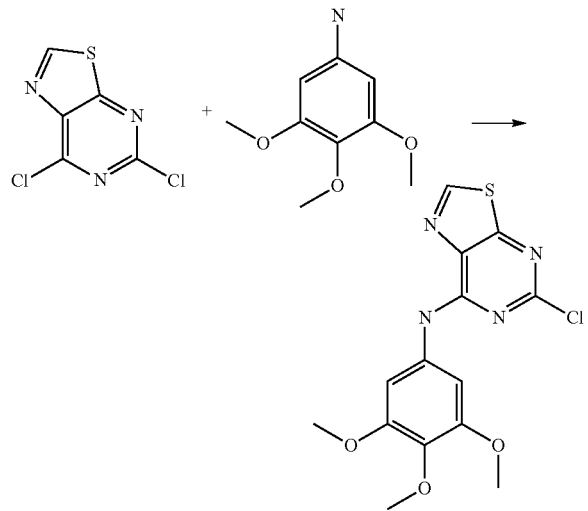

Procedure:

To a stirred solution of 5,7-dichlorothiazolo[5,4-d]pyrimidine (200 mg, 0.97 mmol) and 3,4,5-trimethoxybenzenamine (230 mg, 1.25 mmol) in 7 mL of DMSO was added DIEA (188 mg, 1.45 mmol) in one portion at room temperature. Then the reaction mixture was stirred at room temperature for 16 hours. The reaction mixture was poured into 40 mL of water, and the solid obtained was filtered, washed with water (10 mL) to give a crude product. It was purified by silica gel chromatography (silica gel 200-300 mesh, eluting with ethyl acetate) to give 5-chloro-N-(3,4,5-trimethoxyphenyl)thiazolo[5,4-d]pyrimidin-7-amine (337 mg, 98.6%) as a yellow solid. LC-MS: 353.0 [M+H]$^+$, 726.9 [2M+H]$^+$, $t_R$=1.56 min.

Step 2

3-(7-(3,4,5-Trimethoxyphenylamino)thiazolo[5,4-d]pyrimidin-5-yl)benzamide

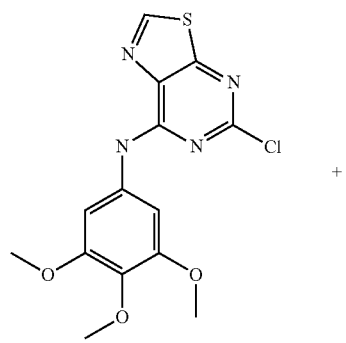

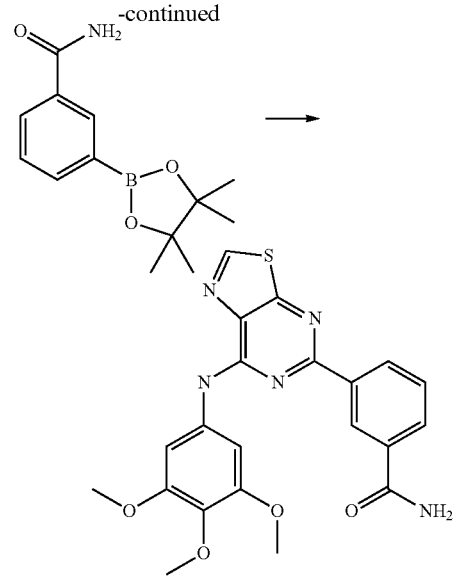

Procedure:

To a stirred solution of 5-chloro-N-(3,4,5-trimethoxyphenyl)thiazolo[5,4-d]pyrimidin-7-amine (337 mg, 0.95 mmol), 3-(4,4,5,5-tetramethyl-1,3,2-dioxaborolan-2-yl)benzamide (190 mg, 1.15 mmol) and Na$_2$CO$_3$ (347 mg, 3.27 mmol) in 2 mL of water and 50 mL of dioxane was added Pd(PPh$_3$)$_4$ (100 mg, 0.086 mmol) in one portion at room temperature under nitrogen. Then the mixture was stirred at 97° C. for 16 hours under nitrogen. The solvent was evaporated at 40° C. at reduced pressure and the residue was purified by silica gel chromatography (silica gel 200-300 mesh, eluting with a mixture of petroleum ether and ethyl acetate (1:2)) to give a crude product. It was purified by preparative HPLC (Gemini 5u C18 150×21.2 mm; inject volume: 3 ml/inj, flow rate: 20 ml/min; wavelength: 214 nm and 254 nm; the gradient conditions are: 20% acetonitrile/80% water (0.1% TFA V/V) initially, and then proceed to 45% acetonitrile/55% water (0.1% TFA V/V) in a linear fashion after just 9 min.) to give 3-(7-(3,4,5-trimethoxyphenylamino)thiazolo[5,4-d]pyrimidin-5-yl)benzamide (120 mg, 27.4%) as a solid. $^1$H NMR (300 MHz, DMSO): δ 10.10 (s, 1H), 9.43 (s, 1H), 8.93 (s, 1H), 8.58 (d, 1H, J=8.1 Hz), 8.03-8.00 (m, 2H), 7.65-7.60 (m, 3H), 7.50 (brs, 1H), 3.87 (s, 3H), 3.71 (s, 3H), 3.30 (s, 3H). LC-MS: 438 [M+H]$^+$, $t_R$=1.43 min. HPLC: 99.77% at 214 nm, 99.84% at 254 nm, $t_R$=5.68 min.

Example 59

1-(7-(3-((S)-2-Methylpyrrolidin-1-yl)phenylamino)thiazolo[5,4-d]pyrimidin-5-yl)piperidin-3-ol hydrochloride

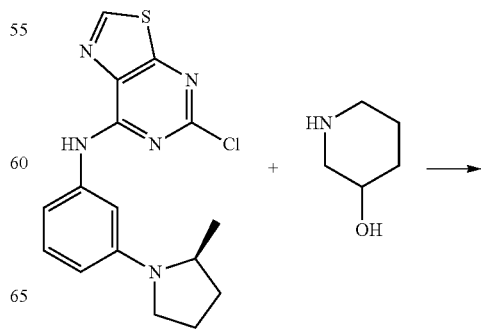

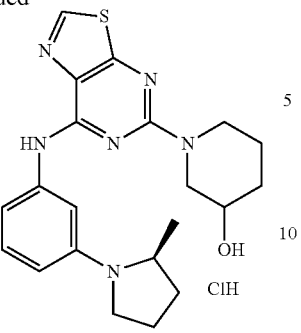

Procedure:

A mixture of (S)-5-chloro-N-(3-(2-methylpyrrolidin-1-yl)phenyl)thiazolo[5,4-d]pyrimidin-7-amine (138 mg, 0.4 mmol), piperidin-3-ol (50 mg, 0.48 mmol), Pd$_2$(dba)$_3$ (24 mg, 0.04 mmol), X-Phos (78 mg, 0.16 mmol), Cs$_2$CO$_3$ (392 mg, 1.2 mmol) and dioxane (10 mL) was heated to 100° C. with stirring for 16 h under N$_2$. The solvent was removed in vacuo and the resulting mixture was purified first by column chromatography (petroleum ether:ethyl acetate=5:1), then by preparative HPLC (Gemini 5u C18 150×21.2 mm; inject volume: 3 ml/inj, flow rate: 20 ml/min; wavelength: 214 nm and 254 nm; the gradient conditions are: 30% acetonitrile/70% water (0.1% TFA V/V) initially, and then proceed to 50% acetonitrile/50% water (0.1% TFA V/V) in a linear fashion after just 9 min.) to give the corresponding trifluoroacetate salt. And then conc. HCl (0.5 mL) was added and the mixture was stirred for 10 minutes and concentrated under reduced pressure to give 1-(7-(3-(((S)-2-methylpyrrolidin-1-yl)phenylamino)thiazolo[5,4-d]pyrimidin-5-yl)piperidin-3-ol hydrochloride (93 mg, 51.8%). $^1$H NMR (300 MHz, DMSO): δ 8.99 (s, 1H), 8.19 (s, 1H), 7.88 (d, 1H, J=8.1 Hz), 7.73 (t, 1H, J=8.1 Hz), 7.61 (d, 1H, J=7.8 Hz), 4.16-4.03 (m, 3H), 3.89-3.69 (m, 5H), 2.57-2.51 (m, 1H), 2.43-2.29 (m, 2H), 2.10-1.99 (m, 3H), 1.77-1.69 (m, 2H), 1.39 (d, 3H, J=6.3 Hz). LC-MS: 411 [M+H]$^+$, t$_R$=1.655 min. HPLC: 97.67% at 214 nm, 97.98% at 254 nm, t$_R$=4.983 min.

Example 60

(S)-4-(7-(3-Methoxy-5-(2-methylpyrrolidin-1-yl)phenylamino)thiazolo[5,4-d]pyrimidin-5-yl)benzamide Step 1

(S)-1-(3-Methoxy-5-nitrophenyl)-2-methylpyrrolidine

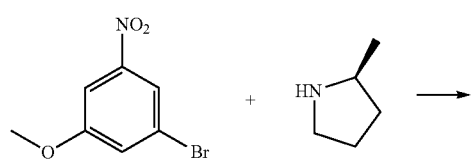

Procedure

A mixture of 1-bromo-3-methoxy-5-nitrobenzene (500 mg, 2.16 mmol), (S)-2-methylpyrrolidine (200 mg, 2.37 mmol), Pd$_2$(dba)$_3$ (248 mg, 0.43 mmol), BINAP (538 mg, 0.86 mmol), Cs$_2$CO$_3$ (2.11 g, 6.48 mmol) and dioxane (20 mL) was heated to 100° C. with stirring for 16 h under N$_2$. The solvent was removed in vacuo and the resulting residue was purified by column chromatography (petroleum ether:ethyl acetate=5:1) to afford (S)-1-(3-methoxy-5-nitrophenyl)-2-methylpyrrolidine (430 mg, 85%) as yellow oil. LC-MS: 237 [M+H]$^+$, t$_R$=1.77 min.

Step 2

(S)-3-Methoxy-5-(2-methylpyrrolidin-1-yl)benzenamine

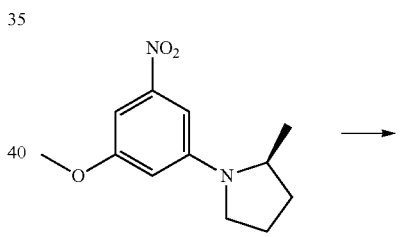

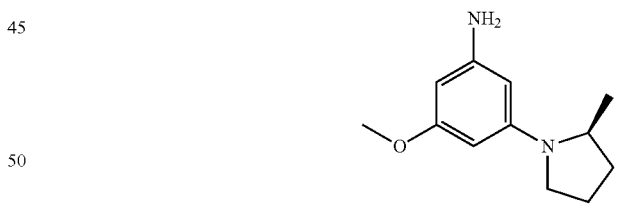

Procedure

To a suspension of (S)-1-(3-methoxy-5-nitrophenyl)-2-methylpyrrolidine (430 mg, 1.82 mmol) and Zinc (1.18 g, 18.2 mmol) in dioxane (20 mL) and H2O (10 mL) was added dropwise conc. HCl (1.8 mL) at room temperature, and the mixture was stirred for 2 h. The reaction mixture was filtered and the filtrate was adjusted to pH~8 by the addition of solid NaHCO$_3$, and then extracted with ethyl acetate (50 mL). The organic layer was dried with Na2SO4, concentrated and the residue was purified by column chromatography (petroleum ether:ethyl acetate=20:1) to afford (S)-3-methoxy-5-(2-methylpyrrolidin-1-yl)benzenamine (269 mg, 72%) as yellow oil. LC-MS: 207 [M+H]$^+$, t$_R$=1.193 min.

Step 3

(S)-5-Chloro-N-(3-methoxy-5-(2-methylpyrrolidin-1-yl)phenyl)thiazolo[5,4-d]pyrimidin-7-amine

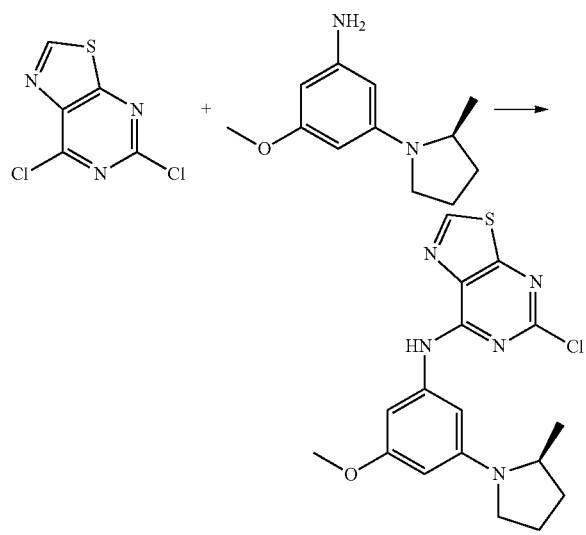

Procedure

The mixture of 5,7-dichlorothiazolo[5,4-d]pyrimidine (200 mg, 0.97 mmol), (S)-3-methoxy-5-(2-methylpyrrolidin-1-yl)benzenamine (220 mg, 1.07 mmol) and DIPEA (150 mg, 1.17 mmol) in DMSO (50 mL) was heated to 30° C. with stirring for 16 h. The mixture was diluted with water, extracted with ethyl acetate (50 mL), combined organics washed with water (10 mL×4) then brine (10 mL×2), dried over Na2SO4 and concentrated to give the residue which was purified by column chromatography (petroleum ether:ethyl acetate=20:1) to afford (S)-5-chloro-N-(3-methoxy-5-(2-methylpyrrolidin-1-yl)phenyl)thiazolo[5,4-d]pyrimidin-7-amine (280 mg, 77%) as yellow oil. LC-MS: 376 [M+H]$^+$, $t_R$=1.825 min.

Step 4

(S)-Methyl 4-(7-(3-methoxy-5-(2-methylpyrrolidin-1-yl)phenylamino)thiazolo[5,4-d]pyrimidin-5-yl)benzoate

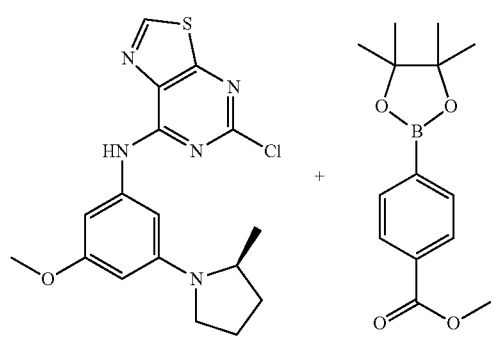

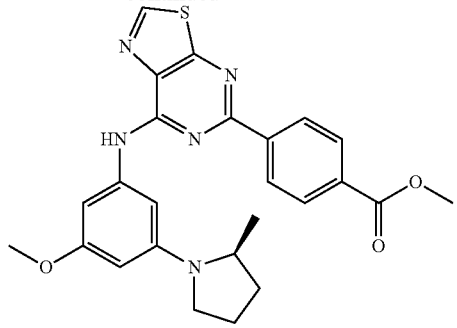

Procedure

The mixture of (S)-5-chloro-N-(3-methoxy-5-(2-methylpyrrolidin-1-yl)phenyl)thiazolo[5,4-d]pyrimidin-7-amine (200 mg, 0.53 mmol), methyl 4-(4,4,5,5-tetramethyl-1,3,2-dioxaborolan-2-yl)benzoate (153 mg, 0.585 mmol), Pd$_2$(dba)$_3$ (61 mg, 0.11 mmol), X-Phos (102 mg, 0.21 mmol) and Na$_2$CO$_3$ (169 mg, 1.6 mmol) in dioxane (20 mL) and water (5 mL) was heated to 100° C. with stirring for 16 h under N$_2$. The solvent was removed in vacuo and the resulting residue was purified by column chromatography (petroleum ether:ethyl acetate=20:1) to afford (S)-methyl 4-(7-(3-methoxy-5-(2-methylpyrrolidin-1-yl)phenylamino)thiazolo[5,4-d]pyrimidin-5-yl)benzoate (121 mg, 48%) as yellow oil. LC-MS: 476 [M+H]$^+$, $t_R$=1.999 min.

Step 5

(S)-4-(7-(3-Methoxy-5-(2-methylpyrrolidin-1-yl)phenylamino)thiazolo[5,4-d]pyrimidin-5-yl)benzoic acid

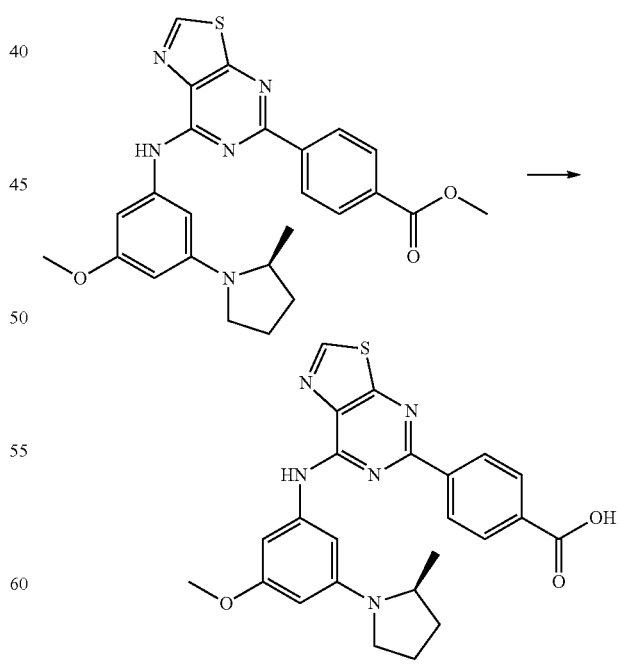

Procedure

The mixture of (S)-methyl 4-(7-(3-methoxy-5-(2-methylpyrrolidin-1-yl)phenylamino)thiazolo[5,4-d]pyrimidin-5- yl)benzoate (121 mg, 0.25 mmol) and NaOH (102 mg, 2.54 mmol) in dioxane (20 mL) and H2O (10 mL) was heated to 30° C. for 2 h. The reaction mixture was concentrated and the aqueous residue was adjusted to pH~4 by the addition of conc. HCl. The solution was extracted with ethyl acetate (10 mL×3), then combined organics dried over Na2SO4 and concentrated to afford (S)-4-(7-(3-methoxy-5-(2-methylpyrrolidin-1-yl)phenylamino)thiazolo[5,4-d]pyrimidin-5-yl)benzoic acid (50 mg, crude) as yellow solid which was used to next step without purification. LC-MS: 462 [M+H]$^+$, $t_R$=1.699 min.

Step 6

(S)-4-(7-(3-Methoxy-5-(2-methylpyrrolidin-1-yl)phenylamino)thiazolo[5,4-d]pyrimidin-5-yl)benzamide

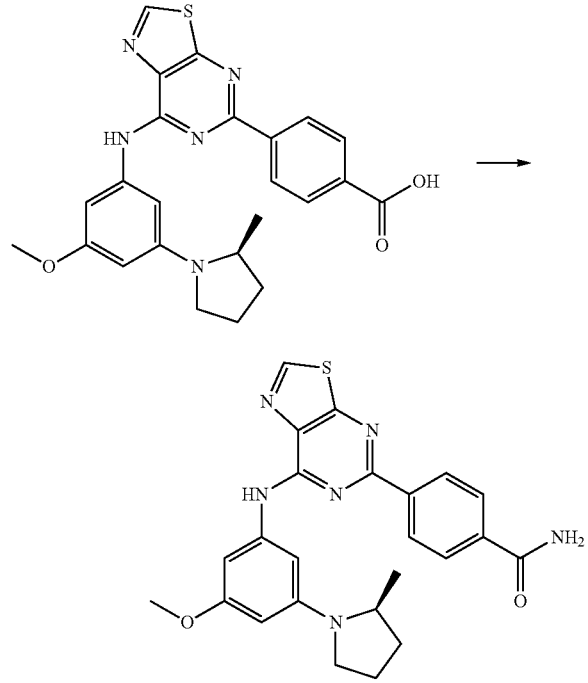

Procedure

The mixture of (S)-4-(7-(3-methoxy-5-(2-methylpyrrolidin-1-yl)phenylamino)thiazolo[5,4-d]pyrimidin-5-yl)benzoic acid, EDCI (56 mg, 0.29 mmol), HOBt (39 mg, 0.29 mmol) and Et3N (39 mg, 0.39 mmol) in DCM (20 mL) was stirred at room temperature for 3 hrs, then ammonia was bubbled into this mixture for 3 h. The mixture was filtered and the filtrate was concentrated to give a residue which was purified by column chromatography (DCM:MeOH=50:1) to afford (S)-4-(7-(3-methoxy-5-(2-methylpyrrolidin-1-yl)phenylamino)thiazolo[5,4-d]pyrimidin-5-yl)benzamide (12 mg, 10%) as yellow solid. $^1$H NMR (300 MHz, DMSO): δ 9.99 (s, 1H), 9.40 (s, 1H), 8.49 (s, 1H), 8.46 (s, 1H), 8.12 (s, 1H), 8.01 (s, 1H), 7.98 (s, 1H), 7.49 (s, 1H), 7.15 (s, 1H), 7.05 (s, 1H), 5.88 (s, 1H), 3.93-3.90 (m, 1H), 3.79 (s, 3H), 3.43-3.40 (m, 1H), 3.18-3.15 (m, 1H), 2.06-1.98 (m, 3H), 1.69 (s, 1H), 1.15 (d, 3H, J=6.0 Hz). LC-MS: 461 [M+H]$^+$, $t_R$=1.6 min. HPLC: 95.06% at 214 nm, 95.01% at 254 nm, $t_R$=5.55 min.

Example 61

(S)-5-(6-Methoxypyridin-3-yl)-N-(3-(2-methylpyrrolidin-1-yl)phenyl)thiazolo[5,4-d]pyrimidin-7-amine Step 1

(S)-2-Methyl-1-(3-nitrophenyl)pyrrolidine

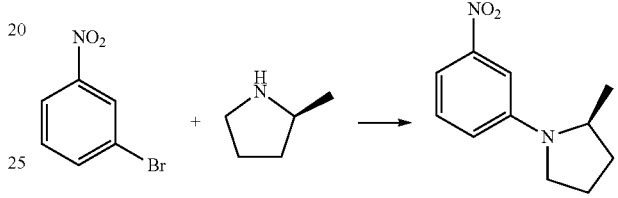

Procedure

A mixture of 1-bromo-3-nitrobenzene (1.43 g, 7.06 mmol), (S)-2-methylpyrrolidine (0.5 g, 5.88 mmol), Pd2(dba)3 (0.34 g, 0.59 mmol), X-Phos (0.56 g, 1.18 mmol) and sodium carbonate (1.77 g, 16.74 mmol) in the mixture of 1,4-dioxane (20 mL) and water (20 mL) was heated to reflux for 16 hours. Then water was added, extracted with ethyl acetate and organic layer washed brine dried over Na$_2$SO$_4$ and filtered. The filtrate was concentrated in vacuo. The crude product was purified by column chromatography (petroleum ether:ethyl acetate=10:1) to give (S)-2-methyl-1-(3-nitrophenyl)pyrrolidine (1.1 g, 91%) as red solid. LC-MS: 207 [M+H]$^+$, $t_R$=1.77 min.

Step 2

(S)-3-(2-Methylpyrrolidin-1-yl)benzenamine

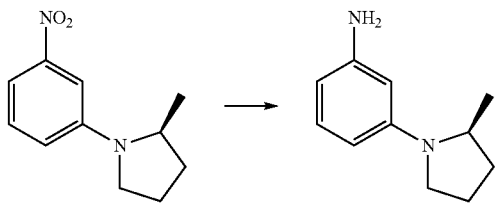

Procedure

A mixture of (S)-2-methyl-1-(3-nitrophenyl)pyrrolidine (1.1 g, 5.34 mmol) and Pd/C (0.2 g) in MeOH (50 mL) was purged with H$_2$ then stirred for 16 hours under H$_2$ atmosphere. Catalyst was removed by filtration and filtrate concentrated to give crude (S)-3-(2-methylpyrrolidin-1-yl)benzenamine (1 g, 100%), used into the next step without further purification.
LC-MS: 177 [M+H]⁺, $t_R$=1.09 min.

Step 3

(S)-5-Chloro-N-(3-(2-methylpyrrolidin-1-yl)phenyl)
thiazolo[5,4-d]pyrimidin-7-amine

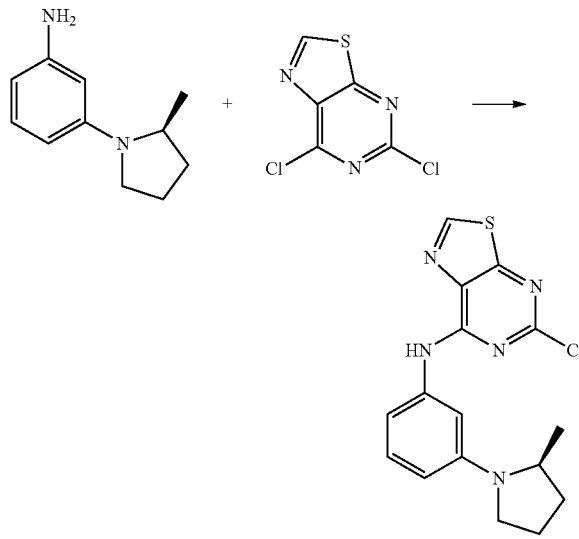

Procedure

A mixture of (S)-3-(2-methylpyrrolidin-1-yl)benzenamine (0.9 g, 5.34 mmol), 5,7-dichlorothiazolo[5,4-d]pyrimidine (1.1 g, 5.34 mmol), DIEA (1.4 g, 10.68 mmol) in IPA (15 mL) was heated to reflux for 2 hours. Then the reaction mixture was concentrated and residue purified by column chromatography (petroleum ether:ethyl acetate=8:1) to give (S)-5-chloro-N-(3-(2-methylpyrrolidin-1-yl)phenyl)thiazolo[5,4-d]pyrimidin-7-amine (1.6 g, 91.4%) as yellow solid. LC-MS: 346 [M+H]⁺, $t_R$=1.82 min.

Step 4

(S)-5-(6-Methoxypyridin-3-yl)-N-(3-(2-methylpyrrolidin-1-yl)phenyl)thiazolo[5,4-d]pyrimidin-7-amine

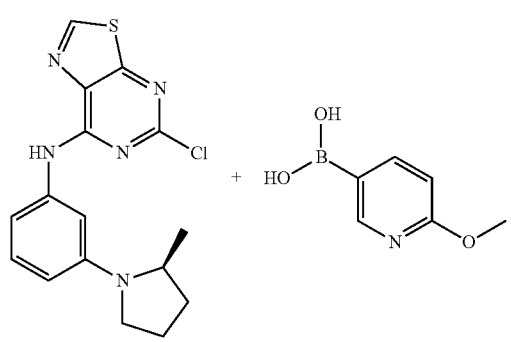

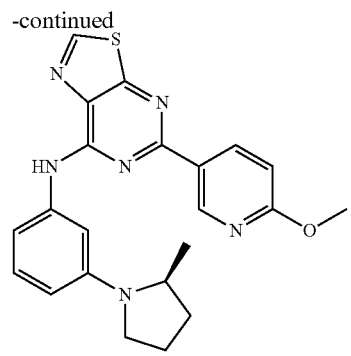

Procedure

A mixture of (S)-5-chloro-N-(3-(2-methylpyrrolidin-1-yl)phenyl)thiazolo[5,4-d]pyrimidin-7-amine (200 mg, 0.58 mmol), 6-methoxypyridin-3-ylboronic acid (134 mg, 0.87 mmol), Pd2(dba)3 (34 mg, 0.058 mmol), X-Phos (0.58 mg, 0.12 mmol) and sodium carbonate (185 mg, 1.74 mmol) in 1,4-dioxane:water (5 mL:5 mL) was heated to reflux for 16 hours. Then water was added, mixture extracted with ethyl acetate, organics combined washed with brine dried over Na2SO4 and filtered. The filtrate was concentrated in vacuo. The crude product was purified by preparative HPLC (Gemini 5u C18 150×21.2 mm; inject volume: 3 ml/inj, flow rate: 20 ml/min; wavelength: 214 nm and 254 nm; the gradient conditions are: 20% acetonitrile/80% water (0.1% TFA V/V) initially, and then proceed to 45% acetonitrile/55% water (0.1% TFA V/V) in a linear fashion after just 9 min.) to give (S)-5-(6-methoxypyridin-3-yl)-N-(3-(2-methylpyrrolidin-1-yl)phenyl)thiazolo[5,4-d]pyrimidin-7-amine (60 mg, 24.8%) as yellow solid. ¹H NMR (300 MHz, CD3OD): δ 9.19 (s, 1H), 9.08 (s, 1H), 8.63 (dd, 1H, J1=8.7 Hz, J2=2.4 Hz), 7.33 (s, 1H), 7.23-7.12 (m, 2H), 6.88 (d, 1H, J=8.7 Hz), 6.42 (d, 1H, J=6.9 Hz), 3.96 (s, 3H), 3.51-3.46 (m, 1H), 3.30-3.24 (m, 2H), 2.17-2.03 (m, 3H), 1.80-1.75 (m, 1H), 1.22 (d, 3H, J=6.3 Hz). LC-MS: 419 [M+H]⁺, $t_R$=2.04 min. HPLC: 100% at 214 nm, 100% at 254 nm, $t_R$=6.299 min.

Example 62

(S)-4-(7-(3-(2-Methylpyrrolidin-1-yl)phenylamino)thiazolo[5,4-d]pyrimidin-5-yl)benzamide Step 1

4-(4,4,5,5-Metramethyl-1,3,2-dioxaborolan-2-yl)benzamide

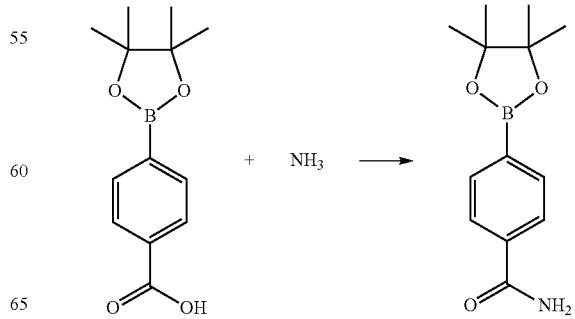

Procedure

To a mixture of 4-(4,4,5,5-tetramethyl-1,3,2-dioxaborolan-2-yl)benzoic acid (200 mg, 0.746 mmol), EDCI (214 mg, 1.12 mmol), HOBt (151 mg, 1.12 mmol) and Et3N (151 mg, 1.49 mmol) in DCM (20 mL) was bubbled ammonia until saturation. The mixture was stirred at room temperature for 3 h, then was filtered and the filtrate was concentrated to give residue which was purified by column chromatography (DCM:MeOH=50:1) to afford 4-(4,4,5,5-tetramethyl-1,3,2-dioxaborolan-2-yl)benzamide (90 mg, 45%) as a yellow solid. LC-MS: 248 [M+H]$^+$, $t_R$=1.421 min.

Step 2

(S)-4-(7-(3-(2-Methylpyrrolidin-1-yl)phenylamino)thiazolo[5,4-d]pyrimidin-5-yl)benzamide

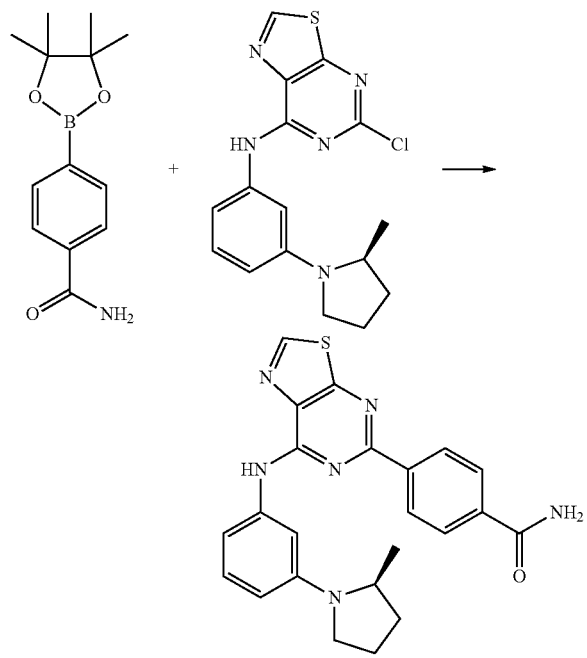

Procedure

The mixture of (S)-5-chloro-N-(3-methoxy-5-(2-methylpyrrolidin-1-yl)phenyl)thiazolo[5,4-d]pyrimidin-7-amine (100 mg, 0.29 mmol), 4-(4,4,5,5-tetramethyl-1,3,2-dioxaborolan-2-yl)benzamide (77 mg, 0.29 mmol), Pd$_2$(dba)$_3$ (33 mg, 0.058 mmol), X-Phos (55 mg, 0.116 mmol) and Na$_2$CO$_3$ (123 mg, 1.16 mmol) in dioxane (20 mL) and water (5 mL) was heated to 100° C. with stirring for 16 h under N$_2$. The solvent was removed in vacuo and the resulting residue was purified by column chromatography (DCM:MeOH=80:1) to afford (S)-4-(7-(3-(2-methylpyrrolidin-1-yl)phenylamino)thiazolo[5,4-d]pyrimidin-5-yl)benzamide (26 mg, 21%) as a yellow solid. $^1$H NMR (300 MHz, DMSO): δ 10.02 (s, 1H), 9.39 (s, 1H), 8.46-8.44 (m, 2H), 8.10 (s, 1H), 8.00-7.97 (m, 2H), 7.48-7.39 (m, 2H), 7.29-7.15 (m, 2H), 6.35 (d, 1H, J=7.8 Hz), 3.91 (brs, 1H), 3.41-3.31 (m, 1H), 3.19-3.16 (m, 1H), 2.08-1.98 (m, 2H), 1.71 (brs, 1H), 1.15 (d, 3H, J=6.3 Hz). LC-MS: 431 [M+H]$^+$, $t_R$=1.57 min. HPLC: 95.67% at 214 nm, 95.15% at 254 nm, $t_R$=3.14 min.

Example 63

3-(7-(3,4-Dimethoxyphenylamino)thiazolo[5,4-d]pyrimidin-5-yl)-N-(4-(2,4-dioxothiazolidin-5-yl)phenyl)benzamide

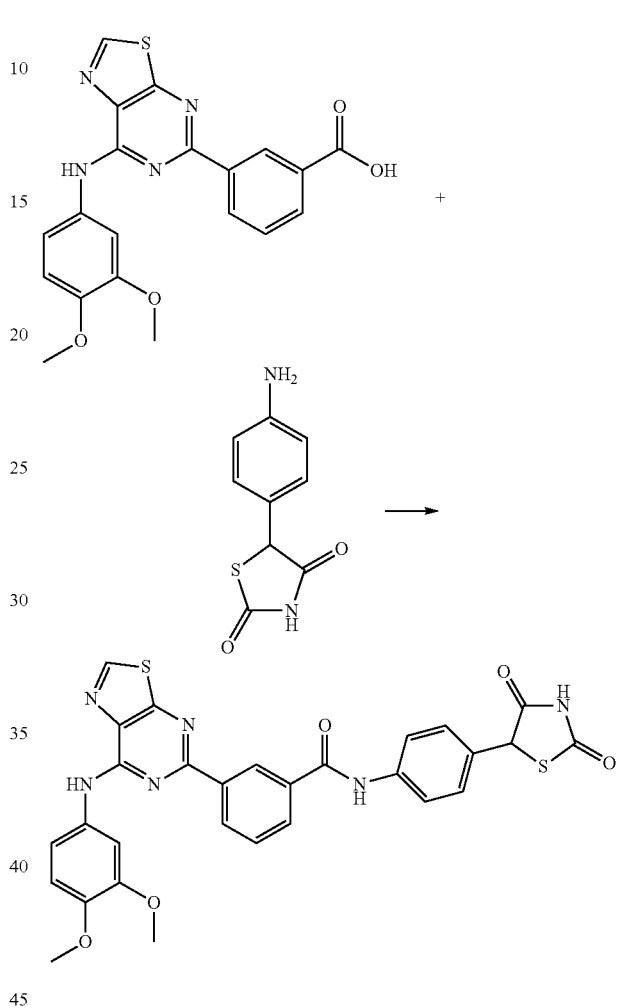

Procedure

To a solution of 3-(7-(3,4-dimethoxyphenylamino)thiazolo[5,4-d]pyrimidin-5-yl)benzoic acid (100 mg, 0.25 mmol) and 5-(4-aminophenyl)thiazolidine-2,4-dione (50 mg, 0.25 mmol) in DCM (10 mL) was added 1-methyl-1H-indozole (78 mg, 1.0 mmol) and EDCI (129 mg, 1.0 mmol) in DCM (5 mL). The reaction mixture was stirred at room temperature for 15 hrs. The solvent was removed in vacuo and the residue was purified by column chromatography (DCM:MeOH=50:1), then by preparative HPLC (Gemini 5u C18 150×21.2 mm; inject volume: 3 ml/inj, flow rate: 20 ml/min; wavelength: 214 nm and 254 nm; the gradient conditions are: 30% acetonitrile/70% water (0.1% TFA V/V) initially, and then proceed to 45% acetonitrile/55% water (0.1% TFA V/V) in a linear fashion after just 9 min.) to give the corresponding trifluoroacetate salt. The obtained salt was suspended in dichloromethane (8 mL) and conc. HCl (0.5 mL) was added dropwise. The mixture was stirred for 15 minutes and then concentrated under reduced pressure to afford 3-(7-(3,4-dimethoxyphenylamino)thiazolo[5,4-d]pyrimidin-5-yl)-N-(4-(2,4-dioxothiazolidin-5-yl)phenyl)benzamide (2.4 mg, 1.5%) as HCl salt. $^1$H NMR (300 MHz, DMSO): δ 12.29 (s, 1H), 10.57 (s, 1H), 10.19 (s, 1H), 9.41 (s, 1H), 8.95 (s, 1H), 8.59 (d, 1H, J=7.5 Hz), 8.07 (d, 1H, J=7.8 Hz), 7.84-7.81 (m, 2H), 7.69 (t, 1H, J=7.5 Hz), 7.55 (d, 2H, J=9.0 Hz), 7.42 (d, 1H, J=8.4 Hz), 6.97 (d, 1H, J=8.4 Hz), 5.74 (s, 1H), 3.80 (s, 3H), 3.72 (s, 3H). LC-MS: 599 [M+H]$^+$, $t_R$=1.54 min. HPLC: 95.59% at 214 nm, 95.99% at 254 nm, $t_R$=4.594 min.

Example 64

4-(7-(3,4-Dimethoxyphenylamino)thiazolo[5,4-d]pyrimidin-5-yl)benzamide

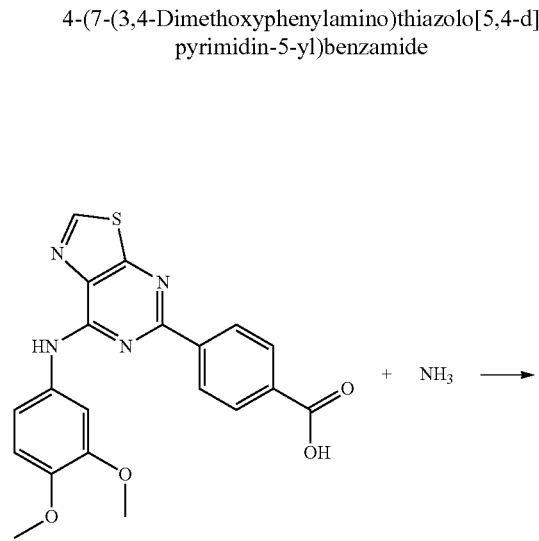

Procedure

To a mixture of 4-(7-(3,4-dimethoxyphenylamino)thiazolo[5,4-d]pyrimidin-5-yl)benzoic acid (210 mg, 0.52 mmol), EDCI (147 mg, 0.77 mmol), HOBt (104 mg, 0.77 mmol) and Et3N (104 mg, 1.07 mmol) in DCM (20 mL) was bubbled ammonia until saturation. The mixture was stirred at room temperature for 3 h, then was filtered and the filtrate was concentrated to give residue which was purified by column chromatography (DCM:MeOH=50:1) to afford 4-(7-(3,4-dimethoxyphenylamino)thiazolo[5,4-d]pyrimidin-5-yl)benzamide (38 mg, 22%) as a yellow solid. $^1$H NMR (300 MHz, DMSO): δ 9.14 (s, 1H), 8.30 (s, 1H), 8.27 (s, 1H), 7.87 (s, 1H), 7.84 (s, 1H), 7.62 (d, 1H, J=2.4 Hz), 7.32-7.28 (m, 1H), 6.92 (d, 1H, J=9.0 Hz), 3.75 (s, 3H), 3.72 (s, 3H). LC-MS: 599 [M+H]$^+$, $t_R$=1.54 min. HPLC: 95.59% at 214 nm, 95.99% at 254 nm, $t_R$=4.594 min. LC-MS: 408 [M+H]$^+$, $t_R$=1.392 min. HPLC: 95.38% at 214 nm, 96.23% at 254 nm, $t_R$=5.259 min.

Example 65

(S)—N-(2-(Dimethylamino)ethyl)-4-(7-(3-(2-methylpyrrolidin-1-yl)phenylamino)thiazolo[5,4-d]pyrimidin-5-yl)benzamide

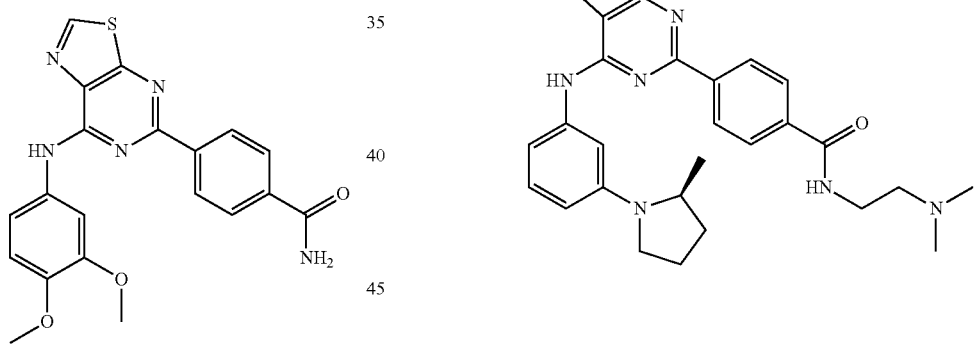

Procedure

To a solution of (S)-4-(7-(3-(2-methylpyrrolidin-1-yl)phenylamino)thiazolo[5,4-d]pyrimidin-5-yl)benzoic acid (80 mg, 0.19 mmol) and N1,N1-dimethylethane-1,2-diamine (18 mg, 0.2 mmol) in DCM (20 mL) was added 1-methyl-1H-indozole (92 mg, 1.12 mmol) and EDCI (217 mg, 1.12 mmol). The reaction mixture was stirred at room temperature for 3 h. The solvent was removed in vacuo and the residue was purified by column chromatography (DCM:MeOH=50:1) and product treated with conc. HCl to give (S)—N-(2-(dimethylamino)ethyl)-4-(7-(3-(2-methylpyrrolidin-1-yl)phenylamino)thiazolo[5,4-d]pyrimidin-5-yl)benzamide (22 mg, 24%) as HCl salt. $^1$H NMR (300 MHz, CD$_3$OD): δ 9.15 (s, 1H), 8.37 (s, 1H), 8.34 (s, 1H), 8.27 (s, 1H), 7.97-7.91 (m, 3H), 7.63-7.57 (m, 1H), 7.41 (d, 1H, J=8.1 Hz), 4.06-3.93 (m, 2H), 3.77-3.68 (m, 3H), 3.37-3.33 (m, 2H), 2.91 (s, 6H), 2.53-2.42 (m, 1H), 2.35-2.18 (m, 2H), 2.06-1.87 (m, 1H), 1.36 (d, 3H, J=6.6 Hz). LC-MS: 502 [M+H]$^+$, $t_R$=1.344 min. HPLC: 97.57% at 214 nm, 97.17% at 254 nm, $t_R$=4.793 min.

Example 66

4-(7-(3,4-Dimethoxyphenylamino)thiazolo[5,4-d]pyrimidin-5-yl)-N-(2-(dimethylamino)ethyl)benzamide

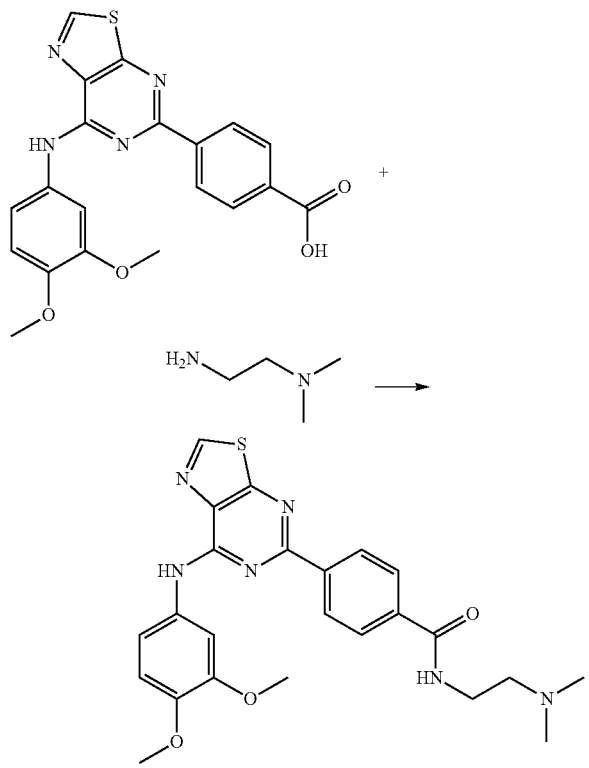

Procedure

The mixture of 4-(7-(3,4-dimethoxyphenylamino)thiazolo[5,4-d]pyrimidin-5-yl)benzoic acid (158 mg, 0.387 mmol) and N1,N1-dimethylethane-1,2-diamine (37 mg, 0.41 mmol), 1-methyl-1H-indozole (127 mg, 1.56 mmol) and EDCI (296 mg, 1.56 mmol) in DCM (20 mL) was stirred at room temperature for 3 h. The solvent was removed in vacuo and the residue was purified by column chromatography (DCM:MeOH=50:1), then by preparative HPLC (Gemini 5u C18 150×21.2 mm; inject volume: 3 ml/inj, flow rate: 20 ml/min; wavelength: 214 nm and 254 nm; the gradient conditions are: 20% acetonitrile/80% water (0.1% TFA V/V) initially, and then proceed to 45% acetonitrile/55% water (0.1% TFA V/V) in a linear fashion after just 9 min.) to give the corresponding trifluoroacetate salt. The salt was suspended in MeOH (10 mL) and conc. HCl (0.5 mL) was added, the mixture was stirred for 15 minutes and concentrated under reduced pressure to give 4-(7-(3,4-dimethoxyphenylamino)thiazolo[5,4-d]pyrimidin-5-yl)-N-(2-(dimethylamino)ethyl)benzamide (49 mg, 25%) as HCl salt. $^1$H NMR (300 MHz, DMSO): δ 9.16 (s, 1H), 8.35 (s, 1H), 8.33 (s, 1H), 7.88 (s, 1H), 7.86 (s, 1H), 7.62 (s, 1H), 7.32-7.29 (m, 1H), 6.96 (d, 1H, J=9.0 Hz), 3.76 (s, 3H), 3.72 (s, 3H), 3.62-3.59 (m, 2H), 3.26-3.23 (m, 2H), 2.79 (s, 6H). LC-MS: 479 [M+H]$^+$, $t_R$=1.23 min. HPLC: 99.54% at 214 nm, 99.49% at 254 nm, $t_R$=4.884 min.

Example 67

(3-(7-(3,4-Dimethoxyphenylamino)thiazolo[5,4-d]pyrimidin-5-yl)phenyl)methanol

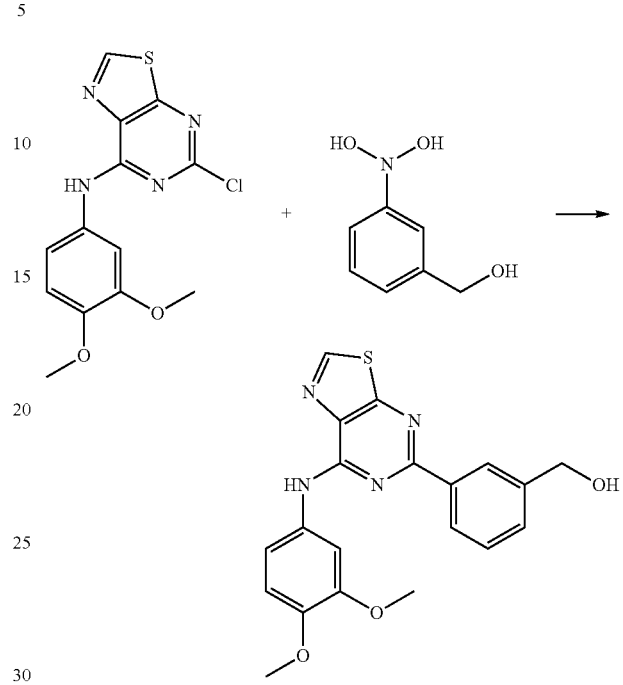

Procedure

A mixture of 5-chloro-N-(3,4-dimethoxyphenyl)thiazolo[5,4-d]pyrimidin-7-amine (200 mg, 0.62 mmol), 3-(hydroxymethyl)phenylboronic acid (104 mg, 0.68 mmol), Pd$_2$(dba)$_3$ (71 mg, 0.12 mmol), X-Phos (118 mg, 0.25 mmol), Na$_2$CO$_3$ (131 mg, 1.2 mmol) in dioxane (20 mL) and H2O (5 mL) was heated to 90° C. with stirring for 16 h under N$_2$. The solvent was removed in vacuo and the resulting mixture was purified by column chromatography (MeOH:DCM=1:80) to give (3-(7-(3,4-dimethoxyphenylamino)thiazolo[5,4-d]pyrimidin-5-yl)phenyl)methanol (51 mg, 21%) as yellow solid. $^1$H NMR (300 MHz, CDCl$_3$): δ 8.84 (s, 1H), 8.49 (s, 1H), 8.42 (d, 1H, J=6.9 Hz), 7.97 (s, 1H), 7.87 (s, 1H), 7.49-7.46 (m, 2H), 7.18 (dd, 1H, J1=8.7 Hz, J2=2.7 Hz), 6.93 (d, 1H, J=8.4 Hz), 4.79 (s, 2H), 4.00 (s, 3H), 3.93 (s, 3H). LC-MS: 395 [M+H]$^+$, $t_R$=1.48 min. HPLC: 98.36% at 214 nm, 98.69% at 254 nm, $t_R$=6.086 min.

Example 68

3-(7-(3,4-Dimethoxyphenylamino)thiazolo[5,4-d]pyrimidin-5-yl)benzamide

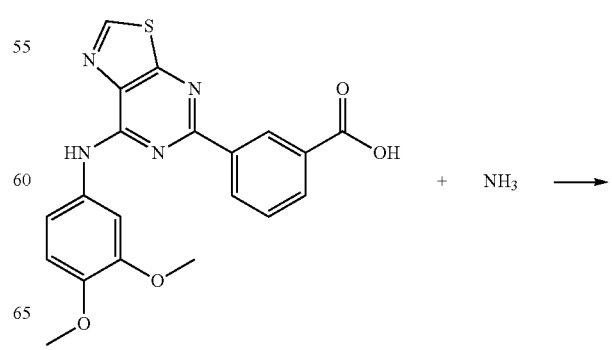

-continued

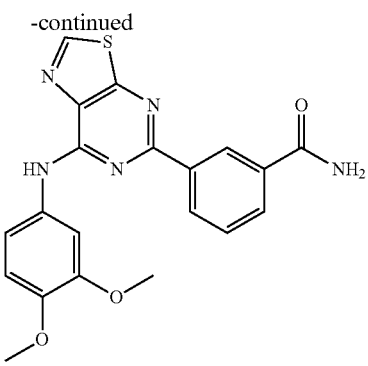

Procedure

To a mixture of 3-(7-(3,4-dimethoxyphenylamino)thiazolo[5,4-d]pyrimidin-5-yl)benzoic acid (100 mg, 0.25 mmol), EDCI (70 mg, 0.37 mmol), HOBt (50 mg, 0.37 mmol) and Et3N (49 mg, 0.49 mmol) in DCM (20 mL) was bubbled ammonia until saturation. The mixture was stirred at room temperature for 3 h, then was filtered and the filtrate was concentrated to give residue which was purified by column chromatography (DCM:MeOH=50:1) to afford 3-(7-(3,4-dimethoxyphenylamino)thiazolo[5,4-d]pyrimidin-5-yl)benzamide (22 mg, 14%) as a yellow solid. $^1$H NMR (300 MHz, DMSO): δ 10.13 (s, 1H), 9.37 (s, 1H), 8.88 (t, 1H, J=1.5 Hz), 8.51 (d, 1H, J=7.8 Hz), 8.10 (s, 1H), 7.98 (d, 1H, J=7.5 Hz), 7.86 (d, 1H, J=2.4 Hz), 7.58 (t, 1H, J=7.8 Hz), 7.49-7.44 (m, 2H), 7.99 (d, 1H, J=8.7 Hz), 3.82 (s, 3H), 3.77 (s, 3H). LC-MS: 408 [M+H]$^+$, $t_R$=1.39 min. HPLC: 97.78% at 214 nm, 97.42% at 254 nm, $t_R$=1.39 min. LC-MS: 408 [M+H]$^+$, $t_R$=1.392 min. HPLC: 95.38% at 214 nm, 96.23% at 254 nm, $t_R$=3.53 min.

Biological Examples

SYK Assay Information

Determination of IC$_{50}$ of Spleen Tyrosine Kinase (SYK) Inhibition:

SYK kinase assay is a standard kinase assay adapted to a 96 well plate format. This assay is performed in 96-well format for IC$_{50}$ determination with 8 samples which represented 10 half log dilutions and a 40 μL reaction volume. The assay measures the incorporation of radiolabeled $^{33}$P γATP into an N-terminally biotinylated peptide substrate, derived from naturally occurring phosphoacceptor consensus sequence (Biotin-11aa DY*E). Phosphorylated products were detected upon termination of reactions with EDTA and the addition of Streptavidin coated beads. Representative results are in Table II above.

Assay plates: 96-well MultiScreen 0.65 um filter plates (Millipore Cat. No.: MADVNOB10)
Streptavidin coated beads: Streptavidin Sepharose™, suspension 5.0 mL, in 50 mM EDTA/PBS diluted (1:100), (Amersham, Cat. No.: 17-5113-01)
Compounds: 10 mM in 100% dimethylsulfoxide (DMSO), final conc.: compound 0.003-100 uM in 10% DMSO
Enzyme: SYK RPA purified, truncated construct of Spleen Tyrosine Kinase aa 360-635, stock solution 1 mg/mL, MW: 31.2 KDa, final conc.: 0.0005 μM.
Peptide 1: biotinylated peptide is derived from a naturally occurring phosphor-acceptor consensus sequence (Biotin-EPEGDYEEVLE), special order from QCB, stock solution 20 mM, final conc.: 5.0 μM.

ATP: Adenosine-5'-triphosphate 20 mM, (ROCHE Cat. No.: 93202720), final concentration: 20 μM
Buffer: HEPES: 2-Hydroxyethyl piperazine-2-ethane-sulfonic acid (Sigma, Cat. No.: H-3375) final concentration: 50 mM HEPES pH7.5
BSA: Bovine Serum Albumin Fraction V, fatty acid free (Roche Diagnostics GmbH, Cat. No. 9100221) diluted to a final concentration of 0.1%
EDTA: EDTA stock solution 500 mM, (GIBCO, Cat. No.: 15575-038) final concentration: 0.1 mM
DTT: 1,4-Dithiothreitol (Roche Diagnostics GmbH, Cat. No.: 197777), final conc.: 1 mM
MgCl$_2$×6H$_2$O: MERCK, Cat. No.: 105833.1000, final concentration: 10 mM
Assay Dilution Buffer (ADB): 50 mM HEPES, 0.1 mM EGTA, 0.1 mM Na Vanadate, 0.1 mM β-glycerophosphate, 10 mM MgCl$_2$, 1 mM DTT, 0.1% BSA, pH 7.5
Bead wash buffer: 10 g/L PBS (Phosphate buffered saline) with 2M NaCl+1% phosphoric acid.

Experimental Method:

In 40 μL volume, 26 μL of ADB diluted, purified recombinant human SYK360-635 [0.5 nM] was mixed with 4 μL of 10× concentrations of the test compounds, [usually 100 μM-0.003 μM] in [10%] DMSO and the mixture was incubated for 10 min at RT.

The kinase reaction was initiated by the addition of 10 μL 4× substrate cocktail containing the DYE peptide substrate [0 or 5 μM], ATP [20 μM] and $^{33}$PγATP [2 μCi/rxn]. After incubation at 30° C. for 15 min, the reaction was terminated by the transfer of 25 μL of the reaction sample to a 96 well 0.65 μm Millipore MADVNOB membrane/plate containing 200 μL 5 mM EDTA and 20% Streptavidine coated beads in PBS.

The unbound radionucleotides were washed under vacuum with 3×250 μL 2M NaCl; 2×250 μL 2M NaCl+1% phosphoric acid; 1×250 μL H$_2$O. After the last wash membrane/plates were transferred to an adaptor plate, heat dried for 15 min at 60° C., and 50 μL scintillation cocktail was added to each well and 4 h later the amount of radioactivity was counted in a top counter.

The percent inhibition was calculated based on the uninhibited enzyme rate:

% Inhibition=100/(1+(IC$_{50}$/Inhibitor conc)$^n$)

The IC$_{50}$ was calculated using a non-linear curve fit with XLfit software (ID Business Solution Ltd., Guilford, Surrey, UK).

| Compound | IC50 h-syk-gst-sf9-c (inactive-dephosphorylated)/ uM |
|---|---|
| I-1 | 0.421 |
| I-2 | 1.114 |
| I-3 | 0.071 |
| I-4 | 0.007 |
| I-5 | 0.749 |
| I-6 | 5.070 |
| I-7 | 1.090 |
| I-8 | 0.882 |
| I-9 | 0.040 |
| I-10 | 0.111 |
| I-11 | 0.406 |
| I-12 | 0.933 |
| I-13 | 0.566 |
| I-14 | 0.487 |
| I-15 | 0.045 |
| I-16 | 0.012 |
| I-18 | 0.980 |

-continued

| Compound | IC50 h-syk-gst-sf9-c (inactive-dephosphorylated)/ uM |
|---|---|
| I-19 | 0.056 |
| I-20 | 0.566 |
| I-21 | 1.854 |
| I-22 | 4.879 |
| I-23 | 0.930 |
| I-24 | 0.916 |
| I-25 | 19.900 |
| I-26 | 2.061 |
| I-27 | 4.605 |
| I-28 | 3.133 |
| I-29 | 1.490 |
| I-30 | 0.018 |
| I-31 | 0.592 |
| I-32 | 0.060 |
| I-33 | 0.350 |
| I-34 | 2.468 |
| I-35 | 0.418 |
| I-37 | 0.912 |
| I-38 | 1.949 |
| I-39 | 0.129 |
| I-40 | 5.409 |
| I-41 | 1.691 |
| I-42 | 0.065 |
| I-43 | 0.164 |
| I-44 | 0.136 |
| I-45 | 0.922 |
| I-46 | 1.034 |
| I-47 | 0.071 |
| I-48 | 4.209 |
| I-49 | 1.519 |
| I-50 | 1.919 |
| I-51 | 0.156 |
| I-52 | 0.441 |
| I-53 | 3.867 |
| I-54 | 0.093 |
| I-55 | 6.152 |
| I-56 | 3.180 |
| I-57 | 4.246 |
| I-58 | 2.247 |
| I-59 | 0.757 |
| I-60 | 1.115 |
| I-61 | 1.036 |
| I-62 | 0.337 |
| I-63 | 0.053 |
| I-64 | 0.113 |
| I-65 | 0.351 |
| I-66 | 0.278 |
| I-67 | 0.079 |
| I-68 | 0.233 |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:
1. A compound of Formula I

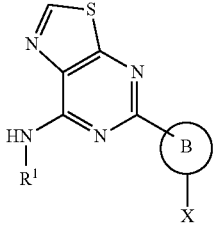

I wherein:
$R^1$ is phenyl, optionally substituted with one or more lower alkyl, lower haloalkyl, hydroxy, hydroxy lower alkyl, lower alkoxy, lower alkyl sulfonyl, halo, nitro, amino, aminoalkyl, amido, cyano, oxo, or $R^{1'}$;
  $R^{1'}$ is heterocycloalkyl or spiro heterocycloalkyl, each optionally substituted with one or more $R^{1''}$;
    $R^{1''}$ is hydroxy, halo, lower alkyl, lower alkoxy, or lower haloalkyl;
B is phenyl, pyridinyl, pyrrolidinyl, or piperidinyl;
X is OH, lower alkoxy, NHC(=O)Y, C(=O)NH$_2$, C(=O)NHY, C(=O)X', C(=O)Y, CH$_2$NHY, CH$_2$CH$_2$Y, CF=CHY, CH=CHY, CH$_2$OH, C(=O)NHCH$_2$CH$_2$N(CH$_3$)$_2$, or C(=O)NHCH$_2$CH$_2$Y;
X' is OH or lower alkoxy;
Y is cycloalkyl, heterocycloalkyl, aryl, or heteroaryl, each optionally substituted with one or more $Y^3$;
$Y^3$ is hydroxy, lower alkyl, lower alkoxy, halo, oxo, lower haloalkyl, hydroxy lower alkyl, amino, amido, C(=O)NH(CH$_3$), C(=O)OH, C(=O)OY$^4$, or heteroaryl optionally substituted by with one or more lower alkyl, oxo or SH;
$Y^4$ is lower alkyl;
or a pharmaceutically acceptable salt thereof.

2. A compound according to claim 1 of Formula I

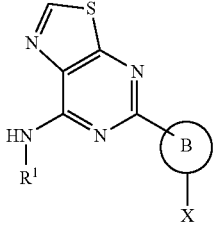

I wherein:
$R^1$ is phenyl, optionally substituted with one or more lower alkyl, lower haloalkyl, hydroxy, hydroxy lower alkyl, lower alkoxy, lower alkyl sulfonyl, halo, nitro, amino, aminoalkyl, amido, cyano, oxo, or $R^{1'}$;
  $R^{1'}$ is heterocycloalkyl or spiro heterocycloalkyl, each optionally substituted with one or more $R^{1''}$;
    $R^{1''}$ is hydroxy, halo, lower alkyl, lower alkoxy, or lower haloalkyl;
B is phenyl, pyrrolidinyl, or piperidinyl;
X is OH, NHC(=O)Y, C(=O)NH$_2$, C(=O)NHY, C(=O)X', C(=O)Y, CH$_2$NHY, CH$_2$CH$_2$Y, CF=CHY, CH=CHY, CH$_2$OH, C(=O)NHCH$_2$CH$_2$N(CH$_3$)$_2$, or C(=O)NHCH$_2$CH$_2$Y;

X' is OH or lower alkoxy;

Y is cycloalkyl, heterocycloalkyl, aryl, or heteroaryl, each optionally substituted with one or more $Y^3$;

$Y^3$ is hydroxy, lower alkyl, lower alkoxy, halo, oxo, lower haloalkyl, hydroxy lower alkyl, amino, amido, C(=O)OH, or C(=O)O$Y^4$;

$Y^4$ is lower alkyl;

or a pharmaceutically acceptable salt thereof.

3. The compound of claim 1, wherein B is phenyl.

4. The compound of claim 1, wherein B is pyrrolidinyl.

5. The compound of claim 1, wherein B is piperidinyl.

6. The compound of claim 1, wherein X is NHC(=O)Y, C(=O)NH$_2$, C(=O)NHY, C(=O)X', C(=O)Y, C(=O)NHCH$_2$CH$_2$N(CH$_3$)$_2$, or C(=O)NHCH$_2$CH$_2$Y.

7. The compound of claim 1, wherein X is NHC(=O)Y, C(=O)NHY, CH$_2$NHY or CH$_2$OH.

8. The compound of claim 1, wherein $R^1$ is 3,4-dimethoxyphenyl.

9. The compound of claim 1, wherein Y is phenyl optionally substituted with one or more $Y^3$.

10. The compound of claim 1, wherein Y is heteroaryl optionally substituted with one or more $Y^3$.

11. The compound of claim 1, wherein Y is heterocycloalkyl optionally substituted with one or more $Y^3$.

12. The compound of claim 1, wherein said compound is selected from the group consisting of:

3-[7-(3,4-Dimethoxy-phenylamino)-thiazolo[5,4-d]pyrimidin-5-yl]-benzoic acid;

[1,4]Diazepan-1-yl-{3-[7-(3,4-dimethoxy-phenylamino)-thiazolo[5,4-d]pyrimidin-5-yl]-phenyl}-methanone;

3-(7-(3,4-Dimethoxyphenylamino)thiazolo[5,4-d]pyrimidin-5-yl)-N-(4-(methylcarbamoyl)phenyl)benzamide;

4-{3-[7-(3,4-Dimethoxy-phenylamino)-thiazolo[5,4-d]pyrimidin-5-yl]-benzoylamino}-benzoic acid;

4-(1-(7-(3,4-Dimethoxyphenylamino)thiazolo[5,4-d]pyrimidin-5-yl)pyrrolidin-3-ylcarbamoyl)benzoic acid;

4-(1-(7-(3,4-Dimethoxyphenylamino)thiazolo[5,4-d]pyrimidin-5-yl)piperidin-3-ylcarbamoyl)benzoic acid;

4-({1-[7-(3,4-Dimethoxy-phenylamino)-thiazolo[5,4-d]pyrimidin-5-yl]-piperidine-3-carbonyl}-amino)-benzoic acid;

N-(1-(7-(3,4-Dimethoxyphenylamino)thiazolo[5,4-d]pyrimidin-5-yl)pyrrolidin-3-yl)-2-oxoindoline-6-carboxamide;

4-(1-(7-(3,4-Dimethoxyphenylamino)thiazolo[5,4-d]pyrimidin-5-yl)pyrrolidin-3-ylcarbamoyl)-2-hydroxybenzoic acid;

4-(1-(7-(3,4-Dimethoxyphenylamino)thiazolo[5,4-d]pyrimidin-5-yl)pyrrolidin-3-ylcarbamoyl)-2-methoxybenzoic acid;

N-(1-(7-(3,4-Dimethoxyphenylamino)thiazolo[5,4-d]pyrimidin-5-yl)pyrrolidin-3-yl)-1H-indazole-6-carboxamide;

N-(1-(7-(3,4-Dimethoxyphenylamino)thiazolo[5,4-d]pyrimidin-5-yl)pyrrolidin-3-yl)pyrazine-2-carboxamide;

6-Amino-N-{1-[7-(3,4-dimethoxy-phenylamino)-thiazolo[5,4-d]pyrimidin-5-yl]-pyrrolidin-3-yl}-nicotinamide;

N-(1-(7-(3,4-Dimethoxyphenylamino)thiazolo[5,4-d]pyrimidin-5-yl)pyrrolidin-3-yl)-2-oxo-2,3-dihydro-1H-benzo[d]imidazole-5-carboxamide;

3-[7-(3,4-Dimethoxy-phenylamino)-thiazolo[5,4-d]pyrimidin-5-yl]-N-[4-(5-mercapto-[1,3,4]oxadiazol-2-yl)-phenyl]-benzamide;

4-(3-(7-(3,4-Dimethoxyphenylamino)thiazolo[5,4-d]pyrimidin-5-yl)benzamido)-2-methoxybenzoic acid;

3-[7-(3,4-Dimethoxy-phenylamino)-thiazolo[5,4-d]pyrimidin-5-yl]-N-[4-(5-oxo-4,5-dihydro-[1,2,4]oxadiazol-3-yl)-phenyl]-benzamide;

3-[7-(3,4-Dimethoxy-phenylamino)-thiazolo[5,4-d]pyrimidin-5-yl]-N-(1H-indazol-5-yl)-benzamide;

3-[7-(3,4-Dimethoxy-phenylamino)-thiazolo[5,4-d]pyrimidin-5-yl]-N-(1H-indazol-6-yl)-benzamide;

4-[7-(3,4-Dimethoxy-phenylamino)-thiazolo[5,4-d]pyrimidin-5-yl]-N-(2-pyridin-4-yl-ethyl)-benzamide;

1-(7-(3,4-Dimethoxyphenylamino)thiazolo[5,4-d]pyrimidin-5-yl)-N-(2-(pyridin-4-yl)ethyl)piperidine-4-carboxamide;

1-(7-(3,4-Dimethoxyphenylamino)thiazolo[5,4-d]pyrimidin-5-yl)-N-(2-(2-oxo-1,2-dihydropyridin-4-yl)ethyl)piperidine-4-carboxamide;

4-(7-(3,4-Dimethoxyphenylamino)thiazolo[5,4-d]pyrimidin-5-yl)-N-(2-(2-oxo-1,2-dihydropyridin-4-yl)ethyl)benzamide;

4-[7-(3,4-Dimethoxy-phenylamino)-thiazolo[5,4-d]pyrimidin-5-yl]-N-[2-(1-methyl-2-oxo-1,2-dihydro-pyridin-4-yl)-ethyl]-benzamide;

1-(7-(3,4-Dimethoxyphenylamino)thiazolo[5,4-d]pyrimidin-5-yl)-N-(2-(pyridin-4-yl)ethyl)piperidine-3-carboxamide;

Methyl 3-(7-(3-(methylsulfonyl)phenylamino)thiazolo[5,4-d]pyrimidin-5-yl)benzoate;

3-[7-(3-Methanesulfonyl-phenylamino)-thiazolo[5,4-d]pyrimidin-5-yl]-benzoic acid;

3-{7-[3-(2-Methoxymethyl-pyrrolidin-1-yl)-phenylamino]-thiazolo[5,4-d]pyrimidin-5-yl}-benzoic acid;

tert-Butyl 4-(3-(7-(3,4-dimethoxyphenylamino)thiazolo[5,4-d]pyrimidin-5-yl)benzylamino)benzoate;

4-(3-(7-(3,4-Dimethoxyphenylamino)thiazolo[5,4-d]pyrimidin-5-yl)benzylamino)benzoic acid;

4-((E)-2-{3-[7-(3,4-Dimethoxy-phenylamino)-thiazolo[5,4-d]pyrimidin-5-yl]-phenyl}-2-fluoro-vinyl)-benzoic acid;

(E)-4-(3-(7-(3,4-Dimethoxyphenylamino)thiazolo[5,4-d]pyrimidin-5-yl)styryl)benzoic acid;

4-(3-(7-(3,4-Dimethoxyphenylamino)thiazolo[5,4-d]pyrimidin-5-yl)phenethyl)benzoic acid;

3-{7-[(1R,5S)-3-(8-Oxa-3-aza-bicyclo[3.2.1]oct-3-yl)-phenylamino]-thiazolo[5,4-d]pyrimidin-5-yl}-benzoic acid;

N-(1-(7-(3,4-Dimethoxyphenylamino)thiazolo[5,4-d]pyrimidin-5-yl)pyrrolidin-3-yl)-1H-indazole-5-carboxamide;

(S)—N-(3-(2-Methylpyrrolidin-1-yl)phenyl)-5-(3-((piperidin-4-ylamino)methyl)phenyl)thiazolo[5,4-d]pyrimidin-7-amine;

N5-(1-(7-(3,4-Dimethoxyphenylamino)thiazolo[5,4-d]pyrimidin-5-yl)pyrrolidin-3-yl)pyridine-2,5-dicarboxamide;

Methyl 5-(1-(7-(3,4-dimethoxyphenylamino)thiazolo[5,4-d]pyrimidin-5-yl)pyrrolidin-3-ylcarbamoyl)picolinate;

5-(1-(7-(3,4-Dimethoxyphenylamino)thiazolo[5,4-d]pyrimidin-5-yl)pyrrolidin-3-ylcarbamoyl)picolinic acid;

1-(7-(3,4-Dimethoxyphenylamino)thiazolo[5,4-d]pyrimidin-5-yl)-N-(2-oxoindolin-5-yl)piperidine-3-carboxamide;

1-(7-(3,4-Dimethoxyphenylamino)thiazolo[5,4-d]pyrimidin-5-yl)-N-(1H-indazol-5-yl)piperidine-3-carboxamide;

5-(1-(7-(3,4-Dimethoxyphenylamino)thiazolo[5,4-d]pyrimidin-5-yl)piperidine-3-carboxamido)picolinic acid;

4-({1-[7-(3,4-Dimethoxy-phenylamino)-thiazolo[5,4-d]pyrimidin-5-yl]-piperidine-3-carbonyl}-amino)-2-methoxy-benzoic acid;

1-(7-(3,4-Dimethoxyphenylamino)thiazolo[5,4-d]pyrimidin-5-yl)-N-(4-(5-oxo-4,5-dihydro-1,2,4-oxadiazol-3-yl)phenyl)piperidine-3-carboxamide;

1-(7-(3,4-Dimethoxyphenylamino)thiazolo[5,4-d]pyrimidin-5-yl)-N-(1H-indazol-6-yl)piperidine-3-carboxamide;

1-(7-(3,4-Dimethoxyphenylamino)thiazolo[5,4-d]pyrimidin-5-yl)-N-(1-oxoisoindolin-5-yl)piperidine-3-carboxamide;

4-(1-(7-(3,4-Dimethoxyphenylamino)thiazolo[5,4-d]pyrimidin-5-yl)piperidine-3-carboxamido)-2-hydroxybenzoic acid;

1-(7-(3,4-Dimethoxyphenylamino)thiazolo[5,4-d]pyrimidin-5-yl)-N-(5-oxopyrrolidin-3-yl)piperidine-3-carboxamide;

1-(7-(3,4-Dimethoxyphenylamino)thiazolo[5,4-d]pyrimidin-5-yl)-N-(pyrazin-2-yl)piperidine-3-carboxamide;

1-(7-(3,4-Dimethoxyphenylamino)thiazolo[5,4-d]pyrimidin-5-yl)-N-(1,3-dioxoisoindolin-5-yl)piperidine-3-carboxamide;

1-(7-(3,4-Dimethoxyphenylamino)thiazolo[5,4-d]pyrimidin-5-yl)-N-(4-(5-mercapto-1,3,4-oxadiazol-2-yl)phenyl)piperidine-3-carboxamide;

1-(7-(3,4-Dimethoxyphenylamino)thiazolo[5,4-d]pyrimidin-5-yl)-N-(4-(5-mercapto-4-methyl-4H-1,2,4-triazol-3-yl)phenyl)piperidine-3-carboxamide;

3-{7-[3-(2-Oxa-6-aza-spiro[3.3]hept-6-yl)-phenylamino]-thiazolo[5,4-d]pyrimidin-5-yl}-benzoic acid;

4-(1-(7-(3,4-Dimethoxyphenylamino)thiazolo[5,4-d]pyrimidin-5-yl)pyrrolidine-3-carboxamido)benzoic acid;

4-(1-(7-(5,6-Dimethoxypyridin-2-ylamino)thiazolo[5,4-d]pyrimidin-5-yl)pyrrolidin-3-ylcarbamoyl)benzoic acid;

Methyl 3-(7-(3-(trifluoromethyl)phenylamino)thiazolo[5,4-d]pyrimidin-5-yl)benzoate;

3-[7-(3-Trifluoromethyl-phenylamino)-thiazolo[5,4-d]pyrimidin-5-yl]-benzoic acid;

3-[7-(3,4,5-Trimethoxy-phenylamino)-thiazolo[5,4-d]pyrimidin-5-yl]-benzamide;

1-(7-(3-((S)-2-Methylpyrrolidin-1-yl)phenylamino)thiazolo[5,4-d]pyrimidin-5-yl)piperidin-3-ol;

4-{7-[3-Methoxy-5-((S)-2-methyl-pyrrolidin-1-yl)-phenylamino]-thiazolo[5,4-d]pyrimidin-5-yl}-benzamide;

(S)-5-(6-Methoxypyridin-3-yl)-N-(3-(2-methylpyrrolidin-1-yl)phenyl)thiazolo[5,4-d]pyrimidin-7-amine;

4-{7-[3-((S)-2-Methyl-pyrrolidin-1-yl)-phenylamino]-thiazolo[5,4-d]pyrimidin-5-yl}-benzamide;

3-[7-(3,4-Dimethoxy-phenylamino)-thiazolo[5,4-d]pyrimidin-5-yl]-N-[4-(2,4-dioxo-thiazolidin-5-yl)-phenyl]-benzamide;

4-[7-(3,4-Dimethoxy-phenylamino)-thiazolo[5,4-d]pyrimidin-5-yl]-benzamide;

(S)—N-(2-(Dimethylamino)ethyl)-4-(7-(3-(2-methylpyrrolidin-1-yl)phenylamino)thiazolo[5,4-d]pyrimidin-5-yl)benzamide;

4-(7-(3,4-Dimethoxyphenylamino)thiazolo[5,4-d]pyrimidin-5-yl)-N-(2-(dimethylamino)ethyl)benzamide;

{3-[7-(3,4-Dimethoxy-phenylamino)-thiazolo[5,4-d]pyrimidin-5-yl]-phenyl}-methanol; and 3-[7-(3,4-Dimethoxy-phenylamino)-thiazolo[5,4-d]pyrimidin-5-yl]-benzamide.

13. A pharmaceutical composition comprising the compound of claim 1, admixed with at least one pharmaceutically acceptable carrier, excipient or diluent.

14. A method for treating rheumatoid arthritis comprising administering to a patient in need thereof a therapeutically effective amount of the compound of claim 1.

15. A method for treating asthma comprising administering to a patient in need thereof a therapeutically effective amount of the compound of claim 1.

\* \* \* \* \*